(12) United States Patent
Kato et al.

(10) Patent No.: US 8,318,782 B2
(45) Date of Patent: Nov. 27, 2012

(54) MITOTIC KINESIN INHIBITOR

(75) Inventors: Kazuhiko Kato, Shizuoka (JP); Yushi Kitamura, Osaka (JP)

(73) Assignees: Kyowa Hakko Kirin Co., Ltd., Tokyo (JP); Fujifilm Corporation, Tokyo (JP)

( * ) Notice: Subject to any disclaimer, the term of this patent is extended or adjusted under 35 U.S.C. 154(b) by 0 days.

(21) Appl. No.: 13/188,819

(22) Filed: Jul. 22, 2011

(65) Prior Publication Data

US 2011/0275827 A1 Nov. 10, 2011

Related U.S. Application Data

(60) Continuation of application No. 12/883,338, filed on Sep. 16, 2010, now abandoned, which is a division of application No. 10/553,222, filed as application No. PCT/JP2004/005489 on Apr. 16, 2004, now Pat. No. 7,851,635.

(30) Foreign Application Priority Data

Apr. 18, 2003 (JP) ................................. 2003-114071
Jun. 10, 2003 (JP) ................................. 2003-164727

(51) Int. Cl.
A61K 31/433 (2006.01)
C07D 285/125 (2006.01)
(52) U.S. Cl. ......... 514/363; 548/125; 548/139; 514/361
(58) Field of Classification Search ................. 548/125, 548/139; 514/361, 363
See application file for complete search history.

(56) References Cited

U.S. PATENT DOCUMENTS

| | | | |
|---|---|---|---|
| 4,338,449 A | 7/1982 | Tao et al. | |
| 4,346,225 A | 8/1982 | Tao et al. | |
| 4,699,913 A | 10/1987 | Farooq et al. | |
| 4,927,822 A | 5/1990 | Brown et al. | |
| 5,643,911 A | 7/1997 | Yamada et al. | |
| 5,814,647 A | 9/1998 | Urban et al. | |
| 6,207,690 B1 | 3/2001 | Urban et al. | |
| 6,235,762 B1 | 5/2001 | Takasugi et al. | |
| 6,414,121 B1 | 7/2002 | Wood et al. | |
| 6,545,004 B1 | 4/2003 | Finer et al. | |
| 6,545,030 B1 | 4/2003 | Barrett et al. | |
| 6,562,831 B1 | 5/2003 | Finer et al. | |
| 6,630,479 B1 | 10/2003 | Finer et al. | |
| 6,831,085 B1 | 12/2004 | Bergnes et al. | |
| 6,992,082 B2 | 1/2006 | Finer et al. | |
| 7,060,705 B2 | 6/2006 | Fraley et al. | |
| 7,105,668 B1 | 9/2006 | Bergnes et al. | |
| 7,119,089 B2 | 10/2006 | Finer et al. | |
| 7,230,000 B1 | 6/2007 | Finer et al. | |
| 7,425,636 B2 | 9/2008 | Murakata et al. | |
| 7,759,371 B2 | 7/2010 | Murakata et al. | |
| 7,851,635 B2 | 12/2010 | Ino | |
| 7,902,234 B2 * | 3/2011 | Murakata et al. | 514/363 |
| 2002/0143026 A1 | 10/2002 | Lombardo et al. | |
| 2002/0165240 A1 | 11/2002 | Kimball et al. | |
| 2003/0008888 A1 | 1/2003 | Kimball et al. | |
| 2004/0023996 A1 | 2/2004 | Finer et al. | |
| 2004/0087548 A1 | 5/2004 | Salvati et al. | |
| 2004/0132719 A1 | 7/2004 | Finer et al. | |
| 2004/0132830 A1 | 7/2004 | Finer et al. | |
| 2004/0254203 A1 | 12/2004 | Finer et al. | |
| 2004/0259826 A1 | 12/2004 | Fraley et al. | |
| 2005/0119484 A1 | 6/2005 | Breslin et al. | |
| 2005/0187232 A1 | 8/2005 | Finer et al. | |
| 2005/0203110 A1 | 9/2005 | Coleman et al. | |
| 2006/0014736 A1 | 1/2006 | Finer et al. | |
| 2006/0074113 A1 | 4/2006 | Murakata et al. | |
| 2006/0100161 A1 | 5/2006 | Hans et al. | |
| 2006/0111424 A1 | 5/2006 | Salvati et al. | |
| 2007/0112044 A1 | 5/2007 | Murakata et al. | |
| 2007/0213380 A1 | 9/2007 | Murakata et al. | |
| 2007/0254902 A1 | 11/2007 | Finer et al. | |

(Continued)

FOREIGN PATENT DOCUMENTS

DE 243930 3/1987

(Continued)

OTHER PUBLICATIONS

CA Registry No. 337501-53-8, indexed in Registry file on STN on May 23, 2001.
CA Registry No. 337501-51-6, indexed in Registry file on STN on May 23, 2001.
CA Registry No. 332389-30-7, indexed in Registry file on STN on Apr. 25, 2001.
CA Registry No. 332389-28-3, indexed in Registry file on STN on Apr. 25, 2001.
CA Registry No. 332389-25-0, indexed in Registry file on STN on Apr. 25, 2001.

(Continued)

Primary Examiner — Golam M M Shameem
(74) Attorney, Agent, or Firm — Greenblum & Bernstein, P.L.C.

(57) ABSTRACT

A mitotic kinesin Eg5 inhibitor which comprises a thiadiazoline derivative represented by the general formula (I) or a pharmacologically acceptable salt thereof as an active ingredient:

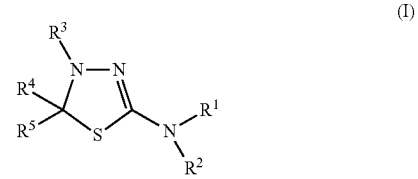

(I)

[wherein $R^1$ represents a hydrogen atom and the like, $R^2$ represents a hydrogen atom, —C(=W)$R^6$ (wherein W represents an oxygen atom or a sulfur atom, and $R^6$ represents substituted or unsubstituted lower alkyl and the like) and the like, $R^3$ represents —C(=Z)$R^{19}$ (wherein Z represents an oxygen atom or a sulfur atom, and $R^{19}$ represents substituted or unsubstituted lower alkyl and the like) and the like, $R^4$ represents substituted or unsubstituted lower alkyl and the like, and $R^5$ represents substituted or unsubstituted aryl and the like] and the like are provided.

3 Claims, No Drawings

U.S. PATENT DOCUMENTS

| | | | |
|---|---|---|---|
| 2007/0276017 A1 | 11/2007 | Murakata et al. |
| 2008/0194653 A1 | 8/2008 | Murakata et al. |
| 2008/0262049 A1 | 10/2008 | Nakai et al. |
| 2010/0029625 A1 | 2/2010 | Nakai et al. |

FOREIGN PATENT DOCUMENTS

| | | |
|---|---|---|
| EP | 0207004 | 12/1986 |
| EP | 0217519 | 4/1987 |
| EP | 1 004 241 | 5/2000 |
| EP | 1454903 | 9/2004 |
| EP | 1 616 866 | 1/2006 |
| EP | 1 632 484 | 3/2006 |
| EP | 1 671 957 | 6/2006 |
| EP | 1 867 640 | 12/2007 |
| EP | 1 870 404 | 12/2007 |
| JP | 62-53976 | 3/1987 |
| JP | 8-34734 | 2/1996 |
| JP | 2000-159756 | 6/2000 |
| JP | 2000-204077 | 7/2000 |
| JP | 2000-229959 | 8/2000 |
| WO | 93/22311 | 11/1993 |
| WO | 00/42029 | 7/2000 |
| WO | 01/30768 | 5/2001 |
| WO | 01/56994 | 8/2001 |
| WO | 01/98278 | 12/2001 |
| WO | 02/056880 | 7/2002 |
| WO | 02/057244 | 7/2002 |
| WO | 02/067939 | 9/2002 |
| WO | 02/079149 | 10/2002 |
| WO | 02/079169 | 10/2002 |
| WO | 03/039460 | 5/2003 |
| WO | 03/051854 | 6/2003 |
| WO | 03/079973 | 10/2003 |
| WO | 2004/039774 | 5/2004 |
| WO | 2004/092147 | 10/2004 |
| WO | 2004/111023 | 12/2004 |
| WO | 2004/111024 | 12/2004 |
| WO | 2005/035512 | 4/2005 |
| WO | 2006/044825 | 4/2006 |
| WO | 2006/101102 | 9/2006 |
| WO | 2006/101103 | 9/2006 |
| WO | 2006/137490 | 12/2006 |

OTHER PUBLICATIONS

Daub et al. Nature Reviews Drug Discovery 3:1001-10, 2004.
Golub et al. *Science* 286:531-37, 1999.
Grachev et al. Journal of Applied Spectroscopy 67(3):461-66, 2000.
Agarwal et al. Nature Reviews Cancer 3:502-16, 2003.
CA Registry No. 400873-00-9, indexed in Registry file on STN on Mar. 14, 2002.
CA Registry No. 400833-35-4, indexed in Registry file on STN on Mar. 14, 2002.
CA Registry No. 385382-44-5, indexed in Registry file on STN on Jan. 22, 2002.
CA Registry No. 382174-71-2, indexed in Registry file on STN on Jan. 11, 2002.
CA Registry No. 356773-31-4, indexed in Registry file on STN on Sep. 14, 2001.
CA Registry No. 356773-11-0, indexed in Registry file on STN on Sep. 14, 2001.
CA Registry No. 355435-20-0, indexed in Registry file on STN on Sep. 10, 2001.
CA Registry No. 353466-59-8, indexed in Registry file on STN on Aug. 29, 2001.
CA Registry No. 352225-16-2, indexed in Registry file on STN on Aug. 21, 2001.
B. G. Szczepankiewicz et al., J. Med. Chem., 2001, vol. 44, No. 25, pp. 4416-4430.
S. M. Hassan et al., J. Chem. Research Synopses, 2000, vol. 12, pp. 544-545 and pp. 1301-1315.
K. N. Zelenin et al., Zhurnal Organicheskoi Khimii, 1984, vol. 20, No. 1, pp. 152-162.
D.M. Evans et al., Journal of the Chemical Society, Perkin Transactions 1, 1986, vol. 8, pp. 1499-1505.
K. Zelenin et al., Chemical Abstracts, 1982, vol. 97, No. 19, p. 708, Abstract No. 162877w.
CA Registry No. 443105-88-2, indexed in Registry file on STN on Aug. 8, 2002.
CA Registry No. 443105-51-9, indexed in Registry file on STN on Aug. 8, 2002.
CA Registry No. 443105-41-7, indexed in Registry file on STN on Aug. 8, 2002.
CA Registry No. 443105-34-8, indexed in Registry file on STN on Aug. 8, 2002.
CA Registry No. 443105-23-5, indexed in Registry file on STN on Aug. 8, 2002.
CA Registry No. 416841-95-7, indexed in Registry file on STN on May 16, 2002.
CA Registry No. 416841-94-6, indexed in Registry file on STN on May 16, 2002.
CA Registry No. 405925-80-6, indexed in Registry file on STN on Apr. 18, 2002.
CA Registry No. 401945-66-2, indexed in Registry file on STN on Mar. 20, 2002.
CA Registry No. 401945-63-9, indexed in Registry file on STN on Mar. 20, 2002.
CA Registry No. 400873-06-5, indexed in Registry file on STN on Mar. 14, 2002.
CA Registry No. 332055-94-4, indexed in Registry file on STN on Apr. 23, 2001.
CA Registry No. 329689-25-0, indexed in Registry file on STN on Apr. 2, 2001.
CA Registry No. 329689-21-6, indexed in Registry file on STN on Apr. 2, 2001.
CA Registry No. 329689-19-2, indexed in Registry file on STN on Apr. 2, 2001.
CA Registry No. 312597-81-2, indexed in Registry file on STN on Jan. 3, 2001.
CA Registry No. 312597-80-1, indexed in Registry file on STN on Jan. 3, 2001.
CA Registry No. 312597-79-8, indexed in Registry file on STN on Jan. 3, 2001.
CA Registry No. 312597-76-5, indexed in Registry file on STN on Jan. 3, 2001.
CA Registry No. 309927-68-2, indexed in Registry file on STN on Dec. 20, 2000.
CA Registry No. 298218-65-2, indexed in Registry file on STN on Oct. 23, 2000.
CA Registry No. 296801-28-0, indexed in Registry file on STN on Oct. 18, 2000.
CA Registry No. 356773-74-5, indexed in Registry file on STN on Sep. 14, 2001.
CA Registry No. 356773-69-8, indexed in Registry file on STN on Sep. 14, 2001.
CA Registry No. 356773-42-7, indexed in Registry file on STN on Sep. 14, 2001.
CA Registry No. 344872-11-3, indexed in Registry file on STN on Jul. 8, 2001.
CA Registry No. 337501-59-4, indexed in Registry file on STN on May 23, 2001.
CA Registry No. 337501-55-0, indexed in Registry file on STN on May 23, 2001.
*Jikken Igaku* (*Experimental Medicine*) 17(4):439-44, 1999.
Moses et al. *N. Engl. J. Med.* 349(14):1315-23, 2003.
Power et al. *J. Chem. Soc. Chem. Commun.* 8:873-74, 1998.
Ross, R. *Nature* 362:801-09, 1993.
Saha et al. CA 117:171340, 1992.
Serruys et al. *N. Engl. J. Med.* 331(8):489-95, 1994.
*Shin-Jikken-Kagaku-Koza* 14:1142-45 (Maruzen 1978).
Stone et al. *N. Engl. J. Med.* 350(3):221-31, 2004.
Su et al. *Proc. Natl. Acad. Sci. USA* 99(7):4465-70, 2002.
Temple et al. *J. Med. Chem.* 25:1045-50, 1982.
Yinglin et al. *Synthesis* 28:615-18, 1990.
Zelenin et al. CA 119:202821, 1993.
Schenone, S., et al. "3-Arylsulphonyl-5-arylamino-1,3,4-thiadiazol-2(3H)ones as Anti-inflammatory and Analgesic Agents", Bioorganic and Medicinal Chemistry, 9, 2001, pp. 2149-2153.

Bhalla, M., et al. "Benzopyran-2-one derivatives: anti-inflammatory, analgesic and antiproteolytic agents" European Journal of Medicinal Chemistry, 29, 1994, pp. 713-717.
Blangy, A., et al., "Phosphorylation by p34$^{cdc2}$ Regulates Spindle Association of Human Eg5, a Kinesin-Related Motor Essential for Bipolar Spindle Formation in Vivo", Cell, vol. 83, 1995, pp. 1159-1169.
Kapoor, T. M., et al., "Probing Spindle Assembly Mechanism with Monastrol, a Small Molecule Inhibitor of the Mitotic Kinesin, Eg5", The Journal of Cell Biology, vol. 150, 2000, pp. 975-988.
Kapoor, T. M., et al., "Allele-specific activators and inhibitors for kinesin" Proc. Natl. Acad. Sci. USA, vol. 96, 1999, pp. 9106-9111.
Lockhart, A. et al., "Kinetics and Motility of the Eg5 Microtubule Motor", Biochemistry, vol. 35, 1999. pp. 2365-2373.
Turner, J., et al., "Crystal Structure of the Mitotic Spindle Kinesin Eg5 Reveals a Novel Conformation of the Neck-linker", The Journal of Biological Chemistry, vol. 276, 2001, pp. 25496-25502.
Maliga, Z. et al., "Evidence that Monastrol Is an Allosteric Inhibitor of the Mitotic Kinesin Eg5", Chemistry and Biology, vol. 9, 2002, pp. 989-996.
Mandelkow, E, et al., "Kinesin motors and disease", Trends in Cell Biology, vol. 12, 2002, pp. 585-591.
Mayer, T. U., et al., "Small Molecule Inhibitor of Mitotic Spindle Bipolarity Identified in a Phenotype-Based Screen", Science, vol. 286, 1999, pp. 971-974.
Hoque, T., et al., "Synthesis of Some 5-spiro-4-acetyl-2-(Acetylamino)-$\Delta^2$-1,3,4-Thiadiazoline from Ketone Thiosemicarbazones", Journal of the Bangladesh Chemical Society, vol. 5 (2), 1992, pp. 127-132.
Kubota, S., et al. "Synthesis of 4-Acyl-2-(acylamino)-$\Delta^2$-1,3,4-thiadiazolines and 4-Acyl-2-amino-$\Delta^2$-1,3,4-thiadiazolines by Acylation of Thiosemicarbazones" J. Org. Chem., vol. 45, No. 8, 1980, pp. 1473-1477.
Tao, E.V.P., et al., J. Heterocyclic Chem., vol. 21, 1984, pp. 599-601.
Huang, T. B., et al. "Reaction of Schiff Base of Thiohydrazines with P(NR$_2$)$_3$" Phosphorus, Sulfur & Silicon, vol. 122, pp. 307-312 (1997).
Kubota, S., et al. "Novel Rearrangement of 3-acyl-5-acylamino-2,3-dihydro-1,3,4-thiadiazole 1-oxides into 1,3,4-oxadiazoles" Heterocycles, vol. 24, No. 1, 1986, pp. 21-24.
Kubota, S., et al. "Stereoselective S-Oxidation of 5-Substituted 4-Acetyl- $\Delta^2$-1,3,4-thiadiazolines: X-Ray Crystal Structure of 4-Acetyl-2-acetylamino-5-methyl-5-phenyl-$\Delta^2$1,3,4-thiadiazolines 1-Oxide" J. Chem. Soc., Chem. Comm. 1982, No. 16, pp. 901-902.
M.A. Khalil et al., Arch. Pharm. (Weinheim), vol. 326, 1993, pp. 489-492.
A.A. Farghaly et al., Arch. Pharm. Pharm. Med. Chem., vol. 333, No. 2-3, 2000, pp. 53-57.
El-S.M. El-Khawass et al., Alexandria Journal of Pharmaceutical. Sciences, vol. 4, No. 1, 1990, pp. 77-79.
H.M. Mokhtar et al., Bull. Pharm. Sci., Assiut University, vol. 18, Part 2, Dec. 1995, pp. 59-67.
M.A. Khalil, Alexandria J. of Pharm. Sciences, vol. 3, No. 2, 1989, pp. 221-224.
L.L. Awad et al., Alexandria J. of Pharm. Sci., vol. 3, No. 2, 1989, pp. 119-121.
S.Y. Hassan et al., J. Saudi Chem. Soc., vol. 3, No. 2, 1999, pp. 171-176.
B. Schulze et al., Zeitschrift fuer Chemie, vol. 29, No. 5, 1989, pp. 166-167.
S. Kubota et al., Heterocycles, vol. 4, 1976, pp. 1909-1912.

A. Wengel et al., Pestic. Sci., vol. 30, 1990, pp. 223-233.
E.E. Ycoba et al., Khim. Geterotsikl. Soedin., vol. 10, 1994, pp. 1337-1344.
Y. Nakayama et al., J. Org. Chem., vol. 49, 1984, pp. 1703-1707.
E.V. Tao et al., Heterocycles, vol. 29, 1989, pp. 133-140.
L. Somogyi, Tetrahedron, vol. 47, 1991, pp. 9305-9316.
L. Somogyi et al., Tetrahedron, vol. 48, 1992, pp. 9355-9362.
Khim. Geterotsiki. Soedin, vol. 12, 1992, pp. 1689-1697.
S. Andreae et al., Journal f. prakt. Chemie., vol. 328, 1986, Heft 2, pp. 205-214.
L. Somogyi, Liebigs Ann. Chem., 1994, pp. 623-627.
L. Somogyi, Liebigs Ann., 1995, pp. 721-724.
Z.M. Nofal et al., Arch. Pharm. Res., vol. 25, 2002, pp. 250-257.
S. Kabilan et al., Asian Journal of Chemistry, vol. 14, 2002, pp. 879-883.
M.A.M. Alho et al., Arkivoc 2000, vol. 1, pp. 627-640.
K.N. Zelenin et al., Chemistry of Heterocyclic Compounds, vol. 35, 1999, pp. 87-92.
I.V.U. Zavedenii, Khimiya I Khimicheskaya Takhnologiya, vol. 43, 2000, pp. 64-68.
N.S. Habib et al., Alex. J. Pharm. Sci., vol. 10, 1996, pp. 53-58.
F.A. Ashour et al., Bull. Fac. Pharm. Cairo Univ., vol. 31, 1993, pp. 381-386.
M.H. Khan et al., J. Pesticide Sci., vol. 19, 1994, pp. 305-308.
Dokl. Aka. Nauk SSSR, vol. 296, 1987, pp. 1133-1137.
Zhurnal Organicheskoi Khimii, 1986, pp. 663-664.
R.J. Kuban et al., Cryst. Res. Technol., vol. 22, 1987, pp. 799-802.
K.N. Thimmaiah et al., Inorganica Chimica Acta, vol. 107, 1985, pp. 1-4.
CAS Registry Nos. 443105-88-2, 443105-83-7, 443105-78-0, 443105-73-5, 443105-64-4, 443105-56-4, 443105-51-9, 443105-46-2, 443105-41-7, 443105-34-8, 442654-91-3, 438540-30-8, 433235-71-3, 432536-58-8, 432518-92-8, 419551-57-8, 405925-79-3, 400833-35-4, 356773-31-4, 356773-12-1, 355435-20-0, 352225-16-2, 332389-28-3, 332389-25-0, 89992-30-3, 356773-98-3, 356773-79-0, 356773-31-4, 356773-13-2, 350581-79-2, 346715-36-4, 332389-27-2, 332389-25-0, 330683-67-5, 330683-65-3, 313558-45-1, 313548-79-7, 313523-91-0, 313523-88-5, 307332-32-7, 307332-31-6, 307332-30-5, 307332-29-2, 307332-28-1, 307332-24-7, 307332-22-5, 300808-92-8, 300719-38-4, 298218-64-1, 296801-28-0, 292066-09-2, 332389-28-3, 332389-25-0, 332389-24-9, 332389-23-8, 296801-28-0, 198069-12-4, 149638-52-8, 149638-50-6, 149638-48-2, 149638-46-0, 149638-44-8, 149638-42-6.various dates in 2000, 2001, 2002.
H. Graubaum et al., Z. Chem., vol. 26, 1986, pp. 99-100.
Yun Ding et al., "Syntheses and Anticancer Activity of Ribonucleoside Analogues Containing Thio-Substituted Five-Membered Heterocyclic Base", Bioorganic and Medicinal Chemistry Letters, vol. 7, No. 13, pp. 1607-1610 (1997).
U.S. Appl. No. 60/620,048, filed Oct. 19, 2004, Hans et al.
Silverman, R. B. (The Org. Chem. of Drug Design and Drug Action, Academic Press, Inc.: San Diego, 1992, pp. 4-51).
Kubinyi (3D QSAR in Drug Design: Ligand-Protein Interactions and Molecular Similarity, vol. 2-3, Springer, 1998, 800 pages).
CAPLUS Abstract of WO 03/051854, Accession # 2003: 491200.
Bulka etal. (CAPLUS abstract of Chemische Berichte (1963), 96(B), 2199-205, Accession #1963:462322).
Extended European Search Report dated Apr. 5, 2011 in EP 11158215.

* cited by examiner

MITOTIC KINESIN INHIBITOR

CROSS-REFERENCE TO RELATED APPLICATION

This application is a continuation of application Ser. No. 12/883,338, filed Sep. 16, 2010, which is a divisional of application Ser. No. 10/553,222, now U.S. Pat. No. 7,851,635, which is a national stage of PCT/JP2004/005489, filed Apr. 16, 2004, which claims priority to Japanese Application No. 2003-114071, filed Apr. 18, 2003 and Japanese Application No. 2003-164727, filed Jun. 10, 2003. The disclosures of application Ser. Nos. 10/553,222, 12/883,338 and PCT/JP2004/005489 are incorporated by reference herein in their entireties.

TECHNICAL FIELD

The present invention relates to a mitotic kinesin Eg5 inhibitor comprising a thiadiazoline derivative or a pharmacologically acceptable salt thereof as an active ingredient, which is effective in treatment of a disease associated with cell proliferation, for example, restenosis, cardiac hypertrophy, immunologic diseases, and the like.

BACKGROUND ART

The mitotic kinesins are proteins that are involved in the mitotic spindle regulation; and play an essential role for progression of the mitotic phase in cell cycle. These proteins have a function of moving proteins along microtubules using the energy produced by ATP hydrolysis, and belong to a class of functional proteins generally called "molecular motors". In the mitotic phase, the proteins are deeply involved in extension and maintenance of mitotic spindles, as well as formation of structure called spindle pole body, and further, they regulate progression of normal cell division through the movement of chromosomes along the spindle microtubules.

The mitotic kinesin Eg5 is one of the mitotic kinesins constituting an evolutionarily conserved subfamily. It is known that Eg5 has a function as a bipolar homotetramer molecule, and is involved in the formation of the bipolar spindle structure by crosslinking two of microtubules of the same direction and moving them in the direction toward the + (plus) end to cause sliding of two of the antiparallel microtubules, thereby keep − (minus) ends of microtubules at a distance and separate spindle pole bodies. The above functions of Eg5 were elucidated on the basis of the analysis of the human cells treated with anti-Eg5 antibody and a specific inhibitor [Cell, Vol. 83, p. 1159 (1995); J. Cell Biol., Vol. 150, p. 975 (2000); Jikken Igaku (Experimental Medicine), Vol. 17, p. 439 (1999)].

The gene of human Eg5 was cloned in 1995, and the expression of a full-length human Eg5 recombinant protein by using an insect cell and functional analysis using the resulting protein were reported [Cell, Vol. 83, p. 1159 (1995)]. The gene was registered in a public database as GenBank accession numbers: X85137, NM004523 and U37426. A biochemical analysis and structure analysis by crystallization of Eg5 utilizing an N-terminus portion of human Eg5, expressed by using *Escherichia coli* cells, were reported [J. Biological Chemistry, Vol. 976, p. 25496 (2001); Chemistry & Biology, Vol. 9, p. 989 (2002)], which applied a technique similar to the analysis utilizing Eg5 derived from *Xenopus laevis* having a high homology to the human Eg5 [Proc. Natl. Acad. Sci. USA, Vol. 96, p. 9106 (1999); Biochemistry, Vol. 35, p. 2365 (1996)].

As described above, the mitotic kinesin Eg5 is important as a target molecule of a novel mitotic phase acting agent and it is considered that an inhibitor against said molecule is promising as an agent for therapeutic treatment of diseases in which cell proliferation is involved (for example, restenosis, cardiac hypertrophy, arthritis, immunologic diseases, and the like) [WO01/98278; WO02/56880; WO02/57244; Trends in Cell Biology, Vol. 12, p. 585 (2002)].

As compounds having inhibitory activity against the human Eg5 enzyme, monastrol [Science, Vol. 286, p. 971 (1999)], quinazoline derivatives (WO01/98278), phenathiazine derivatives (WO02/57244), triphenylmethane derivatives (WO02/56880), dihydropyrimidine derivatives (WO02/79149; WO02/79169), dihydropyrazole derivatives (WO03/79973), and the like were reported.

Thiadiazoline derivatives having inhibitory activity against a transcription factor STAT6 activation or those having integrin antagonistic action are known (Japanese Patent Unexamined Publication (KOKAI) No. 2000-229959; WO01/56994), and further, those having an antibacterial activity, ACE inhibitory activity or the like are also known (WO93/22311; Japanese Patent Unexamined Publication (KOKAI) No. 62-53976; J. Bangladesh Chem. Soc., Vol. 5, p. 127 (1992)).

DISCLOSURE OF THE INVENTION

An object of the present invention is to provide a mitotic kinesin Eg5 inhibitor and the like which comprises a thiadiazoline derivative or a pharmacologically acceptable salt thereof as an active ingredient.

The present invention relates to the following (1) to (27).

(1) A mitotic kinesin Eg5 inhibitor which comprises a thiadiazoline derivative represented by the general formula (I) or a pharmacologically acceptable salt thereof as an active ingredient:

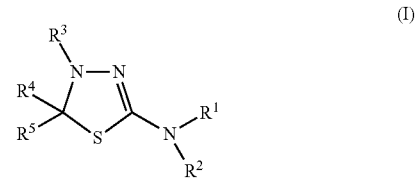

<wherein $R^1$ represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl, or a substituted or unsubstituted heterocyclic group;

$R^2$ represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl, or a substituted or unsubstituted heterocyclic group, —C(=W)$R^6$ [wherein W represents an oxygen atom- or a sulfur atom, and $R^6$ represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl, a substituted or unsubstituted heterocyclic group, —NR$^7$R$^8$ (wherein R$^7$ and R$^8$ are the same or different and each represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl; or a substituted or unsubstituted heterocyclic group, or $R^7$ and $R^8$ are combined together with the adjacent nitrogen atom to form a substituted or unsubstituted heterocyclic group), —$OR^9$ (wherein $R^9$ represents substituted or unsubstituted lower alkyl, substituted or unsubstituted lower alkenyl, substituted or unsubstituted lower alkynyl, substituted or unsubstituted cycloalkyl, substituted or unsubstituted aryl, or a substituted or unsubstituted heterocyclic group) or —$SR^{10}$ (wherein $R^{10}$ has the same meaning as that of the aforementioned $R^9$)], —$NR^{11}R^{12}$ {wherein $R^{11}$ and $R^{12}$ are the same or different and each represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl, a substituted or unsubstituted heterocyclic group, —(=O)$R^{13}$ [wherein $R^{13}$ represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl, a substituted or unsubstituted heterocyclic group, —$NR^{14}R^{15}$ (wherein $R^{14}$ and $R^{15}$ are the same or different and each represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl, or a substituted or unsubstituted heterocyclic group, or $R^{14}$ and $R^{15}$ are combined together with the adjacent nitrogen atom to form a substituted or unsubstituted heterocyclic group), —$OR^{16}$ (wherein $R^{16}$ has the same meaning as that of the aforementioned $R^9$), or —$SR^{17}$ (wherein $R^{17}$ has the same meaning as that of the aforementioned $R^9$)], or $R^{11}$ and $R^{12}$ are combined together with the adjacent nitrogen atom to form a substituted or unsubstituted heterocyclic group), or —$SO_2R^{18}$ (wherein $R^{18}$ represents substituted or unsubstituted lower alkyl, substituted or unsubstituted lower alkenyl, substituted or unsubstituted lower alkynyl, substituted or unsubstituted cycloalkyl, substituted or unsubstituted aryl, or a substituted or unsubstituted heterocyclic group), or $R^1$ and $R^2$ are combined together with the adjacent nitrogen atom to form a substituted or unsubstituted heterocyclic group, $R^3$ represents a hydrogen atom, or —C(=Z)$R^{19}$ [wherein Z represents an oxygen atom or a sulfur atom, and $R^{19}$ represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl, a substituted or unsubstituted heterocyclic group, —$NR^{20}R^{21}$ (wherein $R^{20}$ and $R^{21}$ are the same or different and each represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl, or a substituted or unsubstituted heterocyclic group, or $R^{20}$ and $R^{21}$ are combined together with the adjacent nitrogen atom to form a substituted or unsubstituted heterocyclic group), —$OR^{22}$ (wherein $R^{22}$ represents substituted or unsubstituted lower alkyl, substituted or unsubstituted lower alkenyl, substituted or unsubstituted lower alkynyl, substituted or unsubstituted cycloalkyl, substituted or unsubstituted aryl, or a substituted or unsubstituted heterocyclic group), or —$SR^{23}$ (wherein $R^{23}$ has the same meaning as that of the aforementioned $R^{22}$)], $R^4$ represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl, or a substituted or unsubstituted heterocyclic group, and $R^5$ represents substituted or unsubstituted lower alkyl, substituted or unsubstituted lower alkenyl, substituted or unsubstituted lower alkynyl, substituted or unsubstituted cycloalkyl, substituted or unsubstituted aryl, or a substituted or unsubstituted heterocyclic group, or $R^4$ and $R^5$ are combined together to represent —$(CR^{25A}R^{25B})_{m1}Q(CR^{25C}CR^{25D})_{m2}$— {wherein Q represents a single bond, substituted or unsubstituted phenylene or cycloalkylene, m1 and m2 are the same or different and each represents an integer of from 0 to 4, with the proviso that m1 and m2 are not 0 at the same time, $R^{25A}$, $R^{25B}$, $R^{25C}$ and $R^{25D}$ are the same or different and each represents a hydrogen atom, halogen, substituted or unsubstituted lower alkyl, —$OR^{26}$ [wherein $R^{26}$ represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl, a substituted or unsubstituted heterocyclic group, —$CONR^{27}R^{28}$ (wherein $R^{27}$ and $R^{28}$ are the same or different and each represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl, or a substituted or unsubstituted heterocyclic group, or $R^{27}$ and $R^{28}$ are combined together with the adjacent nitrogen atom to form a substituted or unsubstituted heterocyclic group), —$SO_2NR^{29}R^{30}$ (wherein $R^{29}$ and $R^{30}$ have the same meanings as those of the aforementioned $R^{27}$ and $R^{28}$, respectively), or —$COR^{31}$ (wherein $R^{31}$ represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl, or a substituted or unsubstituted heterocyclic group)], —$NR^{32}R^{33}$ [wherein $R^{32}$ and $R^{33}$ are the same or different and each represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl, a substituted or unsubstituted heterocyclic group, —$COR^{34}$ (wherein $R^{34}$ represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl, a substituted or unsubstituted heterocyclic group, substituted or unsubstituted lower alkoxy, substituted or unsubstituted aryloxy, amino, substituted or unsubstituted lower alkylamino, substituted or unsubstituted di-(lower alkyl)amino, or substituted or unsubstituted arylamino), or —$SO_2R^{35}$ (wherein $R^{35}$ represents substituted or unsubstituted lower alkyl, substituted or unsubstituted lower alkenyl, substituted or unsubstituted lower alkynyl, substituted or unsubstituted cycloalkyl, substituted or unsubstituted aryl, or a substituted or unsubstituted heterocyclic group)], or —$COOR^{36}$ (wherein $R^{36}$ represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl, or a substituted or unsubstituted heterocyclic group), or $R^{26A}$ and $R^{25B}$, or $R^{25C}$ and $R^{25D}$ are combined together to represent an oxygen atom, and when m1 or m2 is an integer of 2 or above, any of $R^{25A}$, $R^{25B}$, $R^{25C}$ and $R^{25D}$ may be the same or different, and any two of $R^{26A}$, $R^{25B}$, $R^{25C}$ and $R^{25D}$ which are bound to the adjacent two carbon atoms may be combined to form a bond}>.

(2) The mitotic kinesin Eg5 inhibitor according to (1), wherein $R^2$ is —C(=W)$R^6$ (wherein W and $R^6$ have the same meanings as those mentioned above, respectively).

(3) The mitotic kinesin Eg5 inhibitor according to (2), wherein $R^6$ is substituted or unsubstituted lower alkyl.

(4) The mitotic kinesin Eg5 inhibitor according to any one of (1) to (3), wherein $R^3$ is —C(=Z)$R^{19}$ (wherein Z and $R^{19}$ have the same meanings as those mentioned above, respectively).

(5) The mitotic kinesin Eg5 inhibitor according to (4), wherein $R^{19}$ is substituted or unsubstituted lower alkyl.

(6) The mitotic kinesin Eg5 inhibitor according to any one of (1) to (5), wherein $R^5$ is substituted or unsubstituted aryl, or a substituted or unsubstituted aromatic heterocyclic group.

(7) The mitotic kinesin Eg5 inhibitor according to any one of (1) to (5), wherein $R^5$ is substituted or unsubstituted aryl.

(8) The mitotic kinesin Eg5 inhibitor according to any one of (1) to (7), wherein $R^4$ is substituted or unsubstituted lower alkyl, or —(CH$_2$)$_n$NHSO$_2$R$^{24}$ (wherein n and $R^{24}$ have the same meanings as those mentioned above, respectively).

(9) The mitotic kinesin Eg5 inhibitor according to any one of (1) to (5), wherein $R^4$ and $R^5$ are combined together to represent —(CR$^{25A}$R$^{25B}$)$_{m1}$Q(CR$^{25C}$R$^{25D}$)$_{m2}$— (wherein $R^{25A}$, $R^{25B}$, $R^{25C}$, $R^{25D}$, m1, m2 and Q have the same meanings as those mentioned above, respectively).

(10) The mitotic kinesin Eg5 inhibitor according to (9), wherein Q is substituted or unsubstituted phenylene.

(11) The mitotic kinesin Eg5 inhibitor according to any one of (1) to (10), wherein $R^1$ is a hydrogen atom.

(12) The mitotic kinesin Eg5 inhibitor according to any one of (1) to (11), wherein W and Z are oxygen atoms.

(13) A thiadiazoline derivative represented by the general formula (IA) or a pharmacologically acceptable salt thereof:

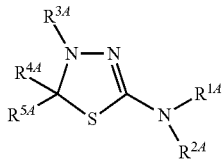

(IA)

<wherein $R^{1A}$ represents a hydrogen atom, $R^{2A}$ represents a hydrogen atom or —COR$^{6A}$ (wherein $R^{6A}$ represents substituted or unsubstituted lower alkyl), or $R^{1A}$ and $R^{2A}$ are combined together with the adjacent nitrogen atom to form a substituted or unsubstituted heterocyclic group, $R^{3A}$ represents —COR$^{19A}$ (wherein $R^{19A}$ represents substituted or unsubstituted lower alkyl), $R^{4A}$ represents —(CH$_2$)$_p$NR$^{4AA}$R$^{4AB}$ [wherein p represents 1 or 2, and $R^{4AA}$ and $R^{4AB}$ are the same or different and each represents a hydrogen atom, lower alkyl or cycloalkyl (with the proviso that when $R^{2A}$ is —COR$^{6A}$, $R^{6A}$ and $R^{19A}$ are tert-butyl and $R^{5A}$ is phenyl, $R^{4AA}$ and $R^{4AB}$ are not methyl at the same time)], —(CH$_2$)$_p$NR$^{4AD}$COR$^{4AC}$ (wherein p has the same meaning as that mentioned above, $R^{4AC}$ represents a hydrogen atom, lower alkyl or lower alkoxy, and $R^{4AD}$ represents a hydrogen atom or lower alkyl), or —(CH$_2$)$_p$NHSO$_2$R$^{29A}$ (wherein p has the same meaning as that mentioned above, $R^{24A}$ represents —(CH$_2$)$_q$NR$^{24AA}$R$^{29AB}$ [wherein q represents an integer of from 0 to 5, and $R^{24AA}$ and $R^{24AB}$ are the same or different and each represents a hydrogen atom, substituted or unsubstituted lower alkyl or cycloalkyl (with the proviso that when $R^{2A}$ is —COR$^{6A}$, $R^{6A}$ is tert-butyl and $R^{19A}$ is methyl or tert-butyl, neither of $R^{24AA}$ and $R^{24AB}$ is methyl, and done of $R^{24AA}$ and $R^{24AB}$ is a hydrogen atom in this case, the other is not ethyl or hydroxyethyl)), 3-chloropropyl, 3-azidopropyl or lower alkenyl (with the proviso that when $R^{2A}$ is —COR$^{6A}$, $R^{6A}$ is tert-butyl and $R^{19A}$ is methyl or tert-butyl, $R^{24A}$ is not vinyl)), and $R^{5A}$ represents substituted or unsubstituted aryl or a substituted or unsubstituted aromatic heterocyclic group>.

(14) The thiadiazoline derivative or a pharmacologically acceptable salt thereof according to (13), wherein $R^{5A}$ is substituted or unsubstituted aryl.

(15) The thiadiazoline derivative or a pharmacologically acceptable salt thereof according to (13), wherein $R^{5A}$ is phenyl.

(16) The thiadiazoline derivative or a pharmacologically acceptable salt thereof according to any one of (13) to (15), wherein $R^{2A}$ is COR$^{6A}$, and $R^{6A}$ is unsubstituted lower alkyl.

(17) The thiadiazoline derivative or a pharmacologically acceptable salt thereof according to any one of (13) to (15), wherein $R^{2A}$ is COR$^{6A}$, and $R^{6A}$ is tert-butyl.

(18) The thiadiazoline derivative or a pharmacologically acceptable salt thereof according to any one of (13) to (17), wherein $R^{19A}$ is unsubstituted lower alkyl.

(19) The thiadiazoline derivative or a pharmacologically acceptable salt thereof according to any one of (13) to (17), wherein $R^{19A}$ is tert-butyl.

(20) The thiadiazoline derivative or a pharmacologically acceptable salt thereof according to any one of (13) to (19), wherein $R^{4A}$ is —(CH$_2$)$_p$NR$^{4AA}$R$^{4AB}$ (wherein p, $R^{4AA}$ and $R^{4AB}$ have the same meanings as those mentioned above, respectively).

(21) The thiadiazoline derivative or a pharmacologically acceptable salt thereof according to any one of (13) to (19), wherein $R^{4A}$ is —(CH$_2$)$_p$NR$^{4AD}$COR$^{4AC}$ (wherein p, $R^{4AC}$ and $R^{4AD}$ have the same meanings as those mentioned above, respectively).

(22) The thiadiazoline derivative or a pharmacologically acceptable salt thereof according to any one of (13) to (19), wherein $R^{4A}$ is —(CH$_2$)$_p$NHSO$_2$R$^{24A}$ (wherein p and $R^{24A}$ have the same meanings as those mentioned above, respectively).

(23) A medicament which comprises the thiadiazoline derivative or a pharmacologically acceptable salt thereof according to any one of (13) to (22) as an active ingredient.

(24) A mitotic kinesin Eg5 inhibitor which comprises the thiadiazoline derivative or a pharmacologically acceptable salt thereof according to any one of (13) to (22) as an active ingredient.

(25) A method for inhibiting a mitotic kinesin Eg5 which comprises administering an effective amount of the thiadiazoline derivative or a pharmacologically acceptable salt thereof according to any one of (1) to (12).

(26) A method for inhibiting a mitotic kinesin Eg5 which comprises administering an effective amount of the thiadiazoline derivative or a pharmacologically acceptable salt thereof according to any one of (13) to (22).

(27) Use of the thiadiazoline derivative or a pharmacologically acceptable salt thereof according to any one of (1) to (12) for the manufacture of a mitotic kinesin Eg5 inhibitor.

(28) Use of the thiadiazoline derivative or a pharmacologically acceptable salt thereof according to any one of (13) to (22) for the manufacture of a mitotic kinesin Eg5 inhibitor.

Hereinafter, compounds represented by the general formula (I) are referred to as "Compound (I)". The compounds having the other formula numbers are referred to in the same manner.

In the definition of each group of the general formula (I) and the general formula (IA), (i) examples of the lower alkyl moiety in the lower alkyl, the lower alkoxy, the lower alkylamino and the di-(lower alkyl)amino include straight or branched chain alkyl having 1 to 10 carbon atoms, for example, methyl, ethyl, propyl, isopropyl, butyl, isobutyl, sec-butyl, tert-butyl, pentyl, isopentyl, neopentyl, hexyl, heptyl, octyl, nonyl, decyl and the like. The two lower alkyl moieties in the di-(lower alkyl)amino may be the same or different.

(ii) Examples of the lower alkenyl include straight or branched chain alkenyl having 2 to 10 carbon atoms, for example, vinyl, allyl, 1-propenyl, butenyl, pentenyl, hexenyl, heptenyl, octenyl, nonenyl, decenyl and the like.

(iii) Examples of the lower alkynyl include straight or branched chain alkynyl having 2 to 10 carbon atoms, for example, ethynyl, propynyl, butynyl, pentynyl, hexynyl, heptynyl, octynyl, nonynyl, decynyl and the like.

(iv) Examples of the cycloalkyl include cycloalkyl having 3 to 8 carbon atoms, for example, cyclopropyl, cyclobutyl, cyclopentyl, cyclohexyl, cycloheptyl, cyclooctyl and the like.

(v) Examples of the aryl moiety in the aryl, the aryloxy and the arylamino include phenyl, naphthyl and the like.

(vi) Examples of the aromatic heterocyclic group include a 5- or 6-membered monocyclic aromatic heterocyclic group containing at least one atom selected from a nitrogen atom, an oxygen atom and a sulfur atom, and a bicyclic or tricyclic condensed aromatic heterocyclic group comprising 4- to 8-membered rings and containing at least one atom selected from a nitrogen atom, an oxygen atom and a sulfur atom, and the like, for example, furyl, thienyl, pyrrolyl, pyrazolyl, imidazolyl, triazolyl, tetrazolyl, thiazolyl, isothiazolyl, oxazolyl, isoxazolyl, thiadiazolyl, oxadiazolyl, pyridyl, pyrazinyl, pyrimidinyl, pyridazinyl, indolyl, isoindolyl, indazolyl, benzoxazolyl, benzothienyl, benzimidazolyl, benzothiazolyl, benzotriazolyl, purinyl, quinolyl, isoquinolyl, quinazolinyl, phthalazinyl, quinoxalinyl, naphthylidinyl, benzodiazepinyl, phenothiazinyl, benzopyranyl, cinnolinyl, pyranyl and the like.

(vii) Examples of the heterocyclic group include an aliphatic heterocyclic group, the aromatic heterocyclic group aforementioned and the like. Examples of the aliphatic heterocyclic group include a 5- or 6-membered monocyclic aliphatic heterocyclic group containing at least one atom selected from a nitrogen atom, an oxygen atom and a sulfur atom, and a bicyclic or tricyclic condensed aliphatic heterocyclic group comprising 3- to 8-membered rings and containing at least one atom selected from a nitrogen atom, an oxygen atom and a sulfur atom and the like, for example, azetidinyl, tetrahydrothienyl, tetrahydrothiopyranyl, imidazolidinyl, pyrrolidinyl, oxazolinyl, dioxolanyl, piperidino, piperidinyl, piperazinyl, morpholino, morpholinyl, thiomorpholinyl, homopiperidinyl, homopiperazinyl, tetrahydropyridinyl, tetrahydroquinolinyl, tetrahydroisoquinolinyl, tetrahydrofuranyl, tetrahydropyranyl, dihydrobenzofuranyl and the like.

(viii) Examples of the heterocyclic group formed together with the adjacent nitrogen atom include an aliphatic heterocyclic group containing at least one nitrogen atom, and the like. Said aliphatic heterocyclic group containing at least one nitrogen atom may contain an oxygen atom, a sulfur atom or another nitrogen atom, and examples thereof include, for example, 1-pyrrolyl, pyrrolidinyl, morpholino, thiomorpholino, pyrazolidinyl, piperidino, piperazinyl, homopiperazinyl, aziridinyl, azetidinyl, azolidinyl, perhydroazepinyl, perhydroazocinyl, tetrahydroquinolinyl, tetrahydroisoquinolinyl, indolyl, isoindolyl, 1,3-dihydroisoindolyl, pyrrolidonyl, succinimidyl, glutarimidyl, piperidonyl and the like.

(ix) Examples of the cycloalkylene include cycloalkylene having 3 to 8 carbon atoms, for example, cyclopropylene, cyclobutylene, cyclopentylene, cyclohexylene, cycloheptylene, cyclooctylene and the like, and examples of the phenylene include 1,2-phenylene, 1,3-phenylene and 1,4-phenylene.

(x) The halogen means each atom of fluorine, chlorine, bromine and iodine.

(xi) The substituents in the substituted lower alkyl, the substituted lower alkoxy, the substituted lower alkenyl, the substituted lower alkynyl, the substituted cycloalkyl, the substituted lower alkylamino and the substituted di-(lower alkyl)amino may be the same or different in number of 1 to 3 substituent(s), and include halogen, hydroxy, oxo, nitro, azido, cyano, substituted or unsubstituted cycloalkyl (the substituents (a) in said substituted cycloalkyl may be the same or different in number of 1 to 3 substituent(s), and include halogen, hydroxy, oxo, carboxy, cyano, lower alkoxy, lower alkanoyloxy, lower alkylthio, aryl, aryloxy, a heterocyclic group, amino, lower alkylamino, di-(lower alkyl)amino and the like), substituted or unsubstituted aryl-(the substituent in said substituted aryl has the same meaning as that of the aftermentioned substituent (xii) in the substituted aryl), a substituted or unsubstituted heterocyclic group (the substituent in said substituted heterocyclic group has the same meaning as that of the after-mentioned substituent (xiii) in the substituted heterocyclic group), —CONR$^{37}$R$^{38}$ <wherein R$^{37}$ and R$^{38}$ may be the same or different and each represents a hydrogen atom, hydroxy, substituted or unsubstituted lower alkyl the substituents (b) in said substituted lower alkyl may be the same or different in number of 1 to 3 substituent(s), and include halogen, hydroxy, oxo, carboxy, cyano, substituted or unsubstituted lower alkoxy (the substituent in said substituted lower alkoxy has the same meaning as that of the aforementioned substituent (a) in the substituted cycloalkyl), substituted or unsubstituted lower alkylthio (the substituent in said substituted lower alkylthio has the same meaning as that of the aforementioned substituent (a) in the substituted cycloalkyl), substituted or unsubstituted lower alkylsulfonyl (the substituent in said substituted lower alkylsulfonyl has the same meaning as that of the aforementioned substituent (a) in the substituted cycloalkyl), substituted or unsubstituted aryl (the substituent in said substituted aryl has the same meaning as that of the after-mentioned substituent (xii) in the substituted aryl), a substituted or unsubstituted heterocyclic group (the substituent in said substituted heterocyclic group has the same meaning as that of the after-mentioned substituent (xiii) in the substituted heterocyclic group), substituted or unsubstituted aryloxy (the substituent in said substituted aryloxy has the same meaning as that of the after-mentioned substituent (xii) in the substituted aryl), —NR$^{39}$R$^{40}$ [wherein R$^{39}$ and R$^{40}$ may be the same or different and each represents a hydrogen atom, substituted or unsubstituted lower alkyl-(the substituent in said substituted lower alkyl has the same meaning as that of the aforementioned substituent (a) in the substituted cycloalkyl), substituted or unsubstituted lower alkenyl (the substituent in said substituted lower alkenyl has the same meaning as that of the aforementioned substituent (a) in the substituted cycloalkyl), substituted or unsubstituted lower alkynyl (the substituent in said substituted lower alkynyl has the same meaning as that of the aforementioned substituent (a) in the substituted cycloalkyl), substituted or unsubstituted cycloalkyl (the substituent in said substituted cycloalkynyl has the same meaning as that of the aforementioned substituent (a) in the substituted cycloalkyl), substituted or unsubstituted substituted aryl (the substituent in said substituted aryl has the same meaning as that of the after-mentioned substituent (xii) in the substituted aryl) or a substituted or unsubstituted heterocyclic group (the substituent in said substituted heterocyclic group has the same meaning as that of the after-mentioned substituent (xiii) in the substituted heterocyclic group), or $R^{39}$ and $R^{40}$ are combined together with the adjacent nitrogen atom to form a substituted or unsubstituted heterocyclic group (the substituent in said substituted heterocyclic group formed together with the adjacent nitrogen atom has the same meaning as that of the after-mentioned substituent in the substituted heterocyclic group formed together with the adjacent nitrogen atom)] and the like), substituted or unsubstituted lower alkenyl (the substituent in said substituted lower alkenyl has the same meaning as that of the aforementioned substituent (a) in the substituted cycloalkyl), substituted or unsubstituted lower alkynyl (the substituent in said substituted lower alkynyl has the same meaning as that of the aforementioned substituent (a) in the substituted cycloalkyl), substituted or unsubstituted cycloalkyl (the substituent in said substituted cycloalkyl has the same meaning as that of the aforementioned substituent (a) in the substituted cycloalkyl), substituted or unsubstituted aryl (the substituent in said substituted aryl has the same meaning as that of the after-mentioned substituent (xii) in the substituted aryl) or a substituted or unsubstituted heterocyclic group (the substituent in said substituted heterocyclic group has the same meaning as that of the after-mentioned substituent (xiii) in the substituted heterocyclic group), or $R^{37}$ and $R^{38}$ are combined together with the adjacent nitrogen atom to form a substituted or unsubstituted heterocyclic group (the substituent in said substituted heterocyclic group formed together with the adjacent nitrogen atom has the same meaning as that of the after-mentioned substituent (xiii) in the substituted heterocyclic group formed together with the adjacent nitrogen atom)>, —COOR$^{41}$ [wherein R$^{41}$ represents a hydrogen atom, substituted or unsubstituted lower alkyl (the substituent in said substituted lower alkyl has the same meaning as that of the aforementioned substituent (b) in the substituted lower alkyl), substituted or unsubstituted lower alkenyl (the substituent in said substituted lower alkenyl has the same meaning as that of the aforementioned substituent (b) in the substituted lower alkyl), substituted or unsubstituted lower alkynyl (the substituent in said substituted lower alkynyl has the same meaning as that of the aforementioned substituent the substituted lower alkyl), substituted or unsubstituted cycloalkyl (the substituent in said substituted cycloalkyl has the same meaning as that of the aforementioned substituent (b) in the substituted lower alkyl), substituted or unsubstituted aryl (the substituent in said substituted aryl has the same meaning as that of the after-mentioned substituent (xii) in the substituted aryl) or a substituted or unsubstituted heterocyclic group (the substituent in said substituted heterocyclic group has the same meaning as that of the after-mentioned substituent (xiii) in the substituted heterocyclic group)], —COR$^{42}$ (wherein R$^{42}$ has the same meaning as that of the aforementioned R$^{41}$), —NR$^{43}$R$^{44}$ <wherein R$^{43}$ and R$^{44}$ may be the same or different and each represents a hydrogen atom, substituted or unsubstituted lower alkyl { the substituents (c) in said substituted lower alkyl may be the same or different in number of 1 to 3 substituent(s), and include halogen, hydroxy, oxo, carboxy, cyano, substituted or unsubstituted lower alkoxy (the substituent in said substituted lower alkoxy has the same meaning as that of the aforementioned substituent (b) in the substituted alkyl), substituted or unsubstituted lower alkylthio (the substituent in said substituted lower alkylthio has the same meaning as that of the aforementioned substituent (b) in the substituted alkyl), substituted or unsubstituted aryl (the substituent in said substituted aryl has the same meaning as that of the after-mentioned substituent (xii) in the substituted aryl), a substituted or unsubstituted heterocyclic group (the substituent in said substituted heterocyclic group has the same meaning as that of the after-mentioned substituent (xiii) in the substituted heterocyclic group), substituted or unsubstituted aryloxy (the substituent in said substituted aryloxy has the same meaning as that of the after-mentioned substituent (xii) in the substituted aryl), —O(CH$_2$CH$_2$O)$_n$R$^{45}$ (wherein n represents an integer of from 1 to 15, and R$^{45}$ represents lower alkyl), —SO$_2$R$^{46}$ [wherein R$^{46}$ represents substituted or unsubstituted lower alkyl (the substituent in said substituted lower alkyl has the same meaning as that of the aforementioned substituent (b) in the substituted alkyl), substituted or unsubstituted lower alkenyl (the substituent in said substituted lower alkenyl has the same meaning as that of the aforementioned substituent (b) in the substituted alkyl), substituted or unsubstituted lower alkynyl (the substituent in said substituted lower alkynyl has the same meaning as that of the aforementioned substituent (b) in the substituted alkyl), substituted or unsubstituted aryl (the substituent in said substituted aryl has the same meaning as that of the after-mentioned substituent (xii) in the substituted aryl), a substituted or unsubstituted heterocyclic group (the substituent in said substituted heterocyclic group has the same meaning as that of the after-mentioned substituent (xiii) in the substituted heterocyclic group), amino, lower alkylamino or di-(lower alkyl)amino], —NR$^{47}$R$^{48}$ (wherein R$^{47}$ and R$^{48}$ may be the same or different and each represents a hydrogen atom, substituted or unsubstituted lower alkyl (the substituent in said substituted lower alkyl has the same meaning as that of the aforementioned substituent (b) in the substituted lower alkyl), substituted or unsubstituted lower alkenyl (the substituent in said substituted lower alkenyl has the same meaning as that of the aforementioned substituent (b) in the substituted lower alkyl), substituted or unsubstituted lower alkynyl (the substituent in said substituted lower alkynyl has the same meaning as that of the aforementioned substituent (b) in the substituted lower alkyl), substituted or unsubstituted cycloalkyl (the substituent in said substituted cycloalkynyl has the same meaning as that of the aforementioned substituent (b) in the substituted lower alkyl), substituted or unsubstituted substituted aryl (the substituent in said substituted aryl has the same meaning as that of the after-mentioned substituent (xii) in the substituted aryl) or a substituted or unsubstituted heterocyclic group (the substituent in said substituted heterocyclic group has the same meaning as that of the after-mentioned substituent (xiii) in the substituted heterocyclic group), or R$^{47}$ and R$^{48}$ may be combined together with the adjacent nitrogen atom to form a substituted or unsubstituted heterocyclic group (the substituent in said substituted heterocyclic group formed together with the adjacent nitrogen atom has the same meaning as that of the after-mentioned substituent (xiii) in the substituted heterocyclic group formed together with the adjacent nitrogen atom)) and the like}, substituted or unsubstituted lower alkenyl (the substituent in substituted lower alkenyl has the same meaning as that of the aforementioned substituent (b) in the substituted lower alkyl), substituted or unsubstituted lower alkynyl (the substituent in said substituted lower alkynyl has the same meaning as that of the aforementioned substituent (b) in the substituted lower alkyl), substituted or unsubstituted cycloalkyl (the substituent in said substituted lower cycloalkyl has the same meaning as that of the aforementioned substituent (b) in the substituted lower alkyl), substituted or unsubstituted aryl (the substituent in said substituted aryl has the same meaning as that of the after-mentioned substituent (xii) in the substituted aryl), a substituted or unsubstituted heterocyclic group (the substituent in said substituted heterocyclic group has the same meaning as that of the after-mentioned substituent (xiii) in the substituted heterocyclic group), —COR$^{49}$ {wherein R$^{49}$ represents a hydrogen atom, substituted or unsubstituted lower alkyl (the substituent in said substituted lower alkyl has the same meaning as that of the aforementioned substituent (b) in the substituted lower alkyl), substituted or unsubstituted lower alkenyl (the substituent in said substituted lower alkenyl has the same meaning as that of the aforementioned substituent (b) in the substituted lower alkyl), substituted or unsubstituted lower alkynyl (the substituent in said substituted lower alkynyl has the same meaning as that of the aforementioned substituent (b) in the substituted lower alkyl), substituted or unsubstituted cycloalkyl (the substituent in said substituted cycloalkyl has the same meaning as that of the aforementioned substituent (b) in the substituted lower alkyl), substituted or unsubstituted aryl (the substituent in said substituted aryl has the same meaning as that of the after-mentioned substituent (xii) in the substituted aryl), a substituted or unsubstituted heterocyclic group (the substituent in said substituted heterocyclic group has the same meaning as that of the after-mentioned substituent (xiii) in the substituted heterocyclic group, —NR$^{59}$R$^{51}$ (wherein R$^{50}$ and R$^{51}$ have the same meanings as those of the aforementioned R$^{47}$ and R$^{48}$, respectively) or —OR$^{52}$ [wherein R$^{52}$ represents substituted or unsubstituted lower alkyl (the substituent in said substituted lower alkyl has the same meaning as that of the aforementioned substituent (b) in the substituted lower alkyl), substituted or unsubstituted lower alkenyl (the substituent in said substituted lower alkenyl has the same meaning as that of the aforementioned substituent (b) in the substituted lower alkyl), substituted or unsubstituted lower alkynyl (the substituent in said substituted lower alkynyl has the same meaning as that of the aforementioned substituent (b) in the substituted lower alkyl), substituted or unsubstituted cycloalkyl (the substituent in said substituted cycloalkyl has the same meaning as that of the aforementioned substituent (b) in the substituted lower alkyl), substituted or unsubstituted aryl (the substituent in said substituted aryl has the same meaning as that of the after-mentioned substituent (xii) in the substituted aryl) or a substituted or unsubstituted heterocyclic group (the substituent in said substituted heterocyclic group has the same meaning as that of the after-mentioned substituent in the substituted heterocyclic group)]} or —SO$_2$R$^{53}$ (wherein R$^{53}$ has the same meaning as that of the aforementioned R$^{49}$), or R$^{43}$ and R$^{44}$ may be combined together with the adjacent nitrogen atom to form a heterocyclic group or a substituted heterocyclic group (the substituent in said substituted heterocyclic group formed together with the adjacent nitrogen atom has the same meaning as that of the after-mentioned substituent (xiii) in the substituted heterocyclic group formed together with the adjacent nitrogen atom)>, —N$^+$R$^{54}$R$^{55}$R$^{55}$X$^-$ (wherein R$^{54}$ and R$^{55}$ may be the same or different and each represents lower alkyl, or R$^{54}$ and R$^{55}$ may be combined together with the adjacent nitrogen atom to form a heterocyclic group, R$^{56}$ represents lower alkyl, and X represents each atom of chlorine, bromine or iodine), —OR$^{57}$ [wherein R$^{57}$ represents substituted or unsubstituted lower alkyl (the substituent in said substituted lower alkyl has the same meaning as that of the aforementioned substituent (b) in the substituted lower alkyl), substituted or unsubstituted lower alkenyl (the substituent in said substituted lower alkenyl has the same meaning as that of the aforementioned substituent (b) in the substituted lower alkyl), substituted or unsubstituted lower alkynyl (the substituent in said substituted lower alkynyl has the same meaning as that of the aforementioned substituent (b) in the substituted lower alkyl), substituted or unsubstituted cycloalkyl (the substituent in said substituted cycloalkyl has the same meaning as that of the aforementioned substituent (b) in the substituted lower alkyl), substituted or unsubstituted aryl (the substituent in said substituted aryl has the same meaning as that of the after-mentioned substituent (xii) in the substituted aryl), or a substituted or unsubstituted heterocyclic group (the substituent in said substituted heterocyclic, group has the same meaning as that of the after-mentioned substituent (xiii) in the substituted heterocyclic group)], —SR$^{58}$ (wherein R$^{58}$ has the same meaning as that of the aforementioned R$^{57}$), —SO$_2$R$^{58}$ [wherein R$^{59}$ represents substituted or unsubstituted lower alkyl (the substituent in said substituted lower alkyl has the same meaning as that of the aforementioned substituent (b) in the substituted lower alkyl), substituted or unsubstituted lower alkenyl (the substituent in said substituted lower alkenyl has the same meaning as that of the aforementioned substituent (b) in the substituted lower alkyl), substituted or unsubstituted lower alkynyl (the substituent in said substituted lower alkynyl has the same meaning as that of the aforementioned substituent (b) in the substituted lower alkyl), substituted or unsubstituted cycloalkyl (the substituent in said substituted cycloalkyl has the same meaning as that of the aforementioned substituent (b) in the substituted lower alkyl), substituted or unsubstituted aryl (the substituent in said substituted aryl has the same meaning as that of the after-mentioned substituent (xii) in the substituted aryl), a substituted or unsubstituted heterocyclic group (the substituent in said substituted heterocyclic group has the same meaning as that of the after-mentioned substituent (xiii) in the substituted heterocyclic group), substituted or unsubstituted lower alkoxy (the substituent in said substituted lower alkoxy has the same meaning as that of the aforementioned substituent (b) in the substituted lower alkyl) or —NR$^{60}$R$^{61}$ (wherein R$^{60}$ and R$^{61}$ have the same meanings as those of the aforementioned R$^{47}$ and R$^{48}$, respectively), —OSO$_2$R$^{62}$ (wherein R$^{62}$ has the same meaning as that of the aforementioned R$^{59}$) and the like.

Herein, the lower alkyl moiety in the lower alkyl, the lower alkoxy, the lower alkylthio, the lower alkylsulfonyl, the lower alkylamino, the di-(lower alkyl)amino and the lower alkanoyloxy, the lower alkenyl, the lower alkynyl, the cycloalkyl, the aryl moiety in the aryl and the aryloxy, the heterocyclic group, the heterocyclic group formed together with the adjacent nitrogen atom and the halogen have the same meanings as those of the aforementioned lower alkyl (i), lower alkenyl (ii), lower alkynyl (iii), cycloalkyl (iv), aryl (v), a heterocyclic group (vii), a heterocyclic group formed together with the adjacent nitrogen atom (viii) and halogen (x), respectively, and two of the lower alkyl moieties in the di-(lower alkyl) amino may be the same or different.

(xii) The substituents in the substituted aryl, the substituted aryloxy, the substituted arylamino, the substituted phenylene and the substituted aromatic heterocyclic group in the substituted heterocyclic group may be the same or different in number of 1 to 3 substituent(s), and include halogen, hydroxy, carboxy, formyl, nitro, cyano, methylenedioxy, substituted or unsubstituted lower alkyl [the substituents (d) in said substituted lower alkyl may be the same or different in number of 1 to 3 substituent(s), and include halogen, hydroxy, oxo, carboxy, substituted or unsubstituted lower alkoxy (the substituents (e) in said substituted lower alkoxy may be the same or different in number of 1 to 3 substituent(s), and include halogen, hydroxy, oxo, carboxy, lower alkoxy, amino, lower alkylamino, di-(lower alkyl) amino, aryl, a heterocyclic group and the like), amino, substituted or unsubstituted lower alkylamino (the substituent in said substituted lower alkylamino has the same meaning as that of the aforementioned substituent (e) in the substituted lower alkoxy), substituted or unsubstituted di-(lower alkyl)amino (the substituent in said substituted di-(lower alkyl)amino has the same meaning as that of the aforementioned substituent (e) in the substituted lower alkoxy), aryl, a heterocyclic group and the like], substituted or unsubstituted lower alkenyl (the substituent in said substituted lower alkenyl has the same meaning as that of the aforementioned substituent (d) in the substituted lower alkyl), substituted or unsubstituted lower alkynyl (the substituent in said substituted lower alkynyl has the same meaning as that of the aforementioned substituent (d) in the substituted lower alkyl), substituted or unsubstituted cycloalkyl (the substituent in said substituted cycloalkyl has the same meaning as that of the aforementioned substituent (d) in the substituted lower alkyl), substituted or unsubstituted lower alkoxy (the substituent in said substituted lower alkoxy has the same meaning as that of the aforementioned substituent (d) in the aforementioned substituted lower alkyl), substituted or unsubstituted lower alkylthio (the substituent in said substituted lower alkylthio has the same meaning as that of the aforementioned substituent (d) in the substituted lower alkyl), amino, substituted or unsubstituted lower alkylamino (the substituent in said substituted lower alkylamino has the same meaning as that of the aforementioned substituent (d) in the substituted lower alkyl), substituted or unsubstituted di-(lower alkyl)amino (the substituent in said substituted di-(lower alkylamino has the same meaning as that of the aforementioned substituent (d) in the aforementioned substituted lower alkyl), substituted or unsubstituted aryl [the substituents (f) in said substituted aryl may be the same or different in number of 1 to 3 substituent(s), and include halogen, hydroxy, carboxy, cyano, nitro, substituted or unsubstituted lower alkyl (the substituent in said substituted lower alkyl has the same meaning as that of the aforementioned substituent (e) in the substituted lower alkoxy); substituted or unsubstituted lower alkoxy (the substituent in said substituted lower alkoxy has the same meaning as that of the aforementioned substituent (e) in the substituted lower alkoxy), amino, substituted or unsubstituted lower alkylamino (the substituent in said substituted lower alkylamino has the same meaning as that of the aforementioned substituent (e) in the substituted lower alkoxy), substituted or unsubstituted di-(lower alkyl)amino (the substituent in said substituted di-(lower alkyl)amino has the same meaning as that of the aforementioned substituent (e) in the substituted lower alkoxy) and the like), a substituted or unsubstituted heterocyclic group (the substituent in said substituted heterocyclic group has the same meaning as that of the aforementioned substituent (f) in the substituted aryl), substituted or unsubstituted aryloxy (the substituent in said substituted aryloxy has the same meaning as that of the aforementioned substituent (f) in the substituted aryl), substituted or unsubstituted arylamino (the substituent in said substituted arylamino has the same meaning as that of the aforementioned substituent (f) in the substituted aryl), substituted or unsubstituted arylthio (the substituent in said substituted arylthio has the same meaning as that of the aforementioned substituent (f) in the substituted aryl), substituted or unsubstituted arylsulfonyl (the substituent in said substituted arylsulfonyl has the same meaning as that of the aforementioned substituent (f) in the substituted aryl), substituted or unsubstituted heterocyclyloxy (the substituent in said substituted heterocyclyloxy has the same meaning as that of the aforementioned substituent (f) in the substituted aryl), substituted or unsubstituted heterocyclylamino (the substituent in said substituted heterocyclylamino has the same meaning as that of the aforementioned substituent (f) in the substituted aryl), substituted or unsubstituted heterocyclylthio (the substituent in said substituted heterocyclylthio has the same meaning as that of the aforementioned substituent (f) in the substituted aryl) and the like.

Herein, the lower alkyl moiety in the lower alkyl, the lower alkoxy, the lower alkylthio, the lower alkylamino and the di-(lower alkyl)amino has the same meaning as that of the aforementioned lower alkyl (i). The lower alkenyl, the lower alkynyl, the cycloalkyl and the halogen have the same meanings as those of the lower alkenyl (ii), the lower alkynyl (iii), the cycloalkyl (iv), and the halogen (x), respectively, and two of the lower alkyl moieties of the di-(lower alkyl)amino may be the same or different. Further, herein, the aryl moiety in the aryl, the aryloxy, the arylthio, the arylamino and the arylsulfonyl has the same meaning as that of the aforementioned aryl (v), and the heterocyclic group moiety of the heterocyclic group, the heterocyclylthio, the heterocyclylamino and the heterocyclyloxy has the same meaning as that of the aforementioned heterocyclic group (vii).

(xiii) Examples of the substituent in the substituted aliphatic heterocyclic group among the substituted heterocyclic group and the substituted heterocyclic group formed together with the adjacent nitrogen atom include axe and the like as well as the groups mentioned in the definition of the aforementioned substituent (xii) in the substituted aryl.

Example of the pharmacologically acceptable salt of Compound (I) and Compound (IA) include pharmacologically acceptable acid addition salts, metal salts, ammonium salts, organic amine addition salts, amino acid addition salts and the like. Examples of the pharmacologically acceptable acid addition salt of Compound (I) and Compound (IA) include an inorganic acid addition salt such as hydrochloride, sulfate and phosphate, an organic acid addition salt such as acetate, maleate, fumarate and citrate, and the like. Examples of the pharmacologically acceptable metal salt include an alkali metal salt such as a sodium salt and a potassium salt, an alkaline-earth metal salt such as a magnesium salt and a calcium salt, an aluminium salt, a zinc salt and the like. Examples of the pharmacologically acceptable ammonium salt include a salt of ammonium, tetramethylammonium or the like. Examples of the pharmacologically acceptable organic amine addition salt include an addition salt of morpholine, piperidine or the like. Examples of the pharmacologically acceptable amino acid addition salt include an addition salt of lysine, glycine, phenylalanine, aspartic acid, glutamic acid or the like.

Next, the methods of preparing the Compound (I) are described as follows.

In the preparing methods as shown below, when the defined group changes under the conditions of the method carried out, or is inappropriate for carrying out the methods, the desired compound can be obtained by using the protection and deprotection methods which are ordinarily used in the organic synthetic chemistry [e.g., Protective Groups in Organic Synthesis, T. W. Greene, John Wiley & Sons Inc. (1981)] and the like. In addition, the order of the steps for introducing a substituent and the like may be changed, if necessary.

Compound (I) can be prepared according to the following preparing methods.

Preparing Method 1

Among Compound (I), Compound (Ia) wherein $R^2$ is a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl, or a substituted or unsubstituted heterocyclic group, or $R^1$ and $R^2$ are combined to form a substituted or unsubstituted heterocyclic group together with the adjacent nitrogen atom, and $R^3$ is —$COR^{19}$ (wherein $R^{19}$ has the same meaning as that mentioned above) can be prepared in accordance with the following Steps 1-1 and 1-2:

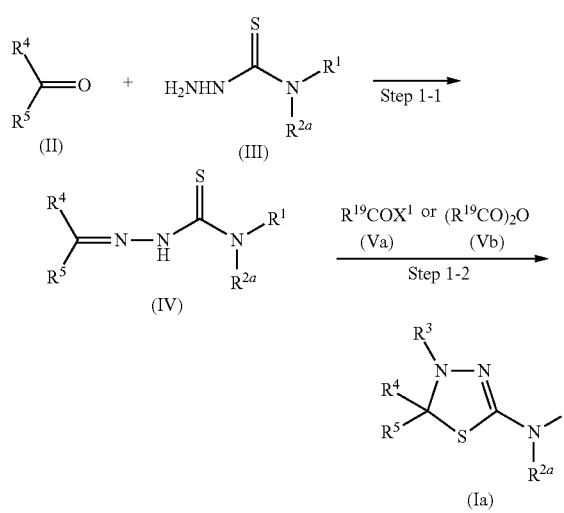

(wherein $R^1$, $R^4$, $R^5$ and $R^{19}$ have the same meanings as those mentioned above, respectively, $X^1$ represents a chlorine atom, a bromine atom or an iodine atom, and $R^{2a}$ represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl or a substituted or unsubstituted heterocyclic group in the definition of the aforementioned $R^2$, or $R^1$ and $R^{2a}$ are combined to form a substituted or unsubstituted heterocyclic group together with the adjacent nitrogen atom.).

Compound (Ia) can be obtained from Compound (II) and Compound (III), via Compound (IV), by known methods [e.g., J. Heterocyclic Chem., Vol. 21, p. 599 (1984) and the like], or the methods similar to the known methods.

Compounds (II), (III), (Va) and (Vb) can be prepared as commercial products, or can be prepared by known methods [e.g., methods described in Shin-Jikken-Kagaku-Koza Vol. 14, p. 1621 (Maruzen, 1978) and the like], or the methods similar to the known methods.

Preparing Method 2

Among Compound (I), Compound (Ib) wherein $R^2$ and $R^3$ are the same to be —$COR^{6a}$ (wherein $R^{6a}$ has the same meaning as that of the aforementioned $R^6$ or $R^{19}$) can be prepared in accordance with the following step:

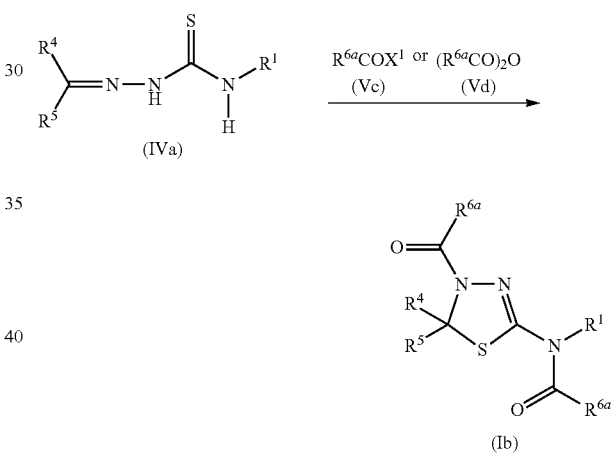

(wherein $R^1$, $R^4$, $R^5$, $R^{6a}$ and $X^1$ have the same meanings as those mentioned above, respectively.)

Compound (Ib) can be prepared from Compound (IVa) wherein $R^{2a}$ is a hydrogen atom in Compound (IV) prepared by Step 1-1 of the preparing method 1, and Compound (Vc) or Compound (Vd) by known methods [e.g., J. Bangladesh Chem: Soc., Vol. 5, p. 127 (1992); J. Org. Chem., Vol. 45, p. 1473 (1980), Patent of East Germany No. 243930, and the like], or the methods similar to the known methods.

Compounds (Vc) and (Vd) can be prepared as commercial products, or can be obtained by known methods [e.g., methods described in Shin-Jikken-Kagaku-Koza Vol. 14, p. 1621 (Maruzen, 1978) and the like], or the methods similar to the known methods.

Preparing Method 3

Among Compound (I), Compound (Ic) wherein $R^2$ is a hydrogen atom and $R^3$ is —$COR^{16}$ (wherein $R^{19}$ has the same meaning as that mentioned above) can also be prepared in accordance with the following step:

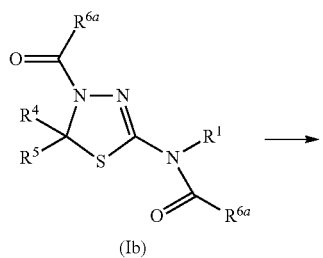

(Ib)

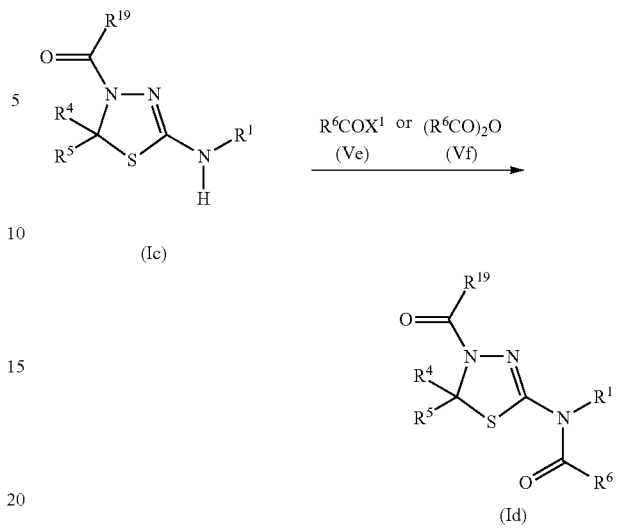

(Ic)

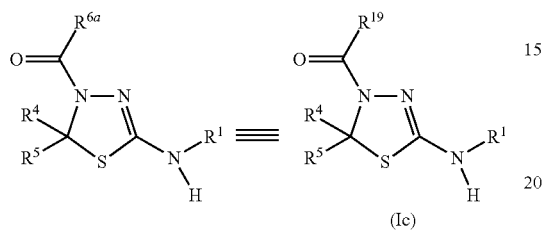

(Ic)

(wherein $R^1$, $R^4$, $R^5$, $R^{6a}$ and $R^{19}$ have the same meanings as those mentioned above, respectively.)

Compound (Ic) can be obtained by treatment of Compound (Ib) prepared in the preparing method 2 in an appropriate solvent in the presence of 1 to 200 equivalents, preferably 1 to 10 equivalents of an appropriate base, at a temperature between −10° C. and the boiling point of the solvent used for 5 minutes to 24 hours.

Examples of the appropriate solvent include, for example, methanol, ethanol, tert-butanol, acetonitrile, dichloromethane, chloroform, ethyl acetate, tetrahydrofuran (THF), dioxane, toluene, xylene, N,N-dimethylformamide (DMF), N-methylpyrrolidone (NMP), pyridine, water and the like, and they can be used alone or as a mixture. Examples of the appropriate base include, for example, sodium hydride, sodium hydroxide, potassium hydroxide, lithium hydroxide, potassium carbonate, hydrazine monohydrate and the like.

As an alternative method, Compound (Ic) can also be obtained by treatment of Compound (Ib) in an appropriate solvent in the presence of 1 to 200 equivalents of an appropriate reducing agent, and an appropriate additive if necessary, at a temperature between −10° C. and 100° C. for 5 minutes to 24 hours.

Examples of the appropriate solvent include, for example, methanol, ethanol, tert-butanol, acetonitrile, dichloromethane, THF, dioxane, toluene, xylene, water and the like, and they can be used alone or as a mixture. Examples of the appropriate reducing agent include, for example, sodium borohydride, triacetoxy sodium borohydride and the like, and examples of the appropriate additive include ceric chloride heptahydrate, hydrochloric acid-sodium acetate buffer and the like.

Preparing Method 4

Among Compound (I), Compound (Id) wherein $R^2$ is —$COR^6$ (wherein $R^6$ has the same meaning as that mentioned above) and $R^3$ is —$COR^{19}$ (wherein $R^{19}$ has the same meaning as that mentioned above) can also be prepared in accordance with the following step:

(wherein $R^1$, $R^4$, $R^5$, $R^6$, $R^{19}$ and $X^1$ have the same meanings as those mentioned above, respectively.)

Compound (Id) can be obtained by reacting Compound (Ic) prepared in the preparing method 1 or 3 with 1 to 20 equivalents, preferably 1 to 3 equivalents of Compound (Ve) or Compound (Vf), without solvent or in an inert solvent in the presence of 1 to 20 equivalents, preferably 1 to 3 equivalents of an appropriate base, at a temperature between −10° C. and 150° C. for 5 minutes to 24 hours.

Examples of the inert solvent include, for example, acetonitrile, dichloromethane, chloroform, acetone, ethyl acetate, THF, dioxane, toluene, xylene, DMF, NMP and the like, and they can be used alone or as a mixture. Examples of the appropriate base include, for example, triethylamine, diisopropylethylamine, 1,8-diazabicyclo[5.4.0]undec-7-ene (DBU), pyridine, 4-(dimethylamino)pyridine (DMAP), sodium hydride, sodium hydroxide, potassium carbonate and the like. Compounds (Ve) and (Vf) can be prepared as commercial products, or can be prepared by known methods [e.g., methods described in Shin-Jikken-Kagaku-Koza Vol. 14, p. 1621 (Maruzen, 1978) and the like], or the methods similar to the known methods.

As an alternative method, Compound (Id) can also be prepared in accordance with the following step:

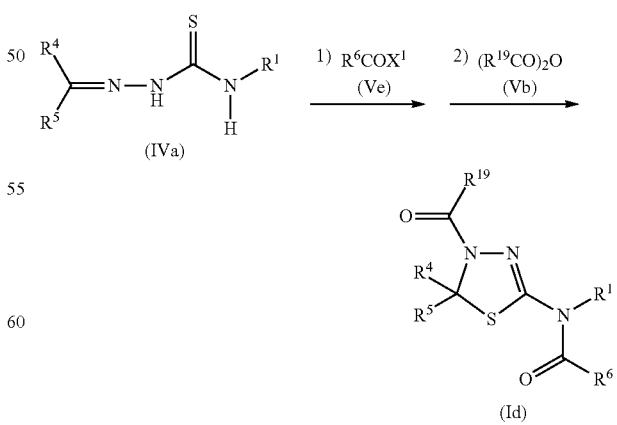

(wherein $R^1$, $R^4$, $R^5$, $R^6$, $R^{19}$ and $X^1$ have the same meanings as those mentioned above, respectively.)

Compound (Id) can be obtained by reacting Compound (IVa) prepared in Step 1-1 of the preparing method 1 with 1 to 5 equivalents of Compound (Ve) in an inert solvent in the presence of 0.5 to 2 equivalents of an appropriate base at a temperature between −78° C. and 100° C., preferably at a temperature between −10° C. and 30° C., for 5 minutes to 24 hours, followed by being added 1 to 5 equivalents of Compound (Vb) and 1 to 5 equivalents of an appropriate base to the reaction mixture, and reacting for 10 to 48 hours.

Examples of the inert solvent include, for example, acetonitrile, dichloromethane, chloroform, acetone, ethyl acetate, THF, dioxane, toluene, xylene, DMF, NMP and the like, and they can be used alone or as a mixture. Examples of the appropriate base used for the first reaction include, for example, 2,6-di-tert-butyl-4-methylpyridine and the like, and examples of the appropriate base used for the subsequent reaction include, for example, pyridine and the like.

Preparing Method 5

Among Compound (I), Compound (Ie) wherein $R^2$ is —$SO_2R^{18}$ (wherein $R^{18}$ has the same meaning as that mentioned above) and $R^3$ is —$COR^{19}$ (wherein $R^{19}$ has the same meaning as that mentioned above) can also be prepared in accordance with the following step:

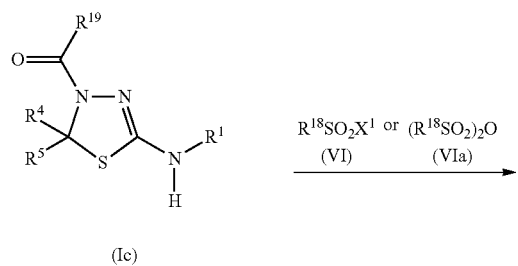

(wherein $R^1$, $R^4$, $R^5$, $R^{18}$, $R^{19}$ and $X^1$ have the same meanings as those mentioned above, respectively.)

Compound (Ie) can be obtained from Compound (Ic) prepared in the preparing method 1 or 3 and Compound (VI) by the methods described in, for example, Shin-Jikken-Kagaku-Koza Vol. 14, p. 1803 (Maruzen, 1978), or the methods similar to thereof.

Compounds (VI) and (VIa) can be prepared as commercial products, or can be prepared by the methods described in Shin-Jikken-Kagaku-Koza Vol. 14, p. 1784 and p. 1799 (Maruzen, 1978) and the like], or the methods similar to thereof.

Preparing Method 6

Among Compound (I), Compound (If) wherein $R^2$ is —$NR^{11}R^{12}$ (wherein $R^{11}$ and $R^{12}$ have the same meanings as those mentioned above, respectively) and $R^3$ is —$COR^{19}$ (wherein $R^{19}$ has the same meaning as that mentioned above) can also be prepared in accordance with the following step:

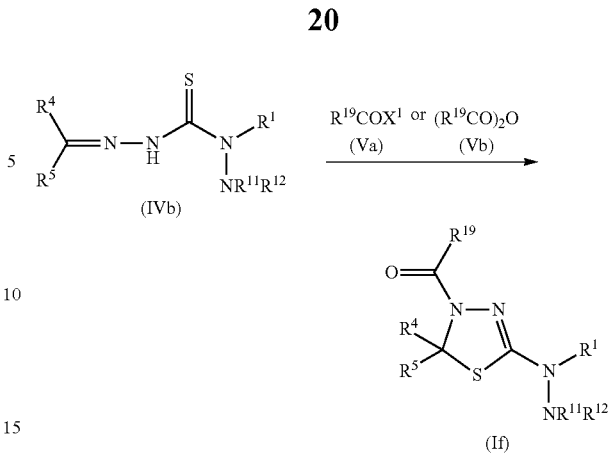

(wherein $R^1$, $R^4$, $R^6$, $R^{11}$, $R^{12}$ and $R^{19}$ have the same meanings as those mentioned above, respectively.)

Compound (If) can be prepared from Compound (IVb) prepared by the methods described in Indian J. Chem., Section B, Vol. 31B(8), p. 547 (1992) and the like, or the methods similar to thereof and Compound (Va) or (Vb) by the methods described in for example, Indian J. Chem., Section B, Vol. 31B(8), p. 547 (1992); Phosphorus Sulfur & Silicon & the Related Elements, Vol. 122, p. 307 (1997) and the like, or the methods similar to thereof.

Preparing Method 7

Among Compound (Id), Compound (Id-b) wherein $R^1$ is substituted or unsubstituted lower alkyl, substituted or unsubstituted lower alkenyl, substituted or unsubstituted lower alkynyl, substituted or unsubstituted cycloalkyl, substituted or unsubstituted aryl or a substituted or unsubstituted heterocyclic group can also be prepared in accordance with the following step:

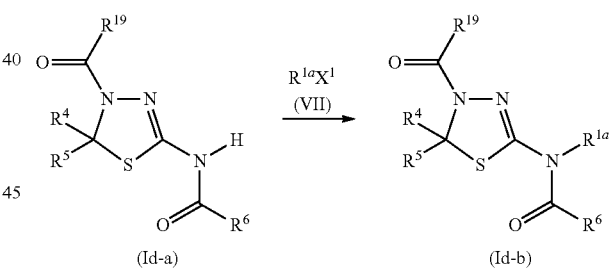

(wherein $R^4$, $R^5$, $R^6$, $R^{19}$ and $X^1$ have the same meanings as those mentioned above, respectively, and $R^{1a}$ represents substituted or unsubstituted lower alkyl, substituted or unsubstituted lower alkenyl, substituted or unsubstituted lower alkynyl, substituted or unsubstituted cycloalkyl, substituted or unsubstituted aryl or a substituted or unsubstituted heterocyclic group in the definition of the aforementioned $R^1$.)

Compound (Id-b) can be prepared by reacting Compound (Id-a) prepared in the preparing method 1, 2 or 4 with 1 to 100 equivalents, preferably 2 to 3 equivalents of Compound (VII), in an inert solvent in the presence of 1 to 100 equivalents, preferably 2 to 5 equivalents of an appropriate base, at a temperature between −10° C. and the boiling point of the solvent used for 5 minutes to 24 hours.

Examples of the inert solvent include, for example, acetonitrile, dichloromethane, chloroform, acetone, ethyl acetate, THF, dioxane, toluene, xylene, DMF, NMP and the like. Examples of the appropriate base include, for example, sodium hydride, potassium carbonate, triethylamine, diisopropylethylamine, DBU, pyridine, DMAP and the like.

Compound (VII) can be prepared as a commercial product, or can be prepared by the methods described in Shin-Jikken-Kagaku-Koza Vol. 14, p. 307 (Maruzen, 1978) and the like, or the methods similar to thereof.

Preparing Method 8

Among Compound (I), Compound (Ig) wherein $R^3$ is a hydrogen atom can be prepared by the methods described in for example, Phosphorus, Sulfur and Silicone and the Related Elements, Vol. 122, p. 307 (1997); Chem. Ber., Vol. 123, p. 691 (1990) and the like, or the methods similar to thereof.

Preparing Method 9

Among Compound (I), Compound (Ih) wherein $R^2$ and/or $R^3$ is —$CSR^6$ (wherein $R^6$ has the same meaning as that mentioned above) and/or —$CSR^{19}$ (wherein $R^{19}$ has the same meaning as that mentioned above), respectively, can be prepared by thiocarbonylation of Compound (IP wherein the corresponding $R^2$ and/or $R^3$ is —$COR^6$ (wherein $R^6$ has the same meaning as that mentioned above) and/or —$COR^{19}$ (wherein $R^{19}$ has the same meaning as that mentioned above), respectively, in Compounds (Ia) to (Ig) prepared in the aforementioned preparing methods 1 to 8.

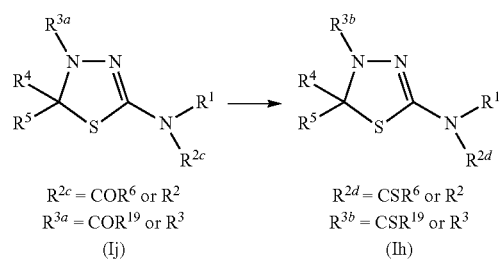

(wherein $R^1$, $R^2$, $R^3$, $R^4$, $R^5$, $R^6$ and $R^{19}$ have the same meanings as those mentioned above, respectively, $R^{2c}$ represents $COR^6$ (wherein $R^6$ has the same meaning as that mentioned above) or $R^2$ having the same meaning as that mentioned above, $R^{3a}$ represents $COR^{19}$ (wherein $R^{19}$ has the same meaning as that mentioned above) or $R^3$ having the same meaning as that mentioned above, $R^{2d}$ represents $CSR^6$ (wherein $R^6$ has the same meaning as that mentioned above) or $R^2$ having the same meaning as that mentioned above, and Rab represents $CSR^{19}$ (wherein $R^{19}$ has the same meaning as that mentioned above) or $R^3$ having the same meaning as that mentioned above.)

Namely, Compound (Ih) can be prepared by treatment of Compound (Ij) with 1 to 50 equivalents, preferably 1 to 10 equivalents of an appropriate thiocarbonylating agent, in an appropriate solvent at a temperature between −10° C. and the boiling point of the solvent used for 5 minutes to 24 hours.

Examples of the appropriate solvent include, for example, toluene, xylene, THF, dioxane, pyridine and the like, and they can be used alone or as a mixture. Examples of the appropriate thiocarbonylating agent include, for example, 2,4-bis(4-methoxyphenyl)-1,3-dithia-2,4-diphophethane-2,4-disulfide (Lawesson's reagent), phosphorus pentasulfide and the like.

Preparing Method 10

Among Compound (I), Compound (Ik) wherein $R^3$ is —$COR^{19}$ (wherein $R^{19}$ has the same meaning as that mentioned above) and $R^1$ and $R^2$ are combined to form a substituted or unsubstituted heterocyclic group together with the adjacent nitrogen atom can be prepared in accordance with the following Steps 10-1 and 10-2:

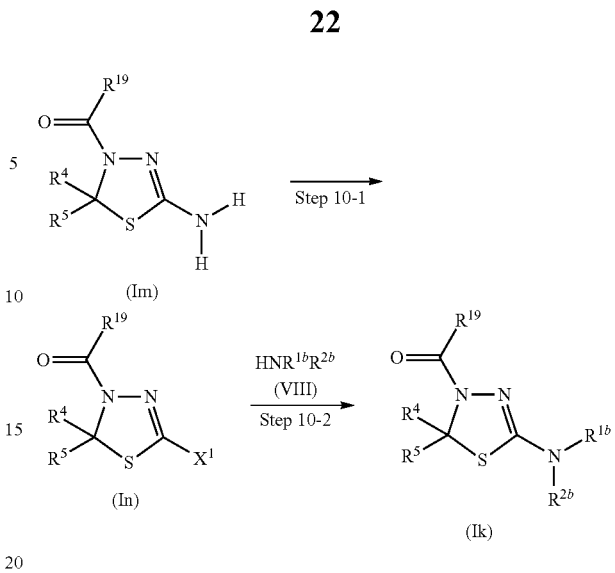

[wherein $R^4$, $R^5$, $R^{19}$ and $X^1$ have the same meanings as those mentioned above, respectively, and $R^{1b}$ and $R^{2b}$ are combined to form a substituted or unsubstituted heterocyclic group together with the adjacent nitrogen atom (said heterocyclic group has the same meaning as the aforementioned heterocyclic group formed together with the adjacent nitrogen atom (viii), and the substituent in said substituted heterocyclic group has the same meaning as the aforementioned substituent (xiii) in the heterocyclic group).]

Step 10-1

Compound (In) can be prepared from Compound (Im) prepared in the preparing method 1 or 3 by the methods described in for example, Chem. Commun., Vol. 8, p. 873 (1998) and the like, or the methods similar to thereof.

Step 10-2

Compound (Ik) can be prepared by reacting Compound (In) prepared in Step 10-1 mentioned above with 1 to 200 equivalents, preferably 2 to 50 equivalents of Compound (VIII), without solvent or in an inert solvent at a temperature between −10° C. and 200° C. for 5 minutes to 24 hours.

Examples of the inert solvent include, for example, acetonitrile, dichloromethane, chloroform, ethyl acetate, THF, dioxane, toluene, xylene, DMF, NMP, pyridine and the like, and they can be used alone or as a mixture.

Compound (VIII) can be prepared as a commercial product, or can be prepared by the methods described in Shin-Jikken-Kagaku-Koza Vol. 14, p. 1332 (Maruzen, 1978) and the like, or the methods similar to thereof.

As alternative methods, Compound (Ik) can also be prepared in accordance with the following two methods (Alternative methods 1 and 2).

Alternative Method 1

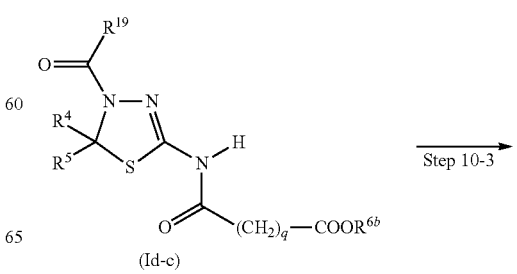

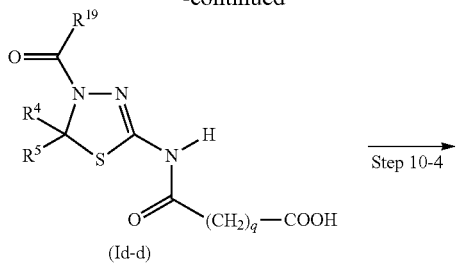

(Id-d)

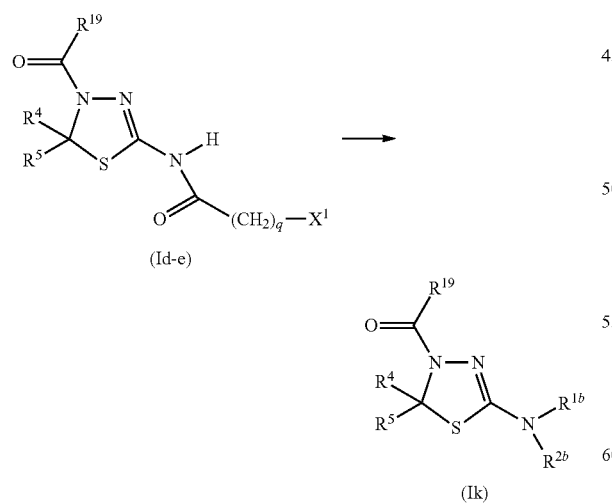

(wherein $R^4$, $R^5$, $R^{19}$, $R^{1b}$ and $R^{2b}$ have the same meanings as those mentioned above, $R^{6b}$ represents methyl, ethyl, tert-butyl or benzyl, and q represents an integer of from 2 to 7.)

Step 10-3

Compound (Id-d) can be prepared by deprotection of Compound (Id-c) wherein $R^1$ is a hydrogen atom, and $R^6$ is an alkyl group substituted with $COOR^{6b}$ (wherein $R^{6b}$ has the same meaning as that mentioned above) in Compound (Id). As the deprotection, deprotection condition of the protective group for carboxyl group ordinarily used in the organic synthetic chemistry [for example, the methods described in Protective Groups in Organic Synthesis, T. W. Greene, John Wiley & Sons Inc., 1981 and the like, or the methods similar to thereof] can be used.

Step 10-4

Compound (Ik) can be prepared from Compound (Id-d) prepared in Step 10-3 mentioned above by the method described in, for example, Synthesis-Stuttgart, Vol. 5, p. 420 (1991), or the methods similar to thereof.

Alternative Method 2

(wherein q, $X^1$, $R^4$, $R^6$, $R^{19}$, $R^{1b}$ and $R^{2b}$ have the same meanings as those mentioned above, respectively.)

Compound (Ik) can be prepared from Compound (Id-e) prepared in the preparing method 2 or 4 wherein $R^1$ is a hydrogen atom and $R^6$ is an alkyl group substituted with a chlorine atom, a bromine atom or an iodine atom in Compound (Id) by the method described in, for example, Shin-Jikken-Kagaku-Koza Vol. 14, p. 1174 (Maruzen, 1978) and the like, or the methods similar to thereof.

Preparing Method 11

Among Compound (I), Compound (Ih-a) wherein $R^3$ is $-CSR^{19}$ (wherein $R^{19}$ has the same meaning as that mentioned above) and $R^1$ and $R^2$ are combined to form a substituted or unsubstituted heterocyclic group together with the adjacent nitrogen atom can be prepared from Compound (Ik) prepared in the preparing method 10 in a manner similar to the preparing method 9.

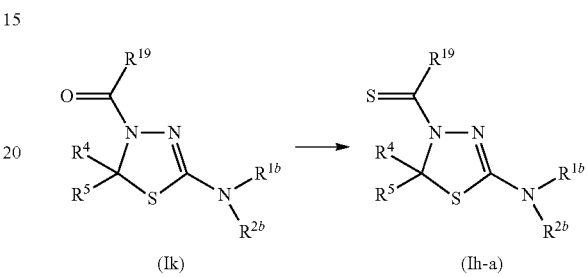

Preparing Method 12

Among Compound (I), Compound (Ip) wherein $R^4$ is $-(CH_2)_n NHBoc$ (wherein n has the same meaning as that mentioned above and Boc represents tert-butyloxycarbonyl), Compound (Iq) wherein $R^4$ is $-(CH_2)_n NH_2$ (wherein n has the same meaning as that mentioned above) and Compound (Io) wherein $R^4$ is $-(CH_2)_n NHSO_2 R^{24}$ (wherein n and $R^{24}$ have the same meanings as those mentioned above, respectively) can also be prepared in accordance with Steps 12-1 to 12-3 mentioned below, respectively:

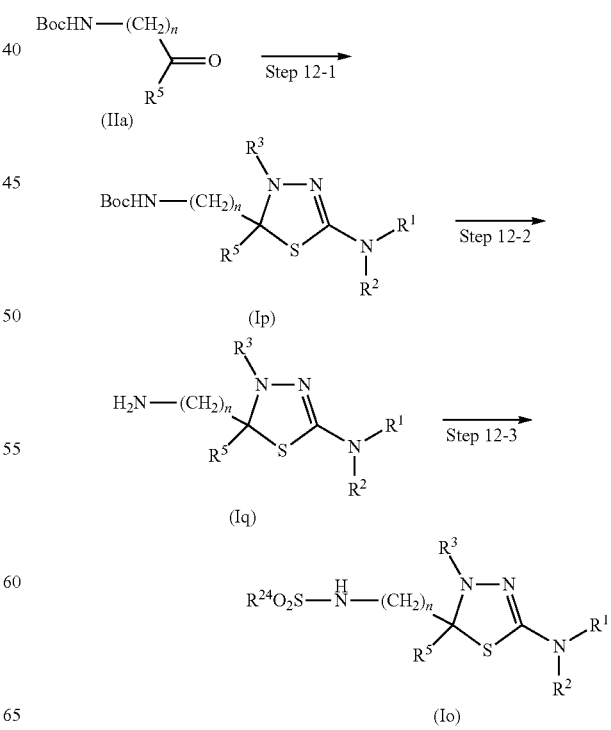

(wherein $R^1$, $R^2$, $R^3$, $R^5$, $R^{24}$, n and Boc have the same meanings as those mentioned above, respectively.)

Step 12-1

Compound (Ip) can be prepared in a manner similar to that of the preparing methods 1 to 11 using Compound (IIa).

Compound (IIa) can be prepared by known methods [e.g., the methods described in, for example, J. Med. Chem., Vol. 41, p. 591 (1998); Angew. Chem. Int. Ed., Vol. 40, p. 3458 (2001) and the like], or the methods similar to the known methods.

Step 12-2

Compound (Iq) can be prepared by the deprotection of Compound (Ip) prepared in the aforementioned Step 12-1. As the deprotection, the deprotection condition of the protective group (tert-butoxycarbonyl group) ordinarily used in the organic synthetic chemistry [e.g., the methods described in Protective Groups in Organic Synthesis, T. W. Greene, John Wiley & Sons Inc., 1981 and the like, or the methods similar to the thereof] can be used.

Step 12-3

Compound (Io) can be prepared by recting Compound (Iq) with 1 to 100 equivalents of $R^{24}SO_2X^1$ (wherein $R^{24}$ and $X^1$ have the same meanings as those mentioned above, respectively) or $(R^{24}SO_2)_2O$ (wherein $R^{24}$ has the same meaning as that mentioned above) without solvent or in an inert solvent, in the presence of 1 to 100 equivalents of an appropriate base if necessary, at a temperature between −30° C. and 150° C. for 5 minutes to 48 hours.

Examples of the inert solvent include, for example, methanol, ethanol, tert-butanol, acetonitrile, dichloromethane, chloroform, ethyl acetate, THF, dioxane, toluene, xylene, DMF, NMP, water and the like, and they can be used alone or as a mixture. Examples of the appropriate base include, for example, pyridine, triethylamine, diisopropylethylamine, DBU, potassium carbonate and the like.

Herein, $R^{24}SO_2X^1$ and $(R^{24}SO_2)_2O$ can be prepared as commercial products, or can be prepared by the methods described in Shin-Jikken-Kagaku-Koza Vol. 14, p. 1784 and p. 1799 (Maruzen, 1978) and the like, or the methods similar to thereof.

Preparing Method 13

Among Compound (1), Compound (It) wherein $R^4$ is —$(CH_2)_n$OH (wherein n has the same meaning as that mentioned above), Compound (Iu) wherein $R^4$ is —$(CH_2)_{n-1}$CHO (wherein n has the same meaning as that mentioned above) and Compound (Ir) wherein $R^4$ is —$(CH_2)_n NR^{43}R^{44}$ (wherein n, $R^{43}$ and $R^{44}$ have the same meanings as those mentioned above, respectively) can also be prepared in accordance with the following steps, respectively:

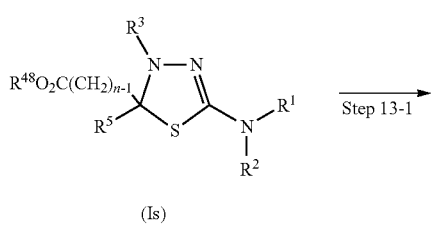

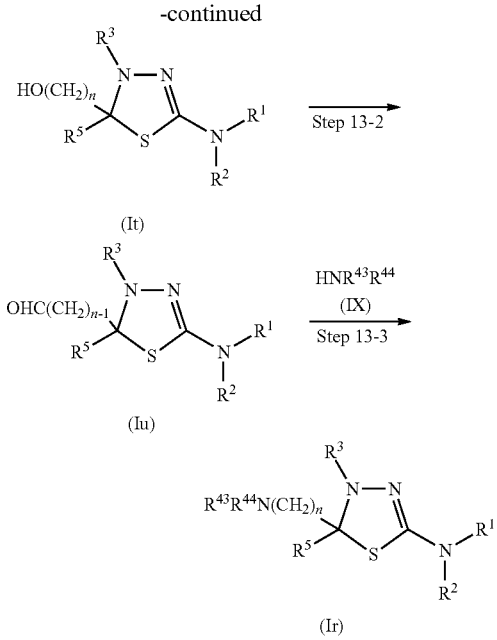

(wherein $R^1$, $R^2$, $R^3$, $R^5$, $R^{43}$, $R^{44}$ and n have the same meanings as those mentioned above, respectively, and $R^{4B}$ represents lower alkyl such as methyl and ethyl.)

Step 13-1

Compound (It) can be prepared by treatment of Compound (Is) prepared in a manner similar to that of the preparing methods 1 to 11 in an inert solvent in the presence of 1 to 10 equivalents of an appropriate reducing agent at a temperature between −78° C. and 150° C., preferably a temperature between −78° C. and 30° C., for 5 minutes to 80 hours.

Examples of the inert solvent include, for example, dichloromethane, THF, dioxane, toluene, xylene, hexane and the like, and they can be used alone or as a mixture. Examples of the appropriate reducing agent include, for example, diisobutylaluminum hydride, aluminum hydride and the like.

Step 13-2

Compound (Iu) can be prepared by treatment of Compound (It) prepared in Step 13-1 mentioned above in an inert solvent in the presence of 1 to 10 equivalents of an appropriate oxidizing agent at a temperature between −78° C. and 100° C., preferably a temperature between 0° C. and 50° C., for 5 minutes to 72 hours.

Examples of the inert solvent include, for example, acetonitrile, dichloromethane, chloroform, acetone, ethyl acetate, THF, dioxane, toluene, xylene, pyridine, water, 1,2-dichloroethane and the like, and they can be used alone or as a mixture. Examples of the appropriate oxidizing agent include, for example, pyridinium dichromate, manganese dioxide and the like.

Step 13-3

Compound (Ir) can be prepared by reacting Compound (Iu) prepared in Step 13-2 mentioned above with 1 to 200 equivalents of Compound (IX) in an inert solvent in the presence of 1 to 50 equivalents, preferably 1 to 10 equivalents of an appropriate reducing agent, and in the presence of catalytic amount to 50 equivalents of an appropriate acid if necessary, at a temperature between −78° C. and 100° C., preferably a temperature between 0° C. and 50° C., for 5 minutes to 48 hours.

Examples of the inert solvent include, for example, methanol, ethanol, tert-butanol, acetonitrile, dichloromethane, chloroform, THF, dioxane, toluene, xylene, water, 1,2-dichloroethane and the like, and they can be used alone or as a mixture. Examples of the appropriate reducing agent include, for example, triacetoxy sodium borohydride, sodium borohydride, sodium cyanoborohydride and the like. Examples of the appropriate acid include, for example, acetic acid, trifluoroacetic acid, hydrochloric acid and the like.

Compound (IX) can be prepared as a commercial product, or can be prepared by the methods described in Shin-Jikken-Kagaku-Koza Vol. 14, p. 1332 (Maruzen, 1978) and the like, or the methods similar to thereof.

Preparing Method 14

Among Compound (I), Compound (Iv) wherein $R^4$ is —$(CH_2)_n NHSO_2(CH_2)_2 NR^{43}R^{44}$ (wherein n has the same meaning as that mentioned above, and $R^{43}$ and $R^{44}$ have the same meanings as those of $R^{43}$ and $R^{44}$ mentioned in the definition of the aforementioned substituent (xi) in the substituted lower alkyl, respectively) can also be prepared in accordance with the following step:

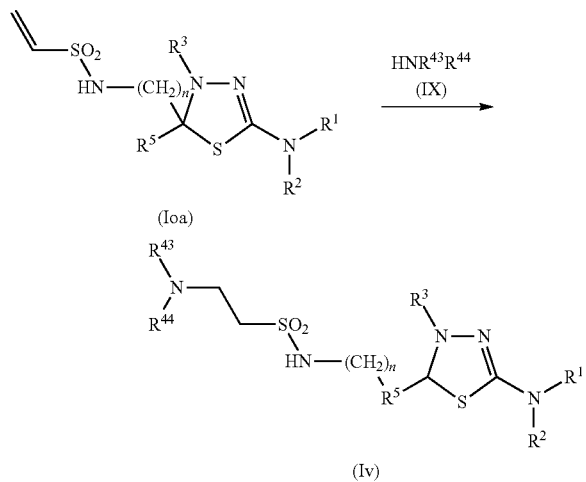

(wherein $R^1$, $R^2$, $R^3$, $R^5$, $R^{43}$, $R^{44}$ and n have the same meanings as those mentioned above, respectively.)

Compound (Iv) can also be prepared by reacting Compound (Ioa) prepared in the preparing methods 1 to 12 with 1 equivalent to large excess amount of Compound (IX) without solvent or in an inert solvent, in the presence of 0.5 equivalent to large excess amount of an appropriate base if necessary, at a temperature between −30° C. and 150° C. for 5 minutes to 72 hours.

Examples of the inert solvent include, for example, methanol, ethanol, tert-butanol, acetonitrile, dichloromethane, chloroform, ethyl acetate, THF, dioxane, toluene, xylene, DMF, NMP, water and the like, and they can be used alone or as a mixture. Examples of the appropriate base include, for example, sodium hydrogencarbonate, sodium carbonate, potassium hydroxide, pyridine, triethylamine, DBU and the like.

Preparing Method 15

Among Compound (I), Compound (Iw) wherein $R^4$ is —$(CH_2)_p NR^{44D}COR^{44C}$ (wherein p, $R^{44D}$ and $R^{44C}$ have the same meanings as those mentioned above, respectively) can also be prepared in accordance with the following step:

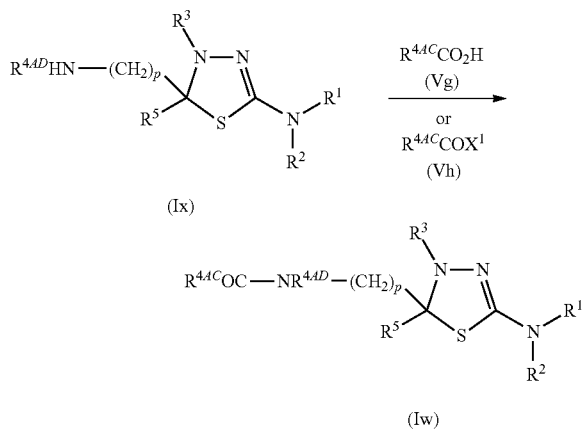

(wherein p, $R^1$, $R^2$, $R^3$, $R^5$, $R^{44C}$, $R^{44D}$ and $X^1$ have the same meanings as those mentioned above, respectively.)

Compound (Iw) can be prepared by reacting Compound (Ix) prepared in the preparing methods 1 to 13 with 1 to 30 equivalents of Compound (Vg) in an inert solvent in the presence of 1 to 30 equivalents of an appropriate condensing agent and 1 to 30 equivalents of an appropriate activating agent at a temperature between −78° C. and 100° C., preferably at a temperature between 0° C. and 50° C., for 5 minutes to 48 hours.

Examples of the inert solvent include, for example, acetonitrile, dichloromethane, chloroform, ethyl acetate, THF, dioxane, toluene, xylene, DMF, NMP, water and the like, and they can be used alone or as a mixture. Examples of the appropriate condensing agent include, for example, 1-ethyl-3-(3'-dimethylaminopropyl)carbodiimide (EDCI), EDCI hydrochloride, dicyclohexylcarbodiimide (DCC) and the like. Examples of the appropriate activating agent include, for example, 1-hydroxybenzotriazole monohydrate and the like.

As an alternative method, Compound (Iw) can be prepared by reacting Compound (Ix) with 1 to 30 equivalents of Compound (Vh) without solvent or in an appropriate solvent in the presence of 0.5 to 50 equivalents of an appropriate base at a temperature between −78° C. and 100° C., preferably at a temperature between −10° C. and 30° C., for 5 minutes to 24 hours.

Examples of the appropriate solvent include, for example, pyridine, acetonitrile, dichloromethane, chloroform, ethyl acetate, THF, dioxane, toluene, xylene, DMF, NMP, water and the like, and they can be used alone or as a mixture. Examples of the appropriate base include, for example, 2,6-di-tert-butyl-4-methylpyridine, pyridine, triethylamine, potassium carbonate and the like.

In Compound (I), conversion of the functional groups can be carried out by the other known methods [e.g., Comprehensive Organic Transformations, R. C. Larock (1989) and the like], or the methods similar to the known methods, as well as by the aforementioned steps.

Compound (I) having the desired functional group at the desired position can be prepared by carrying out the aforementioned methods in appropriate combination.

The intermediates and the desired compounds in the aforementioned preparation methods can be isolated and purified by conducting separation and purification methods ordinarily used in the organic synthetic chemistry such as filtration, extraction, washing, drying, concentration, recrystallization, various chromatography and the like. The intermediates can also be subjected to the next reaction without particular purification.

Specific examples of Compound (I) obtained by the present invention are shown in Tables 1 to 14. However, the compounds of the present invention are not limited to these examples.

TABLE 1

[Chemical structure: a thiadiazoline ring with substituents $R^1$, $R^2$, $R^3$, $R^4$ and a phenyl group]

| Ref. Ex. No. | Compound No. | $R^1$ | $R^2$ | $R^3$ | $R^4$ |
|---|---|---|---|---|---|
| 1 | 1 | H | COCH$_3$ | COCH$_3$ | CH$_3$ |
| 2 | 2 | H | COCH$_3$ | COCH$_3$ | CH$_2$CH$_3$ |
| 3 | 3 | H | COCH$_3$ | COCH$_3$ | (CH$_2$)$_3$CH$_3$ |
| 4 | 4 | H | COCH$_3$ | COCH$_3$ | CH(CH$_3$)$_2$ |
| 5 | 5 | H | COCH$_3$ | COCH$_3$ | cyclopropyl |
| 6 | 6 | H | COCH$_3$ | COCH$_3$ | cyclohexyl |
| 7 | 7 | CH$_3$ | COCH$_3$ | COCH$_3$ | CH$_3$ |
| 8 | 8 | CH$_2$CH$_3$ | CH$_2$CH$_3$ | COCH$_3$ | CH$_3$ |
| 8 | 9 | CH$_2$CH$_3$ | COCH$_3$ | COCH$_3$ | CH$_3$ |
| 9 | 10 | (CH$_2$)$_2$CH$_3$ | (CH$_2$)$_2$CH$_3$ | COCH$_3$ | CH$_3$ |
| 9 | 11 | (CH$_2$)$_2$CH$_3$ | COCH$_3$ | COCH$_3$ | CH$_3$ |
| 10 | 12 | —CH$_2$—phenyl | —CH$_2$—phenyl | COCH$_3$ | CH$_3$ |
| 10 | 13 | —CH$_2$—phenyl | COCH$_3$ | COCH$_3$ | CH$_3$ |
| 11 | 14 | H | H | COCH$_3$ | CH$_3$ |
| 12 | 15 | CH$_3$ | H | COCH$_3$ | CH$_3$ |
| 13 | 16 | CH$_3$ | CH$_3$ | COCH$_3$ | CH$_3$ |
| 14 | 17 | CH$_3$ | H | COCH$_2$CH$_3$ | CH$_3$ |
| 15 | 18 | CH$_3$ | COCH$_3$ | COCH$_2$CH$_3$ | CH$_3$ |
| 16 | 19 | CH$_3$ | COCH$_2$CH$_3$ | COCH$_2$CH$_3$ | CH$_3$ |
| 17 | 20 | CH$_3$ | CO(CH$_2$)$_2$CH$_3$ | CO(CH$_2$)$_2$CH$_3$ | CH$_3$ |
| 18 | 21 | CH$_3$ | COCH(CH$_3$)$_2$ | COCH(CH$_3$)$_2$ | CH$_3$ |

Among Compounds (I), stereoisomers such as position isomers, geometrical isomers, optical isomers, tautomers and the like may be existed, including thereof, all possible isomers and the mixtures thereof can be used as the mitotic kinesin Eg5 inhibitor and the like of the present invention.

To obtain a salt of Compound (I) or Compound (IA), when Compound (I) or Compound (IA) is obtained as a salt form, it may be purified as it When Compound (I) or Compound (IA) is obtained as a free form, it may be dissolved or suspended in an appropriate solvent, and added an appropriate acid or base to form a salt and then be isolated and purified.

In addition, Compound (I) or Compound (IA) or a pharmacologically acceptable salt thereof may exist in the form of adducts with water or varaieous solvents, which also can be used for the mitotic kinesin Eg5 inhibitor and the like of the present invention.

TABLE 2

[Chemical structure with $R^1$, $R^4$, $R^5$ substituents, COCH$_3$ groups]

| Ref. Ex. No. | Compound No. | $R^1$ | $R^4$ | $R^5$ |
|---|---|---|---|---|
| 19 | 22 | H | CH$_3$ | CH$_3$ |
| 20 | 23 | H | CH$_3$ | (CH$_2$)$_3$CH$_3$ |

TABLE 2-continued

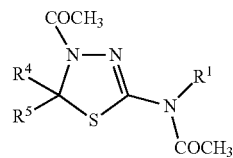

| Ref. Ex. No. | Compound No. | R¹ | R⁴ | R⁵ |
|---|---|---|---|---|
| 21 | 24 | H | CH₃ | —CH₂—CH₂—C₆H₅ |
| 22 | 25 | H | CH₃ | —CH=CH—C₆H₅ |
| 23 | 26 | H | (CH₂)₃CH₃ | (CH₂)₃CH₃ |
| 24 | 27 | H | | -(CH₂)₃-(o-C₆H₄)- |
| 25 | 28 | H | | -CH₂-(o-C₆H₄)-CH₂- |
| 27 | 30 | H | | -(CH₂)₆- |
| 26 | 29 | H | | -CH₂CH₂-(o-C₆H₄)- |
| 28 | 31 | H | | -CH₂-cyclopentyl-CH₂- |
| 29 | 32 | H | CH₃ | 1-naphthyl |

TABLE 2-continued

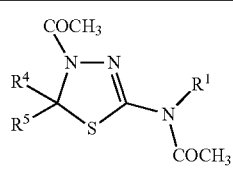

| Ref. Ex. No. | Compound No. | R¹ | R⁴ | R⁵ |
|---|---|---|---|---|
| 30 | 33 | H | CH₃ | 2-naphthyl |
| 31 | 34 | H | CH₃ | 2-pyridyl |
| 32 | 35 | H | CH₃ | 3-pyridyl |
| 33 | 36 | H | CH₃ | 4-pyridyl |
| 34 | 37 | H | CH₃ | 2-pyrazinyl |
| 35 | 38 | H | CH₃ | N-acetyl-2-pyrrolyl |
| 36 | 39 | H | CH₃ | 2-furyl |
| 37 | 40 | H | CH₃ | 2-thienyl |
| 38 | 41 | CH₂CH₃ | CH₃ | 2-thienyl |
| 39 | 42 | H | CH₃ | 3-methyl-2-thienyl |

TABLE 2-continued

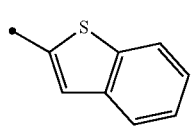

| Ref. Ex. No. | Compound No. | R¹ | R⁴ | R⁵ |
|---|---|---|---|---|
| 40 | 43 | H | $CH_3$ | 2-benzothienyl |
| 41 | 44 | H | $CH_3$ | 3-thienyl |
| 42 | 45 | H | $CH_3$ | 2-thiazolyl |

TABLE 3

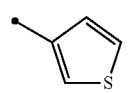

| Ref. Ex. No. | Compound No. | R¹ | R⁴ | Y¹ (Substituting position) |
|---|---|---|---|---|
| 43 | 46 | H | $CH_3$ | $CH_3$ (2) |
| 44 | 47 | H | $CH_3$ | $CH_3$ (3) |
| 45 | 48 | H | $CH_3$ | $CH_3$ (4) |
| 46 | 49 | H | $CH_2CH_3$ | $CH_2CH_3$ (2) |
| 47 | 50 | H | $CH_3$ | $OCH_3$ (2) |
| 48 | 51 | H | $CH_3$ | $OCH_3$ (3) |
| 49 | 52 | H | $CH_3$ | $OCH_3$ (4) |
| 50 | 53 | H | $CH_3$ | F (2) |
| 51 | 54 | H | $CH_3$ | F (3) |
| 52 | 55 | H | $CH_3$ | F (4) |
| 53 | 56 | H | $CH_3$ | Cl (2) |
| 54 | 57 | $CH_2CH_3$ | $CH_3$ | Cl (2) |
| 55 | 58 | H | $CH_3$ | Cl (3) |
| 56 | 59 | H | $CH_3$ | Cl (4) |
| 57 | 60 | H | $CH_3$ | Br (2) |
| 58 | 61 | H | $CH_3$ | $OCOCH_3$ (2) |
| 59 | 62 | H | $CH_3$ | $OCOCH_3$ (3) |
| 60 | 63 | H | H | $OCOCH_3$ (3) |
| 61 | 64 | H | $CH_3$ | $OCOCH_3$ (4) |
| 62 | 65 | H | $CH_3$ | $NO_2$ (2) |
| 63 | 66 | H | $CH_3$ | $NO_2$ (3) |
| 64 | 67 | H | $CH_3$ | $NO_2$ (4) |
| 65 | 68 | H | $CH_3$ | OH (2) |
| 66 | 69 | H | $CH_3$ | OH (3) |
| 67 | 70 | H | $CH_3$ | OH (4) |
| 68 | 71 | H | $CH_3$ | CN (3) |
| 69 | 72 | H | $CH_3$ | CN (4) |
| 70 | 73 | H | $CH_3$ | $CF_3$ (3) |
| 71 | 74 | H | $CH_3$ | COOH (2) |

TABLE 4

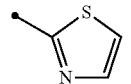

| Ref. Ex. No. | Compound No. | Y¹ (Substituting position) | Y² (Substituting position) |
|---|---|---|---|
| 72 | 75 | $OCH_3$ (2) | $OCH_3$ (6) |
| 73 | 76 | OH (3) | OH (5) |
| 74 | 77 | OH (3) | OH (4) |
| 75 | 78 | $CH_3$ (2) | $CH_3$ (4) |

TABLE 5

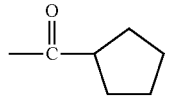

| Ref. Ex. No. | Compound No. | R¹ | R² | R³ |
|---|---|---|---|---|
| 76 | 79 | $CH_2CH=CH_2$ | $COCH_3$ | $COCH_3$ |
| 77 | 80 | $CH_2CH=CH_2$ | H | $COCH(CH_3)_2$ |
| 77 | 81 | $CH_2CH=CH_2$ | $COCH_3$ | $COCH(CH_3)_2$ |
| 78 | 82 | H | $COC(CH_3)_3$ | $COC(CH_3)_3$ |
| 79 | 83 | $CH_3$ | H | $COCH(CH_3)_2$ |
| 79 | 84 | $CH_3$ | $COCH_3$ | $COCH(CH_3)_2$ |
| 80 | 85 | H | $COCH(CH_3)_2$ | $COCH(CH_3)_2$ |
| 81 | 86 | H | H | $COCH(CH_3)_2$ |
| 81 | 87 | H | $COCH_3$ | $COCH(CH_3)_2$ |
| 82 | 88 | H | $COCH(CH_3)_2$ | $COCH_3$ |
| 83 | 89 | H | $-C(O)$-cyclopentyl | $COCH_3$ |
| 84 | 90 | H | H | $COCH_2CH(CH_3)_2$ |
| 84 | 91 | H | $COCH(CH_3)_2$ | $COCH_2CH(CH_3)_2$ |
| 85 | 92 | H | $COCH_3$ | $COC(CH_3)_3$ |
| 86 | 93 | H | $COC(CH_3)_3$ | $COCH_3$ |

TABLE 6

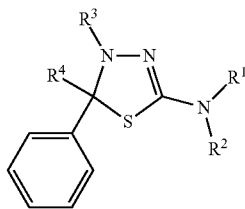

| Ref. Ex. No. | Compound No. | R¹ | R² | R³ | R⁴ |
|---|---|---|---|---|---|
| 87 | 94 | H | COC(CH₃)₃ | COC(CH₃)₃ | CH₂CH₃ |
| 88 | 95 | H | COC(CH₃)₃ | COC(CH₃)₃ | CH₂NHSO₂CH₃ |
| 89 | 96 | —CH₃ | COC(CH₃)₃ | COC(CH₃)₃ | CH₂NHSO₂CH₃ |
| 90 | 97 | H | COC(CH₃)₃ | COC(CH₃)₃ | CH₂NHSO₂CH₂CH₃ |
| 91 | 98 | H | COC(CH₃)₃ | COC(CH₃)₃ | CH₂OCH₃ |
| 92 | 99 | H | COC(CH₃)₃ | COC(CH₃)₃ | (CH₂)₂NHSO₂CH₃ |
| 93 | 100 | H | COCH(CH₃)₂ | COCH(CH₃)₂ | (CH₂)₂NHSO₂CH₃ |
| 94 | 101 | H | COC(CH₃)₃ | COC(CH₃)₃ | CH₂NHCOCF₃ |
| 95 | 102 | COCH(CH₃)₂ | COCH(CH₃)₂ | COCH(CH₃)₂ | CH₂NHSO₂CH₃ |
| 96 | 103 | H | COCH(CH₃)₂ | COCH(CH₃)₂ | CH₂NHSO₂CH₃ |
| 97 | 104 | H | COC(CH₃)₃ | COC(CH₃)₃ | (CH₂)₂N(CH₃)₂ |
| 98 | 105 | H | COC(CH₃)₃ | COC(CH₃)₃ | (CH₂)₂COOCH₃ |
| 99 | 106 | H | COC(CH₃)₃ | COC(CH₃)₃ | (CH₂)₂COOH |
| 100 | 107 | H | COC(CH₃)₃ | COC(CH₃)₃ | (CH₂)₂CONH₂ |
| 101 | 108 | H | COC(CH₃)₃ | COC(CH₃)₃ | (CH₂)₂CONHOH |
| 102 | 109 | H | COC(CH₃)₃ | COC(CH₃)₃ | (CH₂)₂CONHCH₃ |
| 103 | 110 | H | COC(CH₃)₃ | COC(CH₃)₃ | (CH₂)₂CON(CH₃)₂ |
| 104 | 111 | H | COC(CH₃)₃ | COC(CH₃)₃ | (CH₂)₂CONH(CH₂)₂OH |
| 105 | 112 | H | COC(CH₃)₃ | COC(CH₃)₃ | (CH₂)₂CONH(CH₂)₃CH₃ |
| 106 | 113 | H | COC(CH₃)₃ | COC(CH₃)₃ | 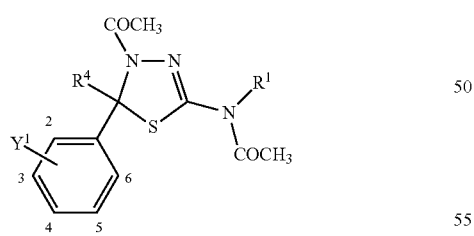 |
| 107 | 114 | H | COC(CH₃)₃ | COC(CH₃)₃ | (CH₂)₃COOCH₃ |
| 108 | 115 | H | COC(CH₃)₃ | COC(CH₃)₃ | (CH₂)₃COOH |
| 109 | 116 | H | COC(CH₃)₃ | COC(CH₃)₃ | (CH₂)₃CONHCH₃ |
| 110 | 117 | H | COC(CH₃)₃ | COC(CH₃)₃ | (CH₂)₃CONH₂ |
| 111 | 118 | H | H | COCH₃ | CH₂NHSO₂CH₃ |
| 112 | 119 | H | COC(CH₃)₃ | COCH₃ | CH₂NHSO₂CH₃ |
| 113 | 120 | H | H | COC(CH₃)₃ | CH₂NHSO₂CH₃ |
| 114 | 121 | H | CO(CH₂)₅Br | COC(CH₃)₃ | CH₂NHSO₂CH₃ |
| 115 | 122 | H | CO(CH₂)₅N₃ | COC(CH₃)₃ | CH₂NHSO₂CH₃ |
| 116 | 123 | H | CO(CH₂)₅NH₂ | COC(CH₃)₃ | CH₂NHSO₂CH₃ |
| 117 | 124 | H | CO(CH₂)₅NHCOCH₃ | COC(CH₃)₃ | CH₂NHSO₂CH₃ |

TABLE 7

| Ref. Ex. No. | Compound No. | R¹ | R⁴ | Y¹ (Substituting position) |
|---|---|---|---|---|
| 118 | 125 | CH₂CH₃ | CH₃ | OCOCH₃ (3) |
| 119 | 126 | CH₂CH₃ | CH₃ | OH (3) |
| 120 | 127 | H | CH₃ | OCONHCH₂CH₃ (3) |

TABLE 8
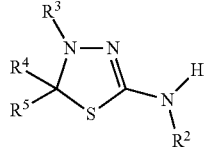
| Ref. Ex. No. | Compound No. | R² | R³ | R⁴ | R⁵ |
|---|---|---|---|---|---|
| 121 | 128 | COCH(CH₃)₂ | COCH(CH₃)₂ | CH₃ | 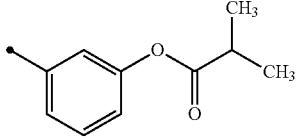 |
| 122 | 129 | COCH(CH₃)₂ | COCH(CH₃)₂ | CH₃ | 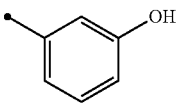 |
| 123 | 130 | COC(CH₃)₃ | COC(CH₃)₃ | CH₃ | 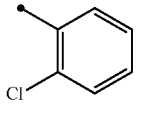 |
| 124 | 131 | COCH(CH₃)₂ | COCH(CH₃)₂ | CH₃ | 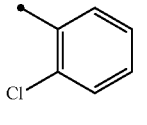 |
| 125 | 132 | COCH₃ | COCH₃ | CH₃ | 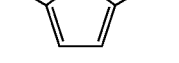 |
| 126 | 133 | COCH₃ | COCH₃ | CH₃ | 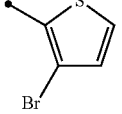 |
| 127 | 134 | COCH₃ | COCH₃ | CH₃ | 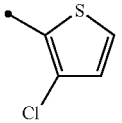 |
| 128 | 135 | COCH(CH₃)₂ | COCH(CH₃)₂ | CH₃ | 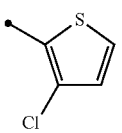 |
| 129 | 136 | CO₂C(CH₃)₃ | COCH₃ | CH₃ | 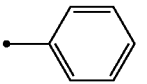 |
| 130 | 137 | CON(CH₃)₂ | COCH₃ | CH₃ | 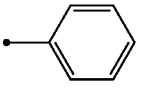 |

TABLE 9

[Structure: 2,3-dihydro-1,3,4-thiadiazole with R³ on N3, R⁴ and phenyl on C5, NR¹R² on C2]

| Ref. Ex. No. | Compound No. | R¹ | R² | R³ | R⁴ |
|---|---|---|---|---|---|
| 131 | 138 | | [heptyl chain, both ends attached] | COCH₃ | CH₃ |
| 132 | 139 | | [branched chain with CH₃] | COCH₃ | CH₃ |
| 133 | 140 | H | CO(CH₂)₄CH₃ | COCH₃ | CH₂NHSO₂CH₃ |
| 134 | 141 | H | COCH=CHCH₃ | COCH₃ | CH₂NHSO₂CH₃ |
| 135 | 142 | | [cyclopropyl-C(O)-] | COCH₃ | CH₂NHSO₂CH₃ |
| 136 | 143 | H | COC(CH₃)₂OCOCH₃ | COCH₃ | CH₂NHSO₂CH₃ |
| 137 | 144 | H | COC(CH₃)₂OH | COCH₃ | CH₂NHSO₂CH₃ |
| 138 | 145 | H | COCH₂OCH₃ | COCH₃ | CH₂NHSO₂CH₃ |
| 139 | 146 | H | COCH₂Cl | COCH₃ | CH₂NHSO₂CH₃ |
| 140 | 147 | H | COCH₂N(CH₃)₂ | COCH₃ | CH₂NHSO₂CH₃ |
| 141 | 148 | H | CO(CH₂)₃CO₂CH₃ | COCH₃ | CH₂NHSO₂CH₃ |
| 142 | 149 | H | CO(CH₂)₃CO₂H | COCH₃ | CH₂NHSO₂CH₃ |
| 143 | 150 | | [-C(O)(CH₂)₃C(O)-] | COCH₃ | CH₂NHSO₂CH₃ |
| 144 | 151 | H | CO(CH₂)₃Br | COCH₃ | CH₂NHSO₂CH₃ |
| 145 | 152 | | [-C(O)(CH₂)₃-] | COCH₃ | CH₂NHSO₂CH₃ |
| 146 | 153 | H | CO(CH₂)₄Br | COCH₃ | CH₂NHSO₂CH₃ |
| 147 | 154 | | [-C(O)(CH₂)₄-] | COCH₃ | CH₂NHSO₂CH₃ |
| 148 | 155 | H | CO(CH₂)₅Br | COCH₃ | CH₂NHSO₂CH₃ |
| 149 | 156 | | [-C(O)(CH₂)₅-] | COCH₃ | CH₂NHSO₂CH₃ |
| 150 | 157 | H | H | COC(CH₃)₃ | (CH₂)₂NHSO₂CH₃ |
| 151 | 158 | H | CO(CH₂)₃Br | COC(CH₃)₃ | (CH₂)₂NHSO₂CH₃ |
| 152 | 159 | | [-C(O)(CH₂)₃-] | COC(CH₃)₃ | (CH₂)₂NHSO₂CH₃ |
| 153 | 160 | H | COC(CH₃)₃ | CSCH₃ | CH₂NHSO₂CH₃ |
| 154 | 161 | H | COC(CH₃)₃ | COC(CH₃)₃ | 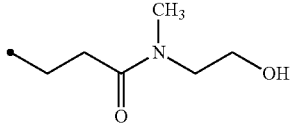 |

TABLE 9-continued

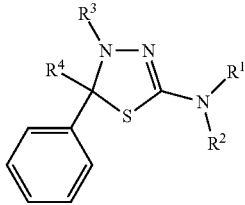

| Ref. Ex. No. | Compound No. | R¹ | R² | R³ | R⁴ |
|---|---|---|---|---|---|
| 155 | 162 | H | COC(CH₃)₃ | COC(CH₃)₃ | 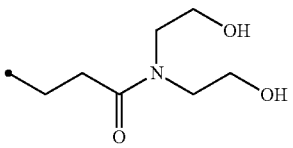 |
| 156 | 163 | H | COC(CH₃)₃ | COC(CH₃)₃ | 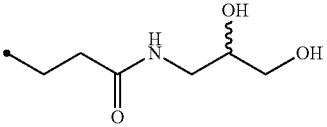 |
| 156 | 164* | H | COC(CH₃)₃ | COC(CH₃)₃ | 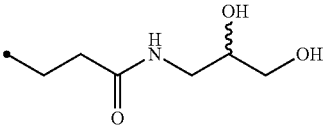 |
| 157 | 165 | H | COC(CH₃)₃ | COC(CH₃)₃ | 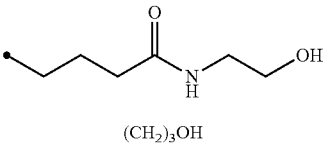 |
| 158 | 166 | H | COC(CH₃)₃ | COC(CH₃)₃ | (CH₂)₃OH |
| 159 | 167 | H | COC(CH₃)₃ | COC(CH₃)₃ | (CH₂)₃OSO₂NH₂ |
| 160 | 168 | H | COC(CH₃)₃ | COCH₃ | CH₂NHSO₂CH₂Cl |
| 160 | 169 | H | COCH₃ | COCH₃ | CH₂NHSO₂CH₂Cl |
| 161 | 170 | H | COC(CH₃)₃ | COCH₃ | CH₂NHSO₂CH=CH₂ |
| 161 | 171 | H | COC(CH₃)₃ | COC(CH₃)₃ | CH₂NHSO₂CH=CH₂ |
| 162 | 172 | H | COC(CH₃)₃ | COCH₃ | 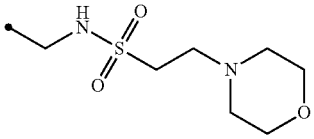 |
| 163 | 173 | H | COC(CH₃)₃ | COCH₃ | CH₂NHSO₂(CH₂)₂NHCH₂CH₃ |
| 164* | 174 | H | COC(CH₃)₃ | COCH₃ | CH₂NHSO₂(CH₂)₂N(CH₃)₂ |
| 165 | 175 | H | COC(CH₃)₃ | COCH₃ | CH₂NHSO₂(CH₂)₂NH(CH₂)₂OH |
| 166 | 176 | H | COC(CH₃)₃ | COC(CH₃)₃ | CH₂NHSO₂(CH₂)₂NHCH₂CH₃ |
| 167 | 177 | H | COC(CH₃)₃ | COC(CH₃)₃ | CH₂NHSO₂(CH₂)₂N(CH₃)₂ |
| 168 | 178 | H | H | COCH₃ | (CH₂)₂CO₂CH₃ |
| 169 | 179 | H | COC(CH₃)₃ | COCH₃ | (CH₂)₂CO₂CH₃ |
| 170 | 180 | H | H | COCH(CH₃)₂ | (CH₂)₂NHSO₂CH₃ |
| 171 | 181 | H | COC(CH₃)₃ | COCH(CH₃)₂ | (CH₂)₂NHSO₂CH₃ |
| 172 | 182 | | 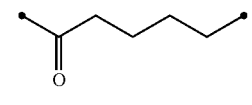 | COCH(CH₃)₂ | (CH₂)₂NHSO₂CH₃ |
| 173 | 183 | | 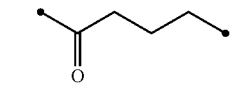 | COCH(CH₃)₂ | (CH₂)₂NHSO₂CH₃ |
| 174 | 184 | | 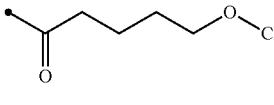 | COCH(CH₃)₂ | (CH₂)₂NHSO₂CH₃ |

TABLE 9-continued

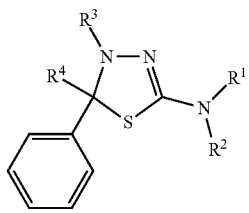

| Ref. Ex. No. | Compound No. | R¹ | R² | R³ | R⁴ |
|---|---|---|---|---|---|
| 175 | 185 | H | COCH$_2$CH$_3$ | COCH$_2$CH$_3$ | (CH$_2$)$_2$NHSO$_2$CH$_3$ |
| 176 | 186 | H | H | COCH$_2$CH$_3$ | (CH$_2$)$_2$NHSO$_2$CH$_3$ |
| 177 | 187 | H | COC(CH$_3$)$_3$ | COCH$_2$CH$_3$ | (CH$_2$)$_2$NHSO$_2$CH$_3$ |
| 178 | 188 | | (cyclopentanone-linked) | COCH$_2$CH$_3$ | (CH$_2$)$_2$NHSO$_2$CH$_3$ |
| 179 | 189 | | (cyclohexanone-linked) | COCH$_2$CH$_3$ | (CH$_2$)$_2$NHSO$_2$CH$_3$ |
| 180 | 190 | H | H | COC(CH$_3$)$_3$ | (CH$_2$)$_2$COOCH$_3$ |
| 181 | 191 | H | COCH$_2$CH$_2$CH$_2$Br | COC(CH$_3$)$_3$ | (CH$_2$)$_2$COOCH$_3$ |
| 182 | 192 | | (cyclopentanone-linked) | COC(CH$_3$)$_3$ | (CH$_2$)$_2$COOCH$_3$ |
| 183 | 193 | | (cyclopentanone-linked) | COC(CH$_3$)$_3$ | (CH$_2$)$_2$COOH |
| 184 | 194 | | (cyclopentanone-linked) | COC(CH$_3$)$_3$ | (CH$_2$)$_2$CONH(CH$_2$)$_2$OH |

*Compound 164: Isomer of Compound 163

TABLE 10

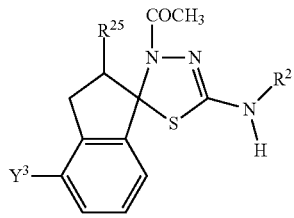

| Ref. Ex. No. | Compound No. | R² | R²⁵ | Y³ |
|---|---|---|---|---|
| 185 | 195 | COC(CH$_3$)$_3$ | OCOCH$_3$ | H |
| 186 | 196 | COC(CH$_3$)$_3$ | OH | H |
| 187 | 197 | H | H | OCOCH$_3$ |
| 188 | 198 | COC(CH$_3$)$_3$ | H | OCOCH$_3$ |
| 189 | 199 | COC(CH$_3$)$_3$ | H | OH |

TABLE 11

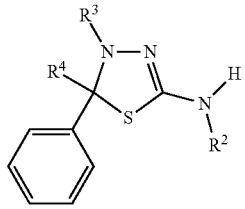

| Ref. Ex. No. | Compound No. | R² | R³ | R⁴ |
|---|---|---|---|---|
| 190 | 200 | COC(CH$_3$)$_3$ | COC(CH$_3$)$_3$ | CH$_2$COOCH$_3$ |
| 191 | 201 | COC(CH$_3$)$_3$ | COC(CH$_3$)$_3$ | CH$_2$CH$_2$OH |
| 192 | 202 | COC(CH$_3$)$_3$ | COC(CH$_3$)$_3$ | CH$_2$CHO |
| 193 | 203 | COCH$_2$CH$_3$ | COCH$_2$CH$_3$ | (CH$_2$)$_2$COOCH$_3$ |
| 194 | 204 | COCH$_3$ | COCH$_3$ | (CH$_2$)$_2$CON(OCH$_3$)CH$_3$ |
| 195 | 205 | COC(CH$_3$)$_3$ | COC(CH$_3$)$_3$ | (CH$_2$)$_2$CON(OCH$_3$)CH$_3$ |

TABLE 12

[Structure: 1,3,4-thiadiazoline with N-COC(CH$_3$)$_3$, R$^4$, R$^5$ substituents, and NHCOC(CH$_3$)$_3$ group]

| Example No. | Compound No. | R$^4$ | R$^5$ |
|---|---|---|---|
| 11 | 206 | (CH$_2$)$_2$NH(CH$_2$)$_2$CH$_3$ | phenyl |
| 12 | 207 | (CH$_2$)$_2$N(CH$_2$CH$_3$)$_2$ | phenyl |
| 13 | 208 | CH$_2$NHCOOC(CH$_3$)$_3$ | phenyl |
| 14 | 209 | (CH$_2$)$_2$NHCOOC(CH$_3$)$_3$ | phenyl |
| 15 | 210 | (CH$_2$)$_2$NH$_2$ | phenyl |
| 16 | 211 | (CH$_2$)$_2$NHCOCH$_3$ | phenyl |

TABLE 12-continued

| Example No. | Compound No. | R$^4$ | R$^5$ |
|---|---|---|---|
| 17 | 212 | (CH$_2$)$_2$NHCOOC(CH$_3$)$_3$ | 3-(OCH$_2$OCH$_3$)phenyl |
| 18 | 213 | (CH$_2$)$_2$NH$_2$ | 3-(OH)phenyl |
| 19 | 214 | (CH$_2$)$_2$NHSO$_2$N(CH$_3$)$_2$ | phenyl |
| 20 | 215 | (CH$_2$)$_2$NHSO$_2$NH$_2$ | phenyl |
| 21 | 216 | CH$_2$NH$_2$ | phenyl |
| 22 | 217 | CH$_2$N(CH$_3$)$_2$ | phenyl |

TABLE 13

[Structure: 1,3,4-thiadiazoline with R$^3$, R$^{4a}$NHCH$_2$–, phenyl, and NR$^1$R$^2$ substituents]

| Example No. | Compound No. | R$^1$ | R$^2$ | R$^3$ | R$^{4a}$ |
|---|---|---|---|---|---|
| 23 | 218 | H | COC(CH$_3$)$_3$ | COC(CH$_3$)$_3$ | SO$_2$(CH$_2$)$_3$Cl |
| 24 | 219 | H | COC(CH$_3$)$_3$ | COC(CH$_3$)$_3$ | SO$_2$(CH$_2$)$_3$N$_3$ |
| 25 | 220* | H | COC(CH$_3$)$_3$ | COC(CH$_3$)$_3$ | SO$_2$(CH$_2$)$_3$NH$_2$ |
| 26 | 221 | H | COC(CH$_3$)$_3$ | COC(CH$_3$)$_3$ | SO$_2$(CH$_2$)$_3$NH$_2$ |
| 27 | 222 | H | H | COC(CH$_3$)$_3$ | COOC(CH$_3$)$_3$ |
| 28 | 223 |  | CO(CH$_2$)$_3$– (cyclic ketone linker) | COC(CH$_3$)$_3$ | COOC(CH$_3$)$_3$ |
| 29 | 224 |  | CO(CH$_2$)$_3$– (cyclic ketone linker) | COC(CH$_3$)$_3$ | SO$_2$CH=CH$_2$ |

TABLE 13-continued

| Example No. | Compound No. | R¹ | R² | R³ | R⁴ᵃ |
|---|---|---|---|---|---|
| 30 | 225 | | O=C(CH₂)₃– (pentanoyl) | COC(CH₃)₃ | SO₂(CH₂)₂NH₂ |
| 31 | 226 | H | COC(CH₃)₃ | COC(CH₃)₃ | SO₂(CH₂)₃NH(CH₂)₂OH |
| 32 | 227 | H | COC(CH₃)₃ | COC(CH₃)₃ | SO₂(CH₂)₃NHCH₂CH₃ |
| 33 | 228 | H | COC(CH₃)₃ | COCH₃ | SO₂(CH₂)₂NH₂ |
| 34 | 229* | H | COC(CH₃)₃ | COCH₃ | SO₂(CH₂)₂NH₂ |
| 35 | 230 | H | COC(CH₃)₃ | COCH₃ | SO₂(CH₂)₂NHC(CH₂OH)₂CH₃ |
| 36 | 231 | H | COCH₃ | COCH₃ | COOC(CH₃)₃ |
| 37 | 232 | H | H | COCH₃ | COOC(CH₃)₃ |
| 38 | 233 | | O=C(CH₂)₃– | COCH₃ | COOC(CH₃)₃ |
| 39 | 234 | | O=C(CH₂)₃– | COCH₃ | SO₂CH=CH₂ |
| 40 | 235 | | O=C(CH₂)₃– | COCH₃ | SO₂(CH₂)₂NH₂ |
| 41 | 236 | | O=C(CH₂)₃– | COCH₃ | SO₂(CH₂)₂N(CH₃)₂ |
| 42 | 237 | H | COC(CH₃)₃ | COC(CH₃)₃ | SO₂(CH₂)₃N(CH₃)₂ |
| 43 | 238* | H | COC(CH₃)₃ | COC(CH₃)₃ | SO₂(CH₂)₃N(CH₃)₂ |
| 44 | 239 | | O=C(CH₂)₃– | COCH₃ | SO₂(CH₂)₃Cl |
| 45 | 240 | | O=C(CH₂)₃– | COCH₃ | SO₂(CH₂)₃N₃ |
| 46 | 241 | | O=C(CH₂)₃– | COCH₃ | SO₂(CH₂)₃NH₂ |
| 47 | 242 | H | COC(CH₃)₃ | COCH₃ | COOC(CH₃)₃ |
| 48 | 243 | H | COC(CH₃)₃ | COCH₃ | H |
| 49 | 244 | H | COC(CH₃)₃ | COCH₃ | SO₂(CH₂)₃Cl |
| 50 | 245 | H | COC(CH₃)₃ | COCH₃ | SO₂(CH₂)₃N₃ |
| 51 | 246 | H | COC(CH₃)₃ | COCH₃ | SO₂(CH₂)₃NH₂ |
| 52 | 247 | | O=C(CH₂)₃– | COCH₃ | SO₂(CH₂)₃N(CH₃)₂ |
| 53 | 248 | | O=C(CH₂)₃– | COCH₃ | SO₂(CH₂)₃NHCH₂CH₃ |
| 54 | 249 | H | COC(CH₃)₃ | COCH₃ | SO₂(CH₂)₃N(CH₃)₂ |

TABLE 13-continued

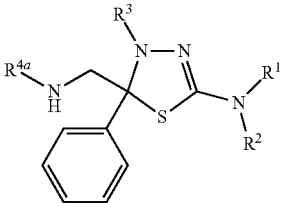

| Example No. | Compound No. | R¹ | R² | R³ | R⁴ᵃ |
|---|---|---|---|---|---|
| 55 | 250 | H | COC(CH₃)₃ | COC(CH₃)₃ | SO₂(CH₂)₂N(CH₂CH₂OCH₃)₂ |
| 56 | 251 | H | COC(CH₃)₃ | COC(CH₃)₃ | SO₂(CH₂)₂NHCH₂CF₃ |
| 57 | 252 | H | COC(CH₃)₃ | COC(CH₃)₃ | 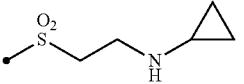 |
| 58 | 253* | H | COC(CH₃)₃ | COC(CH₃)₃ | 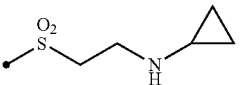 |
| 59 | 254 | H | COC(CH₃)₃ | COC(CH₃)₃ | 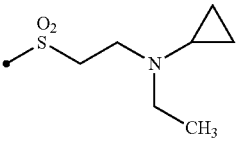 |
| 60 | 255 | H | COC(CH₃)₃ | COC(CH₃)₃ | SO₂(CH₂)₃N(CH₂CH₃)₂ |
| 61 | 256 | H | COC(CH₃)₃ | COC(CH₃)₃ | 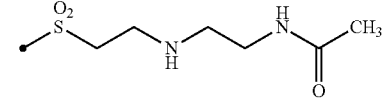 |
| 62 | 257 | H | COC(CH₃)₃ | COC(CH₃)₃ | 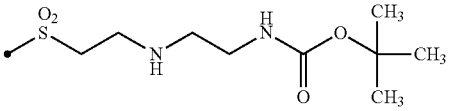 |
| 63 | 258 | H | COC(CH₃)₃ | COC(CH₃)₃ | 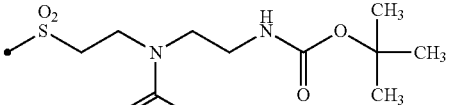 |
| 64 | 259 | H | COC(CH₃)₃ | COC(CH₃)₃ | 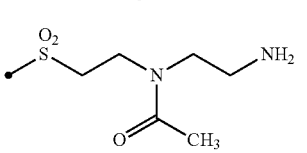 |
| 65 | 260 | H | COC(CH₃)₃ | COC(CH₃)₃ | 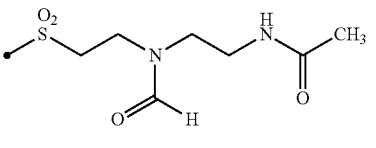 |
| 66 | 261 | H | COC(CH₃)₃ | COC(CH₃)₃ | SO₂(CH₂)₂N(CH₂CH₃)₂ |
| 67 | 262 | H | COC(CH₃)₃ | COC(CH₃)₃ | SO₂(CH₂)₂NHCH₂CH(CH₃)₂ |
| 68 | 263 | H | COC(CH₃)₃ | COC(CH₃)₃ | SO₂(CH₂)₂NH(CH₂)₃CH₃ |
| 69 | 264 | H | COC(CH₃)₃ | COC(CH₃)₃ | SO₂(CH₂)₂N(CH₃)CH₂CH₃ |
| 70 | 265 | H | COC(CH₃)₃ | COC(CH₃)₃ | SO₂(CH₂)₂NHCH₂CN |
| 71 | 266 | H | COC(CH₃)₃ | COC(CH₃)₃ | SO₂NH₂ |
| 72 | 267 | H | COC(CH₃)₃ | COC(CH₃)₃ | SO₂N(CH₃)₂ |
| 73 | 268 | H | COC(CH₃)₃ | COC(CH₃)₃ | SO₂(CH₂)₂NHCH₂CONH₂ |
| 74 | 269 | H | COC(CH₃)₃ | COCH₃ | SO₂(CH₂)₂NHCH₂COOCH₃ |
| 75 | 270 | H | COC(CH₃)₃ | COCH₃ | SO₂(CH₂)₂NH(CH₂)₂COOCH₂CH₃ |

TABLE 13-continued

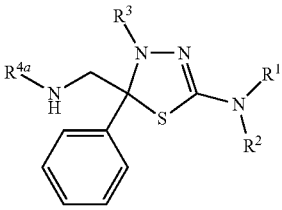

| Example No. | Compound No. | R¹ | R² | R³ | R⁴ᵃ |
|---|---|---|---|---|---|
| 76 | 271 | H | COC(CH₃)₃ | COCH₃ | SO₂(CH₂)₂NHCH₂COOH |
| 77 | 272 | H | COC(CH₃)₃ | COCH₃ | SO₂(CH₂)₂NH(CH₂)₂COOH |
| 78 | 273 | H | COC(CH₃)₃ | COC(CH₃)₃ | SO₂(CH₂)₂NH₂ |
| 79 | 274 | H | COC(CH₃)₃ | COC(CH₃)₃ | ![structure] |
| 80 | 275 | H | COC(CH₃)₃ | COC(CH₃)₃ | SO₂(CH₂)₂NHCOCH₂NH₂ |
| 81 | 276* | H | COC(CH₃)₃ | COC(CH₃)₃ | SO₂(CH₂)₂NHCOCH₂NH₂ |
| 82 | 277 | H | COC(CH₃)₃ | COC(CH₃)₃ | ![structure] |
| 83 | 278 | H | COC(CH₃)₃ | COC(CH₃)₃ | SO₂(CH₂)₂NHCO(CH₂)₂NH₂ |
| 84 | 279 | ![structure] | | COCH₃ | COOC(CH₃)₃ |
| 85 | 280 | ![structure] | | COCH₃ | H |
| 86 | 281 | ![structure] | | COCH₃ | SO₂CH=CH₂ |
| 87 | 282 | ![structure] | | COCH₃ | ![structure] |
| 88 | 283 | H | COC(CH₃)₃ | COCH₃ | ![structure] |
| 89 | 284 | H | COC(CH₃)₃ | COC(CH₃)₃ | ![structure] |

*Compounds 221 and 229 are hydrochlorides of Compounds 220 and 228, respectively.
*Compound 238 is hydrochloride of Compound 237.
*Compound 253 is hydrochloride of Compound 252.
*Compound 276 is hydrochloride of Compound 275.

TABLE 14

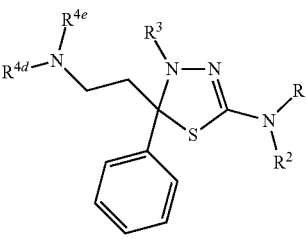

| Example No. | Compound No. | R¹ | R² | R³ | R⁴ᵈ | R⁴ᵉ |
|---|---|---|---|---|---|---|
| 90 | 285 | H | H | | COCH₃ | COOC(CH₃)₃ | H |
| 91 | 286 | | ![ketone] | | COCH₃ | COOC(CH₃)₃ | H |
| 92 | 287 | | ![ketone] | | COCH₃ | H | H |

Bioloigical activities of a typical Compound (I) (Compound 1) will be specifically explained by the following test examples.

TEST EXAMPLE 1

Test for Mitotic Accumulation Effect

The test for mitotic accumulation effect was carried out by referring to the literature [Nature, Vol. 392, p. 300 (1998)]. Human colon carcinoma HCT 116 cells were cultured for 17 hours in the presence of Compound 1. Hoechst 33342 (Sigma Aldrich, Catalog No. B-2261) was added to the cells at a final concentration of 10 μmol/L, and the cells were left for 10 minutes to visualize chromosomes. Fluorescence and phase contrast images were observed using an inverted fluorescence microscope (NIKON CORP., Catalog No. TE300). Rounded cells with condensed chromosomes were regarded as mitotic cells. Mitotic index was expressed as the percentage of mitosis in total cells measured. The mitotic index of untreated cells was approximately 5%, whilst the mitotic index increased by the representative Compound 1 in a concentration-dependent manner, and at the concentration of 3 μmol/L, the mitotic index was approximately 70%. Further, the localization of the condensed chromosomes was different from that of the cells which is accumulated in the mitotic phase by the treatment of microtubule acting agent, and the characteristic phenotype that the localization of the condensed chromosomes distributed in a circular shape in the cells was observed.

The above result suggested that Compound 1 was a different class of mitotic phase acting agent from the microtubule acting agent.

TEST EXAMPLE 2

Analysis of a Mitotic Phenotype by Immunocytochemistry

Analysis of a mitotic phenotype using immunohistochemistry was carried out by referring to the literature [Oncogene, Vol. 19, p. 5303 (2000)]. Human lung cancer A549 cells were cultured for 17 hours in the presence of Compound 1. The cells were washed with phosphate-buffered saline (PBS) and then treated with cold methanol at −20° C. for 1 minute to fix the cells. The cells were washed with PBS and then permeabilized with PBS containing 0.2% Triton-X for 15 minutes. After washing with PBS, the cells were blocked for 30 minutes with a blocking solution [PBS containing 1% fetal bovine serum] and allowed to react for 30 minutes with a primary antibody solution (blocking solution containing 0.2% monoclonal mouse anti-α-tubulin (Sigma Aldrich, Catalog No. T-9026) and 0.2% rabbit anti-γ-tubulin (Sigma Aldrich, Catalog No. T-3559). After washing with PBS, the cells were allowed to react for 30 minutes with a secondary antibody solution (a blocking solution containing 0.025% Alexa Fluor 546-conjugated anti-mouse IgG antibody (Molecular Probe, Catalog No. A-11030), 0.5% Alexa Fluor 488-conjugated anti-rabbit IgG antibody (Molecular Probe, Catalog No. A-11034) and 1 μmol/L Hoechst 33342) to visualize microtubules, centrosomes and chromosomes. Mitotic phenotypes were observed under the inverted fluorescence microscope. The cells accumulated in mitosis by Compound 1 showed characteristic phenotypes of monastral microtubule arrays, monopolar spindles, and circularly distributed localization of chromosomes. These mitotic phenotypes are the same as those of cells treated with neutralizing antibodies for Eg5 described in the literature [Cell, Vol. 83, p. 1159 (1995)] or an Eg5 specific inhibitor, monastrol [Science, Vol. 286, p. 971 (1999)].

The above results suggested that the representative Compound 1 inhibited Eg5.

TEST EXAMPLE 3

Eg5 Enzyme Inhibition Test

A full length recombinant human Eg5 protein was prepared by referring to the literature [Cell, Vol. 83, p. 1159 (1995)]. The Spodoptera frugiperda (Sf) 9 insect cells were infected with a baculovirus expressing a full length human Eg5 fused with a His tag at the N-terminus, and cultured. Then the culture medium was centrifuged to collect cell pellets. The cell pellets were suspended in a buffer, and the suspension was centrifuged to recover the supernatant. The supernatant was passed through a nickel agarose column to obtain the Eg5 fused with a His tag at the N-terminus as a partially purified sample.

Measurement of the ATPase activity of Eg5 was carried out by referring to the literature [EMBO Journal, Vol. 13, p. 751 (1994): Proc. Natl. Acad. Sci. USA, Vol. 89, p. 4884 (1992)]. A reaction solution was prepared which consisted of 25 mmol/L piperazine N,N'-bis(ethanesulfonate) (PIPES)/KOH (pH 6.8), 1 mmol/L ethylene glycol-bis(2-aminoethyl ether) tetraacetic acid (EGTA), 2 mmol/L MgCl₂, 1 mmol/L dithiothreitol (DTT), 100 μg/mL bovine serum albumin (BSA), 5 μmol/L paclitaxel, 25 μg/mL tubulin (Cytoskeleton, Catalog No. TL238), 200 μmol/L MESG substrate (2-amino-6-mercapto-7-methylpurine riboside) (Molecular Probes, Catalog Number E-6646), 1 U/mL purine nucleoside phosphorylase (Molecular Probe, Catalog No. E-6646) and 12.5 μg/mL of the full length human Eg5 partially purified sample. The reaction solution containing serially diluted Compound 1 was added to each well of a 96-well plate. The enzymatic reaction was performed at 30° C. for 30 minutes. Absorbance at 360 nm was measured using a plate reader (Molecular Device, SpectraMax 340PC[384]) as an index of the ATPase activity. The absorbance observed in the presence of Eg5 and absence of Compound 1 was defined 100%, and the absorbance observed in the absence of both Eg5 and Compound 1 was defined 0%. The relative activity was calculated to calculate the $IC_{50}$ value.

Compound 1 inhibited the ATPase activity of Eg5 in a concentration-dependent manner, and the $IC_{50}$ value was 2 µmol/L.

From the results of Test Examples 2 and 3, it was shown that Compound 1 has an inhibitory activity against Eg5.

TEST EXAMPLE 4

Eg5 Enzyme Inhibition Test (2)

A recombinant human Eg5 motor domain protein was prepared by referring to the literature [Biochemistry, Vol. 35, p. 2365 (1996)]. A plasmid expressing the motor domain of human Eg5 was constructed, and transformed into *Escherichia coli* BL21 (DE3). The transformant was cultured at 25° C., and when $OD_{600}$ reached 0.74, isopropyl-β-D-thiogalactoside was added at a final concentration of 0.5 mmol/L. The transformant was further cultured for 4 hours, and then the culture medium was centrifuged to collect the cells. The cells were suspended in a buffer and ultrasonicated, and then the sonicated solution was centrifuged to recover the supernatant. The supernatant was purified by cation exchange column chromatography to obtain a partially-purified sample. Furthermore, the partially purified sample was purified by gel filtration column chromatography to obtain a finally purified sample.

Measurement of the ATPase activity of Eg5 was carried out by referring to the literatures EEMBO Journal, Vol. 13, p. 751 (1994); Proc. Natl. Acad. Sci. USA, Vol. 89, p. 4884 (1992)]. The following two kinds of solutions were prepared: Solution A consisting of 25 mmol/L piperazine N,N'-bis(ethanesulfonate) (PIPES)/KOH (pH 6.8), 1 mmol/L ethylene glycol-bis(2-aminoethyl ether)tetraacetic acid (EGTA), 2 mmol/L $MgCl_2$, 1 mmol/L dithiothreitol (DTT), 5 µmol/L paclitaxel, 167 µg/mL bovine serum albumin (BSA), 41.7 µg/mL tubulin (Cytoskeleton, Catalog No. TL238), 333 µmol/L MESG substrate (2-amino-6-mercapto-7-methylpurine riboside) (Molecular Probes, Catalog Number E-6646), 1.67 U/mL purine nucleoside phosphorylase (Molecular Probe, Catalog No. E-6646) and 1.33 µg/mL of the human Eg5 motor domain purified sample, and Solution B consisting of 25 mmol/L piperazine N,N'-bis(ethanesulfonate) (PIPES)/KOH (pH 6.8), 1 mmol/L ethylene glycol-bis(2-aininoethyl ether)tetraacetic acid (EGTA), 2 mmol/L $MgCl_2$, 1 mmol/L dithiothreitol (DTT), 5 µmol/L paclitaxel and 2.5 mmol/L ATP. Solution A was dispensed into each well of a 96-well plate as 45 µL portions. Solution B was used to serially dilute a test compound. The diluted test compound solutions in a volume of 30 µL were mixed with Solution A added beforehand in each well of the 96-well plate to start the enzymatic reaction. The enzymatic reaction was performed at 30° C. for 30 minutes. Absorbance at 360 nm, which serves as an index of the ATPase activity, was measured using a plate reader (Molecular Device, SpectraMax $340PC^{384}$). The absorbance observed in the presence of Eg5 and absence of the test compound was defined 100%, and the absorbance observed in the absence of both Eg5 and the test compound was defined 0%. The relative activity was calculated to calculate 1050 value.

Compounds 1, 95, 97, 100, 104, 107, 111, 134, 152, 154, 171, 174, 176, 210, 221; 238, 264 and the like inhibited the ATPase activity of Eg5 in a concentration-dependent manner, and $IC_{50}$ values of the compounds were found to be 2 µmol/L or lower.

Compound (I) or a pharmaceutically acceptable salt thereof can be administered alone. However, usually, Compound (I) or a pharmaceutically acceptable salt thereof is preferably provided in various pharmaceutical preparations. Furthermore, these pharmaceutical preparations are used for animals and humans.

The pharmaceutical preparations according to the present invention may comprise Compound (I) or a pharmaceutically acceptable salt thereof alone as an active ingredient. Alternatively, the pharmaceutical preparations may comprise a mixture of Compound (I) or a pharmaceutically acceptable salt thereof with any effective ingredient used for another treatment. Furthermore, these pharmaceutical preparations are prepared by mixing the active ingredient(s) with one or more pharmaceutically acceptable carrier(s) and then employing any method well-known in the technical field of pharmaceutics.

As for administration routes, it is preferred to select the most effective route of administration. Examples of the administration routes include oral administration and parenteral administration such as intravenous administration and the like.

As for the dosage form, for example, tablets, injections and the like are included.

For example, the tablet suitable for oral administration can be prepared with, for example, excipients such as lactose and mannitol; disintegrants such as starch; lubricants such as magnesium stearate; binders such as hydroxypropylcellulose; surfactants such as a fatty acid ester; plasticizers such as glycerol; and the like.

Preparations suitable for parenteral administration preferably comprises of a sterilized aqueous preparation containing the active compound and being isotonic to blood of a recipient. For example, when an injection is prepared, a solution for injection is prepared by using a carrier consisting of a salt solution, glucose solution, a mixture of salt solution and glucose solution, or the like.

Also in these parenteral preparations, one or more kinds of auxiliary components selected from excipients, disintegrants, lubricants, binders, surfactants, plasticizers, diluents which are exemplified for the oral administration, preservatives, flavors and the like may be added.

Compound (I) or a pharmacologically acceptable salt thereof is generally administered systemically or locally in the form of an oral or parenteral preparation when used for the aforementioned purpose. The dose and the frequency of administration may vary depending on the administration form, the age and body weight of a patient, nature and severity of the condition to be treated, and the like. When oral administration is performed, generally 0.01 to 1,000 mg/kg, preferably 0.05 to 500 mg/kg per-single administration for an adult may be administered once a day or a few times a day. When parenteral administration such as intravenous administration is performed, 0.001 to 1,000 mg/kg, preferably 0.01 to 300 mg/kg, per single administration for an adult may be administered once a day or a few times a day, or may be continuously administered intravenously for 1 to 24 hours a day. However, the dose and the frequency of administration may vary depending on the aforementioned various conditions and the like.

The present invention will be explained in detail with reference to the following examples and reference examples.

The spectra of proton nuclear magnetic resonance ($^1H$ NMR) used in Examples and Reference Examples were measured at 270 or 300 MHz, and exchangeable hydrogen may not always be clearly observed depending on the compound and the measurement conditions. For the descriptions of the multiplicity of signals, those generally applied are used, and the symbol "br" represents an apparent broad signal.

BEST MODE FOR CARRYING OUT THE INVENTION

Example 1

Tablets (Compound 1)

Tablets having the following composition are prepared in a conventional manner. Compound 1 (40 g), lactose (286.8 g) and potato starch (60 g) are mixed, and 10% aqueous solution of hydroxypropylcellulose (120 g) is added to the mixture. This mixture is kneaded, granulated and dried in a conventional manner, and then the granules are sized to obtain granules for tablet pressing. Magnesium stearate (1.2 g) is added to the granules for tablet pressing and mixed. Tableting is performed with a tableting machine having a pestle of 8 mm a diameter (Kikusui, RT-15) to obtain tablets (containing 20 mg/tablet of active ingredient).

Formulation

| Compound 1 | 20 mg |
| Lactose | 143.4 mg |
| Potato starch | 30 mg |
| Hydroxypropylcellulose | 6 mg |
| Magnesium stearate | 0.6 mg |
| | 200 mg |

Example 2

Tablets (Compound 134)

The tablets (containing 20 mg/tablet of active ingredient) are obtained by using Compound 134 (40 g) in the same manner as that in Example 1.

Formulation

| Compound 134 | 20 mg |
| Lactose | 143.4 mg |
| Potato starch | 30 mg |
| Hydroxypropylcellulose | 6 mg |
| Magnesium stearate | 0.6 mg |
| | 200 mg |

Example 3

Tablets (Compound 104)

The tablets (containing 20 mg/tablet of active ingredient) are obtained by using Compound 104 (40 g) in the same manner as that in Example 1.

Formulation

| Compound 104 | 20 mg |
| Lactose | 143.4 mg |
| Potato starch | 30 mg |
| Hydroxypropylcellulose | 6 mg |
| Magnesium stearate | 0.6 mg |
| | 200 mg |

Example 4

Injection (Compound 107)

Injection having the following composition is prepared in a conventional manner. Compound 107 (1 g) is dissolved in purified soybean oil, and purified egg yolk lecithin (12 g) and glycerin for injection (25 g) are added to the solution. This mixture is made to have a volume of 1,000 ml with distilled water for injection, kneaded and emulsified in a conventional manner. The resulting dispersion is aseptically filtered through a 0.2 μm disposable type membrane filter and then aseptically filled in glass vials in a volume of 2 ml each to obtain injection (containing 2 mg/vial of the active ingredient).

Formulation

| Compound 107 | 2 mg |
| Purified soybean oil | 200 mg |
| Purified egg yolk lecithin | 24 mg |
| Glycerin for injection | 50 mg |
| Distilled water for injection | 1.72 ml |
| | 2.00 ml |

Example 5

Injection (Compound 104)

The injection (containing 2 mg/vial of active ingredient) is obtained by using Compound 104 (40 g) in the same manner as that in Example 4.

Formulation

| Compound 104 | 2 mg |
| Purified soybean oil | 200 mg |
| Purified egg yolk lecithin | 24 mg |
| Glycerin for injection | 50 mg |
| Distilled water for injection | 1.72 ml |
| | 2.00 ml |

Example 6

Tablets (Compound 95)

The tablets (containing 20 mg/tablet of active ingredient) are obtained by using Compounds 95 (40 g) in the same manner as that in Example 1.

Formulation

| Compound 95 | 20 mg |
| Lactose | 143.4 mg |
| Potato starch | 30 mg |
| Hydroxypropylcellulose | 6 mg |
| Magnesium stearate | 0.6 mg |
| | 200 mg |

Example 7

Tablets (Compound 100)

The tablets (containing 20 mg/tablet of active ingredient) are obtained by using Compound 100 (40 g) in the same manner as that in Example 1.

Formulation

| | |
|---|---|
| Compound 100 | 20 mg |
| Lactose | 143.4 mg |
| Potato starch | 30 mg |
| Hydroxypropylcellulose | 6 mg |
| Magnesium stearate | 0.6 mg |
| | 200 mg |

Example 8

Tablets (Compound 152)

The tablets (containing 20 mg/tablet of active ingredient) are obtained by using Compound 152 (40 g) in the same manner as that in Example 1.

Formulation

| | |
|---|---|
| Compound 152 | 20 mg |
| Lactose | 143.4 mg |
| Potato starch | 30 mg |
| Hydroxypropylcellulose | 6 mg |
| Magnesium stearate | 0.6 mg |
| | 200 mg |

Example 9

Injection (Compound 176)

Injection having the following composition is prepared in a conventional manner. Compound 176 (1 g) and D-mannitol (5 g) are added to distilled water for injection and mixed, and hydrochloric acid and aqueous sodium hydroxide are added to the mixture to adjust the mixture to pH 6, and then the total volume is made 1000 mL with distilled water for injection. The resulting mixture is aseptically filled in glass vials in a volume of 2 mL each to obtain injection (containing 2 mg/vial of the active ingredient).

Formulation

| | |
|---|---|
| Compound 176 | 2 mg |
| D-Mannitol | 10 mg |
| Hydrochloric acid | Optimum amount |
| Aqueous sodium hydroxide | Optimum amount |
| Distilled water for injection | Optimum amount |
| | 2.00 ml |

Example 10

Injection (Compound 174)

The injection (containing 2 mg/vial of active ingredient) is obtained by using Compound 174 (1 g) in the same manner as that in Example 9.

Formulation

| | |
|---|---|
| Compound 174 | 2 mg |
| D-Mannitol | 10 mg |
| Hydrochloric acid | Optimum amount |
| Aqueous sodium hydroxide | Optimum amount |
| Distilled water for injection | Optimum amount |
| | 2.00 ml |

Example 11

Compound 206

Compound 202 (55.8 mg, 0.143 mmol) obtained in Reference Example 192 was dissolved in 1,2-dichloroethane (5 mL). To the solution was successively added acetic acid (0.0450 mL, 0.786 mmol), n-propylamine (0.0538 mL, 0.654 mmol) and triacetoxy sodium borohydride (130 mg, 0.612 mmol), and the mixture was stirred at room temperature for 12 hours. To the reaction mixture was added saturated aqueous sodium hydrogencarbonate (30 mL), and the mixture was extracted with ethyl acetate. The organic layer was washed with saturated aqueous sodium chloride and dried over anhydrous sodium sulfate, and the solvent was evaporated under reduced pressure. The residue was purified by preparative thin layer chromatography (chloroform/methanol/concentrated aqueous ammonia=100/10/1) to give Compound 206 (51.9 mg, 84%).

ESI-MS m/z 865 $(2M+H)^+$.

Example 12

Compound 207

In a manner similar to that in Example 11, Compound 207 (53.0 mg, 90%) was obtained from Compound 202 (51.5 mg, 0.132 mmol) obtained in Reference Example 192, acetic acid (0.0460 mL, 0.804 mmol), diethylamine (0.0690 mL, 0.667 mmol) and triacetoxy sodium borohydride (115 mg, 0.542 mmol).

APCI-MS m/z 447 $(M+H)^+$.

Example 13

Compound 208

Step 1: 2-Aminoacetophenone hydrochloride (2.93 g, 17.1 mmol) was dissolved in acetonitrile (100 mL). To the solution was successively added di-tert-butyl dicarbonate (5.09 g, 22.9 mmol) and 4-dimethylaminopyridine (2.21 g, 18.1 mmol), and the mixture was stirred at room temperature for 10 hours. To the reaction mixture was added saturated aqueous ammonium chloride, and the mixture was extracted with ethyl acetate. The organic layer was washed with saturated aqueous sodium chloride and dried over anhydrous sodium sulfate, and the solvent was evaporated under reduced pressure. The residue was purified by silica gel column chromatography (hexane/ethyl acetate=9/1→4/1) to give 2-(N-tert-butoxycarbonylamino)acetophenone (865 mg, 21%).

Step 2: 2-(N-tert-Butoxycarbonylamino)acetophenone (851 mg, 3.62 mmol) obtained above was dissolved in methanol (20 mL). To the solution was added thiosemicarbazide hydrochloride (1.03 g, 8.04 mmol), and the mixture was stirred at room temperature for 15 hours. To the reaction mixture was added water, and the mixture was extracted with ethyl acetate. The organic layer was washed with saturated aqueous sodium chloride and dried over anhydrous sodium sulfate, and the solvent was evaporated under reduced pressure. The resulting residue was dissolved in dichloromethane (50 mL), to the solution was added pyridine (1.75 mL, 21.7 mmol) and trimethylacetyl chloride (2.23 mL, 18.1 mmol), and the mixture was stirred at room temperature for 16 hours. To the reaction mixture was added saturated aqueous sodium hydrogencarbonate, and the mixture was further stirred at room temperature for 1 hour and then extracted with ethyl acetate. The organic layer was washed with saturated aqueous sodium chloride and dried over anhydrous sodium sulfate, and the solvent was evaporated under reduced pressure. The residue was purified by silica gel column chromatography (hexane/ethyl acetate=9/1→4/1) to give Compound 208 (910 mg, 53%).

APCI-MS m/z 477 (M+H)$^+$.

Example 14

Compound 209

Step 1: Palladium(II) acetate (125 mg, 0.559 mmol) and triphenylphosphine (317 mg, 1.21 mmol) were dissolved in THF (50 mL). To the solution was successively added N-tert-butoxycarbonyl-β-alanine (2.07 g, 10.9 mmol), phenylboronic acid (1.61 g, 13.2 mmol), distilled water (0.477 mL, 26.5 mmol) and trimethylacetic anhydride (3.23 mL, 15.9 mmol), and then the mixture was heated to 60° C. and stirred for 24 hours. The reaction mixture was filtered, then to the filtrate was added saturated aqueous sodium hydrogencarbonate, and the mixture was extracted with ethyl acetate. The organic layer was washed with saturated aqueous sodium chloride and dried over anhydrous sodium sulfate, and the solvent was evaporated under reduced pressure. The residue was purified by silica gel column chromatography (hexane/ethyl acetate=9/1→4/1) to give 2-(N-tert-butoxycarbonylamino)ethyl phenyl ketone (1.85 g, 68%).

Step 2: 2-(N-tert-Butoxycarbonylamino)ethyl phenyl ketone (513 mg, 2.06 mmol) obtained above was dissolved in methanol (40 mL). To the solution was added thiosemicarbazide hydrochloride (562 mg, 4.40 mmol), and the mixture was stirred at room temperature for 8 hours. To the reaction mixture was added water, and the mixture was extracted with ethyl acetate. The organic layer was washed with saturated aqueous sodium chloride and dried over anhydrous sodium sulfate, and the solvent was evaporated under reduced pressure to obtain pale yellow solid (513 mg). A part of the obtained solid (198 mg) was dissolved in dichloromethane (10 mL), to the solution was added pyridine (0.300 mL, 3.73 mmol) and trimethylacetyl chloride (0.415 mL, 3.37 mmol), and the mixture was stirred at room temperature for 22 hours. To the reaction mixture was added saturated aqueous sodium hydrogencarbonate, and the mixture was further stirred at room temperature for 1 hour, and then extracted with ethyl acetate. The organic layer was washed with saturated aqueous sodium chloride and dried over anhydrous sodium sulfate, and the solvent was evaporated under reduced pressure. The residue was purified by preparative thin layer chromatography (hexane/ethyl acetate=2/1) to give Compound 209 (319 mg, 82%).

APCI-MS m/z 491 (M+H)$^+$.

Example 15

Compound 210

Compound 209 (274 mg, 0.557 mmol) obtained in Example 14 was dissolved in dichloromethane (5 mL), to the mixture was added trifluoroacetic acid (1.0 mL), and the mixture was stirred at room temperature for 3 hours. The reaction mixture was evaporated under reduced pressure, and the residue was purified by preparative thin layer chromatography (chloroform/methanol/concentrated aqueous ammonia=100/10/1) to give Compound 210 (252 mg, 90%) as trifluoroacetic acid salt.

APCI-MS m/z 391 (M+H)$^+$.

Example 16

Compound 211

The trifluoroacetic acid salt of Compound 210 (103 mg, 0.240 mmol) obtained in Example 15 was dissolved in acetonitrile (5 mL), to the solution was successively added 4-dimethylaminopyridine (63.0 mg, 0.516 mmol) and acetic anhydride (0.0907 mL, 0.960 mmol), and the mixture was stirred at room temperature for 12 hours. To the reaction mixture was added saturated aqueous sodium hydrogencarbonate (30 mL), and the mixture was extracted with ethyl acetate. The organic layer was washed with saturated aqueous sodium chloride and dried over anhydrous sodium sulfate, and the solvent was evaporated under reduced pressure. The residue was purified by preparative thin layer chromatography (chloroform/methanol=20/1) to give Compound 211 (55.6 mg, 54%).

APCI-MS m/z 431 (M−H)$^−$.

Example 17

Compound 212

Step 1: 1-Bromo-3-(methoxymethoxy)benzene (3.938 g, 18.14 mmol) prepared from 3-bromophenol by the method described in Shin-Jikken-Kagaku-Koza (New Experiment Chemistry Lecture) Vol. 14, p. 568 (Maruzen, 1978) was dissolved in tetrahydrofuran (8 mL), and to the solution was gradually added a 1.56 mol/L solution of n-butyl lithium in hexane (12.2 mL, 19.0 mmol) under cooling at −78° C. Subsequently, to the mixture was added THF (16 mL), and then the mixture was stirred at the same temperature for 30 minutes. The reaction mixture was gradually added to tert-butyl [2-(N-methoxy-N-methylcarbamoyl)ethyl]carbamate (this compound is prepared by condensation of N-tert-butoxycarbonyl-β-alanine and N,O-dimethylhydroxylamine hydrochloride) (2.010 g, 8.653 mmol) dissolved in THF (10 mL) at −18° C. The mixture was stirred at the same temperature for 1 hour, then to the mixture was added water and saturated aqueous ammonium chloride, and the mixture was extracted with ethyl acetate. The organic layer was washed with saturated aqueous sodium chloride and dried over anhydrous sodium sulfate, and the solvent was evaporated under reduced pressure. The residue was purified by silica gel column chromatography (ethyl acetate/n-hexane=1/4) to give tert-butyl{3-[3-(methoxymethoxy)phenyl]-3-oxopropyl} carbamate (1.568 g, 59%).

APCI-MS m/z 310 (M+H)⁺.

Step 2: In a manner similar to that in Step 1 of Reference Example 190, crude 3'-(methoxymethoxy)-3-(tert-butoxycarbonylamino)propiophenone=thiosemicarbazone (1.355 g) was obtained from tert-butyl {3-[3-(methoxymethoxy)phenyl]-3-oxopropyl}carbamate (1.406 g, 4.546 mmol) obtained above and thiosemicarbazide hydrochloride (1.131 g, 8.864 mmol).

Step 3: In a manner similar to that in Step 2 of Reference Example 190, Compound 212 (1.01 g, 41% for the two steps) was obtained from crude 3'-(methoxymethoxy)-3-(tert-butoxycarbonylamino)propiophenone=thiosemicarbazone (1.32 g) obtained above, trimethylacetyl chloride (2.55 mL, 20.7 mmol) and pyridine, (2.10 mL, 26.0 mmol).

$^1$H NMR (270 MHz, CDCl$_3$) δ (ppm): 1.29 (s, 9H), 1.32 (s, 9H), 1.44 (s, 9H), 2.47 (m, 1H), 3.22 (m, 2H), 3.45 (s, 3H), 3.71 (m, 1H), 4.62 (m, 1H), 5.14 (m, 2H), 6.87-6.98 (m, 3H), 7.25 (m, 1H), 7.86 (s, 1H).

APCI-MS m/z 549 (M−H)⁻.

Example 18

Compound 213

Compound 212 (502 mg, 9.12 mmol) obtained in Example 17 was dissolved in dichloromethane (5 mL), to the solution was added trifluoroacetic acid (10 mL), and the mixture was stirred at room temperature for 30 minutes. The reaction mixture was concentrated under reduced pressure, to the resulting residue was added saturated aqueous sodium hydrogencarbonate, and the mixture was extracted with a mixed solvent of ethyl acetate and methanol. The organic layer was washed with saturated aqueous sodium chloride and dried over anhydrous sodium sulfate, and the solvent was evaporated under reduced pressure. The residue was triturated with a mixed solvent of ethyl acetate and diisopropyl ether to give Compound 213 (334 mg, 90%).

$^1$H NMR (270 MHz, DMSO-d$_6$) δ (ppm): 1.15 (s, 9H), 1.22 (s, 9H), 2.25 (m, 1H), 2.44 (m, 1H), 2.81-3.05 (m, 2H), 6.57-6.70 (m, 2H), 6.62 (s, 1H), 7.11 (dd, J=7.5, 8.2 Hz, 1H), 9.40 (br, 1H).

APCI-MS m/z 407 (M+H)⁺.

Example 19

Compound 214

The compound in a free form (50 mg, 0.13 mmol) prepared by treating Compound 210 obtained in Example 15 with saturated aqueous sodium hydrogencarbonate was dissolved in dichloromethane (1 mL), to the solution was added triethylamine (0.072 mL, 0.52 mmol) and dimethylsulfamoyl chloride (0.028 mL, 0.26 mmol), and the mixture was stirred at room temperature for 2 hours. To the reaction mixture was added dichloromethane (1 mL), and the mixture was further stirred for 3.5 hours. Then, to the reaction mixture was added water, and the mixture was extracted with chloroform. The organic layer was washed with saturated aqueous sodium chloride, dried over anhydrous sodium sulfate and concentrated under reduced pressure. The residue was purified by preparative thin layer chromatography (chloroform/methanol=6/1) to give Compound 214 (44 mg, 69%).

$^1$H NMR (300 MHz, CDCl$_3$) δ (ppm): 1.30 (s, 9H), 1.32 (s, 9H), 2.56 (m, 1H), 2.818 (s, 3H), 2.820 (s, 3H), 3.17 (m, 1H), 3.37 (m, 1H), 3.55 (m, 1H), 4.27 (brt, J=6.3 Hz, 1H), 7.21-7.37 (m, 5H), 7.93 (brs, 1H).

APCI-MS m/z: 496 (M−H)⁻.

Example 20

Compound 215

The compound in a free form (63 mg, 0.16 mmol) prepared by treating Compound 210 obtained in Example 15 with saturated aqueous sodium hydrogencarbonate was dissolved in DMF (1 mL), to the solution was added sulfamoyl chloride (57 mg, 0.49 mmol) and triethylamine (0.090 mL, 0.65 mmol), and the mixture was stirred at room temperature for 21.5 hours. To the reaction mixture was added water, and the mixture was extracted with a mixed solvent of chloroform and methanol. The organic layer was washed with saturated aqueous sodium chloride, dried over anhydrous sodium sulfate and concentrated under reduced pressure. The residue was purified by preparative thin layer chromatography (chloroform/methanol=6/1) to give Compound 215 (14 mg, 18%).

APCI-MS m/z: 470 (M+H)⁺.

Example 21

Compound 216

Compound 208 (3.13 g, 6.57 mmol) prepared in Example 13 was added to 4 mol/L hydrogen chloride-ethyl acetate (30 mL), and the mixture was stirred at room temperature for 1 hour. The reaction mixture was concentrated under reduced pressure, and then the residue was triturated with ethyl acetate to give Compound 216 (2.80 g, quantitative) as hydrochloride.

$^1$H NMR (270 MHz, DMSO-d$_6$) δ (ppm): 1.17 (s, 9H), 1.32 (s, 9H), 4.06 (d, J=13.7 Hz, 1H), 4.21 (d, J=13.7 Hz, 1H), 7.20-7.44 (m, 5H), 8.30 (brs, 3H), 11.17 (s, 1H).

Example 22

Compound 217

Hydrochloride of Compound 216 (40 mg, 0.097 mmol) prepared in Example 21 was suspended in 1,2-dichloroethane (1 mL), to the suspension was added 37% aqueous formalin (0.080 mL) and triacetoxy sodium borohydride (100 mg, 0.472 mmol), and the mixture was stirred at room temperature for 2.5 hours. To the reaction mixture was added saturated aqueous sodium hydrogencarbonate, and the mixture was extracted with chloroform. The organic layer was washed with saturated aqueous sodium chloride, dried over anhydrous sodium sulfate and concentrated under reduced pressure. The residue was purified by preparative thin layer chromatography (chloroform/methanol=20/1) to give Compound 217 (27 mg, 69%).

$^1$H NMR (270 MHz, CDCl$_3$) δ (ppm): 1.28 (s, 9H), 1.31 (s, 9H), 2.43 (s, 6H), 3.31 (d, J=14.3 Hz, 1H), 3.88 (d, J=14.3 Hz, 1H), 7.06-7.65 (m, 5H), 7.88 (s, 1H).

APCI-MS m/z: 405 (M+H)⁺.

Example 23

Compound 218

Hydrochloride of Compound 216 (2.80 g, 6.78 mmol) obtained in Example 21 was suspended in dichloromethane (50 mL), to the suspension was added triethylamine (3.80 mL, 27.3 mmol) and 3-chloropropanesulfonyl chloride (1.24 mL, 10.2 mmol) under ice cooling, and the mixture was stirred at the same temperature for 20 minutes. To the reaction mixture was added water and 1 mol/L hydrochloric acid, and the mixture was extracted with chloroform. The organic layer was successively washed with saturated aqueous sodium hydrogencarbonate and saturated aqueous sodium chloride, dried over anhydrous sodium sulfate and concentrated under reduced pressure. The residue was triturated with a mixed solvent of diisopropyl ether and ethyl acetate to give Compound 218 (3.01 g, 86%).

ESI-MS m/z: 515, 517 (M−H)−.

Example 24

Compound 219

Compound 218 (3.01 g, 5.82 mmol) obtained in Example 23, sodium iodide (17.50 g, 116.8 mmol) and sodium azide (3.80 g, 58.5 mmol) were suspended in DMF (50 mL), and the mixture was stirred for 4 hours at 90° C. To the reaction mixture was added water, and the mixture was extracted with ethyl acetate. The organic layer was washed with saturated aqueous sodium chloride, dried over anhydrous sodium sulfate and concentrated under reduced pressure. The residue was triturated with diethyl ether to give Compound 219 (2.29 g, 75%).

APCI-MS m/z: 524 (M+H)+.

Example 25

Compound 220

Compound 219 (2.29 g, 4.37 mmol) obtained in Example 24 was dissolved in THF (75 mL), to the solution was added water (15 mL) and triphenylphosphine (1.73 g, 6.60 mmol), and the mixture was stirred at room temperature for 20 hours. The reaction mixture was concentrated under reduced pressure, and the residue was triturated with diethyl ether and then with ethyl acetate to give Compound 220 (1.74 g, 80%).

$^1$H NMR (300 MHz, CDCl$_3$) δ (ppm): 1.29 (s, 9H), 1.33 (s, 9H), 1.96 (m, 2H), 2.85 (t, J=6.6 Hz, 2H), 3.19 (t, J=7.5 Hz, 2H), 3.99 (d, J=13.7 Hz, 1H), 4.61 (d, J=13.7 Hz, 1H), 7.24-7.39 (m, 5H).

APCI-MS m/z: 498 (M+H)+.

Example 26

Compound 221

Compound 220 (452 mg, 0.909 mmol) obtained in Example 25 was suspended in ethyl acetate (10 mL), to the suspension was added 4 mol/L hydrogen chloride-ethyl acetate (0.5 mL) under ice cooling, and the mixture was stirred at the same temperature for 30 minutes. The reaction mixture was concentrated under reduced pressure, and the residue was triturated with diethyl ether and then crystallized from ethyl acetate and n-hexane to give Compound 221 (431 mg, 89%) as hydrochloride.

$^1$H NMR (270 MHz, CDCl$_3$) δ (ppm); 1.26 (s, 9H), 1.30 (s, 9H), 2.24 (m, 2H), 3.11 (m, 2H), 3.30 (m, 1H), 3.45 (m, 1H), 4.01 (d, J=13.7 Hz, 1H), 4.63 (d, J=13.7 Hz, 1H), 6.00 (br, 1H), 7.18-7.41 (m, 5H), 8.46 (br, 1H).

Example 27

Compound 222

Compound 208 (3.72 g, 9.48 mmol) prepared in Example 13 was dissolved in tert-butanol (150 mL) and aqueous hydrochloric acid-sodium acetate (pH=3; 50 mL). To the solution was added sodium borohydride (3.6 g, 94.8 mmol) at room temperature, and the mixture was stirred at 50° C. for 1 hour. To the reaction mixture was added acetic acid (5.4 mL), and the mixture was stirred at room temperature for 30 minutes. Then, to the mixture was added water, and the mixture was extracted with ethyl acetate. The organic layer was washed with saturated brine and dried over anhydrous sodium sulfate, and the solvent was evaporated under reduced pressure. The residue was reslurried in hexane to give Compound 222 (3.10 g, 99%).

APCI-MS m/z: 393 (M+H)+.

Example 28

Compound 223

Compound 222 (103 mg, 0.262 mmol) obtained in Example 27 was dissolved in dichloromethane (2 mL), to the solution was added pyridine (0.055 mL, 0.68 mmol) and 4-bromobutyryl chloride (0.076 mL, 0.66 mmol), and the mixture was stirred at room temperature for 3 hours. To the reaction mixture was added water, and the mixture was extracted with ethyl acetate. The organic layer was washed with saturated aqueous sodium chloride, dried over anhydrous sodium sulfate and concentrated under reduced pressure. The residue was dissolved in dimethyl sulfoxide (DMSO) (1 mL), to the solution was added sodium acetate (63 mg, 0.77 mmol), and the mixture was stirred for 12 minutes with gradually heating from room temperature to 100° C. After the reaction mixture was left to cool, then to the mixture was added water, and the mixture was extracted with ethyl acetate. The organic layer was washed with saturated aqueous sodium chloride, dried over anhydrous sodium sulfate and concentrated under reduced pressure. The residue was purified by preparative thin layer chromatography (chloroform/methanol=40/1) to give Compound 223 (91 mg, 75%).

APCI-MS m/z: 461 (M+H)+.

Example 29

Compound 224

Compound 223 (79 mg, 0.17 mmol) obtained in Example 28 was added to 4 mol/L hydrogen chloride-ethyl acetate (1 mL), and the mixture was stirred at room temperature for 30 minutes. The reaction mixture was concentrated under reduced pressure, and then the residue was dissolved in dichloromethane (1 mL). To the solution was added triethylamine (0.086 mL, 0.62 mmol) and 2-chloroethanesulfonyl chloride (0.025 mL, 0.24 mmol) under ice cooling, and the mixture was stirred at the same temperature for 30 minutes. To the reaction mixture was added water and 1 mol/L hydrochloric acid, and the mixture was extracted with chloroform. The organic layer was successively washed with saturated aqueous sodium hydrogencarbonate and saturated aqueous sodium chloride, dried over anhydrous sodium sulfate and concentrated under reduced pressure. The residue was purified by preparative thin layer chromatography (chloroform/methanol=30/1) to give Compound 224 (57 mg, 74%).

APCI-MS m/z: 451 (M+H)+.

Example 30

Compound 225

Compound 224 (56 mg, 0.12 mmol) obtained in Example 29 was added to 7 mol/L ammonia-methanol (1 mL) at room temperature. After 16.5 hours, the reaction mixture was concentrated under reduced pressure. The residue was purified by preparative thin layer chromatography (chloroform containing ammonia/methanol/chloroform=1.8/0.2/1) to give Compound 225 (31 mg, 53%).

$^1$H NMR (270 MHz, CDCl$_3$) δ (ppm): 1.34 (s, 9H), 2.15-2.32 (m, 2H), 2.52-2.65 (m, 2H), 3.16 (m, 4H), 3.90-4.02 (m, 2H), 4.01 (d, J=13.3 Hz, 1H), 4.60 (d, J=13.3 Hz, 1H), 5.41 (br, 1H), 7.22-7.40 (m, 5H).

APCI-MS m/z: 468 (M+H)$^+$.

Example 31

Compound 226

Compound 220 (16.6 mg, 0.0334 mmol) obtained in Example 25 was dissolved in a mixed solvent of dichloromethane (0.5 mL) and methanol (0.2 mL), to the solution was added glycol sulfite (0.005 mL, 0.07 mmol), and the mixture was stirred at room temperature for 21 hours. To the reaction mixture was added DMF (0.5 mL) and glycol sulfite (0.010 mL, 0.13 mmol), and the mixture was stirred at 90° C. for 7.5 hours. Then, to the mixture was added water, and the mixture was extracted with ethyl acetate. The organic layer was washed with saturated aqueous sodium chloride, dried over anhydrous sodium sulfate and concentrated under reduced pressure. The residue was purified by preparative thin layer chromatography (chloroform containing ammonia/methanol=9/1) to give Compound 226 (4.7 mg, 26%).

$^1$H NMR (300 MHz, CDCl$_3$) δ (ppm): 1.29 (s, 9H), 1.33 (s, 9H), 1.99 (m, 2H), 2.74-2.84 (m, 4H), 3.18 (t, J=7.4 Hz, 2H), 3.65 (t, J=5.0 Hz, 2H), 3.99 (d, J=13.7 Hz, 1H), 4.58 (d, J=13.7 Hz, 1H), 7.23-7.40 (m, 5H).

APCI-MS m/z: 542 (M+H)$^+$.

Example 32

Compound 227

Compound 220 (19 mg, 0.038 mmol) obtained in Example 25 was dissolved in THF (0.5 mL), and to the solution was added acetaldehyde (0.011 mL, 0.20 mmol). The mixture was stirred at room temperature for 3 hours, then to the mixture was added sodium borohydride (4.5 mg, 0.12 mmol), and the mixture was stirred for 18 hours. To the reaction mixture was added water, and the mixture was extracted with chloroform. The organic layer was washed with saturated aqueous sodium chloride, dried over anhydrous sodium sulfate and concentrated under reduced pressure. The residue was purified by preparative thin layer chromatography (chloroform containing ammonia/methanol=20/1) to give Compound 227 (6.5 mg, 32%).

$^1$H NMR (300 MHz, CDCl$_3$) δ (ppm): 1.26 (m, 3H), 1.29 (s, 9H), 1.35 (s, 9H), 2.20 (m, 1H), 2.30 (m, 1H), 2.64-3.32 (m, 6H), 3.64 (br, 1H), 4.02 (d, J=13.9 Hz, 1H), 4.61 (d, J=13.9 Hz, 1H), 5.25 (br, 1H), 7.23-7.40 (m, 5H), 8.01 (m, 1H).

APCI-MS m/z: 526 (M+H)$^+$.

Example 33

Compound 228

Compound 170 (51 mg, 0.12 mmol) prepared in Reference Example 161 was added to 7 mol/L ammonia-methanol (1 mL), and the mixture was stirred at room temperature for 18.5 hours. Further, to the reaction mixture was added 7 mol/L ammonia-methanol (1 mL), and the mixture was stirred at room temperature for 24 hours and then concentrated under reduced pressure. The residue was purified by preparative thin layer chromatography (chloroform/methanol=6/1) and then triturated with diisopropyl ether to give Compound 228 (26 mg, 49%).

$^1$H NMR (300 MHz, CDCl$_3$) δ (ppm): 1.27 (s, 9H), 2.32 (s, 3H), 3.16 (brs, 4H), 3.98 (d, J=13.8 Hz, 1H), 4.58 (d, J=13.8 Hz, 1H), 7.26-7.42 (m, 5H).

APCI-MS m/z: 442 (M+H)$^+$.

Example 34

Compound 229

In a manner similar to that in Example 26, Compound 228 (181 mg, 0.410 mmol) prepared in Example 33 was treated with 4 mol/L hydrogen chloride-ethyl acetate (0.6 mL) to give Compound 229 (hydrochloride of Compound 228, 184 mg, 94%).

$^1$H NMR (270 MHz, DMSO-d$_6$) δ (ppm): 1.15 (s, 9H), 2.23 (s, 3H), 3.15 (m, 2H), 3.34 (m, 2H), 3.95 (d, J=13.8 Hz, 1H), 4.38 (d, J=13.8 Hz, 1H), 7.22-7.40 (m, 5H), 8.50 (br, 3H), Example 35

Compound 230

Compound 170 (51 mg, 0.12 mmol) prepared in Reference Example 161 was suspended in acetonitrile (1.5 mL), to the suspension was added 2-amino-2-methyl-1,3-propanediol (258 mg, 2.45 mmol), and the mixture was stirred at room temperature for 21 hours. To the reaction mixture was successively added acetonitrile (2 mL) and water (0.6 mL), and the mixture was stirred for 4 days. Then, to the mixture was added water, and the mixture was extracted with chloroform. The organic layer was washed with saturated aqueous sodium chloride, dried over anhydrous sodium sulfate and concentrated under reduced pressure. The residue was purified by preparative thin layer chromatography (chloroform containing ammonia/methanol=9/1) and then triturated with diisopropyl ether to give Compound 230 (31 mg, 49%).

APCI-MS m/z: 530 (M+H)$^+$.

Example 36

Compound 231

2-(tert-Butoxycarbonylamino) acetophenone=thiosemicarbazone (2.91 g, 9.44 mmol) was added to acetic anhydride (30 mL), and the mixture was stirred at 130° C. for 5 minutes and subsequently at 70° C. for 1 hour. The reaction mixture was left to cool and then triturated with a mixed solvent of diisopropyl ether and n-hexane to give Compound 231 (2.06 g, 56%).

APCI-MS m/z: 393 (M+H)$^+$.

Example 37

Compound 232

Compound 231 (2.01 g, 5.12 mmol) obtained in Example 36 was dissolved in acetonitrile (20 mL), to the solution was added hydrazine monohydrate (8.0 mL, 0.16 mol), and the mixture was stirred at room temperature for 6 hours. To the reaction mixture was added water, and the mixture was extracted with ethyl acetate. The organic layer was washed with saturated aqueous sodium chloride, dried over anhydrous sodium sulfate and concentrated under reduced pressure. The residue was purified by using a parallel 12-system preparative chromatography apparatus (Hi-Flash™ column, Yamazen, hexane/ethyl acetate=2/3) to give Compound 232 (1.42 g, 79%).

APCI-MS m/z: 351 (M+H)+.

Example 38

Compound 233

In a manner similar to that in Example 28, Compound 232 (1.01 g, 2.88 mmol) obtained in Example 37 was allowed to react with 4-bromobutyryl chloride (0.840 mL, 7.24 mmol) in the presence of pyridine (0.585 mL, 7.23 mmol) followed by treating with sodium acetate (608 mg, 7.41 mmol) in DMSO (20 mL) to give Compound 233 (0.99 g, 82%).

APCI-MS m/z: 419 (M+H)+.

Example 39

Compound 234

In a manner similar to that in Example 29, Compound 233 (503 mg, 1.20 mmol) obtained in Example 38 was treated with 4 mol/L hydrogen chloride-ethyl acetate (6.0 mL) and then allowed to react with 2-chloroethanesulfonyl chloride (0.377 mL, 3.61 mmol) in the presence of triethylamine (1.34 mL, 9.61 mmol) to give Compound 234 (126 mg, 26%).

APCI-MS m/z: 409 (M+H)+.

Example 40

Compound 235

In a manner similar to that in Example 33, Compound 234 (40 mg, 0.098 mmol) obtained in Example 39 was allowed to react with 7 mol/L ammonia-methanol (3 mL) to give Compound 235 (14 mg, 34%).

$i^1$NMR (300 MHz, CDCl$_3$) δ (ppm): 2.20 (m, 2H), 2.34 (s, 3H), 2.56 (m, 2H), 3.14 (m, 4H), 3.91 (m, 2H), 3.99 (d, J=13.6 Hz, 1H), 4.58 (d, J=13.6 Hz, 1H), 7.25-7.41 (m, 5H).

APCI-MS m/z: 426 (M+H)+.

Example 41

Compound 236

Compound 234 (68 mg, 0.17 mmol) obtained in Example 39 was dissolved in acetonitrile (1.5 mL), to the solution was added 50% aqueous dimethylamine (0.170 mL), and the mixture was stirred at room temperature for 17 hours. The reaction mixture was concentrated under reduced pressure, and the residue was purified by preparative thin layer chromatography (chloroform containing ammonia/methanol=19/1) and then triturated with diisopropyl ether to give Compound 236 (44 mg, 58%).

APCI-MS m/z: 454 (M+H)+.

Example 42

Compound 237

Compound 220 (47 mg; 0.094 mmol) obtained in Example 25 was dissolved in 1,2-dichloroethane (2 mL), to the solution was added 37% aqueous formalin (0.026 mL, 0.94 mmol), acetic acid (0.055 mL, 0.96 mmol) and triacetoxy sodium borohydride (201 mg, 0.948 mmol), and the mixture was stirred at room temperature for 50 minutes. To the reaction mixture was added water and saturated aqueous sodium hydrogencarbonate, and the mixture was extracted with chloroform. The organic layer was washed with saturated aqueous sodium chloride, dried over anhydrous sodium sulfate and concentrated under reduced pressure. The residue was purified by preparative thin layer chromatography (chloroform/methanol=4/1) and then triturated with diisopropyl ether to give Compound 237 (28 mg, 56%).

APCI-MS m/z: 526 (M+H)+.

Example 43

Compound 238

In a manner similar to that in Example 26, Compound 237 (330 mg, 0.628 mmol) prepared in Example 42 was treated with 4 mol/L hydrogen chloride-ethyl acetate (0.32 mL) to give Compound 238 (hydrochloride of Compound 237, 320 mg, 91%).

$^1$H NMR (270 MHz, CDCl$_3$) δ (ppm): 1.31 (s, 9H), 1.36 (s, 9H), 2.37 (m, 2H), 2.77 (s, 6H), 3.10-3.34 (m, 4H), 4.05 (dd, J=4.6, 13.8 Hz, 1H), 4.62 (dd, J=7.9, 13.8 Hz, 1H), 5.44 (m, 1H), 7.23-7.40 (m, 5H), 8.57 (brs, 1H).

Example 44

Compound 239

In a manner similar to that in Example 23, the compound (600 mg, 1.69 mmol) prepared by treating Compound 233 prepared in Example 38 with 4 mol/L hydrogen chloride-ethyl acetate was allowed to react with 3-chioropropanesulfonyl chloride (0.327 mL, 2.69 mmol) in the presence of triethylamine (0.707 mL, 5.07 mmol) to give Compound 239 (620 mg, 80%).

APCI-MS m/z: 459, 461 (M+H)+.

Example 45

Compound 240

In a manner similar to that in Example 24, Compound 239 (600 mg, 1.31 mmol) obtained in Example 44 was allowed to react with sodium azide (0.85 g, 13 mmol) in the presence of sodium iodide (3.91 g, 26.1 mmol) to give Compound 240 (494 mg, 81%).

APCI-MS m/z: 466 (M+H)+.

Example 46

Compound 241

In a manner similar to that in Example 25, Compound 240 (400 mg, 0.859 mmol) obtained in Example 45 was treated with water (3 mL) and triphenyiphosphine (338 mg, 1.29 mmol) to give Compound 241 (300 mg, 79%).

$^1$H NMR (270 MHz, CDCl$_3$) δ (ppm): 1.90 (m, 2H), 2.20 (m, 2H), 2.34 (s, 3H), 2.56 (m, 2H), 2.81 (m, 2H), 3.12 (m, 2H), 3.90 (m, 2H), 3.99 (d, J=13.8 Hz, 1H), 4.58 (d, J=13.8 Hz, 1H), 7.25-7.42 (m, 5H).

APCI-MS m/z: 440 (M+H)+.

Example 47

Compound 242

Compound 232 (6.00 g, 17.1 mmol) prepared in Example 37 was dissolved in dichloromethane (120 mL), to the solution was added pyridine (4.15 mL, 51.3 mmol) and trimethylacetyl chloride (5.27 mL, 42.8 mmol) under ice cooling, and the mixture was stirred at room temperature for 5 days. To the reaction mixture was added 1 mol/L hydrochloric acid, and the mixture was extracted with chloroform. The organic layer was washed with water and saturated aqueous sodium chloride, dried over anhydrous sodium sulfate and concentrated under reduced pressure. The residue was triturated with a mixed solvent of diethyl ether and n-hexane to give Compound 242 (6.90 g, 93%).
$^1$H NMR (270 MHz, CDCl$_3$) δ (ppm): 1.25 (s, 9H), 1.38 (s, 9H), 2.33 (s, 3H), 4.00 (dd, J=5.3, 14.8 Hz, 1H), 4.59 (dd, J=9.7, 14.8 Hz, 1H), 5.69 (m, 1H), 7.18-7.40 (m, 5H), 8.01 (s, 1H).

Example 48

Compound 243

In a manner similar to that in Example 21, Compound 242 (900 mg, 2.07 mmol) obtained in Example 47 was treated with 4 mol/L, hydrogen chloride-ethyl acetate (9 mL) to give Compound 243 (803 mg, quantitative) as hydrochloride.

Example 49

Compound 244

In a manner similar to that in Example 23, hydrochloride of Compound 243 (803 mg, 2.17 mmol) obtained in Example 48 was allowed to react with 3-chloropropanesulfonyl chloride (0.378 mL, 3.11 mmol) in the presence of triethylamine (0.866 mL, 6.21 mmol) to give Compound 244 (325 mg, 32%).
APCI-MS m/z: 475, 477 (M+H)$^+$.

Example 50

Compound 245

In a manner similar to that in Example 24, Compound 244 (323 mg, 0.680 mmol) obtained in Example 49 was allowed to react with sodium azide (0.44 g, 6.8 mmol) in the presence of iodide (2.04 g, 13.6 mmol) to give Compound 245 (216 mg, 66%).
APCI-MS m/z: 482 (M+H)$^+$.

Example 51

Compound 246

In a manner similar to that in Example 25, Compound 245 (212 mg, 0.440 mmol) obtained in Example 50 was treated with water (1.5 mL) and triphenylphosphine (179 mg, 0.682 mmol) to give Compound 246 (173 mg, 86%).
$^1$H NMR (270 MHz, CDCl$_3$) δ (ppm): 1.27 (s, 9H), 1.90 (m, 2H), 2.32 (s, 3H), 2.82 (m, 2H), 3.13 (m, 2H), 3.97 (d, J=13.9 Hz, 1H), 4.59 (d, J=13.9 Hz, 1H), 7.25-7.41 (m, 5H).
APCI-MS m/z: 456 (M+H)$^+$.

Example 52

Compound 247

In a manner similar to that in Example 42, Compound 241 (63 mg, 0.14 mmol) obtained in Example 46 was allowed to react with 37% aqueous formalin (0.039 mL, 1.4 mmol) in the presence of acetic acid (0.082 mL, 1.4 mmol) and triacetoxy sodium borohydride (345 mg, 1.43 mmol) to give Compound 247 (46 mg, 69%).
$^1$H NMR (270 MHz, CDCl$_3$) δ (ppm): 1.93 (m, 2H), 2.20 (s, 6H), 2.21 (m, 2H), 2.34 (s, 3H), 2.35 (t, J=6.8 Hz, 2H), 2.56 (m, 2H), 3.09 (m, 2H), 3.92 (m, 2H), 3.98 (d, J=13.8 Hz, 1H), 4.57 (d, J=13.8 Hz, 1H), 5.73 (m, 1H), 7.26-7.41 (m, 5H).
APCI-MS m/z: 468 (M+H)$^+$.

Example 53

Compound 248

In a manner similar to that in Example 32, Compound 241 (99 mg, 0.23 mmol) obtained in Example 46 was allowed to react with acetaldehyde (0.252 mL, 2.25 mmol) in the presence of sodium borohydride (86 mg, 2.2 mmol) to give the desired compound (15 mg, 14%).
$^1$H NMR (270 MHz, CDCl$_3$) δ (ppm); 1.08 (t, J=7.1 Hz, 3H), 1.95 (m, 2H), 2.20 (m, 2H), 2.34 (s, 3H), 2.56 (m, 2H), 2.63 (q, J=7.1 Hz, 2H), 2.72 (t, J=6.6 Hz, 2H), 3.13 (m, 2H), 3.91 (m, 2H), 3.98 (d, J=13.8 Hz, 1H), 4.57 (d, J=13.8 Hz, 1H), 7.22-7.40 (m, 5H).
APCI-MS m/z: 468 (M+H)$^+$.

Example 54

Compound 249

In a manner similar to that in Example 42, Compound 246 (122 mg, 0.268 mmol) obtained in Example 51 was allowed to react with 37% aqueous formalin (0.074 mL, 2.7 mmol) in the presence of acetic acid (0.153 mL, 2.67 mmol) and triacetoxy sodium borohydride (568 mg, 2.68 mmol) to give Compound 249 (80 mg, 62%).
$^1$H NMR (270 MHz, CDCl$_3$) δ (ppm): 1.27 (s, 9H), 1.95 (m, 2H), 2.21 (s, 6H), 2.31 (s, 3H), 2.37 (t, J=6.8 Hz, 2H), 3.09 (m, 2H), 3.96 (d, J=13.8 Hz, 1H), 4.57 (d, J=13.8 Hz, 1H), 5.77 (br, 1H), 7.22-7.40 (m, 5H), 8.05 (br, 1H).
APCI-MS m/z: 484 (M+H)$^+$.

Example 55

Compound 250

In a manner similar to that in Example 41, Compound 171 (56 mg, 0.12 mmol) prepared in Reference Example 161 was allowed to react with bis(2-methoxyethyl)amine (0.356 mL, 2.41 mmol) under reflux by heating to give Compound 250 (47 mg, 65%).
APCI-MS m/z: 600 (M+H)$^+$.

Example 56

Compound 251

In a manner similar to that in Example 41, Compound 171 (57 mg, 0.12 mmol) obtained in Reference Example 161 was allowed to react with 2,2,2-trifluoroethylamine hydrochloride (681 mg, 5.02 mmol) in acetonitrile (1 mL) and water (0.5 mL) under reflux by heating in the presence of triethylamine (0.686 mL, 4.92 mmol) to give Compound 251 (18 mg, 26%).
APCI-MS m/z: 566 (M+H)+.

Example 57

Compound 252

In a manner similar to that in Example 41, Compound 171 (101 mg, 0.216 mmol) prepared in Reference Example 161 was allowed to react with cyclopropylamine (0.300 mL, 4.33 mmol) to give Compound 252 (105 mg, 93%).
$^1$H NMR (270 MHz, CDCl$_3$) δ (ppm): 0.30-0.48 (m, 4H), 1.29 (s, 9H), 1.34 (s, 9H), 2.12 (m, 1H), 3.11-3.18 (m, 2H), 3.19-3.36 (m, 2H), 3.96 (dd, J=4.9, 13.8 Hz, 1H), 4.57 (dd, J=7.5, 13.8 Hz, 1H), 5.31 (brt, 1H), 7.23-7.39 (m, 5H), 7.93 (brs, 1H).
APCI-MS m/z: 524 (M+H)+.

Example 58

Compound 253

In a manner similar to that in Example 26, Compound 252 (541 mg, 1.03 mmol) prepared in Example 57 was treated with a 4 mol/L hydrogen chloride-ethyl acetate solution (0.52 mL) to give Compound 253 (hydrochloride of Compound 252, 567 mg, 98%).
$^1$H NMR (270 MHz, CDCl$_3$) δ (ppm): 0.75-0.95 (m, 4H), 1.28 (s, 9H), 1.34 (s, 9H), 2.61 (m, 1H), 3.49 (m, 2H), 3.80 (m, 2H), 4.12 (m, 1H), 4.63 (m, 1H), 6.45 (m, 1H), 7.21-7.38 (m, 5H), 8.37 (s, 1H).

Example 59

Compound 254

In a manner similar to that in Example 42, Compound 252 (61 mg, 0.12 mmol) prepared in Example 57 was allowed to react with acetaldehyde (0.065 mL, 1.2 mmol) in the presence of acetic acid (0.066 mL, 1.2 mmol) and triacetoxy sodium borohydride (244 mg, 1.15 mmol) to give Compound 254 (10 mg, 16%).
APCI-MS m/z: 552 (M+H)+.

Example 60

Compound 255

In a manner similar to that in Example 42, Compound 221 (0.0150 g, 0.301 mmol) obtained in Example 26 was allowed to react with acetaldehyde (0.133 g, 3.01 mmol) in the presence of acetic acid (0.136 mL, 2.26 mmol) and triacetoxy sodium borohydride (0.573 g, 2.71 mmol) to give Compound 255 (0.111 g, 68%).
$^1$H NMR (270 MHz, CDCl$_3$) δ (ppm): 0.99 (t, J=7.0 Hz, 6H), 1.14 (s, 9H), 1.29 (s, 9H), 1.40-1.50 (br s, 1H), 1.55-1.63 (m, 1H), 1.88-1.96 (m, 1H), 2.46-2.54 (m, 6H), 3.08-3.14 (m, 2H), 3.95 (d, J=14.3 Hz, 1H), 4.58 (d, J=14.3 Hz, 1H), 7.20-7.38 (m, 6H).
APCI-MS m/z: 554 (M+H)+.

Example 61

Compound 256

In a manner similar to that in Example 41, Compound 171 (0.100 g, 0.215 mmol) prepared in Reference Example 161 was allowed to react with N-acetylethylenediamine (0.110 g, 1.08 mmol) to give Compound 256 (0.0433 g, 35%).
APCI-MS m/z: 569 (M+H)+.

Example 62

Compound 257

In a manner similar to that in Example 41, Compound 171 (0.311 g, 0.666 mmol) prepared in Reference Example 161 was allowed to react with tert-butyl-N-(2-aminoethyl)carbamate (0.200 g, 1.25 mmol) to give Compound 257 (0.290 g, 70%).
$^1$H NMR (270 MHz, CDCl$_3$) δ (ppm): 1.26 (s, 9H), 1.28 (s, 9H), 1.29 (s, 9H), 2.70-2.90 (br m, 2H), 3.10-3.50 (m, 8H), 4.08 (br d, J=13.3 Hz, 1H), 4.57 (br d, J=13.3 Hz, 1H), 5.22 (br s, 1H), 7.20-7.39 (m, 5H), 8.08 (br s, 1H).
APCI-MS m/z: 627 (M+H)+.

Example 63

Compound 258

Compound 257 (0.172 g, 0.274 mmol) obtained in Example 62 was dissolved in dichloromethane (2.0 mL). Then, to the solution was successively added pyridine (0.0488 g, 0.617 mmol) and acetic anhydride (0.0388 mL, 0.411 mmol), and the mixture was stirred at room temperature for 24 hours. To the reaction mixture was added 1 mol/L aqueous hydrochloric acid (3 mL) and water (3 mL), and the mixture was extracted with chloroform. The organic layer was dried over anhydrous sodium sulfate, and the solvent was evaporated under reduced pressure. The residue was purified by preparative thin layer chromatography (chloroform/methanol=9/1) to give Compound 258 (0.0993 g, 53%).

Example 64

Compound 259

Compound 258 (0.0930 g, 0.139 mmol) obtained in Example 63 was dissolved in dichloromethane (2.0 mL). Then, to the solution was added trifluoroacetic acid (1.00 mL, 13.0 mmol), and the mixture was stirred at room temperature for 3 hours. The reaction mixture was evaporated under reduced pressure, and the resulting residue was dissolved in chloroform. To the solution was added saturated aqueous sodium hydrogencarbonate and water, and the mixture was extracted with chloroform. The organic layer was washed with water and dried over anhydrous sodium sulfate, and the solvent was evaporated under reduced pressure. The resulting residue was purified by preparative thin layer chromatography (chloroform/methanol=9/1) to give Compound 259 (0.788 g, 99%).
APCI-MS m/z: 569 (M+H)+.

Example 65

Compound 260

Compound 256 (0.101 g, 0.178 mmol) prepared in Example 61 was dissolved in DMF (0.5 mL), to the solution was added sodium hydride (0.0712 g, 1.78 mmol), and the mixture was stirred at room temperature for 4 hours. To the reaction mixture was added saturated aqueous sodium hydrogencarbonate (3 mL) and water (3 mL), and the mixture was extracted with ethyl acetate. The organic layer was washed with water and saturated brine, and dried over anhydrous sodium sulfate, and the solvent was evaporated under reduced pressure. The resulting residue was purified by preparative thin layer chromatography (chloroform/methanol=9/1) to give Compound 260 (0.0172 g, 18%).

$^1$H NMR (270 MHz, CDCl$_3$) δ (ppm): 1.29 (s, 9H), 1.34 (s, 9H), 1.90 (s, 3H), 2.95-3.35 (m, 8H), 3.99 (d, J=14.0 Hz, 1H), 4.53 (d, J=14.0 Hz, 1H), 5.60 (br s, 1H), 6.34 (br s, 1H), 7.20-7.39 (m, 5H), 8.08 (br s, 1H).

APCI-MS m/z: 597 (M+H)$^+$.

Example 66

Compound 261

In a manner similar to that in Example 41, Compound 171 (100 mg, 0.214 mmol) prepared in Reference Example 161 was allowed to react with diethylamine (0.088 mL, 0.86 mmol) to give Compound 261 (103 mg, 89%).

$^1$H NMR (300 MHz, CDCl$_3$) δ (ppm): 1.03 (t, J=7.2 Hz, 6H), 1.28 (s, 9H), 1.33 (s, 9H), 2.54 (q, J=7.2 Hz, 4H), 2.86-3.03 (m, 2H), 3.10-3.18 (m, 2H), 3.99 (d, J=13.6 Hz, 1H), 4.57 (d, J=13.6 Hz, 1H), 5.79 (brs, 1H), 7.27-7.36 (m, 5H), 7.91 (brs, 1H).

APCI-MS m/z: 540 (M+H)$^+$.

Example 67

Compound 262

In a manner similar to that in Example 41, Compound 171 (100 mg, 0.214 mmol) prepared in Reference Example 161 was allowed to react with isobutylamine (0.086 mL, 0.86 mmol) to give Compound 262 (103 mg, 89%).

APCI-MS m/z: 540 (M+H)$^+$.

Example 68

Compound 263

In a manner similar to that in Example 41, Compound 171 (100 mg, 0.214 mmol) prepared in Reference Example 161 was allowed to react with n-butylamine (0.084 mL, 0.84 mmol) to give Compound 263 (101 mg, 87%).

APCI-MS m/z 540 (M+H)$^+$.

Example 69

Compound 264

In a manner similar to that in Example 41, Compound 171 (100 mg, 0.214 mmol) prepared in Reference Example 161 was allowed to react with ethylmethylamine (0.092 mL, 1.07 mmol) to give Compound 264 (101 mg, 90%).

APCI-MS m/z: 526 (M+H)$^+$.

Example 70

Compound 265

In a manner similar to that in Example 41, Compound 171 (100 mg, 0.214 mmol) prepared in Reference Example 161 was allowed to react with cyanomethylamine-1/2 sulfate (90 mg, 0.86 mmol) to give Compound 265 (43 mg, 39%).

APCI-MS m/z: 523 (M+H)$^+$.

Example 71

Compound 266

Compound 216 (50 mg, 0.12 mmol) prepared in Example 21 was dissolved in dichloromethane (1 mL), to the solution was added triethylamine (0.067 mL, 0.48 mmol) and sulfamoyl chloride (28 mg, 0.24 mmol), and the mixture was stirred at room temperature for 15 minutes. To the reaction mixture was added water, and the mixture was extracted with a mixed solvent of chloroform and methanol. The organic layer was washed with saturated aqueous sodium chloride, dried over anhydrous sodium sulfate and concentrated under reduced pressure. The residue was purified by preparative thin layer chromatography (chloroform/Methanol=9/1) and then crystallized from a mixed solvent of ethanol and water to give Compound 266 (30 mg, 54%).

APCI-MS m/z: 456 (M+H)$^+$.

Example 72

Compound 267

In a manner similar to that in Example 71, Compound 216 (50.7 mg, 0.123 mmol) prepared in Example 21 was allowed to react with dimethylsulfamoyl chloride (0.054 mL, 0.50 mmol) in the presence of triethylamine (0.138 mL, 0.990 mmol) to give Compound 267 (9.2 mg, 15%).

APCI-MS m/z: 482 (M−H)$^-$.

Example 73

Compound 268

In a manner similar to that in Example 33, Compound 171 (60.0 mg, 0.129 mmol) prepared in Reference Example 161 was dissolved in acetonitrile (1 mL), to the solution was added triethylamine (27 μL, 0.193 mmol) and glycinamide hydrochloride (21 mg, 0.193 mmol), and the mixture was stirred at room temperature for 6 hours. To the reaction mixture was added water, and the mixture was extracted with ethyl acetate. The organic layer was washed with saturated aqueous sodium chloride and dried over anhydrous sodium sulfate, and the solvent was evaporated under reduced pressure. The residue was purified by silica gel column chromatography (chloroform/methanol=6/1) to give Compound 268 (48.4 mg, 69%).

$^1$H NMR (270 MHz, CDCl$_3$) δ (ppm): 1.29 (s, 9H), 1.34 (s, 9H), 3.05 (m, 2H), 3.21 (m, 2H), 3.27 (m, 2H), 4.01 (dd, 1H, J=5.6, 13.7 Hz, 1H), 4.59 (dd, J=7.7, 13.7 Hz, 1H), 5.36 (dd, J=5.6, 7.7 Hz, 1H), H), 7.25-7.40 (m, 51), 8.09 (s, 1H).

APCI-MS m/z: 541 (M+H)$^+$.

Example 74

Compound 269

In a manner similar to that in Example 41, Compound 170 (54 mg, 0.13 mmol) of Reference Example 161 was allowed to react with glycine methyl ester hydrochloride (336 mg, 2.67 mmol) in the presence of triethylamine (0.355 mL, 2.55 mmol) to give Compound 269 (48 mg, 73%).

APCI-MS m/z: 514 (M+H)$^+$.

Example 75

Compound 270

In a manner similar to that in Example 41, Compound 170 (52 mg, 0.12 mmol) of Example 161 was allowed to react with β-alanine ethyl ester hydrochloride (381 mg, 2.48 mmol) in the presence of triethylamine (0.345 mL, 2.48 mmol) to give Compound 270 (62 mg, 93%).
APCI-MS m/z: 542 (M+H)$^+$.

Example 76

Compound 271

Compound 269 (28 mg, 0.055 mmol) prepared in Example 74 was dissolved in a mixed solvent of methanol (0.8 mL) and water (10 mL), to the solution was added lithium hydroxide (13 mg, 0.054 mmol), and the mixture was stirred at room temperature for 2 hours. To the reaction mixture was added 1 mol/L hydrochloric acid (1.07 mL), and the mixture was concentrated under reduced pressure. The residue was purified by preparative thin layer chromatography (chloroform/methanol/acetic acid=10/2/0.1), then to the residue was added 1 mol/L hydrochloric acid, and the mixture was concentrated under reduced pressure. The residue was triturated with diisopropyl ether to give Compound 271 (13 mg, 44%).
APCI-MS m/z: 500 (M+H)$^{30}$.

Example 77

Compound 272

In a manner similar to that in Example 76, Compound 272 (25 mg, 55%) was obtained from Compound 270 (45 mg, 0.083 mmol) prepared in Example 75 and lithium hydroxide (21 mg, 0.088 mmol).
APCI-MS m/z: 514 (M+H)$^+$.

Example 78

Compound 273

In a manner similar to that in Example 33, Compound 171 (470 mg, 1.01 mmol) of Reference Example 161 was allowed to react with 7 mol/L ammonia-methanol (10 mL) to give Compound 273 (479 mg, 98%).
APCI-MS m/z: 484 (M+H)$^+$.

Example 79

Compound 274

N-(tert-Butoxycarbonyl)-glycine (35 mg, 0.20 mmol) was dissolved in DMF (1 mL), and to the solution was added EDCI (38 mg, 0.20 mmol) and HOBt monohydrate (31 mg, 0.20 mmol) under ice cooling. The mixture was stirred at the same temperature for 20 minutes, then to the mixture was added Compound 273 (80 mg, 0.17 mmol) prepared in Example 78, and the mixture was stirred at room temperature for 25 hours. To the reaction mixture was added water, and the mixture was extracted with ethyl acetate. The organic layer was successively washed with 1 mol/L hydrochloric acid, saturated aqueous sodium hydrogencarbonate and saturated aqueous sodium chloride, dried over anhydrous sodium sulfate and concentrated under reduced pressure. The residue was triturated with diisopropyl ether to give Compound 274 (87 mg, 82%).
APCI-MS m/z: 641 (M+H)$^+$.

Example 80

Compound 275

Compound 274 (82 mg, 0.13 mmol) obtained in Example 79 was dissolved in dichloromethane (1 mL) and trifluoroacetic acid (1 mL), and the mixture was stirred at room temperature for 1 hour. The reaction mixture was concentrated under reduced pressure, to the residue was added water and saturated aqueous sodium hydrogencarbonate, and the mixture was extracted with ethyl acetate. The organic layer was washed with saturated aqueous sodium chloride, dried over anhydrous sodium sulfate and concentrated under reduced pressure. The residue was purified by preparative thin layer chromatography (chloroform containing ammonia/methanol=9/1) and then triturated with diethyl ether to give Compound 275 (35 mg, 51%).
APCI-MS m/z: 541 (M+H)$^+$.

Example 81

Compound 276

In a manner similar to that in Example 26, Compound 275 (574 mg, 1.06 mmol) obtained in Example 80 was treated with 4 mol/L hydrogen chloride-ethyl acetate (0.53 mL) to give Compound 276 (hydrochloride of Compound 275, 545 mg, 89%).
$^1$H NMR (270 MHz, DMSO-d$_6$) δ (ppm): 1.18 (s, 9H), 1.28 (s, 9H), 3.20-3.46 (m, 4H), 3.51 (s, 2H), 3.75 (m, 1H), 4.34 (m, 1H), 7.21-7.39 (m, 5H), 8.54 (t, J=5.4 Hz, 1H).

Example 82

Compound 277

In a manner similar to that in Example 79, Compound 277 (90 mg, 83%) was obtained from Compound 273 (80 mg, 0.17 mmol) prepared in Example 78, N-(tert-butoxycarbonyl)-δ-alanine (38 mg, 0.20 mmol), EDCI (38 mg, 0.20 mmol) and HOBt monohydrate (31 mg, 0.20 mmol).
APCI-MS m/z: 655 (M+H)$^+$.

Example 83

Compound 278

In a manner similar to that in Example 80, Compound 278 (36 mg, 49%) was obtained from Compound 277 (87 mg, 0.13 mmol) obtained in Example 82 and trifluoroacetic acid (1 mL).
APCI-MS m/z: 555 (M+H)$^+$.

Example 84

Compound 279

In a manner similar to that in Example 28, Compound 279 (1.85 g, 95%) was obtained from Compound 232 (1.57 g, 4.48 mmol) prepared in Example 37, pyridine (1.20 mL, 13.4 mmol), 5-bromovaleryl chloride (1.50 mL, 11.2 mmol) and sodium acetate (3.7 g, 44.8 mmol).
APCI-MS m/z: 433 (M+H)$^+$.

Example 85

Compound 280

Example 85 and Example 86 were carried out in a manner similar to that in Example 29. Specifically, Compound 279 (1.85 g, 4.28 mmol) obtained in Example 84 was treated with 4 mol/L hydrogen chloride-ethyl acetate (20 mL) to give Compound 280 (1.42 g, 90%).
APCI-MS mix 423 (M+H)$^+$.

Example 86

Compound 281

Compound 280 (386 mg, 1.05 mmol) obtained in Example 85 was allowed to react with 2-chloro-1-ethanesulfonyl chloride (0.164 mL, 1.57 mmol) in the presence of triethylamine (0.732 mL, 5.25 mmol) to give Compound 281 (360 mg, 75%).
APCI-MS m/z 333 (M+H)$^+$.

Example 87

Compound 282

In a manner similar to that in Example 41, Compound 281 (332 mg, 0.750 mmol) obtained in Example 86 was allowed to react with cyclopropylamine (1.00 mL, 15.0 mmol) to give Compound 282 (101 mg, 28%).
APCI-MS m/z: 480 (M+H)$^+$.

Example 88

Compound 283

In a manner similar to that in Example 41, Compound 170 (51 mg, 0.12 mmol) prepared in Reference Example 161 was allowed to react with 2-(aminomethyl)pyridine (0.247 mL, 2.40 mmol) to give Compound 283 (43 mg, 67%).
APCI-MS m/z: 533 (M+H)$^+$.

Example 89

Compound 284

In a manner similar to that in Example 41, Compound 171 (43.7 mg, 0.0937 mmol) prepared in Example 161 was allowed to react with 4-picolylamine (0.020 mL, 0.187 mmol) to give Compound 284 (32.4 mg, 60%).
APCI-MS m/z: 575 (M+H)$^+$.

Example 90

Compound 285

3-(tert-Butoxycarbonylamino)-propiophenone=thiosemicarbazone (4.07 g, 12.6 mmol) prepared as an intermediate in Step 2 of Example 14 was dissolved in acetone (20 mL), to the solution was added pyridine (5.4 mL, 63.1 mmol) and acetic anhydride (6.0 mL, 63.1 mmol), and the mixture was stirred at room temperature for 24 hours. To the reaction mixture was added saturated aqueous sodium hydrogencarbonate, and the mixture was extracted with ethyl acetate. The organic layer was washed with saturated brine and dried over anhydrous sodium sulfate, and the solvent was evaporated under reduced pressure. To the residue was added methanol (30 mL) and hydrazine monohydrate (20 mL), and the mixture was stirred at room temperature for 1 hour. To the reaction mixture was added 1 mol/L hydrochloric acid, and the mixture was extracted with ethyl acetate. The organic layer was washed with saturated brine and dried over anhydrous sodium sulfate, and the solvent was evaporated under reduced pressure. The residue was reslurried in diisopropyl ether (30 mL) to give Compound 285 (4.38 g, 91%).
APCI-MS m/z: 365 (M+H)$^+$.

Example 91

Compound 286

In a manner similar to that in Example 38, Compound 286 (103 mg, 84%) was obtained from Compound 285 (103 mg, 0.283 mmol) obtained in Example 90, 4-bromobutyryl chloride (0.082 mL, 0.707 mmol), pyridine (0.072 mL, 0.848 mmol) and sodium acetate (232 mg, 2.83 mmol).
APCI-MS m/z 433 (M+H)$^+$.

Example 92

Compound 287

In a manner similar to that in Example 40, Compound 286 (386 mg, 1.05 mmol) prepared in Example 91 was treated with 4 mol/L hydrogen chloride-ethyl acetate (5 mL) to give Compound 287 (51.7 mg, 59%) as hydrochloride.
APCI-MS m/z 333 (M+H)$^+$.

Reference Example 1

Compound 1

Step 1: Acetophenone (4.00 g, 33.3 mmol) and thiosemicarbazide (3.15 g, 34.6 mmol) were dissolved in methanol (30 mL). To the solution was added hydrochloric acid (0.1 mL) and the mixture was vigorously stirred at room temperature for 15 hours. To the reaction mixture was added water (30 mL), and the deposited crystals were collected by filtration, washed with water and diisopropyl ether, and then dried to give acetophenone=thiosemicarbazone (5.64 g, 88%).
$^1$H NMR (270 MHz, DMSO-d$_6$) δ (ppm): 2.30 (s, 3H), 7.37-7.40 (m, 3H), 7.91-7.94 (m, 3H), 8.27 (br s, 1H), 10.21 (br s, 1H).

Step 2: Acetophenone=thiosemicarbazone (300 mg, 0.889 mmol) obtained above was dissolved in acetic anhydride (1.0 mL, 11 mmol). After being refluxing under heating, the solution was cooled to room temperature with vigorous stirring. To the reaction mixture was added diisopropyl ether (3 mL), and the deposited crystals were collected by filtration. The collected crystals were suspended in diisopropyl ether and stirred for 3 hours, and then the crystals were collected by filtration and dried to give Compound 1 (195 mg, 72%).
$^1$H NMR (270 MHz, CDCl$_3$) δ (ppm): 2.01 (s, 3H), 2.19 (s, 3H), 2.28 (s, 3H), 7.24-7.36 (br s, 5H), 11.63 (br s, 1H).

Reference Example 2

Compound 2

Step 1: In a manner similar to that in Step 1 of Reference Example 1, propiophenone=thiosemicarbazone (759 mg, 88%) was obtained from propiophenone (541 mg, 3.92 mmol) and thiosemicarbazide (382 mg, 4.18 mmol).
$^1$H NMR (270 MHz, DMSO-d$_6$) δ (ppm): 1.01 (t, J=7.4 Hz, 3H), 2.85 (br q, J=7.4 Hz, 2H), 7.39 (m, 3H), 7.89 (m, 3H), 8.24 (br s, 1H), 10.30 (br s, 1H).

Step 2: In a manner similar to that in Step 2 of Reference Example 1, Compound 2 (601 mg, 76%) was obtained from propiophenone=thiosemicarbazone (559 mg, 2.70 mmol) obtained above.

¹H H NMR (270 MHz, DMSO-d₆) δ (ppm): 1.02 (t, J=7.1 Hz, 3H), 2.00 (s, 3H), 2.21 (s, 3H), 2.38 (dt, J=7.1, 7.3 Hz, 1H), 2.85 (dt, J=7.1, 7.3 Hz, 1H), 7.23-7.38 (m, 5H), 11.59 (br s, 1H).

Reference Example 3

Compound 3

Step 1: In a manner similar to that in Step 1 of Reference Example 1, n-butyl(phenyl)methanone=thiosemicarbazone (589 mg, 63%) was obtained from n-butyl(phenyl)methanone (649 mg, 4.00 mmol) and thiosemicarbazide (367 mg, 4.03 mmol).

¹H NMR (270 MHz, DMSO-d₆) δ (ppm): 0.99 (t, J=7.3 Hz, 3H), 1.38-1.49 (m, 4H), 2.96-2.99 (m, 2H), 7.37-7.39 (m, 3H), 7.87-7.91 (m, 3H), 8.26 (br s, 1H), 10.36 (br s, 1H).

Step 2: In a manner similar to that in Step 2 of Reference Example 1, Compound 3 (168 mg, 62%) was obtained from n-butyl(phenyl)methanone=thiosemicarbazone (200 mg, 0.850 mmol) obtained above.

¹H NMR (270 MHz, CDCl₃) δ (ppm): 0.96 (t, J=7.3 Hz, 3H), 1.25-1.34 (m, 1H), 1.36-1.54 (m, 2H), 1.68-1.80 (m, 1H), 2.18 (s, 3H), 2.20-2.26 (m, 1H), 2.26 (s, 3H), 2.99-3.10 (m, 1H), 7.22-7.40 (m, 5H), 8.22 (br s, 1H).

Reference Example 4

Compound 4

Step 1: In a manner similar to that in Step 1 of Reference Example 1, isopropyl(phenyl)methanone= thiosemicarhazone (613 mg, 68%) was obtained from isopropyl(phenyl)methanone (608 mg, 4.10 mmol) and thiosemicarbazide (364 mg, 3.99 mmol).

¹H NMR (270 MHz, DMSO-d₆) δ (ppm): 1.07 (d, J=6.9 Hz, 6H), 2.82 (m, 1H), 7.28 (br d, J=6.3 Hz, 2H), 7.51-7.60 (m, 3H), 7.78 (br s, 1H), 8.23 (br s, 1H), 8.43 (br s, 1H).

Step 2: In a manner similar to that in Step 2 of Reference Example 1, Compound 4 (217 mg, 52%) was obtained from isopropyl(phenyl)methanone=thiosemicarbazone (300 mg, 1.36 mmol) obtained above.

¹H NMR (270 MHz, CDCl₃) δ (ppm): 1.04 (d, J=6.9 Hz, 3H), 1.13 (d, J=6.9 Hz, 3H), 2.09 (s, 3H), 2.19 (s, 3H), 3-86 (m, 1H), 7.25-7.36 (m, 3H), 7.75 (br d, J=7.3 Hz, 2H), 8.08 (br s, 1H).

Reference Example 5

Compound 5

In a manner similar to that in Step 1 and 2 of Reference Example 1, Compound 5 (130 mg, 10%) was obtained from cyclopropyl(phenyl)methanone (649 mg, 4.00 mmol) and thiosemicarbazide (367 mg, 4.03 mmol).

¹H NMR (270 MHz, CDCl₃) δ (ppm): 0.60-0.98 (m, 4H), 1.84 (s, 3H), 2.34 (s, 3H), 2.45 (m, 1H), 7.20-7.35 (m, 3H), 7.54 (br d, J=8.7 Hz, 2H), 9.40 (br s, 1H).

Reference Example 6

Compound 6

In a manner similar to that in Step 1 and 2 of Reference Example 1, Compound 6 (150 mg, 29%) was obtained from benzophenone (0.20 g, 2.19 mmol) and thiosemicarbazide (400 mg, 2.20 mmol).

¹H NMR (270 MHz, CDCl₃) δ (ppm): 1.89 (s, 3H), 2.32 (s, 3H), 7.25-7.52 (m, 10H), 9.13 (br s, 1H).

Reference Example 7

Compound 7

Step 1: In a manner similar to that in Step 1 of Reference Example 1, acetophenone=4-methylthiosemicarbazone (1.51 g, 77%) was obtained from 4-methylthiosemicarbazide (1.00 g, 9.51 mmol) and acetophenone (1.33 mL, 11.4 mmol).

Step 2: In a manner similar to that in Step 2 of Reference Example 1, Compound 7 (1.03 g, 47%) was obtained from acetophenone=4-methylthiosemicarbazone (1.00 g, 9.51 mmol) obtained above.

¹H NMR (270 MHz, DMSO-d₆) δ (ppm): 2.21 (s, 3H), 2.23 (s, 3H), 2.26 (s, 3H), 3.41 (s, 3H), 7.28-7.36 (m, 5H).

Reference Example 8

Compound 8 and Compound 9

To a solution of 60% sodium hydride (110 mg, 2.70 mmol) in DMF (10.0 mL) was added Compound 1 (50.0 mg, 1.80 mmol) prepared in Reference Example 1, and the mixture was stirred at room temperature for 30 minutes. To the reaction mixture was added iodoethane (0.22 mL, 2.70 mmol) and the reaction mixture was further stirred at room temperature for 12 hours. To the reaction mixture was added 5% aqueous ammonium chloride and the mixture was extracted with ethyl acetate. The organic layer was washed with saturated aqueous sodium chloride and dried over anhydrous sodium sulfate, and the solvent was evaporated under reduced pressure. The residue was purified by silica gel column chromatography (ethyl acetate/n-hexane=1/1) to give Compound 8 (120 mg, 22%) and Compound 9 (330 mg, 60%).

Compound 8

¹H NMR (270 MHz, CDCl₃) δ (ppm): 1.19 (t, J=7.0 Hz, 6H), 2.23 (s, 3H), 2.41 (s, 3H), 3.26 (q, J=7.0 Hz, 4H), 7.21-7.45 (m, 5H).

Compound 9

¹H NMR (270 MHz, CDCl₃) δ (ppm): 1.36 (t, J=7.2 Hz, 3H), 2.24 (s, 6H), 2.37 (s, 3H), 3.91 (q, J=7.2 Hz, 2H), 7.22-7.41 (m, 5H).

Reference Example 9

Compound 10 and Compound 11

In a manner similar to that in Reference Example 8, Compound 10 (0.15 g, 26%) and compound 11 (0727 g, 48%) were obtained from Compound 1 (0.50 g, 1.80 mmol) prepared in Reference Example 1 and 1-iodopropane (0.26 mL, 2.70 mmol).

Compound 10

¹H NMR (270 MHz, CDCl₃) δ (ppm): 0.89 (t, J=7.6 Hz, 6H), 1.61 (br q, J=7.6 Hz, 4H), 2.27 (s, 3H), 2.40 (s, 3H), 3.14 (br t, J=7.3 Hz, 4H), 7.21-7.47 (m, 5H).

Compound 11

¹H NMR (270 MHz, CDCl₃) δ (ppm): 1.00 (t, J=7.3 Hz, 3H), 1.74-1.82 (m, 2H), 2.28 (s, 6H), 2.36 (s, 3H), 3.75-3.86 (m, 2H), 7.21-7.44 (m, 5H).

Reference Example 10

Compound 12 and Compound 13

In a manner similar to that in Reference Example 8, Compound 12 (120 mg, 16%) and Compound 13 (0.22 g, 33%) were obtained from Compound 1 (500 mg, 1.80 mmol) prepared in Reference Example 1 and benzyl bromide (0.32 mL, 2.70 mmol).

Compound 12

¹H NMR (270 MHz, CDCl₃) δ (ppm): 2.24 (s, 3H), 2.46 (s, 3H), 4.43 (s, 4H), 7.14-7.49 (m, 15H).

Compound 13

¹H NMR (270 MHz, CDCl₃) δ (ppm): 2.16 (s, 3H), 2.26 (s, 3H), 2.36 (s, 3H), 5.11 (br s, 2H), 7.22-7.38 (m, 10H).

Reference Example 11

Compound 14

To acetophenone=thiosemicarbazone (10.0 g, 51.8 mmol) prepared in Step 1 of Reference Example 1 was added acetic anhydride (4.90 mL, 51.9 mmol) and pyridine (8.40 mL, 104 mmol), and the mixture was stirred at room temperature for 12 hours. After the reaction mixture was concentrated under reduced pressure, to the residue was added 2 mol/L aqueous sodium hydroxide, and the mixture was extracted with ethyl acetate. The organic layer was washed with saturated aqueous ammonium chloride and saturated aqueous sodium chloride, and dried over anhydrous sodium sulfate, and the solvent was evaporated under reduced pressure. The residue was purified by silica gel column chromatography (ethyl acetate/n-hexane=1/1) to give Compound 14 (9.22 g, 76%).

¹H NMR (270 MHz, DMSO-d₆) δ (ppm): 2.12 (s, 3H), 2.31 (s, 3H), 6.49 (br s, 2H), 7.21-7.41 (m, 5H).

Reference Example 12

Compound 15

Compound 7 (550 mg, 1.89 mmol) prepared in Reference Example 7 was dissolved in DMF (10.0 mL). To the solution was added 60% sodium hydride (0.23 g, 5.75 mmol) and the mixture was stirred at room temperature for 30 minutes. To the reaction mixture was added water and the mixture was extracted with ethyl acetate. The organic layer was washed with saturated aqueous ammonium chloride and dried over anhydrous sodium sulfate, and the solvent was evaporated under reduced pressure. The residue was purified by silica gel column chromatography (ethyl acetate/n-hexane=1/1) to give Compound 15 (0.31 g, 66%).

¹H NMR (270 MHz, CDCl₃) δ (ppm): 2.17 (s, 3H), 2.41 (s, 3H), 2.91 (br d, J=5.0 Hz, 3H), 3.92 (br s, 1H), 7.25-7.47 (m, 5H).

Reference Example 13

Compound 16

To a solution of 60% sodium hydride (50.0 mg, 1.20 mmol) in DMF (2.0 mL) was added Compound 14 (100 mg, 0.41 mmol) prepared in Reference Example 11, and the mixture was stirred at room temperature for 30 minutes. To the reaction mixture was added iodomethane (0.08 mL, 1.24 mmol), and the mixture was further stirred at room temperature for 12 hours. To the reaction mixture was added 5% aqueous ammonium chloride and the mixture was extracted with ethyl acetate. The organic layer was washed with saturated aqueous sodium chloride and dried over anhydrous sodium sulfate, and the solvent was evaporated under reduced pressure. The residue was purified by silica gel column chromatography (ethyl acetate/n-hexane=1/1) to give Compound 16 (70.0 mg, 67%).

¹H NMR (270 MHz, CDCl₃) δ (ppm): 2.26 (s, 3H), 2.41 (s, 3H), 2.91 (s, 6H), 7.23-7.48 (m, 5H).

Reference Example 14

Compound 17

In a manner similar to that in Reference Example 12, Compound 17 (580 mg, 71%) was obtained from Compound 19 (1.00 g, 3.13 mmol) obtained in the after-mentioned Reference Example 16.

¹H NMR (270 MHz, CDCl₃) δ (ppm): 1.13 (t, J=7.2 Hz, 3H), 2.39 (s, 3H), 2.61 (q, J=7.2 Hz, 2H), 2.88 (d, J=6.3 Hz, 3H), 4.02 (br d, J=6.3 Hz, 1H), 7.22-7.38 (m, 5H).

Reference Example 15

Compound 18

Compound 17 (100 mg, 0.38 mmol) prepared in Reference Example 14 was dissolved in acetone (2.0 mL). To the solution was added acetyl chloride (0.15 mL, 2.11 mmol) and pyridine (0.15 mL, 1.85 mmol), and the mixture was stirred at room temperature for 2 hours. To the reaction mixture was added 2 mL aqueous sodium hydroxide, and the mixture was extracted with ethyl acetate. The organic layer was washed with saturated aqueous ammonium chloride and saturated aqueous sodium chloride, and dried over anhydrous sodium sulfate, and the solvent was evaporated under reduced pressure. The residue was purified by silica gel column chromatography (ethyl acetate/n-hexane=1/2) to give Compound 18 (0.07 g, 59%).

¹H NMR (270 MHz, CDCl₃) δ (ppm): 1.12 (t, J=7.6 Hz, 3H), 2.27 (s, 3H), 2.35 (s, 3H), 2.65 (q, J=7.6 Hz, 2H), 3.45 (s, 3H), 7.23-7.42 (m, 5H).

Reference Example 16

Compound 19

To acetophenone=4-methylthiosemicarbazone (2.00 g, 9.66 mmol) prepared in Step 1 of Reference Example 7 was added propionic anhydride (8.67 mL, 67.6 mmol), and the mixture was heated and stirred at 100° C. for 3 hours. To the reaction mixture was added ethyl acetate and 2 mol/L aqueous sodium hydroxide. After the mixture was stirred at room temperature for 30 minutes, the mixture was extracted with ethyl acetate. The organic layer was washed with saturated aqueous ammonium chloride and saturated aqueous sodium chloride, and dried over anhydrous sodium sulfate, and the solvent was evaporated under reduced pressure. The residue was purified by silica gel column chromatography (ethyl acetate/n-hexane=1/2) to give Compound 19 (1.39 g, 45%).

$^1$H NMR (270 MHz, CDCl$_3$) δ (ppm): 1.12 (t, J=7.3 Hz, 3H), 1.17 (t, J=7.5 Hz, 3H), 2.36 (s, 3H), 2.54 (q, J=7.3 Hz, 2H), 2.66 (q, J=7.5 Hz, 2H), 3.45 (s, 3H), 7.21-7.42 (m, 5H).

Reference Example 17

Compound 20

In a manner similar to that in Reference Example 16, Compound 20 (1.55 g, 46%) was obtained from acetophenone=4-methylthiosemicarbazone (2.00 g, 9.66 mmol) prepared in Step 1 of Reference Example 7 and butyric anhydride (11.1 mL, 67.8 mmol).

$^1$H NMR (270 MHz, CDCl$_3$) δ (ppm): 0.95 (t, J=7.3 Hz, 3H), 0.98 (t, J=7.4 Hz, 3H), 1.15-1.78 (m, 4H), 2.35 (s, 3H), 2.49 (t, J=7.3 Hz, 2H), 2.61 (t, J=7.4 Hz, 2H), 3.45 (s, 3H), 7.21-7.42 (m, 5H).

Reference Example 18

Compound 21

In a manner similar to that in Reference Example 16, Compound 21 (1.43 g, 43%) was obtained from acetophenone=4-methylthiosemicarbazone (2.00 g, 9.66 mmol) prepared in Step 1 of Reference Example 7 and isobutyric anhydride (11.2 mL, 67.5 mmol).

$^1$H NMR (270 MHz, CDCl$_3$) δ (ppm): 1.05-1.25 (m, 12H), 2.34 (s, 3H), 2.99 (q, J=7.3 Hz, 1H), 3.25 (q, J=7.5 Hz, 1H), 3.50 (s, 3H), 7.21-7.45 (m, 5H).

Reference Example 19

Compound 22

Step 1: In a manner similar to that in Step 1 of Reference Example 1, acetone=thiosemicarbazone (215 mg, 41%) was obtained from acetone (4.8 g, 40 mmol) and thiosemicarbazide (364 mg, 3.99 mmol).

$^1$H NMR (270 MHz, DMSO-d$_6$) δ (ppm): 1.89 (s, 3H), 1.91 (s, 3H), 7.51 (br s, 1H), 7.98 (br s, 1H), 9.90 (br s, 1H).

Step 2: In a manner similar to that in Step 2 of Reference Example 1, Compound 22 (151 mg, 61%) was obtained from acetone=thiosemicarbazone (150 mg, 1.14 mmol) prepared above.

$^1$H NMR (270 MHz, CDCl$_3$) δ (ppm): 1.98 (s, 6H), 2.19 (s, 3H), 2.20 (s, 3H), 9.06 (br s, 1H).

Reference Example 20

Compound 23

Step 1: In a manner similar to that in Step 1 of Reference Example 1, 2-hexanone=thiosemicarbazone (671 mg, 97%) was obtained from 2-hexanone (401 mg, 4.00 mmol) and thiosemicarbazide (364 mg, 3.99 mmol).

$^1$H NMR (270 MHz, DMSO-d$_6$) δ (ppm): 0.88 (t, J=6.9 Hz, 3H), 1.23-1.31 (m, 2H), 1.41-1.50 (m, 2H), 1.88 (s, 3H), 2.17-2.23 (m, 2H), 7.44 (br s, 1H), 8.02 (br s, 1H), 9.88 (br s, 1H).

Step 2: In a manner similar to that in Step 2 of Reference Example 1, Compound 23 (255 mg, 57%) was obtained from 2-hexanone=thiosemicarbazone (300 mg, 1.73 mmol) prepared above.

$^1$H NMR (270 MHz, CDCl$_3$) δ (ppm): 0.90 (t, J=6.9 Hz, 3H), 1.23-1.38 (m, 3H), 1.52-1.56 (m, 1H), 1.84-2.18 (m, 1H), 1.97 (s, 3H), 2.18 (s, 3H), 2.19 (s, 3H), 2.44-2.55 (m, 1H), 8.68 (br s, 1H).

Reference Example 21

Compound 24

Step 1: In a manner similar to that in Step 1 of Reference Example 1, benzylacetone=thiosemicarbazone (788 mg, 89%) was obtained from benzylacetone (593 mg, 4.00 mmol) and thiosemicarbazide (367 mg, 4.03 mmol).

$^1$H NMR (270 MHz, DMSO-d$_6$) δ (ppm): 1.92 (s, 3H), 2.52 (m, 2H), 2.84 (m, 2H), 7.14-7.30 (m, 5H), 7.43 (br s, 1H), 8.03 (br s, 1H), 9.94 (br s, 1H).

Step 2: In a manner similar to that in Step 2 of Reference Example 1, Compound 24 (382 mg, 92%) was obtained from benzylacetone=thiosemicarbazone (300 mg, 1.36 mmol) prepared above.

$^1$H NMR (270 MHz, CDCl$_3$) δ (ppm): 2.00 (s, 3H), 2.13 (dd, J=2.3, 10.2 Hz, 1H), 2.17 (s, 3H), 2.19 (s, 3H), 2.59 (dd, J=2.2, 10.2 Hz, 1H), 2.87 (br d, J=12.2 Hz, 1H), 2.95 (br s, J=11.8 Hz, 1H), 7.14-7.29 (m, 5H), 8.39 (br s, 1H).

Reference Example 22

Compound 25

Step 1: In a manner similar to that in Step 1 of Reference Example 1, benzylideneacetone=thiosemicarbazone (730 mg, 80%) was obtained 1 from benzylideneacetone (610 mg, 4.17 mmol) and thiosemicarbazide (371 mg, 4.07 mmol).

$^1$H NMR (300 MHz, CDCl$_3$) δ (ppm): 2.13 (s, 3H), 6.89 (d, J=16.8 Hz, 1H), 7.10 (d, J=16.8 Hz, 1H), 7.27-7.41 (m, 3H), 7.43-7.56 (m, 2H), 7.78 (br s, 1H), 8.26 (br s, 1H), 10.27 (br s, 1H).

Step 2: In a manner similar to that in Step 2 of Reference Example 1, Compound 25 (195 mg, 72%) was obtained from benzylideneacetone=thiosemicarbazone (300 mg, 0.889 mmol) prepared above.

$^1$H NMR (300 MHz, DMSO-d$_6$) δ (ppm): 2.13 (s, 3H), 2.15 (s, 3H), 2.23 (s, 3H), 6.62 (d, J=12.2 Hz, 1H), 6.65 (d, J=12.2 Hz, 1H), 7.20-7.39 (m, 5H), 8.57 (br s, 1H).

Reference Example 23

Compound 26

Step 1: In a manner similar to that in Step 1 of Reference Example 1, 5-nonanone=thiosemicarbazone (553 mg, 64%) was obtained from 5-nonanone (569 mg, 4.00 mmol) and thiosemicarbazide (364 mg, 3.99 mmol).

$^1$H NMR (270 MHz, DMSO-d$_6$) δ (ppm): 0.87 (t, J=6.9 Hz, 6H), 1.20-1.53 (m, 8H), 2.17-2.22 (m, 2M, 2.31-2.37 (m, 2H), 7.40 (br s, 1H), 8.00 (br s, 1H), 10.03 (br s, 1H).

Step 2: In a manner similar to that in Step 2 of Reference Example 1, Compound 26 (245 mg, 59%) was obtained from 5-nonanone=thiosemicarbazone (300 mg, 1.39 mmol) prepared above.

¹H NMR (270 MHz, CDCl₃) δ (ppm): 0.90 (t, J=6.9 Hz, 6H), 1.18-1.37 (m, 6H), 1.55-1.63 (m, 2H), 1.77-1.88 (m, 2H), 2.18 (s, 3H), 2.19 (s, 3H), 2.45-2.56 (m, 2H), 8.90 (br s, 1H).

Reference Example 24

Compound 27

Step 1: In a manner similar to that in Step 1 of Reference Example 1, α-tetralone=thiosemicarbazone (797 mg, 88%) was obtained from α-tetralone (604 mg, 4.13 mmol) and thiosemicarbazide (368 mg, 4.04 mmol).
¹H NMR (270 MHz, DMSO-d₆) δ (ppm): 1.78-1.82 (m, 2H), 2.65-2.75 (m, 4H), 7.15-7.27 (m, 3H), 7.97 (br s, 1H), 8.20-8.40 (m, 2H), 10.10 (br s, 1H).
Step 2: In a manner similar to that in Step 2 of Reference Example 1, Compound 27 (324 mg, 78%) was obtained from α-tetralone=thiosemicarbazone (300 mg, 1.37 mmol) prepared above.
¹H NMR (270 MHz, CDCl₃) δ (ppm): 1.89 (s, 3H), 2.09-2.22 (m, 2H), 2.28 (s, 3H), 2.36-2.41 (m, 1H), 2.80-2.86 (m, 2H), 2.97-3.08 (m, 1H), 7.01 (br d, J=8.6 Hz, 1H), 7.08-7.18 (m, 2H), 7.40 (br d, J=7.3 Hz, 1H), 9.24 (br s, 1H).

Reference Example 25

Compound 28

Step 1: In a manner similar to that in Step 1 of Reference Example 1, β-tetralone=thiosemicarbazone (684 mg, 75%) was obtained from␣β-tetralone (607 mg, 4.15 mmol) and thiosemicarbazide (379 mg, 4.16 mmol).
Step 2: In a manner similar to that in Step 2 of Reference Example 1, Compound 28 (301 mg, 65%) was obtained from β-tetralone=thiosemicarbazone (334 mg, 1.53 mmol) prepared above.
¹H NMR (270 MHz, DMSO-d₆) δ (ppm): 2.12 (s, 3H), 2.15-2.30 (m, 1H), 2.24 (s, 3H), 3.05-3.09 (m, 2H), 3.14 (br d, J=15.8 Hz, 1H), 3.23-3.41 (m, 1H), 4.38 (br d, J=15.8 Hz, 1H), 6.99-7.00 (m, 1H), 7.02-7.25 (m, 3H), 8.42 (br s, 1H).

Reference Example 26

Compound 29

Step 1: In a manner similar to that in Step 1 of Reference Example 1, 1-indanone=thiosemicarbazone (1.54 g, 94%) was obtained from 1-indanone (1.06 g, 8.00 mmol) and thiosemicarbazide (740 mg, 8.12 mmol).
¹H NMR (270 MHz, DMSO-d₆) δ (ppm): 2.85-2.89 (m, 2H), 3.03-3.08 (m, 2H), 7.28-7.38 (m, 3H), 7.87 (br d, J=7.6 Hz, 1H), 7.92 (br s, 1H), 8.17 (br s, 1H), 10.2 (br s, 1H),
Step 2: In a manner similar to that in Step 2 of Reference Example 1, Compound 29 (184 mg, 44%) was obtained from 1-indanone=thiosemicarbazone (300 mg, 1.46 mmol) prepared above.
¹H NMR (270 MHz, CDCl₃) δ (ppm): 2.17 (s, 3H), 2.24 (s, 3H), 2.58-2.65 (m, 1H), 2.96-3.07 (m, 1H), 3.13-3.21 (m, 2H), 7.15-7.27 (m, 3H), 7.32-7.37 (m, 1H), 9.60 (br s, 1H).

Reference Example 27

Compound 30

Step 1: In a manner similar to that in Step 1 of Reference Example 1, cyclohexanone=thiosemicarbazone (479 mg, 70%) was obtained from cyclohexanone (393 mg, 4.00 mmol) and thiosemicarbazide (364 mg, 3.99 mmol).
¹H NMR (270 MHz, DMSO-d₆) δ (ppm): 1.55 (br s, 6H), 2.19-2.23 (m, 2H), 2.38 (br s, 2H), 7.50 (br s, 1H), 7.93 (br s, 1H), 10.13 (br s, 1H).
Step 2: In a manner similar to that in Step 2 of Reference Example 1, Compound 30 (214 mg, 72%) was obtained from cyclohexanone=thiosemicarbazone (200 mg, 1.17 mmol) prepared above.
¹H NMR (300 MHz, CDCl₃) δ (ppm): 1.25-1.53 (m, 3H), 1.58-1.68 (m, 1H), 1.81-1.86 (m, 2H), 2.03-2.08 (m, 2H), 2.16 (s, 3H), 2.17 (s, 3H), 2.90-3.01 (m, 2H), 7.95 (br s, 1H).

Reference Example 28

Compound 31

In a manner similar to that in Step 1 and 2 of Reference Example 1, Compound 31 (214 mg, 20%) was obtained from 2-norbornanone (452 mg, 4.10 mmol) and thiosemicarbazide (377 mg, 4.14 mmol).
¹H NMR (270 MHz, CDCl₃) δ (ppm): 1.32-1.67 (m, 5H), 1.76-1.89 (m, 3H), 2.18 (s, 3H), 2.19 (br s, 1H), 2.21 (s, 3H), 2.26 (br s, 1H), 3.60 (br d, J=13.9 Hz, 1H), 8.20 (br s, 1H).

Reference Example 29

Compound 32

In a manner similar to that in Step 1 and 2 of Reference Example 1, Compound 32 (214 mg, 32%) was obtained from 1'-acetonaphthone (344 mg, 2.02 mmol) and thiosemicarbazide (190 mg, 2.08 mmol).
¹H NMR (270 MHz, CDCl₃) δ (ppm): 2.06 (s, 3H), 2.07 (s, 3H), 2.33 (s, 3H), 7.45-7.65 (m, 4H), 7.89-7.99 (m, 3H), 11.50 (br s, 1H).

Reference Example 30

Compound 33

Step 1: In a manner similar to that in Step 1 of Reference Example 1, 2'-acetonaphthone=thiosemicarbazone (448 mg, 92%) was obtained from 2'-acetonaphthone (342 mg, 2.10 mmol) and thiosemicarbazide (189 mg, 2.07 mmol).
¹H NMR (270 MHz, DMSO-d₆) δ (ppm): 2.42 (s, 3H), 7.53 (m, 2H), 7.86-8.05 (m, 4H), 8.28-8.34 (m, 3H), 10.28 (br s, 1H).
Step 2: In a manner similar to that in Step 2 of Reference Example 1, Compound 33 (302 mg, 90%) was obtained from 2'-acetonaphthone=thiosemicarbazone (250 mg, 1.03 mmol) prepared above.
¹H NMR (270 MHz, DMSO-d₆) δ (ppm): 2.02 (s, 3H), 2.22 (s, 3H), 2.38 (s, 3H), 7.51-7.55 (m, 3H), 7.85-7.95 (m, 4H), 11.68 (br s, 1H).

Reference Example 31

Compound 34

Step 1: In a manner similar to that in Step 1 of Reference Example 1, 1-(2-pyridyl)ethanone=thiosemicarbazone (694 mg, 88%) was obtained from 2-acetylpyridine (485 mg, 4.00 mmol) and thiosemicarbazide (369 mg, 4.05 mmol).
1H NMR (270 MHz, DMSO-d₆) δ (ppm): 2.38 (s, 3H), 7.37 (br t, J=6.3 Hz, 1H), 7.78 (br t, J=7.2 Hz, 1H), 8.13 (br s, 1H), 8.40 (br s, 1H), 8.41 (br d, J=8.2 Hz, 1H), 8.56 (br d, J=6.6 Hz, 1H), 10.31 (br s, 1H).

Step 2: In a manner similar to that in Step 2 of Reference Example 1, Compound 34 (160 mg, 37%) was obtained from 1-(2-pyridyl)ethanone=thiosemicarbazone (304 mg, 1.56 mmol) prepared above.

$^1$H NMR (270 MHz, CDCl$_3$) δ (ppm): 2.09 (s, 3H), 2.26 (s, 3H), 2.42 (s, 3H), 7.17 (br t, J=6.9 Hz, 1H), 7.38 (br d, J=8.2 Hz, 1H), 7.68 (br t, J=7.7 Hz, 1H), 8.44 (br s, 1H), 8.58 (br d, J=6.3 Hz, 1H).

Reference Example 32

Compound 35

Step 1: In a manner similar to that in Step 1 of Reference Example 1, 1-(3-pyridynethanone=thiosemicarbazone (722 mg, 93%) was obtained from 3-acetylpyridine (484 mg, 4.00 mmol) and thiosemicarbazide (388 mg, 4.00 mmol).

$^1$H NMR (270 MHz, DMSO-d$_6$) δ (ppm): 2.32 (s, 3H), 7.32-742 (m, 1H), 8.07 (br s, 1H), 8.29-8.34 (m, 2H), 8.54-8.57 (m, 1H), 9.09 (br s, 1H), 10.32 (br s, 1H).

Step 2: In a manner similar to that in Step 2 of Reference Example 1, Compound 35 (213 mg, 72%) was obtained from 1-(3-pyridyl)ethanone=thiosemicarbazone (205 mg, 1.05 mmol) prepared above.

$^1$H NMR (270 MHz, CDCl$_3$) δ (ppm): 2.14 (s, 3H), 2.21 (s, 3H), 2.39 (s, 3H), 7.31 (br dd, J=5.4, 7.9 Hz, 1H), 7.75 (br d, J=7.9 Hz, 1H), 8.52 (br d, J=5.4 Hz, 1H), 8.72 (br s, 1H), 9.08 (br s, 1H).

Reference Example 33

Compound 36

Step 1: In a manner similar to that in Step 1 of Reference Example 1, 1-(4-pyridyl)ethanone=thiosemicarbazone (722 mg, 95%) was obtained from 4-acetylpyridine (507 mg, 4.19 mmol) and thiosemicarbazide (408 mg, 4.46 mmol).

Step 2: In a manner similar to that in Step 2 of Reference Example 1, Compound 36 (389 mg, 85%) was obtained from 1-(4-pyridyl)ethanone=thiosemicarbazone (318 mg, 1.64 mmol) prepared above.

$^1$H NMR (270 MHz, CDCl$_3$) δ (ppm): 2.16 (s, 3H), 2.25 (s, 3H), 2.35 (s, 3H), 7.30 (d, J=6.3 Hz, 2H), 8.46 (br s, 1H), 8.60 (d, J=6.3 Hz, 2H).

Reference Example 34

Compound 37

Step 1: In a manner similar to that in Step 1 of Reference Example 1, 1-pyrazinylethanone=thiosemicarbazone (714 mg, 92%) was obtained from acetylpyrazine (489 mg, 4.00 mmol) and thiosemicarbazide (366 mg, 4.00 mmol). Step 2: In a manner similar to that in Step 2 of Reference Example 1, Compound 37 (489 mg, 85%) was obtained from 1-pyrazinylethanone=thiosemicarbazone (400 mg, 2.05 mmol) prepared above.

$^1$H NMR (270 MHz, CDCl$_3$) δ (ppm): 2.16 (s, 3H), 2.26 (s, 3H), 2.42 (s, 3H), 8.96 (br s, 1H), 8.46 (d, J=2.7 Hz, 1H), 8.52 (dd, J=1.7, 2.7 Hz, 1H), 8.71 (d, J=1.7 Hz, 1H).

Reference Example 35

Compound 38

Step 1: In a manner similar to that in Step 1 of Reference Example 1, 1-(2-pyrrolynethanone=thiosemicarbazone (408 mg, 55%) was obtained from 2-acetylpyrrole (437 mg, 4.00 mmol) and thiosemicarbazide (374 mg, 4.09 mmol).

Step 2: In a manner similar to that in Step 2 of Reference Example 1, Compound 38 (504 mg, 95%) was obtained from 1-(2-pyrrolyl)ethanone=thiosemicarbazone (314 mg, 1.72 mmol) prepared above.

$^1$H NMR (270 MHz, CDCl$_3$) δ (ppm): 2.12 (s, 3H), 2.21 (s, 3H), 2.38 (s, 3H), 2.55 (s, 3H), 6.17-6.22 (m, 2H), 7.11 (br s, 1H), 8.13 (br s, 1H).

Reference Example 36

Compound 39

Step 1: In a manner similar to that in Step 1 of Reference Example 1, 1-(2-furyl)ethanone=thiosemicarbazone (441 mg, 60%) was obtained from 2-acetylfuran (444 mg, 4.00 mmol) and thiosemicarbazide (368 mg, 4.03 mmol).

Step 2: In a manner similar to that in Step 2 of Reference Example 1, Compound 39 (217 mg, 83%) was obtained from 1-(2-furyl)ethanone=thiosemicarbazone (180 mg, 0.982 mmol) prepared above.

$^1$H NMR (270 MHz, CDCl$_3$) δ (ppm): 2.13 (s, 3H), 2.22 (s, 3H), 2.30 (s, 3H), 6.31 (m, 2H), 7.36 (br s, 1H), 8.43 (br s, 1H).

Reference Example 37

Compound 40

Step 1: In a manner similar to that in Step 1 of Reference Example 1, 1-(2-thienyl)ethanone=thiosemicarbazone (636 mg, 78%) was obtained from 2-acetylthiophene (521 mg, 4.13 mmol) and thiosemicarbazide (376 mg, 4.11 mmol).

Step 2: In a manner similar to that in Step 2 of Reference Example 1, Compound 40 (549 mg, 78%) was obtained from 1-(2-thienyl)ethanone=thiosernicarbazone (498 mg, 2.50 mmol) prepared-above.

$^1$H NMR (300 MHz, CDCl$_3$) δ (ppm): 2.07 (s, 3H), 2.24 (s, 3H), 2.42 (s, 3H), 6.89 (br t, J=7.2 Hz, 1H), 7.06 (dd, J=6.9, 7.2 Hz 1H), 7.24 (br d, J=6.9 Hz, 1H), 8.81 (br s, 1H).

Reference Example 38

Compound 41

In a manner similar to that in Reference Example 8, Compound 41 (148 mg, 52%) was obtained in from Compound 40 (260 mg, 0.918 mmol) prepared in Reference Example 37.

$^1$H NMR (270 MHz, CDCl$_3$) δ (ppm): 1.36 (t, J=7.0 Hz, 3H), 2.25 (s, 3H), 2.30 (s, 3H), 2.43 (s, 3H), 3.92 (br q, J=7.0 Hz, 2H), 6.91 (br t, J=5.2 Hz, 1H), 7.06 (br d, J=5.2 Hz, 1H), 7.24 (br d, J=5.2 Hz, 1H).

Reference Example 39

Compound 42

Step 1: In a manner similar to that in Step 1 of Reference Example 1, 1-(3-methyl-2-thienypethanone= thiosemicarbazone (410 mg, 48%) was obtained from 2-acetyl-3-methylthiophene (561 mg, 4.00 mmol) and thiosemicarbazide (374 mg, 4.09 mmol).

Step 2: In a manner similar to that in Step 2 of Reference Example 1, Compound 42 (335 mg, 93%) was obtained from 1-(3-methyl-2-thienyl)ethanone=thiosemicarbazone (260 mg, 1.22 mmol) prepared above.

¹H NMR (270 MHz, CDCl₃) δ (ppm): 2.02 (s, 3H), 2.19 (s, 3H), 2.24 (s, 3H), 2.38 (s, 3H), 6.78 (d, J=5.0 Hz, 1H), 7.07 (d, J=5.0 Hz, 1H), 9.37 (br s, 1H).

Reference Example 40

Compound 43

Step 1: In a manner similar to that in Step 1 of Reference Example 1, 1-(benzo[b]thiophen-2-yl)ethanone= thiosemicarbazone (990 mg, 99%) was obtained from 1-(benzo[b]thiophen-2-yl)ethanone (705 mg, 4.00 mmol) and thiosemicarbazide (370 mg, 4.05 mmol).
¹H NMR (270 MHz, DMSO-d₆) δ (ppm): 2.40 (s, 3H), 7.36-7.41 (m, 2H), 7.45 (br s, 1H), 7.81-7.90 (m, 3H), 8.42 (br s, 1H), 10.56 (br s, 1H).
Step 2: In a manner similar to that in Step 2 of Reference Example 1, Compound 43 (599 mg, 90%) was obtained from 1-(benzablthiophen-2-yl)ethanone=thiosemicarbazone (500 mg, 2.01 mmol) prepared above.
¹H NMR (270 MHz, DMSO-d₆) δ (ppm): 2.04 (s, 3H), 2.17 (s, 3H), 2.38 (s, 3H), 7.31-7.40 (m, 3H), 7.79 (br d, J=7.6 Hz, 1H), 7.89 (br d, J=7.8 Hz, 1H), 11.75 (br s, 1H).

Reference Example 41

Compound 44

Step 1: In a manner similar to that in Step 1 of Reference Example 1, 1-(3-thienyl)ethanone=thiosemicarbazone (839 mg, 98%) was obtained from 3-acetylthiophene (520 mg, 4.12 mmol) and thiosemicarbazide (366 mg, 4.00 mmol).
¹H NMR (270 MHz, DMSO-d₆) δ (ppm): 2.27 (s, 3H), 7.52 (br d, J=5.3 Hz, 1H), 7.83 (br d, J=5.3 Hz, 1H), 7.95 (br s, 1H), 8.22 (br s, 1H), 10.08 (br s, 1H).
Step 2: In a manner similar to that in Step 2 of Reference Example 1, Compound 44 (540 mg, 83%) was obtained from 1-(3-thienyDethanone=thiosemicarbazone (458 mg, 2.30 mmol) prepared above.
¹H NMR (270 MHz, DMSO-d₆) δ (ppm): 2.02 (s, 3H), 2.15 (s, 3H), 2.25 (s, 3H), 7.05 (br d, J=6.0 Hz, 1H), 7.37 (br s, 1H), 7.47 (br d, J=6.0 Hz, 1H).

Reference Example 42

Compound 45

Step 1: In a manner similar to that in Step 1 of Reference Example 1, 1-(2-thiazolyl)ethanone=thiosemicarbazone (711 mg, 90%) was obtained from 2-acetylthiazole (379 mg, 4.15 mmol) and thiosemicarbazide (366 mg, 4.00 mmol).
¹H NMR (270 MHz, DMSO-d₆) δ (ppm): 2.42 (s, 3H), 7.67 (br s, 1H), 7.79 (br d, J=4.3 Hz, 1H), 7.87 (br d, J=4.3 Hz, 1H), 8.51 (br s, 1H), 10.65 (br s, 1H).
Step 2: In a manner similar to that in Step 2 of Reference Example 1, Compound 45 (374 mg, 45%) was obtained from 1-(2-thiazolyl)ethanone=thiosemicarbazone (374 mg, 1.87 mmol) prepared above.
¹H NMR (270 MHz, DMSO-d₆) δ (ppm): 2.03 (s, 3H), 2.18 (s, 3H), 2.31 (s, 3H), 7.74-7.79 (m, 2H), 11.70 (br s, Reference Example 43

Compound 46

In a manner, similar to that in Step 1 and 2 of Reference Example 1, Compound 46 (141 mg, 10%) was obtained from 2'-methylacetophenone (627 mg, 4.67 mmol) and thiosemicarbazide (374 mg, 4.09 mmol).
¹H NMR (270 MHz, CDCl₃) δ (ppm): 1.99 (br s, 1H), 2.21 (s, 3H), 2.33 (s, 3H), 2.38 (s, 3H), 7.15-7.20 (m, 3H), 7.38 (m, 1H), 8.90 (br s, 1H).

Reference Example 44

Compound 47

Step 1: In a manner similar to that in Step 1 of Reference Example 1, 3'-methylacetophenone=thiosemicarbazone (791 mg, 89%) was obtained from 3'-methylacetophenone (540 mg, 4.02 mmol) and thiosemicarbazide (369 mg, 4.04 mmol).
Step 2: In a manner similar to that in Step 2 of Reference Example 1, Compound 47 (316 mg, 79%) was obtained from 3'-methylacetophenone=thiosemicarbazone (300 mg, 1.36 mmol) prepared above.
¹H NMR (270 MHz, CDCl₃) δ (ppm): 2.15 (s, 3H), 2.23 (s, 3H), 2.34 (s, 3H), 2.37 (s, 3H), 7.01-7.09 (m, 1H), 7.19-7.30 (m, 3H), 7.90 (br s, 1H).

Reference Example 45

Compound 48

Step 1: In a manner similar to that in Step 1 of Reference Example 1, 4'-methylacetophenone=thiosemicarbazone (767 mg, 93%) was obtained from 4'-methylacetophenone (536 mg, 3.99 mmol) and thiosemicarbazide (382 mg, 4.19 mmol).
¹H NMR (270 MHz, DMSO-d₆) δ (ppm): 2.27 (s, 3H), 2.32 (s, 3H), 7.18 (d, J=7.9 Hz, 2H), 7.82 (d, J=7.9 Hz, 2H), 7.88 (br s, 1H), 8.23 (br s, 1H), 10.15 (br s, 1H).
Step 2: In a manner similar to that in Step 2 of Reference Example 1, Compound 48 (224 mg, 80%) was obtained from 4'-methylacetophenone=thiosemicarbazone (200 mg, 0.965 mmol) prepared above.
¹H NMR (270 MHz, DMSO-d₆) δ (ppm): 2.06 (s, 3H), 2.24 (s, 3H), 2.31 (s, 3H), 2.36 (s, 3H), 7.13 (d, J=8.3 Hz, 2H), 7.31 (d, J=8.3 Hz, 2H), 8.40 (br s, 1H).

Reference Example 46

Compound 49

Step 1: In a manner similar to that in Step 1 of Reference Example 1, 2'-ethylpropiophenone=thiosemicarbazone (672 mg, 71%) was obtained from 2'-ethylpropiophenone (649 mg, 4.00 mmol) and thiosemicarbazide (378 mg, 4.14 mmol).
Step 2: In a manner similar to that in Step 2 of Reference Example 1, Compound 49 (759 mg, 88%) was obtained from 2'-ethylpropiophenone=thiosemicarbazone (300 mg, 1.27 mmol) prepared above.
¹H NMR (270 MHz, CDCl₃) δ (ppm): 1.13 (t, J=6.9 Hz, 3H), 1.24 (t, J=7.3 Hz, 3H), 1.96 (s, 3H), 2.20 (m, 1H), 2.24 (s, 3H), 2.71 (m, 2H), 3.14 (m, 1H), 7.13 (br t, J=7.1 Hz, 1H), 7.21-7.26 (m, 2H), 7.51 (br d, J=7.9 Hz, 1H), 8.87 (br s, 1H).

Reference Example 47

Compound 50

Step 1: In a manner similar to that in Step 1 of Reference Example 1, 2'-methoxyacetophenone=thiosemicarbazone (891 mg, 92%) was obtained from 2'-methoxyacetophenone (601 mg, 4.00 mmol) and thiosemicarbazide (366 mg, 4.00 mmol).

Step 2: In a manner similar to that in Step 2 of Reference Example 1, Compound 50 (64.0 mg, 93%) was obtained from 2'-methoxyacetophenone=thiosemicarbazone (50.0 mg, 0.224 mmol) prepared above.

$^1$H NMR (270 MHz, CDCl$_3$) δ (ppm): 2.08 (s, 3H), 2.29 (s, 3H), 2.45 (s, 3H), 3H), 3.87 (s, 3H), 6.90 (br t, J=7.3 Hz, 1H), 6.91 (br d, J=7.3 Hz, 1H), 7.06 (br d, J=7.3 Hz, 1H), 7.27 (br t, J=7.3 Hz, 1H), 8.31 (br s, 1H).

Reference Example 48

Compound 51

Step 1: In a manner similar to that in Step 1 of Reference Example 1, 3'-methoxyacetophenone=thiosemicarbazone (713 mg, 58%) was obtained from 3'-methoxyacetophenone (601 mg, 4.00 mmol) and thiosemicarbazide (377 mg, 4.12 mmol).

$^1$H NMR (270 MHz, DMSO-d$_6$) δ (ppm): 2.29 (s, 3H), 3.80 (s, 3H), 6.96 (br d, J=7.9 Hz, 1H), 7.30 (br t, J=7.9 Hz, 1H), 7.44 (br s, 1H), 7.46 (br d, J=7.9 Hz, 1H), 7.94 (br s, 1H), 8.28 (br s, 1H), 10.18 (br s, 1H).

Step 2: In a manner similar to that in Step 2 of Reference Example 1, Compound 51 (419 mg, 71%) was obtained from 3'-methoxyacetophenone=thiosemicarbazone (500 mg, 2.24 mmol) prepared above.

$^1$H NMR (270 MHz, CDCl$_3$) δ (ppm): 2.10 (s, 3H), 2.30 (s, 3H), 2.34 (s, 3H), 3.78 (s, 3H), 6.78 (br d, J=7.9 Hz, 1H), 6.94 (br s, 1H), 7.01 (br d, J=7.9 Hz, 1H), 7.25 (br t, J=7.9 Hz, 1H), 9.48 (br s, 1H).

Reference Example 49

Compound 52

Step 1: In a manner similar to that in Step 1 of Reference Example 1, 4'-methoxyacetophenone=thiosemicarbazone (448 mg, 83%) was obtained from 4'-methoxyacetophenone (362 mg, 2.41 mmol) and thiosemicarbazide (225 mg, 2.46 mmol).

Step 2: In a manner similar to that in Step 2 of Reference Example 1, Compound 52 (248 mg, 90%) was obtained from 4'-methoxyacetophenone=thiosemicarbazone (200 mg, 0.896 mmol) prepared above.

$^1$H NMR (270 MHz, CDCl$_3$) δ (ppm): 2.06 (s, 3H), 2.24 (s, 3H), 2.35 (s, 3H), 3.78 (s, 3H), 6.84 (d, J=8.6 Hz, 2H), 7.36 (d, J=8.6 Hz, 2H), 8.56 (br s, 1H).

Reference Example 50

Compound 53

Step 1: In a manner similar to that in Step 1 of Reference Example 1, 2'-fluoroacetophenone=thiosemicarbazone (704 mg, 83%) was obtained from 2'-fluoroacetophenone (558 mg, 4.04 mmol) and thiosemicarbazide (385 mg, 4.12 mmol).

$^1$H NMR (270 MHz, DMSO-d$_6$) δ (ppm): 2.29 (s, 3H), 7.19-7.28 (m, 2H), 7.40-7.48 (m, 1H), 7.74-7.80 (m, 2H), 8.30 (br s, 1H), 10.34 (br s, 1H).

Step 2: In a manner similar to that in Step 2 of Reference Example 1, Compound 53 (199 mg, 71%) was obtained from 2'-fluoroacetophenone=thiosemicarbazone (200 mg, 0.948 mmol) prepared above.

$^1$H NMR (270 MHz, CDCl$_3$) δ (ppm): 2.05 (s, 3H), 2.26 (s, 3H), 2.40 (s, 3H), 7.01-7.12 (m, 2H), 7.23-7.31 (m, 2H), 8.68 (br s, 1H).

Reference Example 51

Compound 54

Step 1: In a manner similar to that in Step 1 of Reference Example 1, 3'-fluoroacetophenone=thiosemicarbazone (772 mg, 92%) was obtained from 3'-fluoroacetophenone (553 mg, 4.00 mmol) and thiosemicarbazide (372 mg, 4.07 mmol).

$^1$H NMR (270 MHz, DMSO-d$_6$) δ (ppm): 2.29 (s, 3H), 7.17-7.24 (m, 1H), 7.38-7.46 (m, 1H), 7.69 (br d, J=8.9 Hz, 1H), 7.88 (br d, J=11.2 Hz, 1H), 8.09 (br s, 1H), 8.31 (br s, 1H), 10.24 (br s, 1H).

Step 2: In a manner similar to that in Step 2 of Reference Example 1, Compound 54 (242 mg, 74%) was obtained from 3'-fluoroacetophenone=thiosemicarbazone (233 mg, 1.10 mmol) prepared above.

$^1$H NMR (270 MHz, CDCl$_3$) δ (ppm): 2.08 (s, 3H), 2.26 (s, 3H), 2.35 (s, 3H), 6.92-6.99 (m, 1H), 7.07-7.13 (m, 1H), 7.18-7.22 (m, 1H), 7.28-7.34 (m, 1H), 8.54 (br s, 1H).

Reference Example 52

Compound 55

Step 1: In a manner similar to that in Step 1 of Reference Example 1, 4'-fluoroacetophenone=thiosemicarbazone (769 mg, 91%) was obtained from 4'-fluoroacetophenone (553 mg, 4.00 mmol) and thiosemicarbazide (376 mg, 4.11 mmol).

Step 2: In a manner similar to that in Step 2 of Reference Example 1, Compound 55 (251 mg, 86%) was obtained from 4'-fluoroacetophenone=thiosemicarbazone (208 mg, 0.986 mmol) prepared above.

$^1$HNMR (270 MHz, CDCl$_3$) δ (ppm): 2.14 (s, 3H), 2.22 (s, 3H), 2.36 (s, 3H), 6.98-7.05 (m, 2H), 7.38-7.44 (m, 2H), 8.09 (br s, 1H).

Reference Example 53

Compound 56

Step 1: In a manner similar to that in Step 1 of Reference Example 1, 2'-chloroacetophenone=thiosemicarbazone (362 mg, 58%) was obtained from 2'-chloroacetophenone (344 mg, 2.23 mmol) and thiosemicarbazide (194 mg, 2.12 mmol).

Step 2: In a manner similar to that in Step 2 of Reference Example 1, Compound 56 (347 mg, 97%) was obtained from 2'-chloroacetophenone=thiosemicarbazone (200 mg, 1.14 mmol) prepared above.

$^1$H NMR (270 MHz, CDCl$_3$) δ (ppm): 1.98 (s, 3H), 2.23 (s, 3H), 2.38 (s, 3H), 7.22-7.27 (m, 2H), 7.37-7.45 (m, 2H), 9.05 (br s, 1H).

Reference Example 54

Compound 57

In a manner similar to that in Reference Example 8, Compound 57 (347 mg, 97%) was obtained from Compound 56 (200 mg, 1.14 mmol) prepared in Reference Example 53.

$^1$H NMR (270 MHz, CDCl$_3$) δ (ppm): 1.35 (t, J=6.9 Hz, 3H), 2.25 (s, 3H), 2.30 (s, 3H), 2.40 (s, 3H), 3.91-3.93 (br s, 2H), 7.22-7.28 (m, 2H), 7.38-7.42 (m, 2H).

Reference Example 55

Compound 58

Step 1: In a manner similar to that in Step 1 of Reference Example 1, 3'-chloroacetophenone=thiosemicarbazone (211 mg, 45%) was obtained from 3'-chloroacetophenone (319 mg, 2.06 mmol) and thiosemicarbazide (188 mg, 2.06 mmol).

Step 2: In a manner similar to that in Step 2 of Reference Example 1, Compound 58 (347 mg, 97%) was obtained from 3'-chloroacetophenone=thiosemicarbazone (200 mg, 1.14 mmol) prepared above.

$^1$H NMR (270 MHz, CDCl$_3$) δ (ppm): 2.01 (s, 3H), 2.19 (s, 3H), 2.25 (s, 3H), 7.29-7.41 (m, 4H), 11.68 (br s, 1H).

Reference Example 56

Compound 59

Step 1: In a manner similar to that in Step 1 of Reference Example 1, 4'-chloroacetophenone=thiosemicarbazone (362 mg, 58%) was obtained from 4'-chloroacetophenone (344 mg, 2.23 mmol) and thiosemicarbazide (194 mg, 2.06 mmol).

Step 2: In a manner similar to that in Step 2 of Reference Example 1, Compound 59 (193 mg, 86%) was obtained from 4'-chloroacetophenone=thiosemicarbazone (164 mg, 0.720 mmol) prepared above.

$^1$H NMR (270 MHz, CDCl$_3$) δ (ppm): 2.11 (s, 3H), 2.23 (s, 3H), 2.24 (s, 3H), 7.30 (d, J=8.6 Hz, 2H), 7.36 (d, J=8.6 Hz, 2H), 8.34 (br s, 1H).

Reference Example 57

Compound 60

Step 1: In a manner similar to that in Step 1 of Reference Example 1, 2'-bromoacetophenone=thiosemicarbazone (392 mg, 69%) was obtained from 2'-bromoacetophenone (415 mg, 2.08 mmol) and thiosemicarbazide (190 mg, 2.08 mmol).

$^1$H NMR (270 MHz, DMSO-d$_6$) δ (ppm): 2.28 (s, 3H), 7.29-7.76 (m, 5H), 8.25 (br s, 1H), 10.35 (br s, 1H).

Step 2: In a manner similar to that in Step 2 of Reference Example 1, Compound 60 (328 mg, 99%) was obtained from 2'-bromoacetophenone=thiosemicarbazone (254 mg, 0.933 mmol) prepared above.

$^1$H NMR (270 MHz, CDCl$_3$) δ (ppm): 2.01 (s, 3H), 2.23 (s, 3H), 2.38 (s, 3H), 7.13 (br t, J=7.6 Hz, 1H), 7.30 (br t, J=7.6 Hz, 1H), 7.47 (br d, J=7.6 Hz, 1H), 7.62 (br s, J=7.6 Hz, 1H), 8.86 (br s, 1H).

Reference Example 58

Compound 61

Step 1: In a manner similar to that in Step 1 of Reference Example 1, 2'-hydroxyacetophenone=thiosemicarbazone (649 mg, 78%) was obtained from 2'-hydroxyacetophenone (544 mg, 4.00 mmol) and thiosemicarbazide (377 mg, 4.12 mmol).

$^1$H NMR (270 MHz, DMSO-d$_6$) δ (ppm): 2.31 (s, 3H), 6.85 (br t, J=7.0 Hz, 1H), 6.88 (br d, J=7.0 Hz, 1H), 7.25 (br t, J=7.0 Hz, 1M), 7.50 (br s, 1H), 7.53 (br d, J=7.0 Hz, 1H), 7.81 (br s, 1H), 8.10 (br s, 1H), 10.35 (br s, 1H).

Step 2: In a manner similar to that in Step 2 of Reference Example 1, Compound 61 (322 mg, 70%) was obtained from 2'-hydroxyacetophenone=thiosemicarbazone (233 mg, 1.10 mmol) prepared above.

$^1$H NMR (270 MHz, DMSO-d$_6$) δ (ppm): 2.04 (s, 3H), 2.06 (s, 3H), 2.23 (s, 3H), 2.24 (s, 3H), 7.12 (br d, J=7.6 Hz, 1H), 7.23 (br t, J=7.6 Hz, 1H), 7.35 (br t, J=7.6 Hz, 1H), 7.39 (br d, J=7.6 Hz, 1H), 10.20 (br s, 1H).

Reference Example 59

Compound 62

Step 1: In a manner similar to that in Step 1 of Reference Example 1, 3'-hydroxyacetophenone=thiosemicarbazone (654 mg, 78%) was obtained from 3'-hydroxyacetophenone (546 mg, 4.01 mmol) and thiosemicarbazide (379 mg, 4.15 mmol).

Step 2: In a manner similar to that in Step 2 of Reference Example 1, Compound 62 (351 mg, 84%) was obtained from 3'-hydroxyacetophenone=thiosemicarbazone (262 mg, 1.25 mmol) prepared above.

$^1$H NMR (270 MHz, DMSO-d$_6$) δ (ppm): 1.96 (s, 3H), 2.27 (s, 3H), 2.28 (s, 3H), 2.34 (s, 3H), 7.07 (br d, J=8.4 Hz, 1H), 7.15 (br s, 1H), 7.32 (br d, J=8.4 Hz, 1H), 7.33 (br t, J=8.4 Hz, 1H), 9.24 (br s, 1H).

Reference Example 60

Compound 63

Step 1: In a manner similar to that in Step 1 of Reference Example 1, 3'-hydroxybenzablehyde=thiosemicarbazone (732 mg, 88%) was obtained from 3'-hydroxybenzaldehyde (488 mg, 4.00 mmol) and thiosemicarbazide (378 mg, 4.15 mmol).

$^1$H NMR (270 MHz, DMSO-d$_6$) δ (ppm): 6.80 (m, 1H), 7.13 (br s, 1H), 7.19 (m, 2H), 7.87 (br s, 1H), 7.96 (s, 1H), 8.14 (br s, 1H), 9.56 (br s, 1H), 11.35 (br s, 1H).

Step 2: In a manner similar to that in Step 2 of Reference Example 1, Compound 63 (322 mg, 70%) was obtained from 3'-hydroxybenzaldehyde=thiosemicarbazone (300 mg, 1.43 mmol) prepared above.

$^1$H NMR (270 MHz, DMSO-d$_6$) δ (ppm): 2.18 (s, 3H), 2.25 (s, 3H), 2.28 (s, 3H), 6.86 (s, 1H), 7.04 (br d, J=7.4 Hz, 1H), 7.05 (s, 1H), 7.19 (br d, J=7.4 Hz, 1H), 7.31 (br t, J=7.4 Hz, 1H), 8.16 (br s, 1H).

Reference Example 61

Compound 64

Step 1: In a manner similar to that in Step 1 of Reference Example 1, 4'-hydroxyacetophenone=thiosemicarbazone (830 mg, 99%) was obtained from 4'-hydroxyacetophenone (544 mg, 4.00 mmol) and thiosemicarbazide (387 me, 4.25 mmol).

$^1$H NMR (270 MHz, DMSO-d$_6$) δ (ppm): 2.23 (s, 3H), 6.75 (d, J=8.5 Hz, 2H), 7.76 (d, J=8.5 Hz, 2H), 7.78 (br s, 1H), 8.14 (br s, 1H), 9.75 (s, 1H), 10.05 (s, 1H).

Step 2: In a manner similar to that in Step 2 of Reference Example 1, Compound 64 (199 mg, 61%) was obtained from 4'-hydroxyacetophenone=thiosemicarbazone (202 mg, 0.965 mmol) prepared above.

$^1$H NMR (270 MHz, CDCl$_3$) δ (ppm): 2.15 (s, 3H), 2.22 (s, 3H), 2.23 (s, 3H), 2.29 (s, 3H), 7.07 (br d, J=8.6 Hz, 2H), 7.43 (br d, J=8.6 Hz, 2H), 7.99 (br s, 1H).

Reference Example 62

Compound 65

Step 1: In a manner similar to that in Step 1 of Reference Example 1, 2'-nitroacetophenone=thiosemicarbazone (785 mg, 81%) was obtained from 2'-nitroacetophenone (673 mg, 4.08 mmol) and thiosemicarbazide (365 mg, 3.99 mmol).

¹H NMR (270 MHz, DMSO-d₆) δ (ppm): 2.27 (s, 3H), 7.32 (br s, 1H), 7.60-7.68 (m, 1H), 7.72-7.79 (m, 2H), 7.96 (br d, J=7.9 Hz, 1H), 8.31 (br s, 1H), 10.52 (br s, 1H).

Step 2: In a manner similar to that in Step 2 of Reference Example 1, Compound 65 (548 mg, 94%) was obtained from 2'-nitroacetophenone=thiosemicarbazone (431 mg, 1.81 mmol) prepared above.

¹H NMR (270 MHz, CDCl₃) δ (ppm): 2.04 (s, 3H), 2.07 (s, 3H), 2.23 (s, 3H), 7.49-7.71 (m, 4H), 11.73 (br s, 1H).

Reference Example 63

Compound 66

Step 1: In a manner similar to that in Step 1 of Reference Example 1, 3'-nitroacetophenone=thiosemicarbazone (910 mg, 75%) was obtained from 3'-nitroacetophenone (661 mg, 4.00 mmol) and thiosemicarbazide (370 mg, 4.05 mmol).

¹H NMR (270 MHz, DMSO-d₆) δ (ppm): 2.37 (s, 3H), 7.67 (br t, J=7.9 Hz, 1H), 8.16 (br s, 1H), 8.23 (br d, J=7.9 Hz, 1H), 8.40 (br s, 1H), 8.43 (br s, J=7.9 Hz, 1H), 8.61 (br s, 1H), 10.40 (br s, 1H).

Step 2: In a manner similar to that in Step 2 of Reference Example 1, Compound 66 (409 mg, 60%) was obtained from 3'-nitroacetophenone=thiosemicarbazone (506 mg, 2.12 mmol) prepared above.

¹H NMR (270 MHz, CDCl₃) δ (ppm): 2.15 (s, 3H), 2.25 (s, 3H), 2.40 (s, 3H), 7.53 (br t, J=8.3 Hz, 1H), 7.73 (br d, J=8.3 Hz, 1H), 8.15 (br d, J=8.3 Hz, 1H), 8.30 (br s 2H).

Reference Example 64

Compound 67

Step 1: In a manner similar to that in Step 1 of Reference Example 1, 4'-nitroacetophenone=thiosemicarbazone (475 mg, 94%) was obtained from 4'-nitroacetophenone (350 mg, 2.12 mmol) and thiosemicarbazide (195 mg, 2.13 mmol).

Step 2: In a manner similar to that in Step 2 of Reference Example 1, Compound 67 (216 mg, 40%) was obtained from 4'-nitroacetophenone=thiosemicarbazone (397 mg, 1.67 mmol) prepared above.

¹H NMR (270 MHz, CDCl₃) δ (ppm): 2.15 (s, 3H), 2.24 (s, 3H), 2.38 (s, 3H), 7.59 (d, J=8.6 Hz, 2H), 8.20 (d, J=8.6 Hz, 2H), 8.30 (br s, 1H).

Reference Example 65

Compound 68

Compound 61 (118 mg, 0.352 mmol) prepared in Reference Example 58 was dissolved in methanol (5 mL), and to the solution was added potassium carbonate (200 mg, 1.48 mmol) and the mixture was stirred at room temperature for 10 minutes. The reaction mixture was filtered, and the filtrate was concentrated under reduced pressure. After the residue was dissolved in ethyl acetate, to the solution was added water and 1 mol/L hydrochloric acid, and the mixture was extracted with ethyl acetate. The organic layer was washed with saturated aqueous sodium chloride and dried over anhydrous sodium sulfate, and the solvent was evaporated under reduced pressure. The resulting yellow oil was dissolved in methanol (3 mL). To the solution was added diisopropyl ether (10 mL), and the deposited crystals were collected by filtration and dried to obtain Compound 68 (96.9 mg, 94%).

¹HNMR (270 MHz, DMSO-d₆) δ (ppm): 1.98 (s, 3H), 2.23 (s, 3H), 2.35 (s, 3H), 6.72 (br t, J=7.6 Hz, 1H), 6.83 (br d, J=7.6 Hz, 1H), 6.88 (br d, J=7.6 Hz, 1H), 7.10 (br t, J=7.6 Hz, 1H), 9.95 (br s, 1H), 11.45 (br s, 1H).

Reference Example 66

Compound 69

In a manner similar to that in Reference Example 65, Compound 69 (101 mg, 82%) was obtained from Compound 62 (140 mg, 0.417 mmol) prepared in Reference Example 59.

¹H NMR (270 MHz, DMSO-d₆) δ (ppm): 2.01 (s, 3H), 2.18 (s, 3H), 2.23 (s, 3H), 6.66 (br t, J=7.9 Hz, 1H), 6.69 (br s, 1H), 6.76 (br d, J=7.9 Hz, 1H), 7.13 (br t, J=7.9 Hz, 1H), 9.46 (br s, 1H), 11.60 (br s, 1H).

Reference Example 67

Compound 70

In a manner similar to that in Reference Example 65, Compound 70 (88 mg, 91%) was obtained from Compound 64 (110 mg, 0.328 mmol) prepared in Reference Example 61.

¹H NMR (270 MHz, CDCl₃) δ (ppm): 2.00 (s, 3H), 2.16 (s, 3H), 2.23 (s, 3H), 6.71 (d, J=8.6 Hz, 2H), 7.15 (d, J=8.6 Hz, 2H), 9.48 (br s, 1H), 11.6 (br s, 1H).

Reference Example 68

Compound 71

Step 1: In a manner similar to that in Step 1 of Reference Example 1, 3'-cyanoacetophenone=thiosemicarbazone (863 mg, 99%) was obtained from 3-acetylbenzonitrile (581 mg, 4.00 mmol) and thiosemicarbazide (370 mg, 4.05 mmol).

Step 2: In a manner similar to that in Step 2 of Reference Example 1, Compound 71 (274 mg, 68%) was obtained from 3'-cyanoacetophenone=thiosemicarbazone (300 mg, 1.34 mmol) prepared above.

¹H NMR (270 MHz, CDCl₃) δ (ppm): 2.08 (s, 3H), 2.26 (s, 3H), 2.36 (s, 3H), 7.46 (m, 1H), 7.56 (m, 1H), 7.68 (m, 1H), 7.71 (br s, 1H), 8.73 (br s, 1H).

Reference Example 69

Compound 72

Step 1: In a manner similar to that in Step 1 of Reference Example 1, 4'-cyanoacetophenone=thiosemicarbazone (430 mg, 98%) was obtained from 4-acetylbenzonitrile (290 mg, 2.0 mmol) and thiosemicarbazide (185 mg, 2.02 mmol).

¹H NMR (270 MHz, DMSO-d₆) δ (ppm): 2.30 (s, 3H), 7.82 (d, J=8.4 Hz, 2H), 8.12 (br s, 1H), 8.14 (d, J=8.4 Hz, 2H), 8.40 (br s, 1H), 10.51 (br s, 1H).

Step 2: In a manner similar to that in Step 2 of Reference Example 1, Compound 72 (494 mg, 94%) was obtained from 4'-cyanoacetophenone=thiosemicarbazone (380 mg, 1.74 mmol) prepared above.

1H NMR (270 MHz, DMSO-d₆) δ (ppm): 2.01 (s, 3H), 2.18 (s, 3H), 2.31 (s, 3H), 7.54 (d, J=11.7 Hz, 2H), 7.81 (d, J=11.7 Hz, 2H), 11.73 (br s, 1H).

Reference Example 70

Compound 73

Step 1: In a manner similar to that in Step 1 of Reference Example 1, 3'-trifluoromethylacetophenone=thiosemicarbazone (888 mg, 63%) was obtained from 3'-trifluoromethylacetophenone (765 mg, 4.07 mmol) and thiosemicarbazide (370 mg, 4.05 mmol).

Step 2: In a manner similar to that in Step 2 of Reference Example 1, Compound 73 (270 mg, 68%) was obtained from 3'-trifluoromethylacetophenone=thiosemicarbazone (300 mg, 1.15 mmol) prepared above.

$^1$H NMR (270 MHz, CDCl$_3$) δ (ppm): 2.01 (s, 3H), 2.27 (s, 3H), 2.37 (s, 3H), 7.43 (br t, J=7.6 Hz, 1H), 7.52 (br d, J=7.6 Hz, 1H), 7.63 (br d, J=7.6 Hz, 1H), 7.65 (br s, 1H), 8.89 (br s, 1H).

Reference Example 71

Compound 74

Step 1: In a manner similar to that in Step 1 of Reference Example 1, 2"carboxyacetophenone=thiosemicarbazone (489 mg, 52%) was obtained from 2-acetylbenzoic acid (381 mg, 4.17 mmol) and thiosemicarbazide (381 mg, 4.17 mmol).

Step 2: In a manner similar to that in Step 2 of Reference Example 1, Compound 74 (313 mg, 64%) was obtained from 2'-carboxyacetophenone=thiosemicarbazone (363 mg, 1.53 mmol) prepared above.

$^1$H NMR (270 MHz, CDCl$_3$) δ (ppm): 2.04 (s, 3H), 2.29 (s, 3H), 2.38 (s, 3H), 3.20-3.30 (br s, 1H), 7.88-8.15 (m, 3H), 8.32-8.33 (br m, 1H).

Reference Example 72

Compound 75

Step 1: In a manner similar to that in Step 1 of Reference Example 1, 2',6'-dimethoxyacetophenone= thiosemicarbazone (747 mg, 83%) was obtained from 2',6'-dimethoxyacetophenone (606 mg, 3.98 mmol) and thiosemicarbazide (374 mg, 4.09 mmol).

$^1$H NMR (270 MHz, DMSO-d$_6$) δ (ppm): 2.09 (s, 3H), 3.77 (s, 6H), 6.80 (d, J=8.2 Hz, 2H), 7.44 (t, J=8.2 Hz, 1H), 7.83 (br s, 1H), 8.04 (br s, 1H), 8.31 (br s, 1H).

Step 2: In a manner similar to that in Step 2 of Reference Example 1, Compound 75 (441 mg, 89%) was obtained from 2',6'-dimethoxyacetophenone=thiosemicarbazone (363 mg, 1.61 mmol) prepared above.

$^1$H NMR (270 MHz, CDCl$_3$) δ (ppm): 2.02 (s, 3H), 2.21 (s, 3H), 2.51 (s, 3H), 3.78 (s, 6H), 6.53 (d, J=8.5 Hz, 2H), 7.15 (t, J=8.5 Hz, 1H), 8.70 (br s, 1H).

Reference Example 73

Compound 76

Step 1: In a manner similar to that in Step 1 of Reference Example 1, 3',5'-dihydroxyacetophenone=thiosemicarbazone (707 mg, 78%) was obtained from 3',5'-dihydroxyacetophenone (613 mg, 4.03 mmol) and thiosemicarbazide (376 mg, 4.11 mmol).

$^1$H NMR (270 MHz, DMSO-d$_6$) δ (ppm): 2.20 (s, 3H), 6.25 (br s, 1H), 6.69 (br s, 2H), 2.74 (br s, 1H), 8.26 (br s, 1H), 9.29 (br s, 2H), 10.19 (br s, 1H).

Step 2: In a manner similar to that in Step 2 of Reference Example 1, the white solid was prepared from 3',5'-dihydroxyacetophenone=thiosemicarbazone (622 mg, 2.76 mmol) obtained above. The resulting white solid was dissolved in methanol (120 mL), to the solution was added potassium carbonate (1.2 g, 8.68 mmol), and the mixture was vigorously stirred for 1.5 hours. The reaction mixture was filtered, and the filtrate was concentrated under reduced pressure. Then, to the residue was added ethyl acetate, and the resulting solution was washed with 1 mol/L hydrochloric acid sunsequently with water. The organic layer was dried over anhydrous sodium sulfate, and the solvent was evaporated under reduced pressure. To the residue was added diisopropyl ether, and the deposited crystals were collected by filtration and dried to give Compound 76 (591 mg, 69%).

$^1$H NMR (270 MHz, CDCl$_3$) δ (ppm): 2.01 (s, 3H), 2.17 (s, 3H), 2.18 (s, 3H), 6.10 (br s, 1H), 6.16 (br s, 2H), 9.27 (br s, 2H), 11.59 (br s, 1H).

Reference Example 74

Compound 77

Step 1: In a manner similar to that in Step 1 of Reference Example 1, 3',4'-dihydroxyacetophenone= thiosemicarbazone (747 mg, 83%) was obtained from 3',4'-dihydroxyacetophenone (606 mg, 3.98 mmol) and thiosemicarbazide (374 mg, 4.09 mmol).

$^1$H NMR (270 MHz, DMSO-d$_6$) δ (ppm): 2.20 (s, 3H), 6.72 (br d, J=8.3 Hz, 1H), 7.18 (br d, J=8.3 Hz, 1H), 7.29 (br s, 1H), 7.65 (br s, 1H), 8.18 (br s, 2H), 9.09 (br s, 2H), 10.09 (br s, 1H).

Step 2: In a manner similar to that in Step 2 of Reference Example 73, CompoUnd 77 (441 mg, 89%) was obtained from 3',4'-dihydroxyacetophenone=thiosemicarbazone (363 mg, 1.61 mmol) prepared above.

$^1$H NMR (270 MHz, CDCl$_3$) δ (ppm): 2.01 (s, 3H), 2.06 (s, 3H), 2.20 (s, 3H), 6.62 (br t, J=7.6 Hz, 1H), 6.66 (br d, J=8.2 Hz, 1H), 6.71 (br s, 1H), 8.93 (s, 1H), 8.97 (s, 1H), 11.56 (br s, 1H).

Reference Example 75

Compound 78

Step 1: In a manner similar to that in Step 1 of Reference Example 1, 2',4'-dimethylacetophenone=thiosemicarbazone (110 mg, 12%) was obtained from 2',4'-dimethylacetophenone (598 mg, 4.04 mmol) and thiosemicarbazide (366 mg, 4.00 mmol).

Step 2: In a manner similar to that in Step 2 of Reference Example 1, Compound 78 (107 mg, 77%) was obtained from 2',4'-dimethylacetophenone=thiosemicarbazone (100 mg, 0.452 mmol) prepared above.

$^1$H NMR (270 MHz, CDCl$_3$) δ (ppm): 2.03 (s, 3H), 2.08 (s, 3H), 2.16 (s, 3H), 2.21 (s, 3H), 2.35 (s, 3H), 6.86 (br s, 1H), 6.92 (d, J=7.9 Hz, 1H), 7.07 (d, J=7.9 Hz, 1H), 8.82 (br s, 1H).

Reference Example 76

Compound 79

Step 1: To a solution of hydrazine monohydrate (1.00 mL, 20.6 mmol) in acetonitrile (5.00 mL) was added allyl isothiocyanate (2.00 mL, 20.4 mmol), and the mixture was stirred at 60° C. for 30 minutes. To the reaction mixture was added diethyl ether (50 mL), and the deposited solid was collected by filtration. The collected solid was dried to obtain 4-allylthiosemicarbazide (1.22 g, 46%).

$^1$H NMR (270 MHz, DMSO-d$_6$) δ (ppm): 4.11 (t, J=5.3 Hz, 2H), 4.47 (br s, 2H), 5.03 (d, J=12.3 Hz, 1H), 5.08 (d, J=19.1 Hz, 1H), 5.86 (m, 1H), 7.88 (br s, 1H), 8.70 (br s, 1H).

Step 2: In a manner similar to that in Step 1 of Reference Example 1, acetophenone=4-allylthiosemicarbazone (1.74 g, 80%) was obtained from acetophenone (1.09 mL, 9.34 mmol) and 4-allylthiosemicarbazide (1.22 g, 9.31 mmol) prepared above.

$^1$H NMR (270 MHz, DMSO-$d_6$) δ (ppm): 2.31 (s, 3H), 4.25 (t, J=5.8 Hz, 2H), 5.10 (d, J=10.5 Hz, 1H), 5.18 (d, J=17.5 Hz, 1H), 5.91 (m, 1H), 7.37-7.42 (m, 3H), 7.81-7.94 (m, 2H), 8.61 (t, J=6.0 Hz, 1H), 10.3 (br s, 1H).

Step 3: Acetophenone=4-allylthiosemicarbazone (30 mg, 0.11 mmol) prepared above was dissolved in chloroform (0.5 mL), and to the solution was added acetyl chloride (0.17 mL, 2.32 mmol) and pyridine (0.190 mL, 2.31 mmol), and the mixture was stirred at room temperature for 5 hours. To the reaction mixture was added 2 mol/L aqueous sodium hydroxide, and the mixture was extracted with ethyl acetate. The organic layer was washed with saturated aqueous ammonium chloride and saturated aqueous sodium chloride, dried over anhydrous sodium sulfate, and the solvent was evaporated. The residue was purified by silica gel column chromatography (ethyl acetate/n-hexane=1/2) to give Compound 79 (25 mg, 89%).

$^1$H NMR (270 MHz, CDCl$_3$) δ (ppm): 2.26 (s, 3H), 2.27 (s, 3H), 2.36 (s, 3H), 4.47-4.53 (m, 2H), 5.24 (d, J=17.3 Hz, 1H), 5.29 (d, J=10.5 Hz, 1H), 5.91 (m, 1H), 7.20-7.45 (m, 5H).

FAB-MS (m/z): 318 (M$^+$+1).

Reference Example 77

Compound 80 and Compound 81

Step 1: In a manner similar to that in Step 3 of Reference Example 76, Compound 80 (42 mg, 5%) was obtained from acetophenone=4-allylthiosemicarbazone (694 mg, 2.97 mmol) prepared in Step 2 of Reference Example 76, isobutyryl chloride (0.63 mL, 5.97 mmol) and pyridine (0.43 mL, 5.26 mmol).

$^1$H NMR (270 MHz, CDCl$_3$) δ (ppm): 1.10 (d, J=6.8 Hz, 3H), 1.13 (d, J=6.9 Hz, 3H), 2.39 (s, 3H), 3.25 (quin., J=7.0 Hz, 1H), 3.84-4.00 (m, 3H), 5.19 (d, J=10.2 Hz, 1H), 5.26 (d, J=17.2 Hz, 1H), 5.93 (m, 1H), 7.20-7.49 (m, 5H).

Step 2: In a manner similar to that in Reference Example 15, Compound 81 (527 mg, 74%) was obtained from Compound 80 (623 mg, 2.05 mmol) prepared above, acetyl chloride (0.59 mL, 8.30 mmol) and pyridine (0.77 mL, 8.28 mmol).

$^1$H NMR (270 MHz, CDCl$_3$) δ (ppm): 1.10 (d, J=6.9 Hz, 3H), 1.12 (d, J=6.9 Hz, 3H), 2.27 (s, 3H), 2.34 (s, 3H), 3.21 (quirt., J=6.9 Hz, 1H), 4.51 (br s, 2H), 5.25 (d, J=17.2 Hz, 1H), 5.30 (d, J=10.7 Hz, 1H), 5.93 (m, 1H), 7.20-7.42 (m, 5H).

AP-MS (m/z): 346 (M$^+$+1).

Reference Example 78

Compound 82

In a manner similar to that in Step 3 of Reference Example 76, Compound 82 (269 mg, 47%) was obtained from acetophenone=thiosemicarbazone (306 mg, 1.59 mmol) prepared in Step 1 of Reference Example 1, pivaloyl chloride (0.40 mL, 3.21 mmol) and pyridine (0.26 mL, 3.22 mmol).

$^1$H NMR (270 MHz, CDCl$_3$) δ (ppm): 1.29 (s, 9H), 1.30 (s, 9H), 2.35 (s, 3H), 7.20-7.43 (m, 5H). 5H), 7.90 (m, 1H)

AP-MS (m/z): 360 (M$^+$−1). .

Reference Example 79

Compound 83 and Compound 84

Step 1: In a manner similar to that in Reference Example 12, Compound 83 (537 mg, 67%) was obtained from Compound 21 (1.00 g, 2.88 mmol) prepared in Reference Example 18.

$^1$H NMR (270 MHz, CDCl$_3$) δ (ppm): 1.12 (d, J=6.9 Hz, 3H), 1.14 (d, J=6.9 Hz, 3H), 2.39 (s, 3H), 2.91 (d, J=4.9 Hz, 3H), 3.30 (m, 1H), 3.90 (br, 1H), 7.20-7.43 (m, 5H).

Step 2: In a manner similar to that in Reference Example 15, Compound 84 (233 mg, 38%) was obtained from Compound 83 (536 mg, 1.93 mmol) prepared above, acetyl chloride (0.28 mL, 3.87 mmol) and pyridine (0.32 mL, 3.90 mmol).

$^1$H NMR (270 MHz, CDCl$_3$) δ (ppm): 1.12 (d, J=6.9 Hz, 3H), 1.14 (d, J=6.9 Hz, 3H), 2.28 (s, 3H), 2.34 (s, 3H), 3.28 (quin., J=6.9 Hz, 1H), 3.46 (br s, 3H), 7.20-7.43 (m, 5H).

FAB-MS (m/z): 320 (M$^+$+1).

Elemental analysis ($C_{16}H_{21}N_3O_2S$): Found (%) C, 60.16; H, 6.63; N, 13.15, Calcd. (%) C, 60.27; H, 6.73; N, 13.20.

Reference Example 80

Compound 85

In a manner similar to that in Step 2 of Reference Example 1, Compound 85 (176 mg, 20%) was obtained from acetophenone=thiosemicarbazone (517 mg, 2.68 mmol) prepared in Step 1 of Reference Example 1 and isobutyric anhydride (2.22 mL, 13.4 mmol).

$^1$H NMR (270 MHz, CDCl$_3$) δppm): 1.09 (d, J=2.6 Hz, 3H), 1.12 (d, J=2.6 Hz, 3H), 1.21 (d, J=2.6 Hz, 3H), 1.23 (d, J=2.6 Hz, 3H), 2.37 (s, 3H), 2.50 (quin., J=6.9 Hz, 1H), 3.20 (quin., J=6.9 Hz, 1H), 7.20-7.48 (m, 513), 7.98 (br s, 1H).

AP-MS (m/z): 334 (M$^+$+1).

Elemental analysis ($C_{17}H_{23}N_3O_2S$): Found (%) C, 61.23; H, 6.95; N, 12.60. Calcd. (%) C, 61.22; H, 6.93; N, 12.63.

Reference Example 81

Compound 86 and Compound 87

Step 1: In a manner similar to that in Reference Example 11, Compound 86 (588 mg, 43%) was obtained from acetophenone=thiosemicarbazone (1.01 g, 5.22 mmol) prepared in Step 1 of Reference Example 1, isobutyric anhydride (1.73 mL, 10.4 mmol) and pyridine (0.84 mL, 10.4 mmol).

$^1$H NMR (270 MHz, CDCl$_3$) δ (ppm): 1.09 (d, J=6.9 Hz, 3H), 1.11 (d, J=6.9 Hz, 3H), 2.40 (s, 3H), 3.21 (quin., J=6.9 Hz, 1H), 4.12 (br s, 2H), 7.20-7.40 (m, 5H).

Step 2: In a manner similar to that in Reference Example 15, Compound 87 (47 mg, 16%) was obtained from Compound 86 (256 mg, 0.97 mmol) prepared above and acetic anhydride (0.46 mL, 4.88 mmol).

$^1$H NMR (270 MHz, CDCl$_3$) δ (ppm): 1.19 (d, J=6.9 Hz, 3H), 1.20 (d, J=6.9 Hz, 3H), 2.25 (s, 3H), 2.38 (s, 3H), 2.47 (quin., J=6.9 Hz, 1H), 7.20-7.50 (m, 5H).

Reference Example 82

Compound 88

In a manner similar to that in Reference Example 15, Compound 88 (53 mg, 8%) was obtained from Compound 14

(502 mg, 2.14 mmol) prepared in Reference Example 11 and isobutyric anhydride (1.77 mL, 10.7 mmol).

$^1$H NMR (270 MHz, CDCl$_3$) δ (ppm): 1.20 (d, J=6.9 Hz, 3H), 1.22 (d, J=6.9 Hz, 3H), 2.24 (s, 3H), 2.38 (s, 3H), 2.48 (quin., J=6.9 Hz, 1H), 7.20-7.46 (m, 5H), 8.08 (br s, 1H).

AP-MS (m/z): 306 (M$^+$+1).

Reference Example 83

Compound 89

In a manner similar to that in Reference Example 15, Compound 89 (274 mg, 64%) was obtained from Compound 14 (303 mg, 1.29 mmol) prepared in Reference Example 11, cyclopentanecarbonyl chloride (0.32 mL, 2.59 mmol) and pyridine (0.21 mL, 2.60 mmol).

$^1$H NMR (270 MHz, CDCl$_3$) δ (ppm): 1.50-1.95 (m, 8H), 2.24 (s, 3H), 2.38 (s, 3H), 2.65 (quin., J=7.9 Hz, 1H), 7.20-7.45 (m, 5H), 8.04 (br s, 1H).

AP-MS (m/z): 330 (M$^+$−1).

Elemental analysis (C$_{17}$H$_{21}$N$_3$O$_2$S.0.4H$_2$O): Found (%) C, 60.30; H, 6.49; N, 12.41. Calcd C. 60.45; H, 6.49; N, 12.05.

Reference Example 84

Compound 90 and Compound 91

Step 1: In a manner similar to that in Reference Example 11, Compound 90 (123 mg, 13%) was obtained from acetophenone=thiosemicarbazone (507 mg, 2.63 mmol) prepared in Step 1 of Reference Example 1, isovaleric anhydride (1.05 mL, 5.30 mmol) and pyridine (0.43 mL, 5.26 mmol).

$^1$H NMR (270 MHz, CDCl$_3$) δ (ppm): 0.82-1.00 (m, 6H), 2.12 (quin., J=6.6 Hz, 1H), 2.38 (s, 3H), 2.45 (d, J=7.7 Hz, 2H), 4.34 (br, 2H), 7.20-7.48 (m, 5H).

Step 2: In a manner similar to that in Reference Example 15, Compound 91 (128 mg, 98%) was obtained from Compound 90 (105 mg, 0.38 mmol) prepared above, isobutyryl chloride (0.08 mL, 0.76 mmol) and pyridine (0.06 mL, 0.80 mmol).

$^1$H NMR (270 MHz, CDCl$_3$) δ (ppm): 0.92 (d, J=6.9 Hz, 3H), 0.93 (d, J=6.9 Hz, 3H), 1.18 (d, J=6.9 Hz, 3H), 1.21 (d, J=6.9 Hz, 3H), 2.37 (s, 3H), 2.50 (quin, J=6.9 Hz, 1H), 3.20 (quin, J=6.9 Hz, 1H), 7.20-7.48 (m, 5H), 7.98 (br s, 1H).

Reference Example 85

Compound 92

Step 1: To a solution of acetophenone (4.00 mL, 34.3 mmol) in ethanol (15 mL) was added hydrazine monohydrate (6.67 mL, 138 mmol), and the mixture was heated under reflux for 4 hours. After cooling, to the mixture was added water, and the mixture was extracted with ethyl acetate. The organic layer was washed with saturated aqueous sodium chloride, and dried over anhydrous sodium sulfate, and the solvent was evaporated. The residue was purified by silica gel column chromatography (ethyl acetate/n-hexane=1/2) to give acetophenone=hydrazone (5.39 g, ~100%).

$^1$H NMR (300 MHz, CDCl$_3$) δ (ppm): 2.00 (s, 3H), 5.34 (br s, 2H), 7.22-7.60 (m, 5H), $^{13}$C NMR (75 MHz, CDCl$_3$) δ (ppm): 11.3, 125.1, 127.7, 127.9, 139.1, 146.7.

Step 2: To a solution of ammonium thiocyanate (3.40 g, 44.6 mmol) in acetone (20 mL) was added acetyl chloride (2.80 mL, 37.1 mmol), and the mixture was stirred at 70° C. for 10 minutes. To the reaction mixture was added acetophenone=hydrazone (5.36 g, 40.0 mmol) prepared above, and the mixture was heated under reflux for 20 minutes. After the reaction mixture was cooled, saturated aqueous ammonium chloride was added to the mixture, and the mixture was extracted with chloroform. The organic layer was washed with saturated aqueous sodium chloride and dried over anhydrous sodium sulfate, and the solvent was evaporated. The residue was purified by silica gel column chromatography (ethyl acetate/n-hexane=1/2) to give acetophenone=4-acetylthiosemicarbazone (148 mg, 2%).

$^1$H NMR (300 MHz, DMSO-d$_6$) δ (ppm): 2.15 (s, 3H), 2.28 (s, 3H), 7.47-7.51 (m, 3H), 7.56-7.59 (m, 2H), 11.6 (br s, 1H), 13.6 (br s, 1H).

Step 3: In a manner similar to that in Step 3 of Reference Example 76, Compound 92 (36 mg, 88%) was obtained from acetophenone=4-acetylthiosemicarbazone (30 mg, 0.13 mmol) prepared above, pivaloyl chloride (32 µL, 0.26 mmol) and pyridine (20 µL, 0.26 mmol).

$^1$H NMR (300 MHz, CDCl$_3$) δ (ppm): 1.27 (s, 9H), 2.25 (s, 3H), 2.38 (s, 3H), 7.23-7.46 (m, 5H), 8.13 (br s, 1H).

$^{13}$C NMR (75 MHz, CDCl$_3$) δ (ppm): 24.0, 27.2, 39.4, 80.5, 125.1, 128.0, 128.6, 143.0, 143.1, 169.0, 176.7.

AP-MS (m/z): 318 (M$^+$+1).

Reference Example 86

Compound 93

In a manner similar to that in Step 2 of Reference Example 1, Compound 93 (123 mg, 45%) was obtained from Compound 14 (201 mg, 0.853 mmol) prepared in Reference Example 11 and pivaloyl chloride (0.21 mL, 1.71 mmol).

$^1$H NMR (270 MHz, CDCl$_3$) δ (ppm): 1.26 (s, 9H), 2.24 (s, 3H), 2.38 (s, 3H), 7.20-7.51 (m, 5H), 8.10 (br s, 1H).

AP-MS (m/z): 319 (M$^+$+1).

Reference Example 87

Compound 94

Step 1: In a manner similar to that in Step 1 of Reference Example 1, propiophenone=thiosemicarbazone (759 mg, 88%) was obtained from propiophenone (382 mg, 4.18 mmol) and thiosemicarbazide (541 mg, 3.92 mmol).

Step 2: In a manner similar to that in Step 3 of Reference Example 76, Compound 94 (270 mg, 58%) was obtained from propiophenone=thiosemicarbazone (256 mg, 1.24 mmol) prepared above, pivaloyl chloride (597 µL, 4.84 mmol) and pyridine (391 µL, 4.84 mmol).

$^1$H NMR (270 MHz, CDCl$_3$) δ (ppm): 1.15 (dd, J=7.1, 7.3 Hz, 3H), 1.29 (s, 9H), 1.34 (s, 9H), 2.29 (qd, J=7.3, 14.6 Hz, 1H), 3.10 (qd, J=7.1, 14.6 Hz, 1H), 7.21-7.40 (m, 5H), 8.31 (br s, 1H).

AP-MS (m/z): 377 (M$^+$+1).

Reference Example 88

Compound 95

Step 1: 2-Aminoacetophenone hydrochloride (6.10 g, 35.5 mmol) was dissolved in dichloromethane (60 mL), and to the solution was added triethylamine (7.56 g, 74.9 mmol). The solution was cooled to 0° C., and to the solution was added methanesulfonyl chloride (2.84 mL, 36.5 mmol). The solution was stirred at the same temperature for 5 minutes, and then at room temperature for 2 hours. To the reaction mixture was added water and 1 raol/L hydrochloric acid, and the mixture was extracted with chloroform. The organic layer was dried over anhydrous sodium sulfate, and the solvent was evaporated under reduced pressure. The residue was suspended in chloroform (5 mL) and the suspension was stirred, and then, the resulted crystals were collected by filtration to give 2-(methylsulfonylamino)acetophenone (4.58 g, 57%).

Step 2: In a manner similar to that in Step 1 of Reference Example 1, 2-(methylsulfonylamino)acetophenone=thiosemicarbazone (3.08 g, 51%) was obtained from 2-(methylsulfonylamino)acetophenone (4.58 g, 20.2 mmol) prepared above and thiosemicarbazide (1.84 g, 20.2 mmol).

Step 3: In a manner similar to that in Step 3 of Reference Example 76, Compound 95 (1.81 g, 91%) was obtained from 2-(methylsulfonylamino)acetophenone=thiosemicarbazone (1.31 g, 4.36 mmol) prepared above, pivaloyl chloride (2.10 g, 17.4 mmol) and pyridine (1.38 g, 17.4 mmol).

$^1$H NMR (270 MHz, CDCl$_3$) δ (ppm): 1.30 (s, 9H), 1.36 (s, 9H), 2.97 (s, 3H), 3.98 (dd, J=5.53, 13.8 Hz, 1H). 4.64 (dd, J=8.5, 13.8 Hz, 1H), 5.10 (br dd, J=5.3, 8.5 Hz, 1H), 7.25-7.39 (m, 5H), 7.93 (br s, 1H).

AP-MS (m/z): 453 (M$^+$−1).

Reference Example 89

Compound 96

Step 1: In a manner similar to that in Step 1 of Reference Example 1, 2-(methylsulfonylamino)acetophenone=4-methylthiosemicarbazone (122 mg) was obtained from 2-(methylsulfonylamino)acetophenone (209 mg, 0.98 mmol) prepared in Step 1 of Reference Example 88 and 4-methylthiosemicarbazide (106 mg, 1.00 mmol).

Step 2: In a manner similar to that in Step 3 of Reference Example 76, Compound 96 (68 mg, 15%) was obtained from 2-(methylsulfonylamino)acetophenone=4-methylthiosemicarbazone (122 mg, 0.41 mmol) obtained above, pivaloyl chloride (128 μL, 1.04 mmol) and pyridine (80 μL, 1.04 mmol).

$^1$H NMR (300 MHz, DMSO-d$_6$) δ (ppm): 1.27 (s, 9H), 1.28 (s, 9H), 2.95 (s, 3H), 3.53 (s, 3H), 3.94 (dd, J=13.9, 6.4 Hz, 1H), 4.27 (dd, J=13.9, 7.9 Hz, 1H), 7.11 (t, J=7.2 Hz, 1H), 7.21-7.38 (m, 5H).

AP-MS (m/z): 467 (M$^+$−1).

Reference Example 90

Compound 97

Step 1: In a manner similar to that in, Step 1 of Reference Example 88, 2-(ethylsulfonylamino)acetophenone (367 mg, 39%) was obtained from 2-aminoacetophenone hydrochloride (714 mg, 4.16 mmol), triethylamine (1.45 mL, 10.4 mmol) and ethanesulfonyl chloride (0.434 mL, 4.58 mmol).

Step 2: In a manner similar to that in Step 1 of Reference Example 1, 2-(ethylsulfonylamino)acetophenone=thiosemicarbazone (327 mg, 43%) was obtained from 2-(ethylsulfonylamino)acetophenone (367 mg, 1.61 mmol) prepared above and thiosemicarbazide (147 mg, 1.61 mmol).

Step 3: In a manner similar to that in Step 2 of Reference Example 1, Compound 97 (39 mg, 25%) was obtained from 2-(ethylsulfonylamino)acetophenone=thiosemicarbazone (99 mg, 0.330 mmol), pivaloyl chloride (162 μL, 1.32 mmol) and pyridine (130 μL, 1.58 mmol).

$^1$H NMR (270 MHz, CDCl$_3$) δ (ppm): 1.26 (s, 9H), 1.28 (t, J=7.8 Hz, 3H), 1.29 (s, 9H), 3.09 (m, 2H), 3.97 (dd, J=5.1, 13.5 Hz, 1H), 4.60 (dd, J=8.1, 13.5 Hz, 1H), 4.99 (br dd, J=5.1, 8.1 Hz, 1H), 7.25-7.38 (br s, 5H), 7.93 (br s, 1H).

Reference Example 91

Compound 98

Step 1: In a manner similar to that in Step 1 of Reference Example 1, 2-methoxyacetophenone=thiosemicarbazone (367 mg, 62%) was obtained from 2-methoxyacetophenone (288 mg, 1.92 mmol) and thiosemicarbazide (179 mg, 1.96 mmol).

Step 2: In a manner similar to that in Step 2 of Reference Example 1, Compound 98 (132 mg, 59%) was obtained from 2-methoxyacetophenone=thiosemicarbazone (128 mg, 0.573 mmol) prepared above, pivaloyl chloride (211 μL, 1.72 mmol) and pyridine (152 μL, 1.88 mmol).

$^1$H NMR (270 MHz, CDCl$_3$) δ (ppm): 1.28 (s, 9H), 1.32 (s, 9H), 3.51 (s, 3H), 4.36 (d, J=9.6 Hz, 1H), 4.48 (d, J=9.6 Hz, 1H), 7.24-7.38 (in, 5H), 7.88 (s, 1H).

AP-MS (m/z): 392 (M$^+$+1).

Reference Example 92

Compound 99

Step 1: Methane sulfonamide (0.476 g, 5.00 mmol) was dissolved in DMF (10 mL), and to the solution was added 60% sodium hydride (0.275 g, 5.00 mmol), and the mixture was stirred in a water bath for 20 minutes. To the reaction mixture was added 3-chloropropiophenone (843 mg, 5.00 mol). The mixture was stirred in a water bath for one hour, and further stirred at room temperature for 15 hours. To the reaction mixture was added water, and the mixture was extracted with ethyl acetate. The organic layer was washed with saturated aqueous sodium chloride and dried over anhydrous sodium sulfate, and the solvent was evaporated under reduced pressure. The residue was purified by silica gel column chromatography (chloroform/methanol=20/1) to give 3-(methylsulfonylamino)propiophenone (240 mg, 21%).

Step 2: In a manner similar to that in Step 1 of Reference Example 1, 3-(methylsulfonylamino)propiophenone= thiosemicarbazone (219 mg, 45%) was obtained from 3-(methylsulfonylamino)propiophenone (388 mg, 1.71 mmol) prepared above and thiosemicarbazide (156 mg, 1.71 mmol).

Step 3: In a manner similar to that in Step 2 of Reference Example 1, Compound 99 (218 mg, 86%) was obtained from 3-(methylsulfonylamino) propiophenone=thiosemicarbazone (200 mg, 0.696 mmol) obtained above, pivaloyl chloride (342 μL, 2.78 mmol) and pyridine (219 μL, 2.78 mmol).

$^1$H NMR (300 MHz, CDCl$_3$) δ (ppm): 1.30 (s, 9H), 1.34 (s, 9H), 2.56-2.65 (m, 1H), 2.94 (s, 3H), 3.21-3.44 (m, 2H), 3.58-3.70 (m, 1H), 4.45 (br s, 1H), 7.28-7.37 (m, 5H), 7.97 (br s, 1H).

AP-MS (m/z): 467 (M$^-$−1).

Reference Example 93

Compound 100

In a manner similar to that in Step 3 of Reference Example 76, an oily compound was obtained from 3-(methylsulfonylamino)propiophenone=thiosemicarbazone (173 mg, 0.604 mmol) prepared in Step 2 of Reference Example 92, isobutyryl chloride (316 μL 3.02 mmol) and pyridine (292 μL, 3.62 mmol). The oily compound was dissolved in methanol (10 mL). To the solution was added potassium carbonate (1.00 g, 7.24 mmol), and the mixture was vigorously stirred for 1 hour. The reaction mixture was filtered, and the filtrate was concentrated. And then, to the residure was added chloroform, water and 1.0 mol/L hydrochloric acid, and the solution was extracted with chloroform. The organic layer was washed with saturated aqueous sodium chloride, and dried over anhydrous sodium sulfate. The solvent was evaporated under reduced pressure, and the residue was purified by preparative thin layer chromatography (chloroform/methanol=20/1) to give Compound 100 (111 mg, 41%).

$^1$H NMR (270 MHz, DMSO-$d_6$) δ (ppm): 0.99-1.07 (m, 12H), 2.55-2.66 (m, 2H), 2.80-3.00 (m, 1H), 2.89 (s, 3H), 3.05-3.17 (m, 1H), 3.24-3.38 (m, 2H), 7.15 (br t, J=5.9 Hz, 1H), 7.24-7.39 (m, 5H), 11.6 (br s, 1H).

Reference Example 94

Compound 101

Step 1: In a manner similar to that in Step 1 of Reference Example 88, 2-(trifluoroacetylamino)acetophenone (4.38 g, 59%) was obtained from 2-aminoacetophenone hydrochloride (5.47 g, 31.9 mmol), triethylamine (11.1 mL, 80.0 mmol) and trifluoroacetic anhydride (4.96 mL, 35.1 mmol).

Step 2: In a manner similar to that in Step 1 of Reference Example 1, 2-(trifluoroacetylamino)acetophenone= thiosemicarbazone was obtained from 2-(trifluoroacetylamino) acetophenone (3.00 g, 13.0 mmol) prepared above and thiosemicarbazide (1.18 g, 13.0 mmol).

Step 3: In a manner similar to that in Step 3 of Reference Example 76, Compound 101 (1.72 g, 28%) was obtained from 2-(trifluoroacetylamino)acetophenone= thiosemicarbazone prepared above, pivaloyl chloride (50 mmol, 6.16 mL) and pyridine (60.0 mmol, 4.85 mL).

$^1$H NMR (270 MHz, CDCl$_3$) δ (ppm): 1.27 (s, 9H), 1.38 (s, 9H), 3.95 (dd, J=3.0, 13.5 Hz, 1H), 4.89 (dd, J=3.7, 13.5 Hz, 1H), 7.15 (br d, J=7.3 Hz, 2H), 7.30-7.40 (m, 3H), 7.92 (br s, 1H), 8.27 (br s, 1H).

AP-MS (m/z): 471 (M$^-$−1).

Reference Example 95

Compound 102

In a manner similar to that in Step 3 of Reference Example 76, Compound 102 (64.6 mg, 39%) was obtained from 2-(methylsulfonylamino) acetophenone=thiosemicarbazone (100 mg, 0.333 mmol) prepared in Step 2 of Reference Example 88, isobutyryl chloride (140 μL, 1.33 mmol) and pyridine (108 μL, 1.33 mmol).

$^1$H NMR (270 MHz, CDCl$_3$) δ (ppm): 1.17 (d, J=6.9 Hz, 3H), 1.19 (d, J=6.9 Hz, 3H), 1.25 (d, J=6.9 Hz, 6H), 1.29 (d, J=6.9 Hz, 6H), 3.05 (s, 3H), 3.10-330 (m, 3H), 4.01 (dd, J=4.8, 14.2 Hz, 1H), 4.74 (dd, J=7.8, 14.2 Hz, 1H), 5.37 (br s, 1H), 7.26-7.40 (m, 5H).

Reference Example 96

Compound 103

Compound 102 (40.0 mg, 0.0805 mg) prepared in Reference Example 95 was dissolved in methanol (10 mL). To the solution was added potassium carbonate (1.00 g, 7.24 mmol), and the mixture was vigorously stirred for 1 hour. The reaction mixture was filtered, and the filtrate was concentrated. Then, to the residue was added chloroform, 1 mol/L hydrochloric acid and water, and the mixture was extracted with chloroform. The organic layer was washed with saturated aqueous sodium chloride, and dried over anhydrous sodium sulfate. The solvent was evaporated under reduced pressure, and the residue was purified by preparative thin layer chromatography (chloroform/methanol=20/1) to give Compound 103 (24.2 mg, 84%).

$^1$H NMR (270 MHz, CDCl$_3$) δ (ppm): 1.13 (d, J=6.9 Hz, 3H), 1.18 (d, J=6.9 Hz, 3H), 1.21 (cl, J=6.9 Hz, 3H), 1.23 (d, J=6.9 Hz, 3H), 2.50 (m, 1H), 2.90 (s, 3H), 3.27 (m, 1H), 3.98 (dd, J=5.0, 13.9 Hz, 1H), 4.60 (dd, J=8.2, 13.9 Hz, 1H), 5.35 (br dd, J=5.0, 8.2 Hz, 1H), 7.26-7.40 (m, 5H), 8.02 (br s, 1H).

Reference Example 97

Compound 104

Step 1: In a manner similar to that in Step 1 of Reference Example 1, 3-(dimethylamino)propiophenone= thiosemicarbazone (491 mg, 46%) was obtained from 3-(dimethylamino) propiophenone (910 mg, 4.26 mmol) and thiosemicarbazide (387 mg, 4.25 mmol).

Step 2: In a manner similar to that in Step 3 of Reference Example 76, Compound 104 (116 mg, 33%) was obtained from 3-(dimethylamino)propiophenone=thiosemicarbazone (210 mg, 0.839 mmol) prepared above, pivaloyl chloride (496 μL, 3.78 mmol) and pyridine (326 μL, 3.78 mmol).

$^1$H NMR (270 MHz, CDCl$_3$) δ (ppm): 1.29 (s, 9H), 1.31 (s, 9H), 2.23-2.29 (m, 1H), 2.26 (br s, 3H), 2.27 (br s, 3H), 2.46 (ddd, J=8.8, 4.3, 11.3 Hz, 1H), 2.87 (m, 1H), 3.31 (m, 1H), 7.20-7.36 (m, 5H), 7.90 (br s, 1H).

Reference Example 98

Compound 105

Step 1: In a manner similar to that in Step 2 of Reference Example 1, 3-carbomethoxypropiophenone=thiosemicarbazone (10.6 g, 94%) was obtained from 3-carbomethoxypropiophenone (8.13 g, 42.3 mmol) and thiosemicarbazide (3.86 g, 42.3 mmol).

Step 2: In a manner similar to that in Step 3 of Reference Example 76, Compound 105 (9.70 g, 77%) was obtained from 3-carbomethoxypropiophenone=thiosemicarbazone (7.76 g, 29.2 mmol) prepared above, pivaloyl chloride (14.4 mL, 117 mmol) and pyridine (11.3 mL, 140 mmol).

$^1$H NMR (270 MHz, CDCl$_3$) δ (ppm): 1.29 (s, 9H), 1.32 (s, 9H), 2.37 (m, 1H), 2.67 (m, 1H), 2.79 (m, 1H), 3.42 (m, 1H), 3.70 (s, 3H), 7.22-7.40 (m, 5H), 7.89 (br s, 1H).

Reference Example 99

Compound 106

Sodium hydroxide (2.7 g, 67 mmol) was dissolved in water (23 mL). Subsequently, to the solution was added methanol (30 mL) and the solution was stirred. To the solution was added Compound 105 (9.65 g, 22.3 mmol) prepared in Reference Example 98, and the mixture was stirred at room temperature for 5 hours. To the reaction mixture was added 1 mol/L hydrochloric acid (20 mL) and water (30 mL), and the deposited white crystals were collected by filtration. The resulting crystals were washed with water and diisopropyl ether, and dried under reduced pressure to give Compound 106 (8.92 g, 96%).

$^1$H NMR (270 MHz, CDCl$_3$) δ (ppm): 1.30 (s, 9H), 1.33 (s, 9H), 2.43 (m, 1H), 2.44 (m, 1H), 2.66 (m, 1H), 2.88 (m, 1H), 3.44 (m, 1H), 7.23-7.40 (m, 5H), 7.92 (br s, 1H).

Reference Example 100

Compound 107

To Compound 106 (1.21 g, 2.88 mmol) prepared in Reference Example 99 was added oxalyl chloride (5 mL) under cooling at 0° C., and the mixture was allowed to react at 0° C. for 1 hour. The solvent was evaporated under reduced pressure from the reaction mixture, and the residue was dried in vacuo. To the residue was added THF, and the mixture was stirred at 0° C. Then, to the reaction mixture was added a 4 mol/L ammonia-methanol solution (5 mL, 20 mmol), and the mixture was stirred at room temperature for 3 hours. To the reaction mixture was added 1 mol/L hydrochloric acid (20 mL) and water (30 mL), and the mixture was extracted with chloroform. The organic layer was washed with saturated aqueous sodium chloride, and dried over anhydrous sodium sulfate. After the solvent was evaporated under reduced pressure, to the resulting residue was added diisopropyl ether, and then the deposited white crystals were collected by filtration. The resulting crystals were washed with water and diisopropyl ether, and then dried under reduced pressure to give Compound 107 (8.92 g, 96%).

$^1$H NMR (270 MHz, DMSO-d$_6$) δ (ppm): 1.17 (s, 9H), 1.28 (s, 9H), 1.81-2.03 (m, 1H), 2.15-2.30 (m, 1H), 2.49-2.75 (m, 1H), 2.95-3.20 (m, 1H), 6.80 (br s, 1H), 7.20-7.41 (m, 5H), 10.93 (br s, 2H).

Reference Example 101

Compound 108

In a manner similar to that in Reference Example 100, Compound 108 (65 mg, 60%) was obtained from Compound 106 (0.104 g, 0.248 mmol) prepared in Reference Example 99, oxalyl chloride (5 mL), hydroxylamine hydrochloride (0.017 g, 0.245 mmol) and triethylamine (0.062 g, 0.614 mmol).
APCI-MS (m/z): 433 (M$^-$−1).

Reference Example 102

Compound 109

In a manner similar to that in Reference Example 100, Compound 109 (1.08 g, 87%) was obtained from Compound 106 (1.20 g, 2.86 mmol) prepared in Reference Example 99, oxalyl chloride (5 mL) and a 4 mol/L methylamine-methanol solution (10 mL, 40 mmol).
AP-MS (m/z): 431 (M$^-$−1).

Reference Example 103

Compound 110

Step 1: In a manner similar to that in Step 1 of Reference Example 1, 3-(dimethylaminocarbonyl)propiophenone= thiosemicarbazone (3.67 g, 79%) was obtained from 3-(dimethylaminocarbonyl)propiophenone (4.00 g, 183 mmol) and thiosemicarbazide (1.70 g, 18.7 mmol).

Step 2: In a manner similar to that in Step 3 of Reference Example 76, Compound 110 (1.64 g, 49%) was obtained from 3-(dimethylaminocarbonyl)propiophenone= thiosemicarbazone (2.00 g, 7.99 mmol) prepared above, pivaloyl chloride (3.94 mL, 32.0 mmol) and pyridine (3.11 mL, 38.4 pima.
AP-MS (m/z): 447 (M$^+$+1).

Reference Example 104

Compound 111

In a manner similar to that in Reference Example 100, Compound 111 (480 mg, 84%) was obtained from Compound 106 (51.8 mg, 0.124 mmol) prepared in Reference Example 99, oxalyl chloride (0.5 mL), ethanolamine (7.58 mg, 0.248 mmol) and triethylamine (18.8 mg, 0.186 mmol).

$^1$H NMR (270 MHz, CDCl$_3$) δ (ppm): 1.29 (s, 9H), 1.33 (s, 9H), 2.16-2.25 (m, 1H), 2.65-2.79 (m, 2H), 3.33-3.44 (m, 3H), 3.72 (m, 2H), 6.18 (br s, 1H), 7.22-7.35 (m, 6H), 8.01 (br s, 1H).

Reference Example 105

Compound 112

In a manner similar to that in Reference Example 100, Compound 112 (400 mg, 68%) was obtained from Compound 106 (51.8 mg, 0.124 mmol) prepared in Reference Example 99, oxalyl chloride (0.5 mL), n-butylamine (18.14 mg, 0.248 mmol) and triethylamine (18.8 mg, 0.186 mmol).

$^1$H NMR (300 MHz, CDCl$_3$) δ (ppm): 0.92 (t, J=7.1 Hz, 3H), 1.25-1.60 (m, 4H), 1.29 (s, 9H), 1.33 (s, 9H), 2.16 (m, 1H), 2.69 (m, 2H), 3.25 (m, 2H), 3.67 (m, 1H), 5.62 (br s, 1H), 7.23-7.34 (m, 5H), 7.94 (br s, 1H).

Reference Example 106

Compound 113

In a manner similar to that in Reference Example 100, Compound 113 (50 mg, 81%) was obtained from Compound 106 (51.8 mg, 0.124 mmol) prepared in Reference Example 99, oxalyl chloride (0.5 mL), cyclohexylamine (24.6 mg, 0.248 mmol) and triethylamine (18.8 mg, 0.186 mmol).

$^1$H NMR (270 MHz, CDCl$_3$) δ (ppm): 1.05-1.50 (m, 6H), 1.28 (s, 9H), 1.33 (s, 9H), 1.65-1.80 (m, 2H), 1.85-1.95 (m, 2H), 2.14 (m, 1H), 2.65 (m, 2H), 3.37 (m, 1H), 3.38 (m, 1H), 5.50 (br s, 1H), 7.10-7.38 (m, 5H), 7.93 (br s, 1H).

Reference Example 107

Compound 114

Step 1: In a manner similar to that in Step 1 of Reference Example 1, 4-carbomethoxybutyrophenone=thiosemicarbazone (0.700 g, 88%) was obtained from 4-carbomethoxybutyrophenone (0.588 g, 2.85 mmol) and thiosemicarbazide (0.260 g, 2.85 mmol).

Step 2: In a manner similar to that in Step 3 of Reference Example 76, Compound 114 (318 mg, 64%) was obtained from 4-carbomethoxybutyrophenone=thiosemicarbazone prepared above, pivaloyl chloride (0.549 mL, 4.45 mmol) and pyridine (0.431 mL, 5.34 mmol).

¹H NMR (300 MHz, CDCl₃) δ (ppm): 1.29 (s, 9H), 1.32 (s, 9H), 1.51-1.60 (m, 1H), 2.10-2.30 (m, 2H), 2.44 (m, 2H), 3.03-3.17 (m, 1H), 3.68 (s, 3H), 7.20-7.36 (m, 5H), 7.95 (br s, 1H).

Reference Example 108

Compound 115

In a manner similar to that in Reference Example 99, Compound 115 (234 mg, 95%) was obtained from Compound 114 (254 mg, 0.567 mmol) prepared in Reference Example 107, sodium hydroxide (70.0 mg, 1.75 mmol), water (2 mL) and ethanol (4 mL).

¹H NMR (270 MHz, CDCl₃) δ (ppm): 1.29 (s, 9H), 1.32 (s, 9H), 1.65-1.75 (m, 1H), 2.10-2.35 (m, 2H), 2.50 (m, 2H), 3.10-3.20 (m, 1H), 7.23-7.35 (m, 6H), 7.92 (br s, 1H),

Reference Example 109

Compound 116

In a manner similar to that in Reference Example 100, Compound 116 (0.028 g, 55%) was obtained from Compound 115 (50.0 mg, 0.115 mmol) prepared in Reference Example 108, oxalyl chloride (0.5 mL) and a 40% methylamine-methanol solution (5 mL).

¹H NMR (270 MHz, CDCl₃) δ (ppm): 1.29 (s, 9H), 1.32 (s, 9H), 1.50-1.65 (m, 1H), 2.21-2.35 (m, 4H), 2.80 (d, J=4.8 Hz, 3H), 3.13 (m, 1H), 5.71 (br s, 1H), 7.20-7.35 (m, 5H), 7.97 (br s, 1H).

Reference Example 110

Compound 117

In a manner similar to that in Reference Example 100, Compound 117 (0.024 g, 47%) was obtained from Compound 115 (51.5 mg, 0.119 mmol) prepared in Reference Example 108, oxalyl chloride (0.5 mL) and a 4 mol/L ammonia-methanol solution (5 mL).

AP-MS (m/z): 431 (M⁻−1).

Reference Example 111

Compound 118

In a manner similar to that in Step 3 of Reference Example 76, Compound 118 (302 mg, 26%) was obtained from 2-(methylsulfonylamino)acetophenone=thiosemicarbazone (1.00 g, 3.49 mmol) prepared in Step 2 of Reference Example 88, acetic anhydride (659 μL, 6.98 mmol) and pyridine (565 μL, 6.98 mmol).

¹H NMR (270 MHz, CDCl₃) δ (ppm): 2.29 (s, 3H), 2.99 (s, 3H), 4.04 (d, J=14.0 Hz, 1H), 4.55 (d, J=14.0 Hz, 1H), 7.30-7.41 (m, 5H).

AP-MS (m/z): 329 (M⁺+1).

Reference Example 112

Compound 119

Compound 118 (10.6 mg, 0.0323 mmol) prepared in Reference Example 111 was dissolved in THF (80 mL). To the solution was added dimethylaminopyridine (7.9 mg, 0.0646 mmol) and pyridine (7.8 μL, 0.0969 mmol), and the mixture was cooled to 0° C. To the solution was added pivaloyl chloride (20 μL, 0.162 mmol), and the mixture was stirred at 0° C. for 5 minutes, and further stirred at room temperature for 4 hours. To the reaction mixture was added water and 1 raolfL hydrochloric acid, and the mixture was extracted with ethyl acetate. The organic layer was dried over anhydrous sodium sulfate, and the solvent was evaporated under reduced pressure. The residue was purified by preparative thin layer chromatography (chloroform/methanol=12/1) to give Compound 119 (5.3 mg, 40%).

¹H-NMR (270 MHz, CDCl₃) δ (ppm): 1.27 (s, 9H), 2.32 (s, 3H), 2.95 (s, 3H), 3.98 (dd, J=5.2, 14.0 Hz, 1H), 4.60 (dd, J=8.1, 13.9 Hz, 1H), 5.40 (m, 1H), 7.29-7.40 (m, 5H), 8.11 (br s, 1H).

Reference Example 113

Cmpound 120

2-(Methylsulfonylamino)acetophenone=thiosemicarbazone (300 mg, 1.05 mmol) prepared in Step 2 of Reference Example 88 was dissolved in THF (18 mL). To the solution was added DMAP (641 mg, 5.25 mmol) and pivaloyl chloride (0.13 mL, 1.1 mmol), and the mixture was stirred at room temperature. To the mixture was further added, after 1 hour and after 2 hours each, pivaloyl chloride (0.065 mL, 0.53 mmol), and the mixture was stirred for 3.6 hours in total. To the reaction mixture was added water, and the mixture was extracted with ethyl acetate. The organic layer was washed with saturated aqueous sodium chloride, and dried over anhydrous sodium sulfate. The solvent was evaporated under reduced pressure, and the residue was purified by preparative thin layer chromatography (chloroform/methanol=20/1) to give Compound 120 (88 mg, yield 22%).

¹H NMR (270 MHz, CDCl₃) δ (ppm): 1.34 (s, 9H), 2.96 (s, 3H), 4.06 (dd, J=6.2, 13.7 Hz, 1H), 4.19 (br s, 2H), 4.58 (dd, J=7.0, 13.7 Hz, 1H), 5.20 (t, J=6.4 Hz, 1H), 7.27-7.56 (m, 5H).

AP-MS (m/z): 371 (M⁺+1).

Reference Example 114

Compound 121

6-Bromohexanoic acid (469 mg, 2.41 mmol) was dissolved in dichloromethane (15 mL). To the solution was added oxalyl chloride (0.28 mL, 3.2 mmol), and the mixture was stirred at room temperature for 2 hours. The reaction mixture was concentrated under reduced pressure, and the resulting residue was dissolved in dichloromethane (15 mL). To the solution was added Compound 120 (297 mg, 0.802 mmol) prepared in Reference Example 113 and pyridine (0.20 mL, 2.4 mmol), and the mixture was stirred at room temperature for 1 hour. After the reaction mixture was concentrated under reduced pressure, water was added to the residue, and the mixture was extracted with ethyl acetate. The organic layer was washed with saturated aqueous sodium chloride, and dried over anhydrous sodium sulfate. The solvent was evaporated under reduced pressure, and the residue was purified by preparative thin layer chromatography (chloroform/methanol=30/1) to give Compound 121 (315 mg, yield 72%).

¹H NMR (270 MHz, CDCl₃) δ (ppm): 1.32 (s, 9H), 1.50 (m, 2H), 1.67 (m, 2H), 1.86 (q, J=6.7 Hz, 2H), 2.34 (t, J=7.3 Hz, 2H), 2.98 (s, 3H), 3.40 (t, J=6.6 Hz, 2H), 3.99 (dd, J=5.2, 13.6 Hz, 1H), 4.63 (dd, J=8.2, 13.6 Hz, 1H), 5.24 (dd, J=5.5, 7.9 Hz, 1H), 7.26-7.38 (m, 5H), 8.40 (br s, 1H)

AP-MS (m/z): 547 (M⁺+1). .

Reference Example 115

Compound 122

Compound 121 (315 mg, 0.575 mmol) prepared in Reference Example 114 was dissolved in N,N-diethylformamide (9.5 mL). To the solution was added sodium azide (187 mg, 2.88 mmol), and the mixture was stirred at 80° C. for 2 hours. To the reaction mixture was added water and the mixture was extracted with ethyl acetate. The organic layer was washed with saturated aqueous sodium chloride, and dried over anhydrous sodium sulfate. The solvent was evaporated under reduced pressure, and the residue was purified by preparative thin layer chromatography (hexane/ethyl acetate=1/2) to give Compound 122 (211 mg, yield 72%).

$^1$H NMR (270 MHz, CDCl$_3$) δ (ppm): 1.32 (s, 9H), 1.42 (m, 2H), 1.55-1.74 (m, 4H), 2.35 (t, J=7.3 Hz, 2H), 2.97 (s, 3H), 3.28 (t, J=6.7 Hz, 2H), 4.13 (dd, J=7.2, 14.3 Hz, 1H), 4.63 (dd, J=8.3, 13.5 Hz, 1H), 5.21 (dd, J=5.2, 8.0 Hz, 1H), 7.26-7.38 (m, 5H), 8.37 (s, 1H).

AP-MS (m/z): 510 (M$^+$+1).

Reference Example 116

Compound 123

Compound 122 (23.6 mg, 0.0463 mmol) prepared in Reference Example 115 was dissolved in THF (1.0 mL). To the solution was added triphenylphosphine (36.4 mg, 0.139 mmol), and the mixture was stirred at room temperature for 25 minutes. To the reaction mixture was added water, and the mixture was extracted with ethyl acetate. The organic layer was washed with saturated aqueous sodium chloride, and dried over anhydrous sodium sulfate. The solvent was evaporated under reduced pressure, and the residue was purified by preparative thin layer chromatography (chloroform/methanol/ammonia=5/0.8/0.2) to give Compound 123 (7.1 mg, yield 32%).

$^1$H-NMR (270 MHz, CDCl$_3$) δ (ppm): 1.31 (s, 9H), 1.47 (m, 2H), 1.57 (m, 2H), 1.70 (m, 2H), 2.39 (m, 2H), 2.82 (m, 2H), 2.97 (s, 3H), 3.95 (d, J=13.7 Hz, 1H), 4.14 (br s, 3H), 4.65 (d, J=13.5 Hz, 1H), 7.24-7.35 (m, 5H).

AP-MS (m/z): 484 (M$^+$+1).

Reference Example 117

Compound 124

Compound 123 (5.0 mg, 0.010 mmol) prepared in Reference Example 116 was dissolved in dichloromethane (0.4 mL). To the solution was added pyridine (0.0025 mL, 0.031 mmol) and acetyl chloride (0.0015 mL, 0.021 mmol), and the mixture was stirred at room temperature for 0.8 hour. To the reaction mixture was added water and the mixture was extracted with ethyl acetate. The organic layer was washed with saturated aqueous sodium chloride, and dried over anhydrous sodium sulfate. The solvent was evaporated under reduced pressure, and the residue was purified by preparative thin layer chromatography (chloroform/methanol=20/1) to give Compound 124 (3.9 mg, yield 72%).

$^1$H NMR (270 MHz, CDCl$_3$) δ (ppm): 1.32 (s, 9H), 1.37 (m, 2H), 1.53 (m, 2H), 1.69 (m, 2H), 1.98 (s, 3H), 2.39 (t, J=7.4 Hz, 2H), 2.97 (s, 3H), 3.24 (m, 2H), 3.98 (dd, J=5.2, 13.6 Hz, 1H), 4.64 (dd, J=8.2, 13.5 Hz, 1H), 5.22 (dd, J=5.4, 8.2 Hz, 1H), 5.68 (m, 1H), 7.24-7.38 (m, 5H), 9.08 (s, 1H)

FAB-MS (m/z): 526 (M$^+$+1).

Reference Example 118

Compound 125

Step 1: In a manner similar to that in Step 1 of Reference Example 1, 3'-hydroxyacetophenone=4-ethylthiosemicarbazone (342 mg, 70%) was obtained from 3'-hydroxyacetophenone (279 mg, 2.05 mmol) and 4-ethylthiosemicarbazide (242 mg, 2.03 mmol).

Step 2: In a manner similar to that in Step 2 of Reference Example 1, Compound 125 (90 mg, 60%) was obtained from 3'-hydroxyacetophenone=4-etlaylthiosemicarbazone (200 mg, 0.843 mmol) prepared above, acetic anhydride (260 mg, 2.53 mmol) and pyridine (108 μL, 1.34 mmol).

$^1$H NMR (270 MHz, CDCl$_3$) δ (ppm): 1.34 (t, J=8.4 Hz, 3H), 2.26 (s, 3H), 2.28 (s, 3H), 2.29 (s, 3H), 2.35 (s, 3H), 3.40 (br s, 2H), 6.71 (br s, 1H), 7.05 (d, J=8.5 Hz, 1H), 7.40 J=8.5 Hz, 1H), 8.02 (br s, 1H).

Reference Example 119

Compound 126

In a manner similar to that in Reference Example 65, Compound 126 (81 mg, 49%) was obtained from Compound 125 (187 mg, 0.515 mg) prepared in Reference Example 118, methanol (10 mL) and potassium carbonate (1.00 g, 7.24 mmol).

$^1$H NMR (270 MHz, CDCl$_3$) δ (ppm): 1.36 (t, J=8.4 Hz, 3H), 2.15 (s, 3H), 2.27 (s, 3H), 2.31 (s, 3H), 3.38 (br s, 2H), 6.65 (br s, 1H), 7.02 (d, J=8.3 Hz, 1H), 7.43 (d, J=8.3 Hz, 1H), 8.13 (br s, 11-1).

Reference Example 120

Compound 127

Compound 69 (50.5 mg, 0.172 mmol) prepared in Reference Example 66 was dissolved in dichloromethane (0.5 mL). To the solution was added triethylamine (17.4 mg, 0.172 mmol) and ethyl isocyanate (13.6 μL, 0.172 mmol), and the mixture was stirred at room temperature for 12 hours. To the reaction mixture was added 1 mol/L hydrochloric acid and water, and the mixture was extracted with dichloromethane. The organic layer was washed with saturated aqueous sodium chloride and dried over anhydrous sodium sulfate. The solvent was evaporated under reduced pressure, and the residue was purified by preparative thin layer chromatography (chloroform/methanol/water=90/10/1) to give Compound 127 (53.3 mg, 85%).

$^1$H NMR (270 MHz, CDCl$_3$) δ (ppm): 1.21 (t, J=7.0 Hz, 3H), 2.09 (s, 3H), 2.22 (s, 3H), 2.35 (s, 3H), 3.31 (m, 2H), 5.03 (br s, 1H), 7.06 (br d, J=8.4 Hz, 1H), 7.24-7.35 (m, 3H), 8.41 (br s, 1H).

Reference Example 121

Compound 128

In a manner similar to that in Step 3 of Reference Example 76, Compound 128 (500 mg, 63%) was obtained from 3'-hydroxyacetophenone=thiosemicarbazone (398 mg, 1.90 mmol) prepared in Step 1 of Reference Example 59, isobutyryl chloride (1.56 mL, 7.60 mmol) and pyridine (721 mg, 9.12 mmol).

¹H NMR (270 MHz, CDCl₃) δ (ppm): 1.09 (d, J=6.8 Hz, 3H), 1.10 (d, J=6.8 Hz, 3H), 1.21 (d, J=6.8 Hz, 3H), 1.22 (d, J=6.8 Hz, 3H), 1.29 (d, J=7.3 Hz, 6H), 2.34 (s, 3H), 2.51 (m, 1H), 2.78 (m, 1H), 3.18 (m, 1H), 7.00 (br d, J=7.3 Hz, 1H), 7.13 (br s, 1H), 7.25-7.33 (m, 2H), 7.93 (br s, 1H).

Reference Example 122

Compound 129

In a manner similar to that in Reference Example 65, Compound 129 (298 mg, 85%) was obtained from Compound 128 (420 mg, 1.00 mmol) prepared in Reference Example 121 and potassium carbonate (1.00 g, 7.24 mmol).
¹H NMR (270 MHz, CDCl₃) δ (ppm): 1.11 (d, J=7.0 Hz, 3H), 1.12 (d, J=7.0 Hz, 3H), 1.22 (d, J=7.0 Hz, 3H), 1.23 (d, J=7.0 Hz, 3H), 2.23 (s, 3H), 2.51 (m, 1H), 3.20 (m, 1H), 5.60 (br s, 1H), 6.63 (br d, J=7.3 Hz, 1H) 6.85 (br s, 1H), 6.94 (br d, J=7.9 Hz, 1H), 7.15 (br t, J=7.9 Hz, 1H), 8.00 (br s, 1H).

Reference Example 123

Compound 130

In a manner similar to that in Step 3 of Reference Example 76, Compound 130 (389 mg, 88%) was obtained from 2'-chloroacetophenone=thiosemicarbazone (253 mg, 1.11 mmol) prepared in Step 1 of Reference Example 53, pivaloyl chloride (546 μL, 4.44 mmol) and pyridine (389 μL, 4.80 mmol).
¹H NMR (270 MHz, CDCl₃) δ (ppm): 1.29 (s, 9H), 1.30 (s, 9H), 2.35 (s, 3H), 7.20-7.27 (m, 2H), 7.35-7.43 (m, 2H), 7.95 (br s, 1H).

Reference Example 124

Compound 131

In a manner similar to that in Step 3 of Reference Example 76, Compound 131 (389 mg, 86%) was obtained from 2'-chloroacetophenone=thiosemicarbazone (400 mg, 1.89 mmol) prepared in Step 1 of Reference Example 53, isobutyryl chloride (594 μL, 5.67 mmol) and pyridine (538 mg, 6.80 mmol).
¹H NMR (270 MHz, CDCl₃) δ (ppm): 1.10 (d, J=6.6 Hz, 3H), 1.12 (d, J=6.6 Hz, 3H), 1.23 (d, J=6.9 Hz, 3H), 1.25 (d, J=6.9 Hz, 3H), 2.39 (s, 3H), 2.52 (m, 1H), 3.18 (m, 1H), 7.22-7.28 (m, 2H), 7.37-7.45 (m, 2H), 7.96 (br s, 1H).

Reference Example 125

Compound 132

Step 1: In a manner similar to that in Step 1 of Reference Example 1, 1-(5-bromo-2-thienyl)ethanone= thiosemicarbazone (7.33 mg, 86%) was obtained from 1-(5-bromo-2-thienyl)ethanone (630 mg, 3.07 mmol) and thiosemicarbazide (281 mg, 3.07 mmol).
Step 2: In a manner similar to that in Step 2 of Reference Example 1, Compound 132 (158 mg, 58%) was obtained from 1-(5-bromo-2-thienyl)ethanone=thiosemicarbazone (2.11 mg, 0.758 mmol) prepared above and acetic anhydride (10 mL).
¹H NMR (270 MHz, CDCl₃) δ (ppm): 2.15 (s, 3H), 2.19 (s, 3H), 2.36 (s, 3H), 6.84 (br s, 1H), 6.86 (br s, 1H), 8.29 (br s, 1H).

Reference Example 126

Compound 133

Step 1: In a manner similar to that in Step 1 of Reference Example 1, 1-(3-bromo-2-thienyl)ethanone= thiosemicarbazone was obtained from 1-(3-bromo-2-thienyl)ethanone (108 mg, 0.388 mmol) and thiosemicarbazide (36.5 mg, 0.399 mmol).
Step 2: In a manner similar to that in Step 2 of Reference Example 1, Compound 133 (139 mg, 99%) was obtained from 1-(3-broma-2-thienyl)ethanone=thiosemicarbazone prepared above and acetic anhydride (10 mL).
¹H NMR (270 MHz, CDCl₃) δ (ppm): 2.04 (s, 3H), 2.14 (s, 3H), 2.27 (s, 3H), 6.96 (br s, 1H), 7.07 (br s, 1H), 9.08 (br s, 1H).

Reference Example 127

Compound 134

Step 1: In a manner similar to that in Step 1 of Reference Example 1, 1-(3-chloro-2-thienyl)ethanone= thiosemicarbazone was obtained from 1-(3-chloro-2-thienyl)ethanone (137 mg, 0.853 mmol) and thiosemicarbazide (78 mg, 0.853 mmol).
Step 2: In a manner similar to that in Step 2 of Reference Example 1, Compound 134 (158 mg, 58%) was obtained from 1-(3-chloro-2-thienyl)ethanone=thiosemicarbazone prepared above and acetic anhydride (10 mL).
¹H NMR (270 MHz, CDCl₃) δ (ppm): 2.14 (s, 3H), 2.21 (s, 3H), 2.43 (s, 3H), 6.89 (d, J=5.3 Hz, 1H), 7.18 (d, J=5.3 Hz, 1H), 8.28 (br s, 1H).

Reference Example 128

Compound 135

Step 1: In a manner similar to that in Step 1 of Reference Example 1, 1-(3-chloro-2-thienyl)ethanone= thiosemicarbazone (96.1 mg, 71%) was obtained from 1-(3-chloro-2-thienyl)ethanone (92.9 mg, 0.578 mmol) and thiosemicarbazide (52.9 mg, 0.578 mmol).
Step 2: In a manner similar to that in Step 3 of Reference Example 76, Compound 134 (90 mg, 60%) was obtained from 1-(3-chloro-2-thienyl)ethanone=thiosemicarbazone (86.9 mg, 0.372 mmol) prepared above, pivaloyl chloride (138 μL, 1.12 mmol) and pyridine (108 μL, 1.34 mmol).
¹H NMR (270 MHz, CDCl₃) δ (ppm): 1.33 (s, 9H), 1.35 (s, 9H), 2.43 (s, 3H), 6.90 (d, J=6.3 Hz, 1H), 7.20 (d, J=6.3 Hz, 1H), 7.97 (br s, 1H).

Reference Example 129

Compound 136

Compound 14 (41 mg, 0.17 mmol) prepared in Reference Example 11 was dissolved in acetonitrile (0.5 mL). To the solution was added di-tert-butyl dicarbonate (0.114 mg, 0.522 mmol) and DMAP (43 mg, 0.35 mmol), and the mixture was stirred at room temperature for 1 hour. To the reaction mixture was added water, and the mixture was extracted with ethyl acetate. The organic layer was washed with saturated aqueous sodium chloride, and dried over anhydrous sodium sulfate, and the solvent was evaporated under reduced pressure. The residue was purified by preparative thin layer chromatography (chloroform/methanol=20/1) to give Compound 136 (24 mg, 41%).

$^1$H NMR (270 MHz, CDCl$_3$) δ (ppm): 1.47 (s, 9H), 2.21 (s, 3H), 2.40 (s, 3H), 7.14-7.48 (m, 6H).

AP-MS (m/z): 334 (M$^-$−1).

Reference Example 130

Compound 137

Compound 14 (74 mg, 0.31 mmol) prepared in Reference Example 11 was dissolved in DMF (2 mL). To the solution was added 60% sodium hydride (50 mg, 1.3 mmol) and dimethylcarbamoyl chloride (0.116 mL, 1.26 mmol), and the mixture was stirred at room temperature for 1 hour. To the reaction mixture was added water, and the mixture was extracted with ethyl acetate. The organic layer was washed with saturated aqueous sodium chloride, and dried over anhydrous sodium sulfate, and the solvent was evaporated under reduced pressure. The residue was purified by preparative thin layer chromatography (chloroform/methanol=40/1, then ethyl acetate/n-hexane=3/1) to give Compound 137 (44 mg, 46%).

$^1$H NMR (270 MHz, CDCl$_3$) δ (ppm): 2.23 (s, 3H), 2.37 (s, 3H), 3.00 (s, 6H), 7.20-7.46 (m, 5H).

AP-MS (m/z): 307 (M$^+$+1).

Reference Example 131

Compound 138

Step 1: Copper (II) bromide (130 mg, 0.583 mmol) was dissolved in acetonitrile (5.4 mL). To the solution was added tert-butyl nitrite (0.093 mL, 0.78 mmol) under ice cooling. After being stirred for 10 minutes, to the mixture was added Compound 14 (180 mg, 0.486 mmol) prepared in Reference Example 11, and the mixture was stirred for 1 hour with gradually raising the temperature up to room temperature. To the reaction mixture was added water, and the mixture was extracted with ethyl acetate. The organic layer was washed with saturated aqueous sodium chloride and dried over anhydrous sodium sulfate, and the solvent was evaporated under reduced pressure. The residue was purified by silica gel column chromatography (ethyl acetate/n-hexane=1/18) to give 3-acetyl-5-bromo-2-methyl-2-phenyl-1,3,4-thiadialine (145 mg, 84%).

Step 2: 3-Acetyl-5-bromo-2-methyl-2-phenyl-1,3,4-thiadialine (50 mg, 0.17 mmol prepared above was dissolved in dichloromethane (0.5 mL). To the solution was added piperidine (0.033 mL, 0.33 mmol), and the mixture was stirred at room temperature for 20 minutes. To the reaction mixture was further added piperidine (0.165 mL, 1.67 mmol), and the mixture was stirred at the same temperature for 5.5 hours. To the reaction mixture was added water, and the mixture was extracted with ethyl acetate. The organic layer was washed with saturated aqueous sodium chloride and dried over anhydrous sodium sulfate, and the solvent was evaporated under reduced pressure. The residue was purified by preparative thin layer chromatography (chloroform) to give Compound 138 (12 mg, 24%).

1H NMR (270 MHz, CDCl$_3$) δ (ppm): 1.60 (m, 6H), 2.25 (s, 3H), 2.40 (s, 3H), 3.24 (m, 4H), 7.20-7.39 (m, 3H), 7.45 (m, 2H).

AP-MS (m/z): 304 (M$^+$1).

Reference Example 132

Compound 139

In a manner similar to that in Step 2 of Reference Example 131, Compound 139 (38 mg, 59%) was obtained from 3-acetyl-5-bromo-2-methyl-2-phenyl-1,3,4-thiadiallyn (61 mg, 0.20 mmol) prepared in Step 1 of Reference Example 131 and 4-methylpiperidine (0.483 mL, 4.08 mmol).

$^1$H NMR (270 MHz, CDCl$_3$) δ (ppm): 0.96 (d, J=6.4 Hz, 3H), 1.25 (m, 2H), 1.44-1.71 (m, 3H), 2.25 (s, 3H), 2.40 (s, 3H), 2.88 (m, 2H), 3.61 (m, 2H), 7.20-7.49 (m, 2H), 7.46 (m, 2H).

AP-MS (m/z): 318 (M$^+$+1).

Reference Example 133

Compound 140

Compound 118 (50 mg, 0.15 mmol) prepared in Reference Example 111 was dissolved in dichloromethane (2 mL). To the solution was added pyridine (0.031 mL, 0.38 mmol) and hexanoyl chloride (0.053 mL, 0.38 mmol), and the mixture was stirred at room temperature for 2.5 hours. To the reaction mixture was further added pyridine (0.012 mL, 0.15 mmol) and hexanoyl chloride (0.021 mL, 0.15 mmol), and the mixture was stirred at the same temperature for 1 hour. To the reaction mixture was added water, and the mixture was extracted with ethyl acetate. The organic layer was washed with saturated aqueous sodium chloride, and dried over anhydrous sodium sulfate and the solvent was evaporated under reduced pressure. The residue was purified by preparative thin layer chromatography (chloroform/methanol=15/1) to give Compound 140 (52 mg, 80%).

$^1$H NMR (270 MHz, CDCl$_3$) δ (ppm): 0.90 (t, J=6.6 Hz, 3H), 1.22-1.41 (m, 4H), 1.64 (m, 2H), 2.31 (s, 3H), 2.32 (t, J=7.5 Hz, 2H), 2.96 (s, 3H), 3.98 (dd, J=5.4, 13.9 Hz, 1H), 4.60 (dd, J=8.1, 13.9 Hz, 1H), 5.38 (dd, J=5.4, 8.1 Hz, 1H), 7.20-7.44 (m, 5H), 8.02 (s, 1H).

AP-MS (m/z): 427 (M$^+$+1).

Reference Example 134

Compound 141

In a manner similar to that in Reference Example 133, Compound 141 (22 mg, 18%) was obtained from Compound 118 (100 mg, 0.305 mmol) prepared in Reference Example 111, pyridine (0.062 mL, 0.78 mmol) and crotonoyl chloride (0.075 mL, 0.78 mmol).

$^1$H NMR (270 MHz, CDCl$_3$) δ (ppm): 1.91 (dd, J=1.7, 7.0 Hz, 3H), 2.32 (s, 3H), 2.97 (s, 3H), 3.99 (dd, J=5.6, 13.9 Hz, 1H), 4.61 (dd, J=7.6, 13.9 Hz, 1H), 5.51 (dd, J=5.6, 7.6 Hz, 1H), 5.86 (dd, J=1.7, 15.2 Hz, 1H), 7.03 (dd, J=7.0, 15.2 Hz, 1H), 7.22-7.41 (m, 5H), 8.49 (s, 1H).

AP-MS (m/z): 397 (M$^+$+1).

Reference Example 135

Compound 142

In a manner similar to that in Reference Example 133, Compound 142 (42 mg, 70%) was obtained from Compound 118 (50 mg, 0.15 mmol) prepared in Reference Example 111, pyridine (0.062 mL, 0.76 mmol) and cyclopropanecarbonyl chloride (0.070 mL, 0.76 mmol).

¹H NMR (270 MHz, CD₃OD) δ (ppm): 0.87-0.98 (m, 4H), 1.77 (m, 1H), 2.28 (s, 3H), 3.01 (s, 3H), 3.97 (d, J=14.0 Hz, 1H), 4.55 (d, J=14.0 Hz, 1H), 7.22-7.42 (m, 5H).
AP-MS (m/z): 397 (M⁺+1).

Reference Example 136

Compound 143

In a manner similar to that in Reference Example 133, Compound 143 (24 mg, 22%) was obtained from Compound 118 (80 mg, 0.24 mmol) prepared in Reference Example 111, pyridine (0.069 mL, 0.85 mmol) and 2-acetoxyisobutyryl chloride (0.12 mL, 0.85 mmol). ¹H NMR (270 MHz, CDCl₃) δ (ppm): 1.65 (s, 3H), 1.67 (s, 3H), 2.15 (s, 3H), 2.32 (s, 3H), 2.97 (s, 3H), 3.99 (dd, J=5.5, 14.0 Hz, 1H), 4.61 (dd, J=8.1, 14.0 Hz, 1H), 5.39 (dd, J=5.5, 8.1 Hz, 1H), 7.29-7.46 (m, 5H), 8.53 (s, 1H).
AP-MS (m/z): 457 (M⁺1H).

Reference Example 137

Compound 144

Compound 143 (21 mg, 0.045 mmol) prepared in Reference Example 136 was dissolved in a mixed solvent of methanol (1.6 mL) and water (0.8 mL). To the solution was added lithium hydroxide (11 mg, 0.45 mmol), and the mixture was stirred at room temperature for 3.5 hours. To the reaction mixture was added water, and the mixture was extracted with ethyl acetate. The organic layer was washed with saturated aqueous sodium chloride, and dried over anhydrous sodium sulfate, and the solvent was evaporated under reduced pressure. The residue was purified by preparative thin layer chromatography (chloroform/methanol=9/1) to give Compound 144 (11 mg, 56%).
¹H NMR (270 MHz, CDCl₃) δ (ppm): 1.44 (s, 3H), 1.48 (s, 3H), 2.32 (s, 3H), 2.85 (br s, 1H), 2.97 (s, 3H), 3.98 (dd, J=5.6, 13.9 Hz, 1H), 4.63 (dd, J=7.8, 13.9 Hz, 1H), 5.53 (dd, J=5.6, 7.8 Hz, 1H), 7.25-7.42 (m, 5H), 9.36 (s, 1H).
AP-MS (m/z): 415 (M⁺+1).

Reference Example 138

Compound 145

In a manner similar to that in Reference Example 133, Compound 145 (53 mg, 86%) was obtained from Compound 118 (50 mg, 0.15 mmol) prepared in Reference Example 111, pyridine (0.031 mL, 0.38 mmol) and methoxyacetyl chloride (0.035 mL, 0.38 mmol).
¹H NMR (270 MHz, CDCl₃) δ (ppm): 2.32 (s, 3H), 2.96 (s, 3H), 3.49 (s, 3H), 4.00 (s, 2H), 4.00 (dd, J=5.8, 13.9 Hz, 1H), 4.61 (dd, J=7.8, 13.9 Hz, 1H), 5.46 (dd, J=5.8, 7.8 Hz, 1H), 7.25-7.44 (m, 5H), 8.94 (s, 1H).
AP-MS (m/z): 401 (M⁺+1).

Reference Example 139

Compound 146

In a manner similar to that in Reference Example 133, Compound 146 (105 mg, 85%) was obtained from Compound 118 (100 mg, 0.305 mmol) prepared in Reference Example 111, pyridine (0.062 mL, 0.76 mmol) and chloroacetyl chloride (0.061 mL, 0.76 mmol).

¹H NMR (270 MHz, CDCl₃) δ (ppm): 2.34 (s, 3H), 2.97 (s, 3H), 4.02 (dd, J=5.6, 14.0 Hz, 1H), 4.11 (d, J=15.9 Hz, 1H), 4.18 (d, J=15_9 Hz, 1H), 4.62 (dd, J=7.8, 14.0 Hz, 1H), 5.28 (dd, J=5.6, 7.8 Hz, 1H), 7.22-7.43 (m, 5H), 8.87 (s, 1H).
AP-MS (m/z): 405 (M⁺+1).

Reference Example 140

Compound 147

Compound 146 (50 mg, 0.12 mmol) prepared in Reference Example 139 was dissolved in methanol (1 mL). To the solution was added 50% aqueous dimethylamine (0.033 mL), and the mixture was stirred at room temperature for 1 hour. To the reaction mixture was further added 50% aqueous dimethylamine (0.033 mL), and the mixture was stirred at the same temperature for 1.5 hours. To the reaction mixture was added water, and the mixture was extracted with ethyl acetate. The organic layer was washed with saturated aqueous sodium chloride and dried over anhydrous sodium sulfate, and the solvent was evaporated under reduced pressure. The residue was purified by preparative thin layer chromatography (chloroform/acetone=1/1) to give Compound 147 (20 mg, 39%).
¹H NMR (270 MHz, CDCl₃) δ (ppm): 2.34 (s, 3H), 2.38 (s, 6H), 2.96 (s, 3H), 3.06 (d, J=17.3 Hz, 11-1), 3.10 (d, J=17.3 Hz, 1H), 4.00 (d, J=13.9 Hz, 1H), 4.61 (d, J=13.9 Hz, 1H), 5.36 (br, 1H), 7.25-7.41 (m, 5H).
AP-MS (m/z): 414 (M⁺+1).

Reference Example 141

Compound 148

In a manner similar to that in Reference Example 133, Compound 148 (304 mg, 74%) was obtained from Compound 118 (297 mg, 0.903 mmol) prepared in Reference Example 111, pyridine (0.183 mL, 2.26 mmol) and methyl 4-(chloroformyl)butyrate (0.312 mL, 2.26 mmol).
¹H NMR (270 MHz, CDCl₃) δ (ppm): 2.00 (m, 2H), 2.32-2.56 (m, 4H), 2.34 (s, 3H), 2.99 (s, 3H), 3.71 (s, 3H), 4.01 (dd, J=5.4, 13.9 Hz, 1H), 4.63 (dd, J=7.9, 13.9 Hz, 1H), 5.45 (m, 1H), 7.21-7.49 (m, 5H), 8.54 (s, 1H).
AP-MS (m/z): 457 (M⁺+1).

Reference Example 142

Compound 149

In a manner similar to that in Reference Example 137, after Compound 148 (262 mg, 0.573 mmol) prepared in Reference Example 141 was treated with lithium hydroxide monohydrate (206 mg, 4.91 mmol), to the reaction mixture was added ice and 0.5 mol/L hydrochloric acid, and the mixture was extracted with a mixed solvent of chloroform and methanol. After the organic layer was concentrated, the residue was purified by silica gel column chromatography (chloroform/methanol=43/7) to give Compound 149 (222 mg, 88%).
¹H NMR (270 MHz, CD₃OD) δ (ppm): 1.89 (m, 2H), 2.28 (s, 3H), 2.33 (t, J=7.3 Hz, 2H), 2.43 (t, J=7.5 Hz, 2H), 3.01 (s, 3H), 3.99 (d, J=14.0 Hz, 1H), 4.56 (d, J=14.0 Hz, 1H), 7.20-7.45 (m, 5H).
AP-MS (m/z): 441 (M⁻1).

Reference Example 143

Compound 150

Compound 149 (83 mg, 0.19 mmol) prepared in Reference Example 142 was dissolved in 1,2-dichloroethane (3.2 mL).

To the solution was added thionyl chloride (3.2 mL), and the mixture was stirred at 60° C. for 2.5 hours. The reaction mixture was concentrated under reduced pressure, and then the residue was purified by preparative thin layer chromatography (chloroform/methanol=20/1) to give Compound 150 (61 mg, 76%).

$^1$H NMR (270 MHz, CDCl$_3$) δ (ppm): 2.09 (m, 2H), 2.29 (s, 3H), 2.80 (t, J=6.5 Hz, 4H), 3.05 (s, 3H), 3.95 (dd, J=3.7, 13.9 Hz, 1H), 4.82 (dd, J=9.6, 13.9 Hz, 1H), 5.70 (dd, J=3.7, 9.6 Hz, 1H), 7.29-7.47 (m, 3H), 7.58 (m, 2H).

AP-MS (m/z): 425 (M$^+$+1).

Reference Example 144

Compound 151

In a manner similar to that in Reference Example 133, Compound 151 (113 mg, 78%) was obtained from Compound 118 (100 mg, 0.305 mmol) prepared in Reference Example 111, pyridine (0.062 mL, 0.76 mmol) and 4-bromobutyryl chloride (0.088 mL, 0.76 mmol).

$^1$H NMR (270 MHz, CDCl$_3$) δ (ppm): 2.20 (m, 2H), 2.31 (s, 3H), 2.55 (t, J=6.9 Hz, 2H), 2.96 (s, 3H), 3.47 (t, J=6.2 Hz, 2H), 3.99 (dd, J=5.5, 13.9 Hz, 1H), 4.61 (dd, J=7.9, 13.9 Hz, 1H), 5.37 (dd, J=5.5, 7.9 Hz, 1H), 7.23-7.42 (m, 5H), 8.18 (s, 1H).

AP-MS (m/z): 476 (M$^-$−1).

Reference Example 145

Compound 152

Compound 151 (70 mg, 0.15 mmol) prepared in Reference Example 144 was dissolved in DMF (1.8 mL). To the solution was added 60% sodium hydride (9 mg, 0.2 mmol), and the mixture was stirred at room temperature for 2 hours. To the reaction mixture was added water, and the mixture was extracted with ethyl acetate. The organic layer was washed with saturated aqueous sodium chloride and dried over anhydrous sodium sulfate, and the solvent was evaporated under reduced pressure. The residue was purified by preparative thin layer chromatography (chloroform/methanol=9/1) to give Compound 152 (51 mg, 88%).

$^1$H NMR (270 MHz, CDCl$_3$) δ (ppm): 2.20 (m, 2H), 2.35 (s, 3H), 2.57 (m, 2H), 2.95 (s, 3H), 3.93 (m, 2H), 3.99 (dd, J=5.5, 13.9 Hz, 1H), 4.61 (dd, J=8.1, 13.9 Hz, 1H), 5.33 (dd, J=5.5, 8.1 Hz, 1H), 7.25-7.44 (m, 5H).

AP-MS (m/z): 397 (M$^+$+1).

Reference Example 146

Compound 153

In a manner similar to that in Reference Example 133, Compound 153 (120 mg, 80%) was obtained from Compound 118 (100 mg, 0.305 mmoD prepared in Reference Example 111, pyridine (0.087 mL, 1.1 mmol) and 5-bromovaleryl chloride (0.143 mL, 1.07 mmol).

$^1$H NMR (270 MHz, CDCl$_3$) δ (ppm): 1.75-1.98 (m, 4H), 2.31 (s, 3H), 2.36 (t, J=7.0 Hz, 2H), 2.96 (s, 3H), 3.40 (t, J=6.2 Hz, 2H), 3.99 (dd, J=5.5, 13.9 Hz, 1H), 4.61 (dd, J=7.9, 13.9 Hz, 1H), 5.40 (dd, J=5.5, 7.9 Hz, 1H), 7.23-7.42 (m, 5H), 8.22 (s, 1H)

AP-MS (m/z): 491, 493 (M$^+$+1).

Reference Example 147

Compound 154

In a manner similar to that in Reference Example 145, Compound 154 (36 mg, 72%) was obtained from Compound 153 (60 mg, 0.12 mmol) prepared in Reference Example 146 and 60% sodium hydride (7 mg, 0.2 mmol).

$^1$H NMR (270 MHz, CDCl$_3$) δ (ppm): 1.81-2.02 (m, 41-1), 2.36 (s, 3H), 2.54 (m, 2H), 2.94 (s, 3H), 3.85 (m, 2H), 3.95 (dd, J=4.8, 13.8 Hz, 1H), 4.56 (dd, J=8.4, 13.8 Hz, 1H), 5.41 (dd, J=4.8, 8.4 Hz, 1H), 7.25-7.41 (m, 5H).

AP-MS (m/z): 411 (M$^+$+1).

Reference Example 148

Compound 155

In a manner similar to that in Reference Example 133, Compound 155 (122 mg, 80%) was obtained from Compound 118 (99 mg, 0.30 mmol) prepared in Reference Example 111, pyridine (0.061 mL, 0.75 mmol) and 6-bromohexanoyl chloride (0.115 mL, 0.754 mmol).

$^1$H NMR (270 MHz, CDCl$_3$) δ (ppm): 1.40-1.77 (m, 4H), 1.87 (m, 2H), 2.31 (s, 3H), 2.35 (t, J=7.4 Hz, 2H), 2.96 (s, 3H), 3.40 (t, J=6.6 Hz, 2H), 3.99 (dd, J=5.4, 14.0 Hz, 1H), 4.60 (dd, J=7.9, 14.0 Hz, 1H), 5.36 (dd, J=5.4, 7.9 Hz; 1H), 7.20-7.43 (m, 5H), 8.06 (s, 1H).

AP-MS (m/z): 505, 507 (M$^+$+1).

Reference Example 149

Compound 156

In a manner similar to that in Reference Example 145, Compound 156 (17 mg, 32%) was obtained from Compound 155 (63 mg, 0.12 mmol) prepared in Reference Example 148 and 60% sodium hydride (7 mg, 0.2 mmol).

$^1$H NMR (270 MHz, DMSO-d$_6$) δ (ppm): 1.55-1.78 (m, 6H), 2.19 (s, 3H), 2.68 (m, 2H), 2.95 (s, 3H), 3.87 (dd, J=7.9, 13.7 Hz, 1H), 4.12 (m, 21-1), 4.29 (dd, J=5.6, 13.7 Hz, 1H), 7.20-7.41 (m, 6H).

AP-MS (m/z): 425 (M$^+$+1).

Reference Example 150

Compound 157

Compound 99 (1.50 g, 3.21 mmol) prepared in Reference Example 92 was dissolved in methanol (30 mL). To the solution was gradually added sodium borohydride (1.21 g, 32.0 mmol) at 50° C., and the mixture was stirred at the same temperature for 1.5 hours. To the reaction mixture was added water, and the mixture was extracted with ethyl acetate. The organic layer was washed with saturated aqueous sodium chloride, and dried over anhydrous sodium sulfate, and the solvent was evaporated under reduced pressure. The residue was purified by silica gel column chromatography (chloroform/methanol=20/1) to give Compound 157 (0.26 g, 21%).

$^1$H NMR (270 MHz, CDCl$_3$) δ (ppm): 1.31 (s, 9H), 2.62 (m, 1H), 2.94 (s, 3H), 3.22 (m, 1H), 3.41 (m, 1H), 3.61 (m, 1H), 4.21 (s, 2H), 4.79 (m, 1H), 7.19-7.38 (m, 5H), AP-MS (m/z): 385 (M$^+$+1).

Reference Example 151

Compound 158

In a manner similar to that in Reference Example 133, Compound 158 (114 mg, 85%) was obtained from Compound 157 (97 mg, 0.25 mmol) prepared in Reference Example 150, pyridine (0.051 nab, 0.63 mmol) and 4-bromobutyryl chloride (0.073 mL, 0.63 mmol).

$^1$H NMR (270 MHz, CDCl$_3$) δ (ppm): 1.32 (s, 9H), 2.22 (m, 2H), 2.58 (t, J=7.4 Hz, 2H), 2.65 (m, 1H), 2.97 (s, 3H), 3.27 (m, 1H), 3.39 (m, 1H), 3.49 (t, J=6.2 Hz, 2H), 3.62 (m, 1H), 4.45 (br t, 1H), 7.21-7.39 (m, 5H), 8.00 (s, 1H).

AP-MS (m/z): 533, 535 (M$^+$+1).

Reference Example 152

Compound 159

In a manner similar to that in Reference Example 145, Compound 159 (64 mg, 68%) was obtained from Compound 158 (110 mg, 0.206 mmol) prepared in Reference Example 151 and 60% sodium hydride (12 mg, 0.31 mmol).

$^1$H NMR (270 MHz, CDCl$_3$) δ (ppm): 1.34 (s, 9H), 2.23 (m, 2H), 2.56 (m, 2H), 2.61 (m, 1H), 2.97 (s, 3H), 3.27 (m, 1H), 3.40 (m, 11-1), 3.63 (m, 1H), 3.98 (m, 2H), 4.01 (br t, J=3.5 Hz, 1H), 7.20-7.37 (m, 5H).

AP-MS (m/z): 453 (M$^+$+1).

Reference Example 153

Compound 160

Compound 119 (21 mg, 0.052 mmol) prepared in Reference Example 112 was dissolved in a mixed solvent of toluene (1 mL) and THF (1 mL). To the solution was added 2,4-bis(4-methoxyphenyl)-1,3-dithia-2,4-diphosphethane-2,4-disulfide (Lawesson's reagent) (43 mg, 0.11 mmol), and the mixture was stirred at 90° C. for 5 hours. The reaction mixture was purified by preparative thin layer chromatography (chloroform/methanol=20/1) to give Compound 160 (15 mg, 67%).

$^1$H NMR (270 MHz, CDCl$_3$) δ (ppm): 1.30 (s, 9H), 2.76 (s, 3H), 3.08 (s, 3H), 4.08 (dd, J=7.3, 13.8 Hz, 1H), 5.03 (t, J=7.3 Hz, 1H), 5_54 (dd, J=7.3, 13.8 Hz, 1H), 7.26-7.42 (m, 5H), 8.16 (s, 1H).

AP-MS (m/z): 429 (M$^+$+1).

Reference Example 154

Compound 161

In a manner similar to that in Reference Example 100, Compound 161 (70 mg, 37%) was obtained from Compound 106 (0.165 g, 0.393 mmol) prepared in Reference Example 99, oxalyl chloride (2 mL), 2-(methylamino)ethanol (295 mg, 3.93 mmol) and triethylamine (476 mg, 4.72 mmol).

AP-MS (ra/z): 475 (M$^-$−1).

Reference Example 155

Compound 162

In a manner similar to that in Reference Example 100, Compound 162 (135 mg, 68%) was obtained from Compound 106 (0.165 g, 0.393 mmol) prepared in Reference Example 99, oxalyl chloride (2 mL) and diethanolamine (413 mg, 3.93 mmol).

AP-MS (m/z): 507 (M$^-$−1).

Reference Example 156

Compound 163 and Compound 164

In a manner similar to that in Reference Example 100, Compound 163 (6.2 mg, 5%) and Compound 164 (36.1 mg, 31%) were obtained from Compound 106 (0.099 g, 0.237 mmol) prepared in Reference Example 99, oxalyl chloride (1.25 mL) and 3-amino-1,2-propanediol (92 μL, 1.19 mmol).

Compound 163

AP-MS (m/z): 493 (M$^+$+1).

Compound 164

AP-MS (m/z): 493 (M$^+$+1).

Reference Example 157

Compound 165

In a manner similar to that in Reference Example 100, Compound 165 (37 mg, 33%) was obtained from Compound 115 (0.102 g, 0.236 mmol) prepared in Reference Example 108, oxalyl chloride (1.25 mL) and 2-aminoethanol (144 mg, 2.36 mmol).

AP-MS (m/z): 477 (M$^+$+1).

Reference Example 158

Compound 166

Compound 105 (0.200 g, 0.461 mmol) prepared in Reference Example 98 was dissolved in THF (2 mL). To the solution was added lithium aluminium hydride (30 mg, 0.791 mmol) at 0° C., and the mixture was stirred at room temperature for 2 hours. To the reaction mixture was added water and 30% aqueous sodium hydroxide. The insoluble precipitate was filtrated off, and the filtrate was concentrated under reduced pressure. The residue was purified by preparative thin layer chromatography (chloroform/methanol=9/1) to give Compound 166 (64.0 mg, 34%).

$^1$H NMR (270 MHz, CDCl$_3$) δ (ppm): 1.29 (s, 9H), 1.32 (s, 9H), 1.65 (m, 1H), 2.08 (m, 1H), 2.33 (m, 1H), 3.16 (m, 1H), 3.78 (m, 2H), 7.21-7.38 (m, 5H), 7.95 (br s, 1H)

AP-MS (m/z): 404 (M$^-$−1).

Reference Example 159

Compound 167

Compound 166 (0.0448 g, 0.110 mmol) prepared in Reference Example 158 was dissolved in N,N-dimethylacetamide (0.5 mL). To the solution was added sulfamoyl chloride (51.1 mg, 0.442 mmol) at 0° C. under stirring, and the mixture was stirred at 0° C. for 20 minutes. To the reaction mixture was added water, and the mixture was stirred. Then, the deposited solid was collected by filtration, and dried under reduced pressure. The resulting solid was purified by preparative thin layer chromatography (chloroform/methanol=30/1) to give Compound 167 (30.2 mg, 57%).

¹H NMR (270 MHz, CDCl₃) δ (ppm): 1.29 (s, 9H), 1.33 (s, 9H), 1.89 (m, 1H), 2.14 (m, 1H), 2.38 (m, 1H), 3.32 (m, 1H), 4.28 (m, 1H), 4.43 (m, 1H), 5.08 (br s, 1H), 7.29 (m, 5H), 7.93 (br s, 1H).

AP-MS (m/z): 483 (M⁻−1).

Reference Example 160

Compound 168 and Compound 169

Step 1: 2-Aminoacetophenone hydrochloride (4.56 g, 26.6 mmol) was dissolved in dichloromethane (250 mL). To the solution was added triethylamine (9.30 mL, 66.7 mmol), and the mixture was stirred at room temperature for 10 minutes. After the reaction mixture was cooled to 0° C., chloromethanesulfonyl chloride (purity 90%, 3.60 mL, 36.3 mmol) was added, and the mixture was stirred at the same temperature for 1 hour. To the reaction mixture was added 2 mol/L hydrochloric acid, and the mixture was extracted with chloroform. The organic layer was washed with saturated aqueous sodium chloride and dried over anhydrous sodium sulfate, and the solvent was evaporated under reduced pressure. To the residue was added diethyl ether, and the deposited crystals were collected by filtration and dried to give 2-(chloromethylsulfonylamino)acetophenone (5.00 g, 76%).

¹H NMR (300 MHz, DMSO-d₆) δ (ppm): 4.67 (s, 2H), 4.94 (s, 2H), 7.54 (t, J=8.1 Hz, 2H), AP-MS (m/z): 247 (M+).

Step 2: 2-(Chloromethylsulfonylamino)acetophenone (1.00 g, 4.05 mmol) prepared above and thiosemicarbazide hydrochloride (1.03 g, 8.07 mmol) were dissolved in methanol (60 mL). To the solution was added concentrated hydrochloric acid (1.00 mL), and the mixture was stirred at 60° C. for 2 hours. The reaction mixture was concentrated, to the residue was added saturated aqueous sodium hydrogencarbonate, and the mixture was extracted with ethyl acetate. The organic layer was washed with saturated aqueous sodium chloride, and dried over anhydrous sodium sulfate, and the solvent was evaporated under reduced pressure. The residue was purified by silica gel column chromatography (ethyl acetate/n-hexane=1/1 and 2/1) to give 2-(chloromethylsulfonylamino)acetophenone=thiosemicarbazone (0.51 g, 40%).

¹HNMR (300 MHz, DMSO-d₆) δ (ppm): 4.17 (s, 2H), 4.93 (s, 2H), 7.37-7.42 (m, 3H), 7.52-7.56 (m, 2H), 8.13 (br s, 1H), 8.48 (br, 2H), 8.85 (br s, 1H).

AP-MS (m/z): 319 (M+).

Step 3: 2-(Chloromethylsulfonylamino)acetophenone=thiosemicarbazone (7.48 g, 23.4 mmol) prepared above was dissolved in chloroform (250 mL). To the solution was added pyridine (11.4 mL, 141 mmol) and pivaloyl chloride (8.70 mL, 70.6 mmol), and the mixture was stirred at room temperature for 30 minutes. To the reaction mixture was added acetic anhydride (4.40 mL, 46.6 mmol), and the mixture was further stirred at room temperature for 15 hours. To the reaction mixture was added 2 mol/L hydrochloric acid, and the mixture was extracted with chloroform. The organic layer was washed with saturated aqueous sodium chloride and dried over anhydrous sodium sulfate, and the solvent was evaporated under reduced pressure. The residue was purified by silica gel column chromatography (ethyl acetate/n-hexane=1/1 and 2/1) to give Compound 168 (3.56 g, 25%) and Compound 169 (1.77 g, 14%).

Compound 168

¹H NMR (300 MHz, DMSO-d₆) δ (ppm): 1.16 (s, 9H), 2.23 (s, 3H), 4.00 (dd, J=11.3, 8.0 Hz, 1H), 4.47 (dd, J=11.3, 2.5 Hz, 1H), 4.91 (d, J=12.0 Hz, 1H), 4.97 (d, J=12.0 Hz, 1H), 7.28-7.39 (m, 5H), 8.10 (br s, 1H), 11.2 (br s, 1H).

AP-MS (m/z): 446 (M+).

Compound 169

¹H NMR (300 MHz, DMSO-d₆) δ (ppm): 2.01 (s, 3H), 2.18 (s, 3H), 3.95 (d, J=14.3 Hz, 1H), 4.45 (d, J=14.3 Hz, 1H), 4.91 (d, J=12.0 Hz, 1H), 4.97 (d, J=12.0 Hz, 1H), 7.25-7.39 (m, 5H), 8.08 (br s, 1H), 11.6 (br s, 1H).

AP-MS (m/z): 404 (M+).

Reference Example 161

Compound 170 and Compound 171

Step 1: 2-Aminoacetophenone hydrochloride (1.00 g, 5.85 mmol) was dissolved in dichloromethane (50 mL). To the solution was added triethylamine (2.50 mL, 17.9 mmol), and the mixture was stirred at room temperature for 10 minutes. After the reaction mixture was cooled to 0° C., chloroethanesulfonyl chloride (0.92 mL, 8.80 mmol) was added, and the mixture was stirred at the same temperature for 15 minutes. To the reaction mixture was added 2 mol/L hydrochloric acid and the mixture was extracted with chloroform. The organic layer was washed with saturated aqueous sodium chloride and dried over anhydrous sodium sulfate, and the solvent was evaporated under reduced pressure. To the residue was added a mixed solvent of ethyl acetate and n-hexane for crystallization to obtain 2-(vinylsulfonylamino)acetophenone (0.42 g, 32%).

¹H NMR (300 MHz, CDCl₃) δ (ppm): 4.54 (d, J=4.5 Hz, 2H), 5.42 (br s, 1H), 5.94 (d, J=9.9 Hz, 1H), 6.28 (d, J=16.5 Hz, 1H), 6.53 (br dd, J=16.2, 9.9 Hz, 1H), 7.52 (t, J=7.5 Hz, 3H), 7.65 (t, J=7.8 Hz, 1H), 7.93 (t, J=5.1 Hz, 1H).

AP-MS (m/z): 225 (M+).

Step 2: 2-(Vinylsulfonylamino)acetophenone (0.32 g, 1.42 mmol) prepared above and thiosemicarbazide hydrochloride (0.27 g, 2.13 mmol) were dissolved in methanol (20 mL). To the solution was added concentrated hydrochloric acid (2 drops), and the mixture was stirred at room temperature for 3 hours. The reaction mixture was concentrated. To the residue was added saturated aqueous sodium hydrogencarbonate, and the mixture was extracted with ethyl acetate. The organic layer was washed with saturated aqueous sodium chloride and dried over anhydrous sodium sulfate, and the solvent was evaporated under reduced pressure. The residue was purified by silica gel column chromatography (ethyl acetate/n-hexane=1/1) to give 2-(vinylsulfonylamino)acetophenone= thiosemicarbazone (0.25 g, 58%).

¹H NMR (300 MHz, CDCl₂) δ (ppm): 4.10 (s, 2H), 5.97 (d, J=9.9 Hz, 1H), 6.25 (d, J=16.8 Hz, 1H), 6.54 (dd, J=16.8, 9.9 Hz, 1H), 7.24-7.27 (m, 2H), 7.42 (br s, 1H), 7.52-7.53 (m, 3H), 7.81 (br s, 1H), 8.70 (m, 1H).

AP-MS (m/z): 297 (M+).

Step 3: 2-(Vinylsulfonylamino)acetophenone= thiosemicarbazone (0.25 g, 0.83 mmol) prepared above was dissolved in acetone (10 mL). To the solution was added pyridine (0.34 mL, 4.17 mmol) and pivaloyl chloride (0.31 mL, 2.50 mmol), and the mixture was stirred at room temperature for 30 minutes. To the reaction mixture was added acetic anhydride (0.16 mL, 1.66 mmol), and the mixture was further stirred for 3 days at room temperature. The reaction mixture was concentrated, to the residue was added 2 mol/L hydrochloric acid, and the mixture was extracted with ethyl acetate. The organic layer was washed with saturated aqueous sodium chloride and dried over anhydrous sodium sulfate, and the solvent was evaporated under reduced pressure. The residue was purified by silica gel column chromatography (ethyl acetate/n-hexane=1/1) to give Compound 170 (0.18 g, 52%) and Compound 171 (0.10 g, 26%).

Compound 170

$^1$H NMR (300 MHz, CDCl$_3$) δ (ppm): 1.27 (s, 9H), 2.31 (s, 3H), 3.87 (dd, J=13.4, 5.0 Hz, 1H), 4.45 (dd, J=13.4, 7.9 Hz, 1H), 5.57 (br s, 1H), 5.92 (d, J=9.9 Hz, 1H), 6.25 (d, J=16.5 Hz, 1H), 6.49 (dd, J=16.5, 9.9 Hz, 1H), 7.27-7.34 (m, 5H), 8.22 (br s, 1H).
AP-MS (m/z): 424 (M+).

Compound 171

$^1$H NMR (300 MHz, CDCl$_3$) δ (ppm): 1.29 (s, 9H), 1.33 (s, 9H), 3.85 (dd, J=13.5, 4.8 Hz, 1H), 4.49 (dd, J=13.5, 8.1 Hz, 1H), 5.29 (br s, 1H), 5.93 (br d, J=9.9 Hz, 1H), 6.27 (br d, J=16.5 Hz, 1H), 6.53 (br dd, J=16.4, 9.6 Hz, 1H), 7.27-7.34 (m, 5H), 8.06 (br s, 1H).
AP-MS (m/z): 466 (M+).

Reference Example 162

Compound 172

Compound 170 (0.05 g, 0.11 mmol) prepared in Step 3 of Reference Example 161 was dissolved in acetonitrile (3 mL). To the solution was added morpholine (0.10 mL), and the mixture was stirred at 80° C. for 2 hours. The reaction mixture was concentrated, and the residue was purified by silica gel column chromatography (chloroform/methanol=10/1) to give Compound 172 (0.04 g, 77%).
$^1$H NMR (300 MHz, CDCl$_3$) δ (ppm): 1.27 (s, 9H), 2.33 (s, 3H), 2.42-2.45 (m, 4H), 2.78 (dquin, J=16.5, 6.0 Hz, 2H), 3.19 (t, J=6.6 Hz, 2H), 3.65-3.68 (m, 4H), 4.04 (dd, J=14.1, 4.8 Hz, 1H), 4.55 (dd, J=14.1, 7.5 Hz, 1H), 5.73 (br s, 1H), 7.30-7.38 (m, 5H), 8.05 (br s,
AP-MS (m/z): 511 (M+).

Reference Example 163

Compound 173

In a manner similar to that in Reference Example 162, Compound 173 (0.03 g, 66%) was obtained from Compound 170 (0.05 g, 0.11 mmol) prepared in Step 3 of Reference Example 161 and 70% aqueous ethylamine (0.10 mL).
$^1$H NMR (300 MHz, CDCl$_3$) δ (ppm): 1.10 (t, J=6.9 Hz, 3H), 1.27 (s, 9H), 2.32 (s, 3H), 2.65 (quin, J=7.2 Hz, 210, 3.05-3.09 (m, 210, 3.18-3.20 (m, 2H), 4.00 (d, J=1H), 4.55 (d, J=13.8 Hz, 1H), 7.30-7.37 (m, 5H), 8.07 (br s, 1H).
AP-MS (m/z): 470 (M$^+$+1).

Reference Example 164

Compound 174

In a manner similar to that in Reference Example 162, Compound 174 (0.03 g, 67%) was obtained from Compound 170 (0.05 g, 0.11 mmol) prepared in Step 3 of Reference Example 161 and a 2 mol/L dimethylamine methanol solution (0.10 mL).
$^1$H NMR (300 MHz, CDCl$_3$) δ (ppm): 1.26 (s, 9H), 2.24 (s, 6H), 2.31 (s, 3H), 2.71-2.81 (m, 2H), 3.12-3.19 (m, 2H), 4.00 (d, J=13.5 Hz, 1H), 4.56 (d, J=13.5 Hz, 1H), 1H), 7.31-7.36 (m, 5H), 8.06 (br s, 1H).
AP-MS (m/z): 469 (M+).

Reference Example 165

Compound 175

In a manner similar to that in Reference Example 162, Compound 175 (0.03 g, 52%) was obtained from Compound 170 (0.05 g, 0.11 mmol) prepared in Step 3 of Reference Example 161 and 2-aminoethanol (0.10 mL).
$^1$H NMR (300 MHz, CDCl$_3$) δ (ppm): 1.26 (s, 9H), 2.35 (s, 3H), 2.65-2.78 (m, 2H), 3.08-3.30 (m, 4H), 3.64 (t, J=5.1 Hz, 2H), 3.98 (d, J=13.5 Hz, 1H), 1H), 7.26-7.38 (m, 5H), 8.25 (br s, 1H).
AP-MS (m/z): 485 (M+).

Reference Example 166

Compound 176

In a manner similar to that in Reference Example 162, Compound 176 (0.01 g, 26%) was obtained from Compound 171 (0.05 g, 0.11 mmol) prepared in Step 3 of Reference Example 161 and 70% aqueous ethylamine (0.10 mL).
$^1$H NMR (300 MHz, CDCl$_3$) δ (ppm): 1.18 (m, 3H), 1.28 (s, 9H), 1.34 (s, 9H), 2.63 (quin, J=7.0 Hz, 2H), 2.73 (br q, J=6.3 Hz, 1H), 2.84 (br q, J=6.2 Hz, 1H), 3.18 (br t, J=6.6 Hz, 2H), 4.02 (d, J=13.2 Hz, 1H), 4.58 (d, J=13.2 Hz, 1H), 5.85 (br s, 1H), 7.27-7.35 (m, 5H), 8.02 (br s, 1H).
AP-MS (m/z): 512 (M$^+$+1).

Reference Example 167

Compound 177

In a manner similar to that in Reference Example 162, Compound 177 (0.02 g, 39%) was obtained from Compound 171 (0.05 g, 0.11 mmol) prepared in Step 3 of Reference Example 161 and a 2 mol/L dimethylamine methanol solution (0.10 mL).
$^1$H NMR (300 MHz, CDCl$_3$) δ (ppm): 1.28 (s, 9H), 1.34 (s, 9H), 2.25 (s, 6H), 2.73 (br q, J=6.3 Hz, 1H), 2.84 (br q, J=6.2 Hz, 1H), 3.18 (br t, J=6.6 Hz, 2H), 4.02 (d, J=13.2 Hz, 1H), 4.58 (d, J=13.2 Hz, 1H), 5.85 (br s, 1H), 7.27-7.35 (m, 5H), 8.02 (br s, 1H).
AP-MS (m/z): 512 (M$^+$+1).

Reference Example 168

Compound 178

In a manner similar to that in Reference Example 11, Compound 178 (64.0 mg, 38%) was obtained from carbomethoxypropiophenone=thiosemicarbazone (0.144 g, 0.543 mol) prepared in Step 1 of Reference Example 98, acetic anhydride (77 μL, 0.814 mmol) and pyridine (79 μL, 0.977 mmol).
$^1$H NMR (270 MHz, CDCl$_3$) δ (ppm): 2.13 (s, 3H), 2.20-2.70 (m, 41-1), 3.61 (s, 3H), 6.52 (br s, 2H), 7.20-7.35 (m, 5H).

Reference Example 169

Compound 179

In a manner similar to that in Reference Example 15, Compound 179 (24.0 mg, 94%) was obtained from Compound 178 (0.0200 g, 0.0650 mol) prepared in Reference Example 168, pivaloyl chloride (16 μL, 0.130 mmol) and pyridine (15 μL, 0.182 mmol).

$^1$H NMR (270 MHz, CDCl$_3$) δ (ppm): 1.30 (s, 9H), 2.10 (s, 3H), 2.17-2.75 (m, 4H), 3.57 (s, 3H), 7.18-7.32 (m, 5H), 8.02 (br s, 1H).

AP-MS (m/z): 390 (M$^-$–1).

Reference Example 170

Compound 180

Compound 100 (304 mg, 0.0690 mmol) prepared in Reference Example 93 and cerium chloride heptahydrate (257 mg, 0.690 mmol) were dissolved in methanol (800 mL). To the solution was gradually added sodium borohydride (522 mg, 13.8 mmol), and the mixture was stirred at room temperature for 20 minutes. The reaction mixture was concentrated under reduced pressure. To the residue was added 1 mol/L hydrochloric acid (100 mL), and the mixture was extracted with chloroform. The organic layer was dried over anhydrous sodium sulfate, and the solvent was evaporated under reduced pressure. The residue was purified by silica gel column chromatography (chloroform/acetone/ethyl acetate/n-hexane=9/1/1/1) to give Compound 180 (217 mg, 85%).

$^1$H NMR (270 MHz, CDCl$_3$) δ (ppm): 1.14 (t, J=7.0 Hz, 6H), 2.68 (in, 1H), 2.98 (s, 3H), 3.27 (m, 2H), 3.44 (m, 1H), 3.63 (m, 1H), 4.18 (br s, 2H), 4.51 (br s, 1H), 7.30 (m, 5H), AP-MS (ra/z): 371 (M$^+$1).

Reference Example 171

Compound 181

In a manner similar to that in Reference Example 15, Compound 181 (87.3 mg, 71%) was obtained from Compound 180 (100 mg, 0.270 mmol) prepared in Reference Example 170, pyridine (65.4 μL, 0.810 mmol) and pivaloyl chloride (83.4 μL, 0.676 mmol).

AP-MS (m/z): 455 (M$^+$+1).

Reference Example 172

Compound 182

Compound 180 (60.6 mg, 0.170 mmol) obtained in Reference Example 170 was dissolved in dichloromethane. To the solution was added pyridine (63.2 μL, 0.188 mmol) and 5-bromovaleryl chloride (23.0 μL, 0.172 mmol), and the mixture was stirred at room temperature for 5 hours. To the reaction mixture was added 1 mol/L hydrochloric acid, and the mixture was extracted with chloroform. The organic layer was dried over anhydrous sodium sulfate, and the solvent was evaporated under reduced pressure. The residue was dissolved in DMSO (0.3 mL). To the solution was added sodium acetate (58.7 mg), and the mixture was stirred at 100° C. for 5 minutes. To the reaction mixture was added water (20 mL) and 1 mol/L hydrochloric acid (20 mL), and the mixture was extracted with chloroform. The organic layer was dried over anhydrous sodium sulfate, and the solvent was evaporated under reduced pressure. The residue was purified by preparative thin layer chromatography (chloroform/acetone/ethyl acetate/n-hexane=9/1/1/1) to give Compound 182 (42.5 mg, 45%).

AP-MS (m/z): 453 (M$^+$1).

Reference Example 173

Compound 183

Compound 180 (100 mg, 0.270 mmol) prepared in Reference Example 170 and pyridine (31.5 μL, 0.389 mmol) were dissolved in dichloromethane (2 mL). To the solution was added 4-bromobutyryl chloride (37.5 μL, 0.324 mmol) at 0° C., and the mixture was stirred at room temperature for 5 hours. To the reaction mixture was added 1 mol/L hydrochloric acid, and the mixture was extracted with chloroform. The organic layer was dried over anhydrous sodium sulfate, and the solvent was evaporated under reduced pressure. To the residue was added methanol (20 mL) and potassium carbonate (1.0 g), and the mixture was vigorously stirred at room temperature for 20 minutes. To the reaction mixture was added water and 1 mol/L hydrochloric acid, and the mixture was extracted with chloroform. The organic layer was dried over anhydrous sodium sulfate, and the solvent was evaporated. The residue was purified by silica gel column chromatography (chloroform/acetone/ethyl acetate/n-hexane=9/1/1/1) to give Compound 183 (27.6 mg, 37%).

$^1$H NMR (270 MHz, CDCl$_3$) δ (ppm): 1.15 (d, J=6.6 Hz, 6H), 2.22 (m, 2H), 2.55-2.67 (m, 3H), 2.94 (s, 3H), 3.31-3.47 (m, 3H), 3.61 (m, 1H), 3.91-3.98 (m, 2H), 5.0 (br s, 1H), 7.20-7%35 (m, 5H).

AP-MS (m/z): 437 (M$^-$–1).

Reference Example 174

Compound 184

In a manner similar to that in Reference Example 173, Compound 180 (84.1 mg, 0.227 mmol) prepared in Reference Example 170 was treated with pyridine (88.0 mL, 1.09 mmol) and 5-bromovaleryl chloride (121 μL, 0.908 mmol), and then treated with methanol and potassium carbonate (1.0 g) to give Compound 184 (89.1 mg, 81%).

AP-MS (m/z): 485 (M$^-$–1).

Reference Example 175

Compound 185

In a manner similar to that in Step 3 of Reference Example 92, Compound 185 (16.7 g, 85%) was obtained from 3-(methylsulfonylamino)propiophenone=thiosemicarbazone (14.4 g, 47.9 mmol), propionyl chloride (16.7 mL, 192 mmol) and pyridine (18.6 mL, 230 mmol).

$^1$H NMR (270 MHz, CDCl$_3$) δ (ppm): 1.12 (t, J=7.5 Hz, 3H), 1.19 (t, J=7.3 Hz, 3H), 2.37 (m, 2H), 2.63 (m, 3H), 2.96 (s, 3H), 3.35 (m, 2H), 3.58 (m, 1H), 4.55 (br s, 1H), 7.20-7.35 (m, 5H), 8.01 (br s, 1H).

Reference Example 176

Compound 186

In a manner similar to that in Reference Example 170, Compound 186 (11.7 g, 81%) was obtained from Compound 185 (16.7 g, 40.5 mmol) prepared in Reference Example 175, cerium chloride heptahydrate (15.1 g, 40.5 mol) and sodium borohydride (12.8 g, 338 mol).

$^1$H NMR (270 MHz, CDCl$_3$) δ (ppm): 1.13 (t, J=8.7 Hz, 3H), 2.61-2.71 (m, 3H), 2.97 (s, 3H), 3.27-3.47 (m, 2H), 3.60-3.67 (m, 1H), 4.21 (br s, 2H), 4.65 (br s, 1H), 7.26-7.36 (m, 5H).

Reference Example 177

Compound 187

In a manner similar to that in Reference Example 15, Compound 187 (90.3 mg, 76%) was obtained from Compound 186 (96.0 mg, 0.269 mmol) prepared in Reference Example 176, pyridine (65.4 μL, 0.810 mmol) and pivaloyl chloride (83.4 μL, 0.676 mmol).

$^1$H NMR (270 MHz, CDCl$_3$) δ (ppm): 1.13 (t, J=6.0 Hz, 3H), 128 (s, 9H), 2.66 (m, 3H), 2.97 (s, 3H), 3.35 (m, 2H), 3.61 (m, 1H), 4.58 (br s, 1H), 7.32 (m, 5H), 8.08 (br s, 1H).

AP-MS (m/z): 441 (M$^+$+1).

Reference Example 178

Compound 188

Compound 186 (100 mg, 0.221 mmol) obtained in Example 176 was dissolved in dichloromethane, to the solution was added pyridine (85 μL, 1.05 mmol) and 4-bromobutyryl chloride (110 μL, 0.949 mmol), and the mixture was stirred at room tempterature for 5 hours. To the reaction mixture was added 1 mol/L hydrochloric acid, and the mixture was extracted with chloroform. The organic layer was dried over anhydrous sodium sulfate, and the solvent was evaporated under reduced pressure. The residue was dissolved in methanol (50 mL), to the solution was added potassium carbonate (1.0 g, 7.24 mmol), and the mixture was vigorously stirred. After 1.5 hours, the reaction mixture was filtered, and the filtrate was concentrated under reduced pressure. To the residue was added ethyl acetate, and the mixture was washed with 1 mol/L hydrochloric acid and then with water. The organic layer was dried over sodium sulfate, and the solvent was evaporated under reduced pressure. The residue was purified by preparative thin layer chromatography (chloroform/methanol=20/1) to give Compound 188 (42.5 mg, 45%).

$^1$H NMR (270 MHz, CDCl$_3$) δ (ppm): 1.14 (t, J=7.5 Hz, 3H), 2.19 (m, 2H), 2.50-2.81 (m, 5H), 2.96 (s, 3H), 3.35 (m, 2H), 3.59 (m, 1H), 3.93 (m, 2H), 4.52 (br s, 1H), 7.20-7.34 (m, 5H).

AP-MS (m/z): 424 (M$^-$−1).

Reference Example 179

Compound 189

In a manner similar to that in Reference Example 178, Compound 189 (27.6 mg, 37%) was obtained from Compound 186 (60.6 mg, 0.170 mmol) prepared in Reference Example 176, pyridine (63.2 μL, 0.788 mmol), 5-bromovaleryl chloride (110 μL, 0.949 mmol) and potassium carbonate (1.0 g, 7.24 mmol).

$^1$H NMR (270 MHz, CDCl$_3$) δ (ppm): 1.14 (t, J=7.5 Hz, 3H), E79-1.99 (m, 4H), 2.54-2.75 (m, 510, 2.96 (s. 3H), 3.19-3.27 (m, 2H), 3.57-3.68 (m, 1H), 3.83-3.95 (m, 2H), 4.36 (br s, 1H), 7.20-7.37 (m, 5H).

AP-MS (m/z): 439 (M$^+$+1).

Reference Example 180

Compound 190

In a manner similar to that in of Reference Example 170, Compound 190 (86.5 mg, 0.248 mmol) was obtained from Compound 105 (1.01 g, 2.33 mmol) prepared in Reference Example 98 and sodium borohydride (2.20 g, 58.2 mmol).

$^1$H NMR (270 MHz, CDCl$_3$) δ (ppm): 1.30 (s, 91-1), 2.37-2.46 (m, 1H), 2.63-2.86 (m, 2H), 3.41-3.51 (m, 1H), 3.71 (s, 3H), 4.09 (br s, 2H), 7.22-7.43 (m, 5H).

Reference Example 181

Compound 191

In a manner similar to that in of Reference Example 133, Compound 191 (89.5 mg, 29%) was obtained from Compound 190 (86.5 mg, 0.248 mmol) obtained in Reference Example 180 and 4-bromobutyryl chloride (57 μL, 0.495 mmol).

AP-MS (m/z): 496 (M$^-$−1).

Reference Example 182

Compound 192

Compound 191 (89.5 mg, 0.18 mmol) prepared in Reference Example 181 was dissolved in DMF (2.0 mL). To the solution was added 60% sodium hydride (14 mg, 0.359 mmol), and the mixture was stirred at room temperature for 1 hour. To the reaction mixture was added acetic acid and water, and the mixture was extracted with ethyl acetate. The organic layer was washed with saturated saline, dried over anhydrous sodium sulfate, and the solvent was evaporated under reduced pressure. The residue was purified by silica gel column chromatography (ethyl acetate/n-hexane=2/1) to give Compound 192 (30.2 mg, 40%).

$^1$H NMR (270 MHz, CDCl$_3$) δ (ppm): 1.36 (s, 9H), 2.17-2.42 (m, 3H), 2.53-2.84 (m, 4H), 3.38-3.50 (s, 1H), 3.72 (s, 3H), 3.97 (m, 2H), 7.22-7.39 (m, 5H).

Reference Example 183

Compound 193

In a manner similar to that in Reference Example 99, Compound 193 (21.7 mg, 74%) was obtained from Compound 192 (30.2 mg, 0.723 mmol) prepared in Reference Example 182 and sodium hydroxide (8.7 mg, 0.217 mmol).

AP-MS (m/z): 402 (M$^-$−1).

Reference Example 184

Compound 194

In a manner similar to that in Reference Example 100, Compound 194 (7.3 mg, 30%) was obtained from Compound 193 (21.7 mg, 0.054 mmol) prepared in Reference Example 183, oxalyl chloride (0.25 ml) and 2-aminoethanol (16 μL, 26.9 mmol).

$^1$H NMR (270 MHz, CDCl$_3$) δ (ppm): 1.34 (s, 9H), 2.17-2.28 (m, 3H), 2.54-2.82 (m, 4H), 3.34-3.46 (m, 3H), 3.72 (dd, J=4.0, 6.0 Hz, 2H), 3.96 (br q, J=7.0 Hz, 2H), 7.32-7.34 (m, 5H), 6.11 (br s, 1H).

Reference Example 185

Compound 195

Step 1: In a manner similar to that in Step 1 of Reference Example 1, 2-acetoxy-1-indanone=thiosemicarbazone (3.23 g, 57%) was obtained from 2-acetoxy-1-indanone (4.1 g, 21.6 mmol) and thiosemicarbazide hydrochloride (3.0 g, 23.7 mmol).

Step 2: In a manner similar to that in Step 2 of Reference Example 1, 3-acetyl-5-aminospiro[1,3,4-thiadiazolin-2,1'-indane]-2'-yl acetate (187.4 obtained from 2-acetoxy-1-indanone=thiosemicarbazone (335.5 mg, 1.27 mmol) prepared above, pyridine (13 mL) and acetic anhydride (136 µL, 1.53 mmol).

Step 3: 3-Acetyl-5-aminospiro[1,3,4-thiadiazolin-2,1'-indane]-2'-yl acetate (163.8 mg) prepared above was dissolved in dichloromethane (2.0 mL). To the solution was added pyridine (520 µL, 6.44 mmol) and pivaloyl chloride (661 µL, 5.36 mmol), and the mixture was stirred at room temperature for 24 hours. To the reaction mixture was added water, and the mixture was extracted with chloroform. The organic layer was washed with saturated aqueous sodium chloride and dried over anhydrous sodium sulfate, and the solvent was evaporated under reduced pressure. The residue was purified by silica gel column chromatography (chloroform/ethyl acetate=3/2) to give Compound 195 (118.0 mg, 57%) as a diastereomixture.

AP-MS (m/z): 390 (M$^+$+1).

Reference Example 186

Compound 196

Compound 195 (90.3 mg, 0.233 mmol) prepared in Reference Example 185 was dissolved in a methanol solution of 10% ammonia (4.8 mL), and the solution was stirred at room temperature for 6 hours. The reaction mixture was concentrated, and the residue was purified by silica gel column chromatography (chloroform/ethyl acetate 3/2) to give Compound 196 (16.6 mg, 20%) as a diastereoisomixture.

FAB-MS (m/z): 348 (M$^+$+1).

Reference Example 187

Compound 197

Step 1: In a manner similar to that in Step 1 of Reference Example 1, 4-acetoxy-1-indanone=thiosemicarbazone (2.78 g, 80%) was obtained from 4-acetoxy-1-indanone (2.51 g, 13.2 mmol) and thiosemicarbazide hydrochloride (1.85 g, 14.5 mmol).

Step 2: In a manner similar to that in Reference Example 11, Compound 197 (193.9 mg, 39%) was obtained from 4-acetoxy-1-indanone=thiosemicarbazone (364.5 mg, 1.38 mmol) prepared above, acetic anhydride (123 µL, 1.38 mmol) and pyridine (112 µL, 1.38 mmol).

$^1$H NMR (300 MHz, CDCl$_3$) δ (ppm): 2.18 (s, 3H), 2.30 (s, 3H), 2.59-2.68 (m, 1H), 2.76-2.86 (m, 1H), 3.09-3.30 (m, 2H), 4.17 (br s, 2H), 6.99 (dd, J=7.7, 1.5 Hz, 1H), 7.31 (m, 2H).

Reference Example 188

Compound 198

In a manner similar to that in Reference Example 15, Compound 198 (136 mg, 98%) was obtained from Compound 197 (108.8 mg, 0.356 mmol) prepared in Reference Example 187, pyridine (346 µL, 4.28 mmol) and pivaloyl chloride (439 µL, 3.56 mmol).

$^1$H NMR (270 MHz, CDCl$_3$) δ (ppm): 1.34 (s, 9H), 2.18 (s, 3H), 2.29 (s, 3H), 2.56-2.63 (m, 1H), 2.79-2.92 (m, 1H), 3.08-3.22 (m, 2H), 6.98-7.03 (m, 1H), 7.28-7.31 (m, 2H), 8.08 (br s, 1H).

Reference Example 189

Compound 199

In a manner similar to that in Reference Example 186, Compound 199 (70.0 mg, 94%) was obtained from Compound 198 (83.1 mg, 0.214 mmol) prepared in Reference Example 188 and a methanol solution of 10% ammonia (4.2 mL).

$^1$H NMR (300 MHz, CDCl$_3$) δ (ppm): 1.34 (s, 9H), 2.21 (s, 3H), 2.58-2.67 (m, 1H), 2.81-2.91 (m, 1H), 3.07-3.27 (m, 2H), 5.25 (br s, 1H), 6.62 (d, J=7.7 Hz, 1H), 6.94 (d, J=7.7 Hz, 1H), 7.10 (t, J=7.7 Hz, 1H), 7.99 (br s, 1H).

Reference Example 190

Compound 200

Step 1: Thiosemicarbazide hydrochloride (8.30 g, 65.1 mmol) was dissolved in a mixed solvent of methanol (50 mL) and distilled water (50 mL). To the solution was added ethyl benzoylacetate (17.0 mL, 98.2 mmol) and concentrated hydrochloric acid (1.00 mL, 12.0 mmol), and the mixture was stirred at room temperature for 11 hours. The deposited solid was collected by filtration, washed (methanol) and then dried to give 3-phenyl-3-thiosemicarbazonopropionic acid ethyl ester (thiosemicarbazone) (11.1 g, 64%).

Step 2: Thiosemicarbazone (2.03 g, 7.65 mmol) obtained above was dissolved in dichloromethane (40 mL). To the solution was added pyridine (4.00 mL, 49.7 mmol) and trimethylacetyl chloride (5.60 mL, 45.5 mmol), and the mixture was stirred at room temperature for 12 hours. To the reaction mixture was added saturated aqueous sodium hydrogencarbonate, and the mixture was further stirred at room temperature for 1 hour and then extracted with ethyl acetate. The organic layer was washed with saturated aqueous sodium chloride and dried over anhydrous sodium sulfate, and the solvent was evaporated under reduced pressure. The residue was purified by silica gel column chromatography (hexane/ethyl acetate=20/1→9/1) to give Compound 200 (3.25 g, 98%).

Reference Example 191

Compound 201

Compound 200 (519 mg, 1.20 mmol) obtained in Reference Example 190 was dissolved in THF (10 mL). This solution was cooled to 0° C., and then to the solution was added a 0.93 mol/L solution of diisobutylaluminum hydride (5.30 mL, 4.93 mmol) in hexane, and the mixture was stirred for 2.5 hours. To the reaction mixture was added anhydrous sodium sulfate and saturated aqueous sodium sulfate, and the mixture was further stirred for 1 hour, then filtered. To the filtrate was added water, and the mixture was extracted with ethyl acetate. The organic layer was washed with saturated aqueous sodium chloride and dried over anhydrous sodium sulfate, and the solvent was evaporated under reduced pressure. The residue was purified by silica gel column chromatography (hexane/ethyl acetate=4/1→2/1) to give Compound 201 (348 mg, 74%)

ESI-MS m/z 392 (M+H)⁺..

Reference Example 192

Compound 202

Compound 201 (234 mg, 0.597 mmol) obtained in Reference Example 191 was dissolved in dichloromethane (10 mL). To the solution was added pyridinium dichromate (783 mg, 2.08 mmol), and the mixture was stirred at room temperature for 60 hours. The reaction mixture was filtered, and then the resulting filtrate was concentrated under reduced pressure. The residue was purified by silica gel column chromatography (hexane/ethyl acetate=41→2/1H) to give Compound 202 (155 mg, 67%).

Reference Example 193

Compound 203

In a manner similar to that in Reference Example 190, 3-carbomethoxy-1-propanone=thiosemicarbazone (1.85 g, 6.62 mmol) obtained from 3-carbomethoxy-1-phenyl-1-propanone and thiosemicarbazide was allowed to react with propionyl chloride (2.87 mL, 33.1 mmol) in the presence of pyridine (3.42 mL, 39.7 mmol) and then treated with methanol (50 mL) and potassium carbonate (3.00 g, 21.7 mmol) to give Compound 203 (1.08 g, 43%).

APCI-MS m/z: 376 (M−H)⁻.

Reference Example 194

Compound 204

Step 1: 3-Benzoylpropionic acid (3.56 g, 20.0 mmol) was dissolved in dichloromethane (50 mL), to the solution was added triethylamine (2.22 g, 22.0 mmol) and trimethylacetyl chloride (2.41 g, 20.0 mmol) at 0° C., and the mixture was stirred at room temperature for 60 hours. Subsequently, to the reaction mixture was successively added triethylamine (4.04 g, 40.0 mmol) and N,O-dimethylhydroxylamine (1.95 g, 20.0 mmol), and the mixture was further stirred at room temperature for 5 hours. To the reaction mixture was added water and 1 mol/L hydrochloric acid, and the mixture was extracted with chloroform. The organic layer was washed with aqueous sodium hydrogencarbonate and water and dried over anhydrous sodium sulfate, and the solvent was evaporated under reduced pressure. The resulting residue was purified by column chromatography (chloroform/methanol=50/1→40/1) to give 3-(N-methoxy-N-methylcarbamoyl)-propiophenone (1.53 g, 35%).

Step 2: In a manner similar to that in Step 1 of Reference Example 190, 3-(N-methoxy-N-methylcarbamoyl)-propiophenone=thiosemicarbazone (1.77 g, 87%) was obtained from 3-(N-methoxy-N-methylcarbamoyl)-propiophenone (1.53 g, 6.92 mmol) obtained above and thiosemicarbazide (0.630 g, 6.91 mmol).

Step 3: In a manner similar to that in Step 2 of Reference Example 190, Compound 204 (0.459 g, 51%) was obtained from 3-(N-methoxy-N-methylcarbamoyl)-propiophenone=thiosemicarbazone (0.703 g, 2.39 mmol) obtained above and acetic anhydride (5 mL, 45.3 mmol).

APCI-MS m/z: 379 (M+H)⁺.

Reference Example 195

Compound 205

In a manner similar to that in Step 2 of Reference Example 190, Compound 205 (0.318 g, 81%) was obtained from thiosemicarbazone (0.250 g, 0.849 mmol) obtained in Step 2 of Reference Example 194, pyridine (0.242 g, 3.06 mmol) and trimethylacetyl chloride (0.307 g, 2.55 mmol).

APCI-MS m/z: 463 (M+H)⁺.

INDUSTRIAL APPLICABILITY

According to the present invention, a mitotic kinesin Eg5 inhibitor comprising a thiadiazoline derivative or a pharmacologically acceptable salt thereof as an active ingredient and a thiadiazoline derivative or a pharmacologically acceptable salt thereof having an inhibitory activity against mitotic kinesin Eg5 are provided.

What is claimed is:

1. A thiadiazoline derivative represented by formula (208) or (216), or a pharmacologically acceptable salt thereof

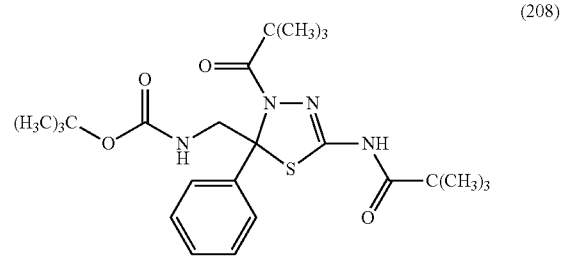

(208)

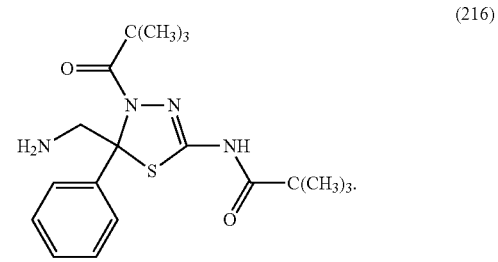

(216)

2. A thiadiazoline derivative according to claim 1, represented by formula (208), or a pharmacologically acceptable salt thereof

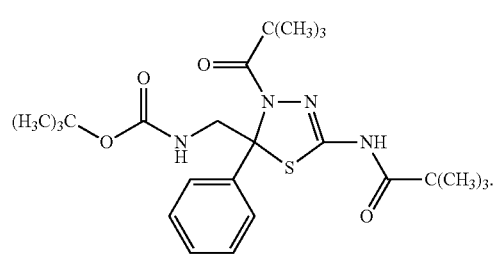 (208)
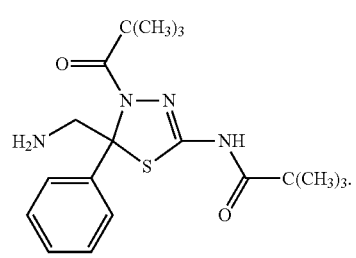 (216)
3. A thiadiazoline derivative according to claim 1 represented by formula (216), or a pharmacologically acceptable salt thereof
* * * * *